US008088359B2

(12) United States Patent
Krause et al.

(10) Patent No.: US 8,088,359 B2
(45) Date of Patent: Jan. 3, 2012

(54) MEANS AND METHODS OF USING A NADPH OXIDASE INHIBITOR FOR THE TREATMENT OF HEARING LOSS AND PHANTOM HEARING

(75) Inventors: Karl-Heinz Krause, Geneva (CH); Botond Banfi, North Liberty, IA (US)

(73) Assignee: University of Geneva, Geneva (CH)

(*) Notice: Subject to any disclaimer, the term of this patent is extended or adjusted under 35 U.S.C. 154(b) by 1123 days.

(21) Appl. No.: 11/628,419

(22) PCT Filed: Jun. 6, 2005

(86) PCT No.: PCT/EP2005/006061
§ 371 (c)(1),
(2), (4) Date: Oct. 3, 2007

(87) PCT Pub. No.: WO2005/119251
PCT Pub. Date: Dec. 15, 2005

(65) Prior Publication Data
US 2009/0263323 A1    Oct. 22, 2009

(30) Foreign Application Priority Data

Jun. 4, 2004 (EP) ..................... 04013266

(51) Int. Cl.
 A61K 49/00  (2006.01)
 C12N 9/00   (2006.01)
 C12N 9/02   (2006.01)
 C12N 1/20   (2006.01)
 C12N 15/00  (2006.01)
 C07H 21/04  (2006.01)
(52) U.S. Cl. ... 424/9.1; 435/183; 435/252.3; 435/320.1; 536/23.2
(58) Field of Classification Search .................. None
See application file for complete search history.

(56) References Cited

U.S. PATENT DOCUMENTS

| | | | |
|---|---|---|---|
| 6,846,672 B2 | 1/2005 | Lambeth et al. | 435/325 |
| 7,029,673 B2 | 4/2006 | Lambeth et al. | 424/94.4 |
| 7,056,704 B2 | 6/2006 | Tuschl et al. | 435/91.1 |
| 7,078,196 B2 | 7/2006 | Tuschl et al. | 435/91.1 |
| 7,202,052 B2 | 4/2007 | Lambeth et al. | 435/25 |
| 7,202,053 B2 | 4/2007 | Lambeth et al. | 435/25 |
| 7,226,769 B2 | 6/2007 | Lambeth et al. | 435/192 |
| 2004/0001818 A1 | 1/2004 | Aird et al. | 424/94.4 |
| 2004/0009901 A1 | 1/2004 | Holmdahl et al. | 514/8 |
| 2005/0255487 A1 | 11/2005 | Khvorova et al. | 435/6 |
| 2008/0108583 A1 | 5/2008 | Feinstein | 514/44 A |
| 2009/0156524 A1 | 6/2009 | Feinstein et al. | 514/44 R |
| 2010/0273854 A1 | 10/2010 | Kalinski et al. | 514/44 A |

FOREIGN PATENT DOCUMENTS

| | | |
|---|---|---|
| EP | 0914821 | 5/1999 |
| EP | 1410798 | 4/2004 |
| WO | WO 97/19679 | 6/1997 |
| WO | WO 00/44895 | 8/2000 |
| WO | WO 02/30453 | 4/2002 |
| WO | WO 02/066047 | 8/2002 |
| WO | WO 02/079224 | 10/2002 |
| WO | WO 03/087399 | 10/2003 |
| WO | WO 2004/007689 | 1/2004 |

OTHER PUBLICATIONS

Kurreck. J Biomed Biotechnol. 2006; 2006(4):83757.*
Amarzguioui et al., "Tolerance for mutations and chemical modifications in a siRNA," *Nucleic Acids Research*, 31(2):589-595, 2003.
Bedard and Krause, "The NOX family of ROS-generating NADPH oxidases: Physiology and Pathophysiology," *Physiol. Rev.*, 87:245-313, 2007.
Borghi et al., "Possible role of HMG-CoA reducatse inhibitors for the treatment of sudden sensorineural hearing loss (SSHL)," *Medical Hypotheses*, 58(5):399-402, 2002.
Braasch et al., "RNA interference in mammalian cells by chemically-modified RNA," *Biochemistry*, 42:7967-7975, 2003.
Caplen et al., "Specific inhibition of gene expression by small double-stranded RNAs in invertebrate vertebrate systems," *Proc. Natl. Acad. Sci.*, 98(17):9472-9747, 2001.
Chakraborty, "Potentiality of small interfering RNAs (siRNA) as rcent therapeutic targets for gene-silencing," *Current Drug Targets*, 8(3):469-82, 2007.
Chalk et al., "Improved and automated prediction of effective siRNA," *Biochem. Biophys. Res. Commun.*, 319(1):264-274, 2004.
Chiu and Rana, "RNAi in human cells: Basic structural and function features of small interfering RNA," *Molecular Cell*, 19:549-561, 2002.
Chiu and Rana, "SiRNA function in RNAi: a chemical modification analysis," *RNA*, 9:1034-1048, 2003.

(Continued)

*Primary Examiner* — Christian Fronda
(74) *Attorney, Agent, or Firm* — Fulbright & Jaworski L.L.P.

(57) ABSTRACT

This invention relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, and optionally with one or more NADPH oxidase subunits, under conditions allowing binding of said test compound to said protein or, if present, said subunit(s); (b) optionally determining whether said test compound binds to said protein or, if present, said subunit(s); and (c) determining whether (ca) said test compound, upon contacting in step (a); or (cb) said test compound, upon binding in step (b) modulates the expression and/or activity of said protein or, if present, said subunit(s). Also provided are pharmaceutical compositions, medical uses and diagnostic uses of compounds of the invention.

17 Claims, 10 Drawing Sheets

OTHER PUBLICATIONS

Figure 1:
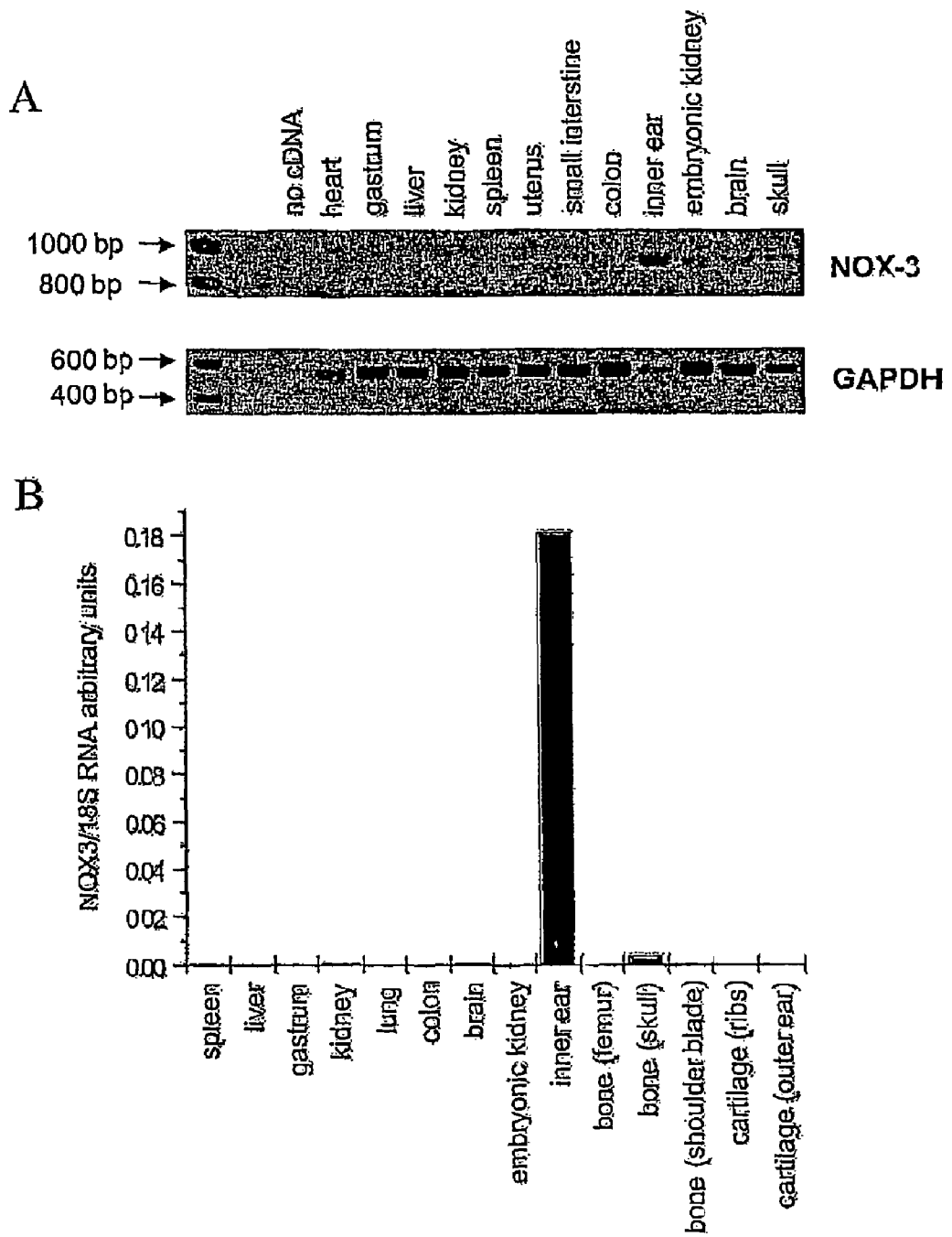

Czauderna et al., "Structural variations and stabilizing modification of synthetic siRNA in mammalian cells," *Nucleic Acids Research*, 31(11):2705-2716, 2003.

Elbashir et ai., "Duplexes of 21-nucleotide mediated RNA intereference in cultured mammalian cells," *Nature*, 411:494-498, 2001.

Elbashir et al., "Analysis of gene function in somatic mammalian cells using small interfering RNAs," *Methods*, 26:199-213, 2002.

European Search Report, issued in European patent Application No. EP 08004076, dated Jul. 4, 2008.

Fire et al., "Potent and scientific genetic interference by double-stranded RNA in caenorhabditis elegans," *Nature*, 391:806-811, 1998.

Holen et al., "Positional effects of short interfering RNAs targeting the human coagulation trigger tissue factor," *Nucleic Acids Research*, 30(8):1757-1766, 2002.

Holen et al., "Similar behavior of single-strand and double-strand siRNAs suggests they act through a common RNAi pathway," *Nucleic Acids Research*, 31(9):2401-2407, 2003.

Levenkova et al., "Gene specific siRNA selector," *Bioinformatics*, 20(3):430-432, 2004.

Mahato et al., "Modulation of gene expression by antisense and antigene oligodeoxynucleotides and small interfering RNA," *Expert Opinion on Drug Delivery*, 2(10):3-28, 2005.

Novotny et al., "Treatment of tinnitus with phenothiazines," abstract XP002353104, Database accession No. EMB-1986243373, *Ceskoslovenska Otolaryngologie*, 35:291-5, 1986.

Paffenholz et al., "Vestibular defects in head-tilt mice result from mutations in NOX3, encoding a NADPH oxidase," *Genes & Development*, 15(5):486-491, 2004.

PCT International Preliminary Report on Patentability, issued in International application No. PCT/EP2005/006061, dated Dec. 4, 2006.

PCT International Search Report and Written Opinion, issued in International application No. PCT/EP2005/006061, dated Apr. 5, 2006.

Prakash, "Positional effect of chemical modifications on short interference RNA activity in mammalian cells," *J. Med. Chem.*, 48(13):4247-53, 2005.

Scherer and Rossi, "Therapeutic applications of RNA interference: Recent advances in siRNA design," *Advances in Genetics*, 52:1-21, 2004.

Sioud et al., "Potential design rules and enzymatic synthesis of siRNAs," *Methods in Molec. Biol.*, 252:457-468, 2004.

Krause et al., "Tissue distribution and putative physiological function of NOX family NADPH oxidases," *Jpn. J. Infect. Dis.*, 57: S28-S29, 2004.

Mukherjea et al., "Transtympanic Administration of short interfering (si)RNA for the NOX3 isoform of NADPH oxidase protects against cisplatin-induced hearing loss in the rat," *Antioxidants & Redox Signaling*, 13(5):589-598, 2010.

Naito et al., "siDirect: highly effective, target-specific siRNA design software for mammalian RNA interference," *Nucleic Acids Research*, 32: W124-W129, 2004. Web Server Issue DOI: 10.1093/nar/gkh442.

Tuschl, "RNA interference and small interfering RNAs," *Chembiochem*, 2:239-245, 2001.

Zamore, "RNA interference: listening to the sound of silence," *Nature Structural Biology*, 8(9):746-750, 2001.

Babior et al., "The neutrophil NADPH oxidase," *Arch. Biochem. Biophys.*, 397:342-344, 2002.

Babior, "NADPH oxidase: an update," *Blood*, 93:1464-1476, 1999.

Banfi et al., "A $Ca^{2+}$-activated NADPH oxidase in testis, spleen, and lymph nodes," *J. Biol. Chem.*, 276:37594-37601, 2001.

Banfi et al., "A mammalian H+ channel generated through alternative splicing of the NADPH oxidase homolog NOH-1," *Science*, 287:138-142, 2000.

Banfi et al., "NOX3, a superoxide-generating NADPH oxidase of the inner ear," *J. Biol. Chem.*, 279:46065-46072, 2004.

Banfi et al., "Two novel proteins activate superoxide generation by the NADPH oxidase NOX1," *J. Biol. Chem.*, 278:3510-3513, 2003.

Bokoch and Knaus, "NADPH oxidases: not just for leukocytes anymore!" *Trends Biochem. Sci.*, 28:502-508, 2003.

Caillou et al., "Expression of reduced nicotinamide adenine dinucleotide phosphate oxidase (*ThoX, LNOX, Duox*) genes and proteins in human thyroid tissues," *J. Clin. Endocrinol. Metab.*, 86:3351-3358, 2001.

Cheng et al., "Homologs of gp91*phox*: cloning and tissue expression of Nox3, Nox4, and Nox5," *Gene*, 269:131-140, 2001.

Clerici et al., "Direct detection of ototoxicant-induced reactive oxygen species generation in cochlear explants," *Hear. Res.*, 98:116-124, 1996.

Darlington and Smith, "Vestibulotoxicity following aminoglycoside antibiotics and its prevention," *Curr. Opin. Investig. Drugs*, 4:841-846, 2003.

De Deken et al., "Cloning of two human thyroid cDNAs encoding new members of the NADPH oxidase family," *J. Biol. Chem.*, 275:23227-23233, 2000.

Geiszt et al., "Identification of renox, an NAD(P)H oxidase in kidney," *Proc. Natl. Acad. Sci. USA*, 97:8010-8014, 2000.

Geiszt et al., "Proteins Homologous to p47*phox* support superoxide production by NAD(P)H oxidase 1 in colon epithelial cells," *J. Biol. Chem.*, 278:20006-20012, 2003.

Henderson et al., "The role of antioxidants in protection from impulse noise," *Ann. N.Y. Acad. Sci.*, 884:368-380, 1999.

Holland et al., "Endothelial cell oxidant production: effect of NADPH oxidase inhibitors," *Endothelium*, 7:109-119, 2000.

Jones et al., "Effect of trans-bullar gentamicin treatment on guinea pig angular and linear vestibulo-ocular reflexes," *Exp. Brain Res.*, 153:293-306, 2003.

Kikuchi et al., "NADPH oxidase subunit, gp91*phox* homologue, preferentially expressed in human colon epithelial cells," *Gene*, 254:237-243, 2000.

Kopke et al., "Toxins and trauma share common pathways in hair cell death," *Ann. N.Y. Acad. Sci.*, 884:171-191, 1999.

Kopke et al., "Use of organotypic cultures of Corti's organ to study the protective effects of antioxidant molecules on cisplatin-induced damage of auditory hair cells," *Am. J. Otol.*, 18:559-571, 1997.

Lalucque and Silar, "NADPH oxidase: an enzyme for multicellularity?" *Trends Microbiol.*, 11:9-12, 2003.

Lambeth, "Nox/Duox family of nicotinamide adenine dinucleotide (phosphate) oxidases," *Curr. Opin. Hematol.*, 9:11-17, 2002.

Maak et al., "Oxygen free radical release in human failing myocardium is associated with increased activity of Rac1-GTPase and represents a target for statin treatment," *Circulation*, 108:1567-1574, 2003.

Malgrange et al., "Expression of growth factors and their receptors in the postnatal rat cochlea," *Neurochem. Res.*, 23:1133-1138, 1998.

McFadden et al., "Cu/Zn SOD deficiency potentiates hearing loss and cochlear pathology in aged 129,CD-1 mice," *J. Comp. Neurol.*, 413:101-112, 1999.

Mocsai et al., "Differential effects of tyrosine kinase inhibitors and an inhibitor of the mitogen-activated protein kinase cascade on degranulation and superoxide production of human neutrophil granulocytes," *Biochem. Pharmacol.*, 54:781-789, 1997.

NCBI Entrez protein database entry NP_056533, (Mar. 25, 2007).

Neri et al., "Tinnitus and oxidative stress in a selected series of elderly patients," *Arch. Gerontol. Geriatr.*, Suppl. 8:219-223, 2002.

Ohinata et al., "Intense noise induces formation of vasoactive lipid peroxidation products in the cochlea," *Brain Res.*, 878:163-173, 2000.

Ohlemiller et al., "Early elevation of cochlear reactive oxygen species following noise exposure," *Audiol. Neurootol.*, 4:229-236, 1999.

Schneider et al., "*Gingko biloba* (Rökan) therapy in tinnitus patients and measurable interactions between tinnitus and vestibular disturbances," *Int. Tinnitus J.*, 6:56-62, 2000.

Seifert and Scachtele, "Studies with protein kinase C inhibitors presently available cannot elucidate the role of protein kinase C in the activation of NADPH oxidase," *Biochem. Biophys. Res. Commun.*, 152:585-592, 1988.

Sergi et al., "Cisplatin ototoxicity in the guinea pig: vestibular and cochlear damage," *Hear. Res.*, 182:56-64, 2003.

Sha and Schacht, "Formation of reactive oxygen species following bioactivation of gentamicin," *Free Radic. Biol. Med.*, 26:341-347, 1999.

Suh et al., "Cell transformation by the superoxide-generating oxidase Mox1," *Nature* 401:79-82, 1999.

Takeya et al., "Novel human homologues of p47*phox* and p67*phox* participate in activation of superoxide-producing NADPH oxidases," *J. Biol. Chem.*, 278:25234-25246, 2003.

Takumida and Anniko, "Simultaneous detection of both nitric oxide and reactive oxygen species in guinea pig vestibular sensory cells," *ORL J. Otorhinolaryngol. Relat. Spec.*, 64:143-147, 2002.

Takumida et al., "Neuroprotection of vestibular sensory cells from gentamicin ototoxicity obtained using nitric oxide synthase inhibitors, reactive oxygen species scavengers, brain-derived neurotrophic factors and calpain inhibitors," *Acta Otolaryngol.*, 123:8-13, 2003.

Tsunawaki et al., "Fungal metabolite gliotoxin inhibits assembly of the human respiratory burst NADPH oxidase," *Infect Immun.*, 72:3373-3382, 2004.

Van Campen et al., "Oxidative DNA damage is associated with intense noise exposure in the rat," *Hear. Res.*, 164:29-38, 2002.

Wang et al., "Identification of a novel partner of Duox," *J. Biol. Chem.*, 280:3096-3103, 2005.

Yanai et al., "Expression of mouse osteocalcin transcripts, OG1 and OG2, is differently regulated in bone tissues and osteoblast cultures," *J. Bone Miner. Metab.*, 19:345-351, 2001.

Yoshida et al., "Fungal gliotoxin targets the onset of superoxide-generating NADPH oxidase of human neutrophils," *Biochem. Biophys. Res. Commun.*, 268:716-723, 2000.

\* cited by examiner

A
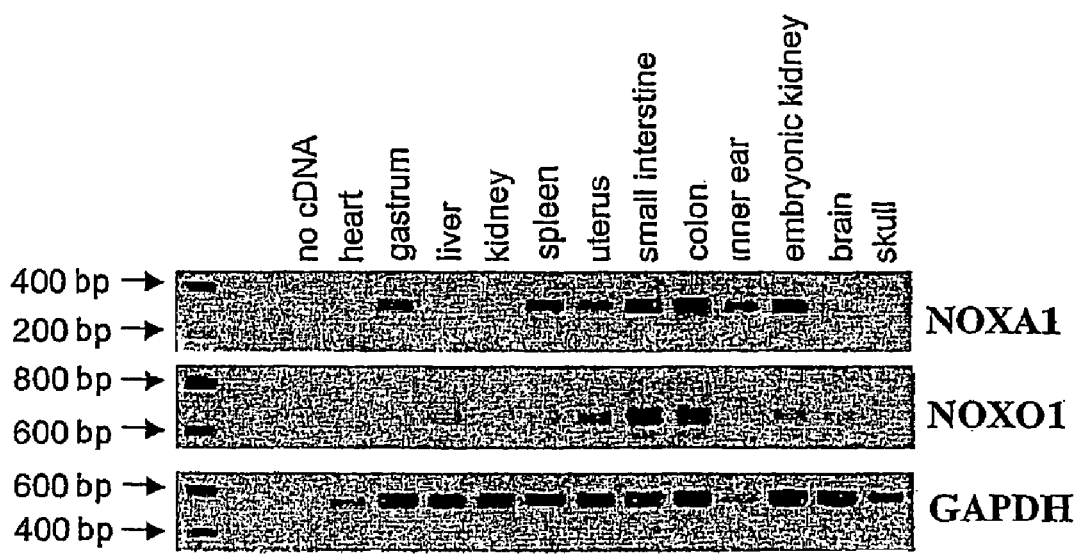
B
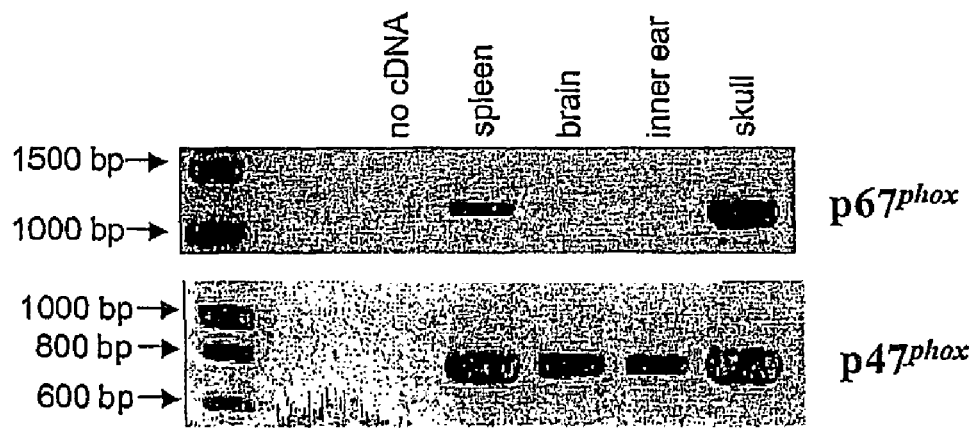
Figure 2

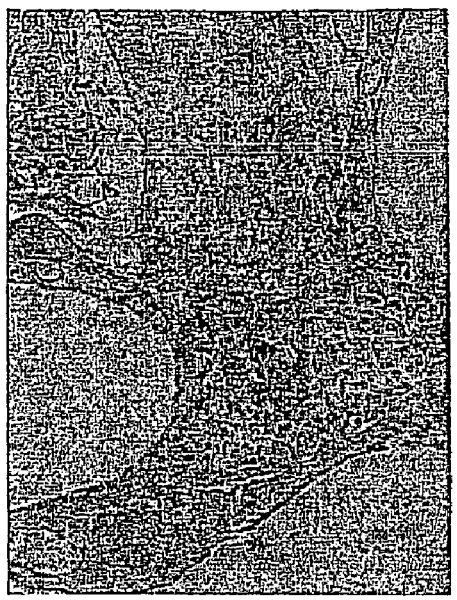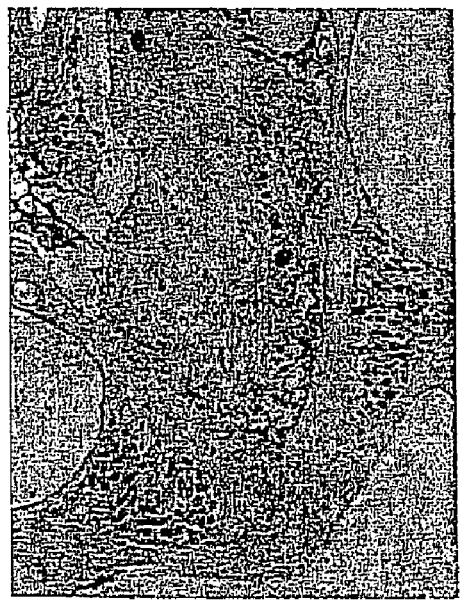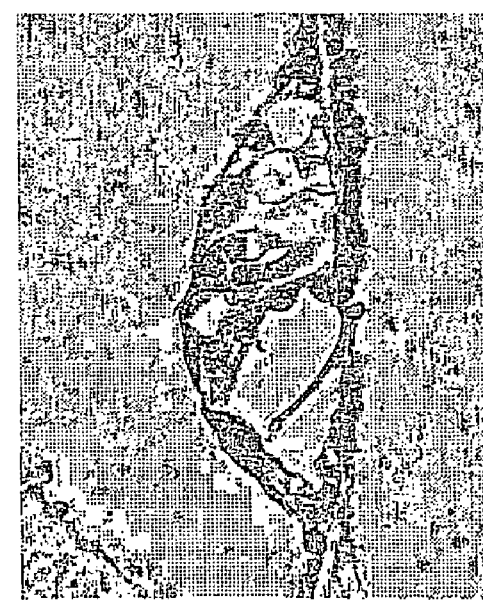
Figure 4A – D

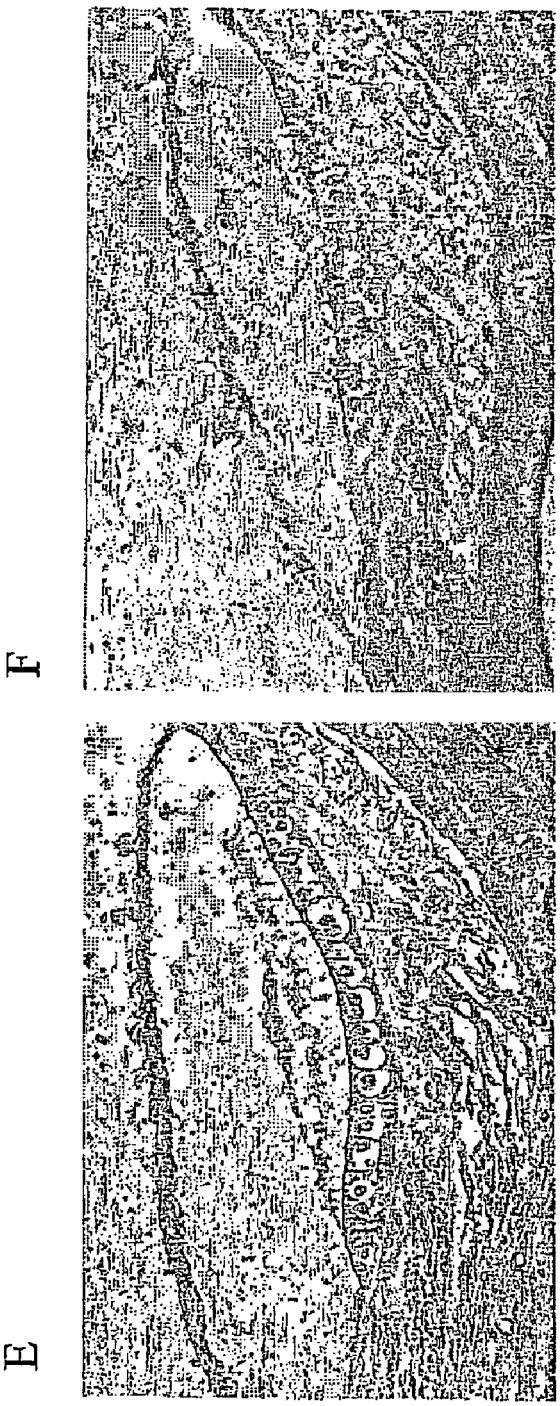
Figure 4E + F

MEANS AND METHODS OF USING A NADPH OXIDASE INHIBITOR FOR THE TREATMENT OF HEARING LOSS AND PHANTOM HEARING

This application is a national phase application under 35 U.S.C. §371 of International Application No. PCT/EP2005/006061 filed Jun. 6, 2005, which claims priority to European Application No. 04013266.4 filed Jun. 4, 2004, the entire text and figures of which disclosures are incorporated herein by reference without disclaimer.

This invention relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, and optionally with one or more NADPH oxidase subunits, under conditions allowing binding of said test compound to said protein or, if present, said subunit(s); (b) optionally determining whether said test compound binds to said protein or, if present, said subunit(s); and (c) determining whether (ca) said test compound, upon contacting in step (a); or (cb) said test compound, upon binding in step (b) modulates the expression and/or activity of said protein or, if present, said subunit(s). Also provided are pharmaceutical compositions, medical uses and diagnostic uses of compounds of the invention.

In this specification, a number of documents is cited. The disclosure of these documents, including manufacturer's manuals, is herewith incorporated by reference in its entirety.

Hearing impairment is a widespread and severe sensory deficit. It is the third most prevalent major chronic disability in the over 65-year-old age group, but also found in younger persons. Slightly more than 1 percent of people under the age of 17 have hearing loss, the prevalence rises to 12 percent between the ages of 45 and 64, to 24 percent between the ages of 65 and 74, and up to 39 percent for ages over 75. There are three major causes of hearing loss: noise-dependent hearing loss, drug-associated hearing loss and age-associated hearing loss. Interestingly, there appears to be a common mechanism to three major causes of hearing loss, namely destruction of sensory epithelium and cochlear neurons through reactive oxygen species. In terms of treatment, no efficient drug treatment or prophylaxis of hearing loss are available at this point and the only option at present is the use of hearing aids. This situation is further aggravated by the limited understanding of the molecular processes involved in hearing loss and the scarcity of suitable molecular targets for therapeutic intervention.

The inner ear is a highly complex structure involved in hearing and balancing. The conversion of sound into electrical signals occurs within the cochlea, in the organ of Corti, and the electrical signals are conducted by the axons of spiral ganglion neurons to the brain. The linear movement of the head is sensed by the otolith organs (utricle and saccule) and the rotation movements by the ampullas of the semicircular canals. The signals generated in the vestibular system are transmitted by the vestibular ganglion neurons to the central nervous system.

Hearing impairment due to loss of cochlear function occurs frequently, if not invariably over lifetime. Noise and ototoxic chemicals may lead to a precocious, rapid hearing loss, while age itself leads to a more insidious, chronic loss of hearing. Research over the last decades has identified reactive oxygen species (ROS[1]) as the major factor mediating hearing loss [1]. ROS is generated within the cochlea after exposure to ototoxic drugs (e.g. cisplatin [2, 3], aminoglycoside antibiotics [3]) or to noise [4]. Signs of oxidative stress, such as DNA damage and lipid peroxidation, have been documented in vivo in response to those challenges [5, 6], as well as in cochlear aging [7]. The vestibular system is also damaged by ototoxic drugs [8, 9] in a process that includes excessive ROS production [10, 11].

[1] The abbreviations used are: bp, base pair; DPI, diphenylene iodonium; DUOX, dual domain oxidase; 5-FU, 5-Fluorouracil; GAPDH, glyceraldehyde-3-phosphate dehydrogenase; gp91$^{phox}$, 91-kDa glycoprotein subunit of the phagocyte NADPH oxidase; NOX, NADPH oxidase; NOXA1, NOX activator 1; NOXO1, NOX organizer 1; PMA, phorbol 12-myristate 13-acetate; PCR, polymerase chain reaction; ROS, reactive oxygen species; RT-PCR, reverse transcription-PCR; SOD, superoxide dismutase.

While the role of oxidative stress in inner ear damage is well established, its source is poorly understood. A role of non-enzymatic generation of ROS by ototoxic compounds has been suggested [12]. The possibility that a superoxide-generating enzyme could be localized within the inner ear, and thereby account for the oxidative damage of this organ, has received little attention.

Over the last decade, it has been proven that the expression of superoxide-generating NADPH oxidases is not restricted to phagocytes. Beside the well-known catalytic subunit of the phagocyte NADPH oxidase, gp91$^{phox}$/NOX2 (for review see [13]), six other superoxide-producing enzymes have been identified in mammals [14, 15]. For most NOX and DUOX enzymes, a predominant tissue localization has been described, e.g. colon epithelium for NOX1 [16, 17], kidney cortex for NOX4 [18], lymphoid organs and testis for NOX5 [19], and the thyroid gland for DUOX1 and DUOX2 [20, 21]. For NOX3, with the exception of some very low level expression in the embryonic kidney [22], no convincing tissue localization had been found so far.

Our knowledge of the activation mechanisms of members of the NOX/DUOX family varies considerably among individual enzymes. NOX1 and gp91$^{phox}$/NOX2 are subunit-dependent enzymes that need to assemble with an activator subunit (NOXA1 and p67$^{phox}$, respectively) and an organizer subunit. (NOXO1 and p47$^{phox}$, respectively) to generate superoxide [23-26]. NOX5, DUOX1 and DUOX2, on the other hand, have N-terminal $Ca^{2+}$-binding motifs (EF-hand domains), and so far one of them, NOX5, has been shown to be activated by increased $Ca^{2+}$ concentration [27]. The mechanism of NOX4 activation is less clear. There are indications that it might be a constitutively active enzyme [18].

Tinnitus, also referred to as phantom hearing, is a common and in some instances invalidating medical complaint. Presently, the pathophysiology of the disease is poorly understood and there is not proven causative treatment available. There is however evidence that reactive oxygen species might play a role in the pathophysiology of tinnitus (Neri S. Tinnitus and oxidative stress in a selected series of elderly patients. Arch Gerontol Geriatr. 2002; 35 Suppl: 219-23) and there are at least some reports that suggest a beneficial effect of antioxidant medication such as Gingko extract on the course of the disease (e.g. Schneider D et al. Gingko biloba (Rokan) therapy in tinnitus patients and measurable interactions between tinnitus and vestibular disturbances. Int Tinnitus J. 2000; 6(1):56-62). Thus, NOX3 might also be involved in the pathophysiology of tinnitus and the use of a NOX3 modulator or inhibitor is an interesting new concept for the treatment of tinnitus.

US-A1 20040001818 and WO-A1 0230453 describe methods of inhibiting angiogenesis, endothelial cell migration or endothelial cell proliferation using NADPH oxidase inhibitors.

EP-A2 1410798 describes a pharmaceutical composition comprising and uses of inhibitors of the production or the release of reactive oxygen metabolites (ROMs) and of compounds effective to scavenge ROMs. The uses are directed to the manufacture of a medicament for the treatment of Adult Respiratory Distress Syndrome (ARDS), ischemia or reperfusion injury, infectious disease, autoimmune or inflammatory diseases, and neurodegenerative diseases. Compounds effective to inhibit enzymatic ROM production or release comprise NADPH oxidase inhibitors.

EP-A2 0914821 relates to a method for diagnosis of atherosclerosis involving measurement of NADPH oxidase activity.

WO-A2 9719679 describes the use of NADPH oxidase inhibitors for the manufacture of a medicament for prevention of atherosclerosis.

US-A1 20040009901 relates to a method of treating a mammal having an autoimmune condition involving NADPH oxidase deficiency. Also, a method for identifying an agent that enhances NADPH oxidase activity is described.

WO-A2 02079224 relates to human peptides and proteins that are related to NADPH oxidase subfamily and methods for identifying modulators thereof. The proteins are described as being substantially similar to p47phox.

WO-A2 04007689 describes regulatory proteins for Nox enzymes, which are referred to as p41 Nox proteins, and nucleic acid sequences encoding these proteins. Furthermore, a method for identifying a compound that modulates superoxide production is described, the method involving administration of the protein. The envisaged medical indications relate to abnormal cell growth and proliferation and include cancer, prostatic hypertrophy and atherosclerosis.

NCBI Entrez protein database entry NP_056533 comprises the amino acid sequence of human NADPH oxidase 3 (NOX3). The sequence is 568 amino acids in length. The database entry recites similarity to gp91phox.

In view of the limited understanding of processes leading to hearing loss and phantom hearing, the technical problem underlying the present invention was therefore the provision of means and methods for the development of drugs for treatment of hearing loss and phantom hearing.

Accordingly, this invention relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, and optionally with one or more NADPH oxidase subunits, under conditions allowing binding of said test compound to said protein or, if present, said subunit(s); (b) optionally determining whether said test compound binds to said protein or, if present, said subunit(s); and (c) determining whether (ca) said test compound, upon contacting in step (a); or (cb) said test compound, upon binding in step (b) modulates the expression and/or activity of said protein or, if present, said subunit(s).

The term "modulator" designates a compound modulating the activity of a target molecule, preferably by performing one or more of the following effects: (i) the transcription of the gene encoding the protein to be modulated is modulated, (ii) the translation of the mRNA encoding the protein to be modulated is modulated, (iii) the protein performs its biochemical function with modulated efficiency in presence of the modulator, and (iv) the protein performs its cellular function with modulated efficiency in presence of the modulator. It is understood that the term "modulator" includes inhibitors and activators at all regulatory levels mentioned above.

The term "NADPH oxidase" comprises any NADPH oxidase. It includes NOX enzymes such as NOX1, NOX2, NOX3, NOX4 and NOX5 as well as DUOX enzymes such as DUOX1 and DUOX2 (see references 13 to 27).

The term "lead compound" designates a compound which is a drug candidate and which may require chemical modifications in order to optimize its pharmacological properties and eventually become a drug to be formulated as a medicament. Methods of optimization are known in the art and further detailed below.

The term "hearing loss" according to the invention embraces drug-, noise- and age-related hearing loss. Age-related hearing loss is also referred to as presbyacusis. The term "phantom hearing", also known as "tinnitus", is a common and in some instances invalidating medical complaint.

The term "protein" recited in the main claim extends to homologues having at least 75% sequence identity. Preferably, the sequence identity level is 80% or 85%, more preferred 90% or 95%, and yet more preferred 98% or 99%. For the purpose of determining the level of sequence identity, two nucleotide or protein sequences can be aligned electronically using suitable computer programs known in the art. Such programs comprise BLAST (Altschul et al. (1990), J. Mol. Biol. 215, 403-410), variants thereof such as WU-BLAST (Altschul & Gish (1996), Methods Enzymol. 266, 460-480), FASTA (Pearson & Lipman (1988), Proc. Natl. Acad. Sci. USA 85, 2444-2448) or implementations of the Smith-Waterman algorithm (SSEARCH, Smith & Waterman (1981), J. Mol. Biol. 147, 195-197). These programs, in addition to providing a pairwise sequence alignment, also report the sequence identity level (usually in percent identity) and the probability for the occurrence of the alignment by chance (P-value). Programs such as CLUSTALW (Higgins et al. (1994), Nucleic Acids Res. 22, 4673-4680) can be used to align more than two sequences.

The optional presence of one or more NADPH oxidase subunits relates inter alia to embodiments, wherein not only modulators exerting their effect exclusively directly on the NADPH oxidase are to be identified, but also modulators which act by interfering with the association of the NADPH oxidase with said subunit(s) are to be identified. Such modulators may be compounds binding to regions of the NADPH oxidase and/or of the subunit(s) involved in subunit association. In other words, a test compound identified by the method of the invention which interferes with association (e.g. binds to regions of the NADPH oxidase and/or of the subunit(s) involved in subunit association) is an example of a test compound according to the invention which either modulates expression and/or activity of the protein defined in the main embodiment or modulates the expression and/or activity of said subunit(s).

Also embraced by the invention is a method as defined above, wherein test compounds may be identified which modulate the expression and/or activity of both the protein defined in the main embodiment and said subunits.

In the following, the interactions of an NADPH oxidase with its subunits is exemplified for the NADPH oxidase 3 (NOX3). NOX3 activity requires the widely distributed membrane NOX subunit p22$^{phox}$. However, in the absence of further, viz. cytoplasmic subunits, no high level, but only low level ROS generation occurs. In contrast in the presence of the combination of one activator subunit (either NOXA1 or p67phox/NOXA2) and one organizer subunit (either NOXO1 or p47$^{phox}$/NOXO2) NOX3 is capable of generating high levels of ROS. In addition, the NOX3 activity most likely also involves the ubiquitous GTP-binding protein Rac. The interaction sites between the partners are depicted in the following scheme.

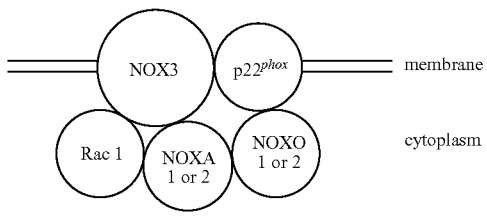

A key interaction is the binding of the activator domain of the activator subunits (amino acids 202-212 for hNOXA1 and amino acids 200-210 for hp67$^{phox}$/NOXA2) to NOX3. It is not clear whether there is a direct interaction of the organizer subunits with NOX3, but there is an indirect interaction with NOX3 through binding to p22$^{phox}$ via the tandem SH3 domain (amino acids 158-217 and 233-289 for hNOXO1 and amino acids 156-216 and 226-286 for hp47$^{phox}$/NOXO2) and through binding to an SH3 domain of the activator subunit (amino acids 402-463 for hNOXA1 and amino acids 457-513 for hp67$^{phox}$/NOXA2) through its proline-rich region (amino acids 321-331 for hNOXO1 and 360-370 for hp47$^{phox}$/NOXO2). The precise site of interaction between NOX3 and p22$^{phox}$, as well as the sites of interaction of Rac1 with NOX3 and the activator subunits (NOXA1 or p67$^{phox}$) are not known. The table below provides a compilation of the interaction sites.

| binding region of the subunit | target |
| --- | --- |
| activator region of activator subunit (aa 202-212 for hNOXA1 and aa 200-210 for hp67$^{phox}$/NOXA2) | NOX3 |
| tandem SH3 domain of organizer subunit (aa 158-217 and aa 233-289 for hNOXO1 and aa 156-216 and 226-286 for hp47$^{phox}$/NOXO2) | p22$^{phox}$ |
| proline-rich region of organizer subunit (aa 321-331 for hNOXO1 and 360-370 for hp47$^{phox}$/NOXO2) | SH3 domain of activator subunit (aa 402-463 for hNOXA1 and aa 457-513 for hp67$^{phox}$/NOXA2) |

The optional determination of binding test compounds in step (b) relates to any biophysical binding assay, which may be used to identify binding test molecules prior to performing the functional assay with the binding test molecules only. Suitable biophysical binding assays are known in the art and comprise fluorescence polarization (FP) assay, fluorescence resonance energy transfer (FRET) assay and surface plasmon resonance (SPR) assay. Step (b) is particularly advantageous if said biophysical assay is more amenable to high throughput than the functional assay.

Step (c) relates to the above mentioned functional assay. Determining whether a test compound, or a binding test compound, modulates the expression of a target protein may be accomplished by measuring the expression level. In a more preferred embodiment, the expression level to be determined is the mRNA expression level. Methods for the determination of mRNA expression levels are known in the art and comprise Real Time PCR, Northern blotting and hybridization on microarrays or DNA chips equipped with one or more probes or probe sets specific for transcripts encoding proteins of the NADPH oxidase family.

In another more preferred embodiment, the expression level to be determined is the protein expression level. The skilled person is aware of methods for the quantitation of proteins. Amounts of purified protein in solution can be determined by physical methods, e.g. photometry. Methods of quantifying a particular protein in a mixture rely on specific binding, e.g. of antibodies. Specific detection and quantitation methods exploiting the specificity of antibodies comprise immunohistochemistry (in situ) and surface plasmon resonance. Western blotting combines separation of a mixture of proteins by electrophoresis and specific detection with antibodies.

The present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; and (b) determining whether said test compound, upon contacting in step (a) modulates the expression and/or activity of said protein.

The present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; (b) determining whether said test compound, upon contacting in step (a) modulates the expression and/or activity of said protein; and (c) performing clinical trials with said modulator.

In a preferred embodiment of the method of the invention, said contacting comprises contacting with one or more NADPH oxidase subunits, under conditions allowing binding of said test compounds to said subunit(s), and wherein said determining comprises determining whether said test compound modulates the expression and/or activity of said subunit(s).

In a further preferred embodiment the method further comprises, prior to step (b), the step of (b') determining whether said test compound binds to said protein or, if present, said subunit(s), wherein said determining in step (b) is effected upon binding in step (b'). The method according to this preferred embodiment comprises both determining of whether a test compound, upon contacting in step (a), modulates expression and/or activity and the determining of whether a test compound, upon binding in step (b'), modulates expression and/or activity. The term "expression and/or activity" relate to, as defined herein above, the expression and/or activity of the protein as defined in the main embodiment and/or of said subunit(s).

Quantitation of the modulation of the activity of an NADPH oxidase may be effected by quantifying the reactive oxygen species production. Accordingly, said modulation preferably involves modulating the ROS production of said protein, and determining in step (c) comprises quantifying ROS production. Methods of quantifying ROS are known in the art and are further exemplified in Example 4 enclosed herewith.

The inventors for the first time demonstrated high-level expression of the NADPH oxidase NOX3 in the inner ear. Thereby, a protein suitable as a target for therapeutic intervention in hearing loss and phantom hearing is provided.

Vestibular and cochlear sensory epithelia develop from a common ectodermal thickening at the head region, called placode [34]. The otic placode also gives rise to the neurons that will form the inner ear ganglia [35]. The data presented in the Examples and Figures enclosed herewith suggest that the expression of NOX3 mRNA may follow this pattern.

Furthermore, the inventors demonstrated for the first time that NOX3 is a superoxide-generating enzyme. It is also demonstrated that the pattern of subunit- and stimulus-dependence that is distinct from other known NOX family NADPH oxidases. NOX3, as opposed to NOX1 and NOX2, produces low levels of superoxide upon PKC activation without the need of subunits. While the activation of phagocyte NADPH oxidase is thought to occur through PKC-dependent phosphorylation of p47$^{phox}$ [13], this, obviously, cannot be the mechanism of the subunit-independent activation of NOX3. At this point, there are numerous possible pathways how PKC might activate NOX3 (e.g. direct phosphorylation of NOX3, activation of the small GTPase protein Rac1, or changes in the lipid environment). The subunit-independent ROS-generation by NOX3 is of low level in the transfected cells. Given the localization of NOX3 in the inner ear, close to or within highly ROS-sensitive cells, it is tempting to speculate that low, rather than high level superoxide generation is the default mode of NOX3 function.

However, NOX3 activity can be massively enhanced by known NOX organizer and regulator/activator subunits. Searches of mouse and human genomic databases suggest that there are probably no other close homologues of p47$^{phox}$ and p67$^{phox}$ than NOXO1 and NOXA1, respectively. Thus, if NOX3 functions in a subunit-dependent manner in vivo, it would have to use subunits of other NOX enzymes. Based on PCR data shown in FIG. 2, NOX3 could potentially interact with NOXA1 and/or p47$^{phox}$ in the inner ear. However, it cannot be excluded that, under specific circumstances or in a very limited number of cells, other NOX subunits may also be expressed in the inner ear.

Therefore, in a preferred embodiment, said NADPH oxidase subunit(s) is/are the activating subunit(s) NOXA1 and/or p67$^{phox}$/NOXA2, and/or the organising subunit(s) NOXO1 and/or p47$^{phox}$/NOXO2.

In a further preferred embodiment said protein and, if present, said subunit(s) is/are comprised in a membrane preparation. Membrane preparations according to the invention may be membrane fractions obtained, for example, by centrifugation upon cell disruption. Alternatively, said membrane preparation is obtained by reconstituting the protein(s) according to the main embodiment with membrane- or micelle-forming amphiphilic lipids.

In a further preferred embodiment said protein and, if present, said subunit(s) is/are comprised in a cell transfected with a nucleic acid encoding said protein. This embodiment relates to a cellular screen.

In a further preferred embodiment of the method of the invention, said protein and, if present, said subunit(s) is/are comprised in a non-human animal. This embodiment relates to an in vivo screen. While less amenable to high throughput, the in vivo screen offers the advantage of the assessment of the disease state of the non-human animal. Accordingly, in a more preferred embodiment, the modulation of ROS production involves improving the hearing of said animal and determining in step (c) involves quantifying said hearing.

In a further preferred embodiment, prior to said contacting, (a') an ototoxic agent and/or an agent increasing the activity and/or the expression of said protein or subunit(s), is brought into contact with said protein or subunit(s) is/are administered to said cell or said animal. Administration of an ototoxic agent and/or an agent increasing the activity and/or the expression of said protein or subunit(s) may be used as a means of modelling (at the cellular level), or inducing/enhancing (at the organismic level) the disease or disease-related conditions.

Interestingly, while there is almost no literature on the physiological function of ROS in the inner ear, there is a considerable number of studies on the pathological effect of excessive ROS production in this organ (for reviews see [1] and [4]). It has been shown in several publications that specific ototoxic drugs (such as platinum derivatives or aminoglycoside antibiotics) lead to accumulation of ROS in both the cochlea [3] and the vestibular system [8, 11, 36], and noise trauma has been demonstrated to be a prominent cause of ROS production in the cochlea [37]. A permanent increase of ROS concentration, in turn, leads primarily to the death of sensory epithelial cells, and, to a lesser extent, to the death of innervating neurons [1]. Based on the surprising observations presented herein and relating to its localization and its capacity to generate ROS, NOX3 is likely to be a major source of ROS in the inner ear. The unexpected observation that cisplatin markedly enhances NOX3-dependent superoxide production, evokes the possibility that NOX3 is a mediator of cisplatin-dependent ototoxicity. Time course and dose-response of the cisplatin-dependent NOX3 activation is compatible with the time course [2] and dose-response [38] of cisplatin toxicity to inner ear sensory cells.

In a more preferred embodiment, said ototoxic agent is selected from the group consisting of salicylates, non-steroidal antiinflammatories, antibiotics, diuretics, cytostatics, quinine derivatives and gastroprotective drugs.

Salicylates include Aspirine and methyl-salicylates.

Non-steroidal antiinflammatories include diclofenac, etocolac, fenprofen, ibuprofen, indomethacin, naproxen, piroxicam and sulindac.

Preferred antibiotics are aminoglycosides such as amikacin, gentamycin, kanamycin, neomycin, netilmicin, streptomycin and tobramycin. Further preferred antibiotics include erythromycin, vancomycin, minocycline, polymixin B, amphotericin B and capreomycin.

Exemplary diuretics according to the invention are bendroflumethazide, bumetadine, chlorthalidone, ethacrynic acid and furosemide.

Cytostatics, or antineoplastic drugs according to the invention include bleomycine, bromocriptine, carboplatinum, cisplatin, methotrexate, nitrogen mustard, vinblastin and vincristine.

Quinine derivatives, being used as antimalarial and antiarrhythmic drugs, include chloroquine phosphate, quinacrine hydrochloride and quinine sulphate.

Misoprostol is among the envisaged gastroprotective drugs.

In a preferred embodiment of the method of the invention, said NADPH oxidase is NOX3. In a further preferred embodiment said NADPH oxidase is the protein defined in claim 1.

In a further preferred embodiment, the method of the invention further comprises the step of formulating said modulator with a pharmaceutically acceptable carrier. By "pharmaceutically acceptable carrier" is meant a non-toxic solid, semisolid or liquid filler, diluent, encapsulating material or formulation auxiliary of any type.

More preferred, and prior to said formulating, the affinity, specificity and/or pharmacological properties of the modulator are optimized and/or clinical trials are performed with said modulator or the optimized modulator.

Accordingly, the present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; (b) determining whether said test compound, upon contacting in step (a) modulates the expression and/or activity of said protein; and (c) performing clinical trials with said modulator.

Methods for the optimization of the pharmacological properties of compounds identified in screens, generally referred to as lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physicochemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiozolidines or combinations thereof; said method optionally further comprising the steps of the above described methods.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

Individuals to be selected for said clinical trials comprise healthy individuals, individuals with a disposition or at risk to develop hearing loss or phantom hearing and patients suffering from hearing loss or phantom hearing. Hearing loss is understood to comprise drug-, noise- and age-related hearing loss.

Moreover, the present invention also relates to a pharmaceutical composition comprising (a) an antibody, aptamer, or a fragment or derivative thereof binding specifically the protein defined in the main embodiment; (b) an antisense nucleic acid, an siRNA, or a ribozyme binding specifically a nucleic acid encoding said protein; (c) a iodonium derivative and/or a substituted catechol such as apocynin; (d) a compound comprising the fragment of SEQ ID NO: 11 from position 202 to position 212, the fragment of SEQ ID NO: 11 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370; and/or (e) a nucleic acid comprising a sequence encoding any of the fragments according to (d). The fragments according to (d) are regions of the sequences of the respective SEQ ID NOs known or expected to be involved in subunit association.

Said compounds according to (d) may furthermore comprise a cell-penetrating peptide. The term "cell-penetrating peptide" relates to a peptide which is capable of entering into cells. This capability may be exploited for the delivery of fragments defined in (d) to cells.

For example, said compounds may be peptides or polypeptides comprising both a fragment as defined in (d) above and a cell-penetrating peptide. Alternatively, other means of functionally linking a fragments as defined in (d) and a cell-penetrating peptide are envisaged. Preferably, said compounds comprising both a fragment as defined in (d) above and a cell-penetrating peptide act as dominant negative cell-permeating inhibitors.

Said cell-penetrating peptides according to the invention include Tat-derived cell-penetrating peptides [46, 47], Antennapedia peptides or penetratins [48, 49] such as the peptide having the sequence Arg-Gln-Ile-Lys-Ile-Trp-Phe-Gln-Asn- Arg-Arg-Met-Lys-Trp-Lys-Lys (SEQ ID NO: 25), peptides derived from HSV-1 VP22 [50], transportans [51], MAP peptides [52] such as the peptide with the sequence KLALKLA-LKALKAALKLA (SEQ ID NO: 26), signal sequence-based cell-penetrating peptides (NLS) [53], hydrophobic membrane translocating sequence (MTS) peptides [53] and arginine-rich transporters for drugs. According to an overview of cell-penetrating peptides is provided in [45], CPPs are divided into two classes: the first class consists of amphipathic helical peptides, such as transportan and model amphipathic peptide (MAP), where lysine (Lys) is the main contributor to the positive charge, while the second class includes arginine (Arg)-rich peptides, such as TAT and Antp or penetratin.

The nucleic acids according to (e) include the sequences with the SEQ ID NOs: 12, 16, 8 and 20 as well those fragments thereof which comprise a sequence encoding any of the fragments according to (d). Said nucleic acid may optionally comprise a sequence encoding a cell-penetrating peptide.

Also embraced by the present invention are pharmaceutical compositions comprising fragments of proteins orthologous or homologous to hNOXA1, hNOXO1, hp47phox/NOXO2 or hp67phox/NOXA2, whereby said fragments align with the fragments of hNOXA1, hNOXO1, hp47phox/NOXO2 or hp67phox/NOXA2 recited under (d), as are pharmaceutical compositions comprising nucleic acids encoding these aligning fragments. It is understood that these pharmaceutical compositions are considered equivalents of the above described embodiment directed to pharmaceutical compositions. Said orthologous or homologous proteins include the respective murine proteins, i.e., proteins having an amino acid sequence set forth in any one of SEQ ID NO: 13, 17, 9 or 21. The nucleic acids encoding the latter are set forth in SEQ ID NO: 14, 18, 10 and 22.

Two nucleotide or protein sequences can be aligned electronically using suitable computer programs known in the art. Such programs comprise BLAST (Altschul et al. (1990), J. Mol. Biol. 215, 403-410), variants thereof such as WU-BLAST (Altschul & Gish (1996), Methods Enzymol. 266, 460-480), FASTA (Pearson & Lipman (1988), Proc. Natl. Acad. Sci. USA 85, 2444-2448) or implementations of the Smith-Waterman algorithm (SSEARCH, Smith & Waterman (1981), J. Mol. Biol. 147, 195-197). These programs, in addition to providing a pairwise sequence alignment, also report the sequence identity level (usually in percent identity) and the probability for the occurrence of the alignment by chance (P-value). Programs such as CLUSTALW (Higgins et al. (1994), Nucleic Acids Res. 22, 4673-4680) can be used to align more than two sequences.

Furthermore embraced by the present invention are pharmaceutical compositions comprising (a) peptidomimetic compound(s) which has been obtained by using any of the fragments according to (d) as a lead compound.

Pharmaceutical compositions comprising a nucleic acid according to (e) and/or the above described equivalents thereof are also envisaged to be used for gene therapy. For this purpose, the nucleic acid may be part of an expression, a gene transfer or gene targeting vector. Gene therapy, which is based on introducing therapeutic genes into cells by ex-vivo or in-vivo techniques is one of the most important applications of gene transfer. Transgenic mice expressing a neutralizing antibody directed against nerve growth factor have been generated using the "neuroantibody" technique; Capsoni, Proc. Natl. Acad. Sci. USA 97 (2000), 6826-6831 and Biocca, Embo J. 9 (1990), 101-108. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. The nucleic acid molecules according to (e) may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention. The introduction and gene therapeutic approach should, preferably, lead to the expression of a fragment according to (d) of the invention, whereby said expressed fragment is particularly useful in the treatment, amelioration and/or prevention of hearing loss and/or phantom hearing.

Said antibody, which is monoclonal antibody, polyclonal antibody, single chain antibody, or fragment thereof that specifically binds said peptide or polypeptide also including bispecific antibody, synthetic antibody, antibody fragment, such as Fab, a F(ab$_2$)', Fv or scFv fragments etc., or a chemically modified derivative of any of these (all comprised by the term "antibody"). Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

Preferably, the antibody, aptamer, fragment or derivative thereof according to the invention specifically binds the target protein, (poly)peptide or fragment or epitope thereof whose presence or absence is to be monitored.

The term "specifically binds" in connection with the antibody used in accordance with the present invention means that the antibody etc. does not or essentially does not cross-react with (poly)peptides of similar structures. Cross-reactivity of a panel of antibodies etc. under investigation may be tested, for example, by assessing binding of said panel of antibodies etc. under conventional conditions (see, e.g., Harlow and Lane, (1988), loc. cit.) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides which are preferably expressed by the same tissue as the (poly)peptide of interest, are considered specific for the (poly)peptide/protein of interest and selected for further studies in accordance with the method of the invention.

In a particularly preferred embodiment of the method of the invention, said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

The term "aptamer" as used herein refers to DNA or RNA molecules that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/.

An antisense nucleic acid according to the invention is a nucleic acid molecule complementary to a nucleic acid molecule encoding a protein according to the main embodiment which may be used for the repression of expression of said protein. The construction of small interfering RNAs (siRNAs) (see, e.g. Zamore Nat Struct Biol 2001, 8(9):746-50 or Tuschl T. CHEMBIOCHEM. 2001, 2:239-245) or of appropriate ribozymes (see, e.g., EP-B1 0 291 533, EP-A1 0 321 201, EP-A2 0 360 257) which specifically cleave the (pre)-mRNA of a gene comprising a nucleic acid encoding said protein are also suitable for the repression of expression. The techniques underlying said repression of expression are well known in the art. Selection of appropriate target sites and corresponding ribozymes can be done as described for example in Steinecke et al. (Methods in Cell Biology (1995) 50:449-460). Standard methods relating to antisense technology have also been described (Melani et al., Cancer Res. (1991) 51:2897-2901). Said nucleic acid molecules may be chemically synthesized or transcribed by an appropriate vector containing a chimeric gene which allows for the transcription of said nucleic acid molecule in the cell. Such nucleic acid molecules may further contain ribozyme sequences as described above.

Iodonium derivatives or, more specifically, aryliodonium compounds include diphenylene iodonium (DPI, also referred to as iodoniumdiphenyl or iodonium biphenyl), di-2-thienyliodonium (also referred to as iodonium thiophene) and phenoxaiodonium. These compounds act as arylating agents and directly and irreversibly inhibit NOX enzymes.

Apocynin (4-hydroxy-3-methoxy-acetophenone) is a methoxy-substituted catechol and exerts its effect on NOX enzymes through the inhibition of subunit assembly.

Also embraced by the present invention are pharmaceutical compositions comprising (i) naphthoquinones such as plumbagin, acetylshikonin; (ii) inhibitors of HMG-CoA reductase including statins such as lovastatin, simvastatin, atorvastatin; (iii) gliotoxin; (iv) phenothiazines such as phenothiazine, trifluoperazine, and/or (v) a derivative of any one of (i) to (v).

Plumbagin is a naphtoquinone derived from *Plumbago Zeylanica* (Chitrak, an indian medicinal plant).

Gliotoxin is a metabolite of pathogenic fungi (*Aspergillus* and *Candida* spp) and has been implicated in infectious pathways. It exhibits immunosupressive action and antitumor activity and inhibits activation process of NOX2 (Yoshida et al., 2000) and the assembly of the enzyme (Tsunawaki et al., 2004). It is available from Sigma.

Statins are inhibitors of HMG-CoA. They decrease plasma cholesterol and block rac-1 dependent activation of NADPH oxidases (Maack et al. 2003). Furthermore, they inhibit myristoylation of rac.

Trifluoperazine is an inhibitor of PKC/calmodulin and prevents the activation of NADPH oxidases (Seifert and Schachtele, 1988, Holland et al., 2000).

The term derivative relates to compounds having the same core or backbone structure while one or more of the substituents are modified, for example by replacing a methyl group with a trifluoromethyl group. These modifications are such that the biological/pharmacological activity is not substantially altered. Said activity may be monitored by the assays disclosed herein.

The present invention also relates to a pharmaceutical composition consisting of (a) ortho-methoxy-substituted catechols such as apocynin, acetosyringone, vanillin, vanillic acid, syringaldehyde, syringic acid; and (b) a pharmaceutically acceptable carrier, excipient or diluent.

Also provided by the present invention is a pharmaceutical composition comprising (a) an ototoxic agent; and (b) a compound selected from the group consisting of: (i) an antibody, aptamer, or a fragment or derivative thereof binding specifically the protein defined in claim 1; (ii) an antisense nucleic acid, an siRNA, or a ribozyme binding specifically a nucleic acid encoding said protein; (iii) a compound comprising the fragment of SEQ ID NO: 11 from position 202 to position 212, the fragment of SEQ ID NO: 11 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370, wherein said compound may furthermore comprise a cell-penetrating peptide; (iv) a nucleic acid comprising a sequence encoding any of the fragments according to (c), wherein said nucleic acid may optionally comprise a sequence encoding a cell-penetrating peptide; (v) aryliodonium compounds such as diphenylene iodonium (DPI), di-2-thienyliodonium, phenoxaiodonium; (vi) naphthoquinones such as plumbagin, acetylshikonin; (vii) inhibitors of HMG-CoA reductase including statins such as lovastatin, simvastatin, atorvastatin; (viii) gliotoxin; (ix) phenothiazines such as phenothiazine, trifluoperazine, and/or (x) a derivative of any one of (v) to (ix). Said ototoxic agent may be any agent detailed herein above. Preferably, said ototoxic agent is a medicament, wherein said medicament causes ototoxicity as a side effect. Therefore, and in view of the disclosure of the mechanism of ototoxicity in this application, a combination therapy with a medicament with ototoxic side effect and an inhibitor of the protein defined in the main embodiment is provided. Also provided is the use of an ototoxic agent and of a compound as defined in (b) above for the manufacture of pharmaceutical composition, wherein said compound as defined in (b) prevents, alleviates or cures the ototoxic effect of said ototoxic agent.

In a preferred embodiment of said pharmaceutical composition, said ototoxic agent is an antibiotic.

In a more preferred embodiment of said pharmaceutical composition, said ototoxic agent is an aminoglycoside antibiotic, preferably gentamycin. This type of combination therapy is particularly envisaged for those regions or countries where aminoglycoside antibiotics such as gentamycin, owing to their low cost, are widely used.

The present invention also relates to the use of a modulator of the protein defined in the main embodiment for the preparation of a pharmaceutical composition for the treatment and/or prevention of hearing loss and/or phantom hearing, wherein said modulator is selected from the group consisting of (a) an antibody, aptamer, or a fragment or derivative thereof binding specifically said protein; (b) an antisense nucleic acid, an siRNA, or a ribozyme binding specifically a nucleic acid encoding said protein; (c) a known modulator of NOX3 and/or NADPH oxidases and/or electron transport proteins; (d) a compound comprising the fragment of SEQ ID NO: 11 from position 202 to position 212, the fragment of SEQ ID NO: 11 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370; (e) a nucleic acid comprising a sequence encoding any of the fragments according to (d); and (f) a modulator identified by the method of any one of claims 1 to 13. The fragments according to (d) are regions of the sequences of the respective SEQ ID NOs known or expected to be involved in subunit association. Said compounds according to (d) may furthermore comprise a cell-penetrating peptide. The term "cell-penetrating peptide" is defined herein above.

The nucleic acids according to (e) include the sequences with the SEQ ID NOs: 12, 16, 8 and 20 as well those fragments thereof which comprise a sequence encoding any of the fragments according to (d). Said nucleic acid may optionally comprise a sequence encoding a cell-penetrating peptide.

Also embraced by the present invention are uses of fragments of proteins orthologous or homologous to hNOXA1, hNOXO1, hp47phox/NOXO2 or hp67phox/NOXA2, whereby said fragments align with the fragments of hNOXA1, hNOXO1, hp47phox/NOXO2 or hp67phox/NOXA2 recited under (d), as are uses of nucleic acids encoding these aligning fragments. It is understood that these uses are considered equivalents of the above described embodiment. Said orthologous or homologous proteins include the respective murine proteins, i.e., proteins having an amino acid sequence set forth in any one of SEQ ID NO: 13, 17, 9 or 21. The nucleic acids encoding the latter are set forth in SEQ ID NO: 14, 18, 10 and 22.

Furthermore embraced by the present invention are uses of (a) peptidomimetic compound(s) which has been obtained by using any of the fragments according to (d) as a lead compound.

Uses of a nucleic acid according to (e) and/or of the above described equivalents thereof are also envisaged for gene therapy.

The present invention also relates to the use of a cisplatin and/or hydrogen hexachloroplatinate for the preparation of a pharmaceutical composition for the treatment and/or prevention of tinnitus. Cisplatin and hydrogen hexachloroplatinate are activators of the protein defined the main embodiment. Surprisingly, in many incidences of tinnitus a positive response to a treatment with compounds known to induce oxidative stress in the inner ear is observed.

Also provided is a method of diagnosing hearing loss and/or phantom hearing and/or an individual's disposition or risk to develop said loss and/or said phantom hearing, comprising the steps of: (a) determining (a) polymorphism(s) in a NOX3 gene or cDNA and/or in a gene or cDNA encoding an NADPH oxidase subunit in a sample obtained from said individual; and (b) associating said polymorphism(s) with a disease state or disposition state. Preferably, said sample is a blood sample. Preferably, said NOX3 gene comprises or consists of the sequence set forth in SEQ ID NO: 23 or 24. Preferably said NOX3 cDNA (or equivalently mRNA) comprises or consists of the sequence set forth in SEQ ID NO: 2, 4 or 6. Preferably said cDNA encoding an NADPH oxidase subunit comprises or consists of the sequence set forth in any one of SEQ ID NOs: 8, 10, 12, 14, 16, 18, 20 or 22.

The term "polymorphism", or "nucleotide polymorphism" refers to the occurrence of one or more different nucleotides or bases at a given location on a chromosome. Usually, polymorphisms are distinguished from mutations based on their prevalence. Sometimes a threshold of 1% prevalence in a population of individuals is considered for separating polymorphisms (more frequent) from mutations (less frequent). A single nucleotide polymorphism (SNP) is a polymorphism of a single nucleotide or base. The SNP database maintained at NCBI (http://www.ncbi.nlm.nih.gov/SNP/) divides SNPs into SNPs in the proximity of a known locus and such that are 5' further away than 2 kb from the most 5' feature of a gene and 3' further away than 500 bases from the most 3' feature of a gene. SNPs in the proximity of a known locus are further divided into SNPs occurring at an mRNA location and such that do not. SNPs occurring at an mRNA location comprise coding and non-coding SNPs.

It is understood that the term "polymorphism(s) in a NOX3 gene and/or in a gene encoding an NADPH oxidase subunit" embraces polymorphisms in exons, introns and regulatory regions such as promoters. Polymorphisms in exons may be determined or analysed using genomic DNA or cDNA (or equivalently mRNA). Polymorphisms in introns or regulatory regions such as promoters may be determined or analysed using cDNA (or equivalently mRNA).

Said associating of polymorphism(s) with a disease state or disposition state refers to classifying of individuals and patients. The term "classifying" refers to the assignment of individuals or patients to two or more groups or classes. In other words, individuals, previously unclassified, get labelled by their respective class. The assigned class label may refer to parameters used for classification, e.g. polymorphisms, or may refer to parameters not used for classification because their values are not known beforehand, e.g. fast or slow response to therapy. In the first case, class discovery methods, e.g. clustering may be applied, whereas in the second case predictive classification methods are used. Classification may be done manually by a trained person or by a computer program provided with the values of the parameters used for class distinction. Patients have to give informed consent. Data have to be handled and kept secret in accordance with national laws.

The present invention also provides the use of a compound binding to the protein defined in the main embodiment or to a NADPH oxidase subunit for the preparation of a diagnostic composition for the diagnosis of hearing loss and/or phantom hearing and/or an individual's disposition or risk to develop said loss and/or said phantom hearing, wherein said compound is selected from the group consisting of (a) an antibody, aptamer, or a fragment or derivative thereof binding specifically said protein; and (b) a known modulator of NOX3 and/or NADPH oxidases and/or electron transport proteins.

In a preferred embodiment of the use according to the invention, said known modulator is selected from the group consisting of iodonium derivatives, substituted catechols such as apocynin, platinum derivatives and palladium derivatives.

Known modulators to be used for the preparation of a pharmaceutical composition according to the invention are selected from the group consisting of (i) aryliodonium compounds such as diphenylene iodonium (DPI), di-2-thienyliodonium, phenoxaiodonium; (ii) ortho-methoxy-substituted catechols such as apocynin, acetosyringone, vanillin, vanillic acid, syringaldehyde, syringic acid; (iii) naphthoquinones such as plumbagin, acetylshikonin; (iv) inhibitors of HMG-CoA reductase including statins such as lovastatin, simvastatin, atorvastatin; (v) gliotoxin; (vi) phenothiazines such as phenothiazine, trifluoperazine; and (vii) a derivative of any one of (i) to (vi). Said known modulators act as inhibitors of the protein defined in the main embodiment.

Known modulators to be used for the preparation of a diagnostic composition according to the invention are selected from the known modulators to be used for the preparation of a pharmaceutical composition and cisplatin and hexachloroplatinate as well as derivatives thereof. Cisplatin and hexachloroplatinate bind and activate the protein defined in the main embodiment and are therefore specifically envisaged for the manufacture of a diagnostic composition.

Cisplatin, as demonstrated by the inventors, is a preferred platinum derivative which modulates NOX3 activity. The platinum derivative hydrogen hexachloroplatinate and palladium derivatives are known to modulate the activity of NOX2 (phagocyte NADPH oxidase). In both cases, there are indications that modulation is a direct effect on the NOX enzymes.

Also envisaged is the use of a compound binding to a nucleic acid encoding the protein defined in the main embodiment or an NADPH oxidase subunit for the preparation of a diagnostic composition for the diagnosis of hearing loss and/or phantom hearing and/or an individual's disposition or risk to develop said loss and/or said phantom hearing, wherein said compound is a nucleic acid complementary to said nucleic acid and at least 15 nucleotides in length. This embodiment is directed to oligonucleotide probes for the detection of genomic DNA or mRNA. With regard to genomic DNA, also the detection and distinction of polymorphisms is envisaged.

Preferably, said compound is detectably labelled.

More preferred, said diagnosis to be performed involves imaging of the human or animal body.

In a preferred embodiment of the method or the use of the invention, said animal is a rodent. More preferred, said rodent is mouse or rat.

In a preferred embodiment of the method or the use of the present invention, said modulator is an inhibitor.

The term "inhibitor" designates a compound lowering the activity of a target molecule, preferably by performing one or more of the following effects: (i) the transcription of the gene encoding the protein to be inhibited is lowered, (ii) the translation of the mRNA encoding the protein to be inhibited is lowered, (iii) the protein performs its biochemical function with lowered efficiency in presence of the inhibitor, and (iv) the protein performs its cellular function with lowered efficiency in presence of the inhibitor.

Compounds falling in class (i) include compounds interfering with the transcriptional machinery and/or its interaction with the promoter of said gene and/or with expression control elements remote from the promoter such as enhancers. Compounds of class (ii) comprise antisense constructs and constructs for performing RNA interference well known in the art (see, e.g. Zamore (2001) or Tuschl (2001)). Compounds of class (iii) interfere with molecular function of the protein to be inhibited, in case of an NADPH oxidase with its enzymatic activity and/or its capability to associate with NADPH oxidase subunits. Accordingly, active site binding compounds, in particular compounds capable of binding to the active site of any NADPH oxidase, are envisaged, as are compounds interfering with the association of NADPH oxidase with said subunits. More preferred are compounds specifically binding to an active site of NADPH oxidase. Also envisaged are compounds binding to or blocking substrate binding sites of NADPH oxidase. Class (iv) includes compounds which do not necessarily directly bind to NADPH oxidase, but still interfere with NADPH oxidase activity, for example by binding to and/or inhibiting the function or inhibiting expression of members of a pathway which comprises NADPH oxidase. These members may be either upstream or downstream of NADPH oxidase within said pathway.

In a preferred embodiment, the inhibitor is a low molecular weight compound. Low molecular weight compounds are compounds of natural origin or chemically synthesized compounds, preferably with a molecular weight between 100 and 1000, more preferred between 200 and 750, and even more preferred between 300 and 600.

The efficiency of the inhibitor can be quantitized by comparing the level of activity in the presence of the inhibitor to that in the absence of the inhibitor. For example, as an activity measure may be used: the change in amount of mRNA formed, the change in amount of protein formed, the change in amount of substrate converted or product formed, and/or the change in the cellular phenotype or in the phenotype of an organism.

In a preferred embodiment, the level of activity is less than 90%, more preferred less than 80%, 70%, 60% or 50% of the activity in absence of the inhibitor. Yet more preferred are inhibitors lowering the level down to less than 25%, less than 10%, less than 5% or less than 1% of the activity in absence of the inhibitor.

The present invention also relates to a nucleic acid (i) comprising or consisting of the sequence of SEQ ID NO: 6, or (ii) encoding a protein comprising or consisting of the sequence of SEQ ID NO: 5, or (iii) encoding a fragment of the protein according to (ii), wherein said fragment exhibits NADPH oxidase activity, or (iv) encoding a protein having a sequence at least 95% identical with the protein according to (ii) or with the fragment according to (iii) and exhibiting NADPH oxidase activity.

Preferably, said protein having at least 95% sequence identity with the protein according to (ii) or with the fragment according to (iii), has 98% or 99% identity with said protein or fragment.

An alternative embodiment of the invention relates to a vector comprising the above defined nucleic acid.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector of the present invention may, in addition to the nucleic acids of the invention, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid of the invention is operably linked to said expression control sequences allowing expression in eukaryotic or prokaryotic cells.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook (1989), loc. cit., and Ausubel, Current Protocols in Molecular Biology, Green Publishing Associates and Wiley Interscience, N.Y. (1989), (1994). Alternatively, the nucleic acids and vectors of the invention can be reconstituted into liposomes for delivery to target cells. According to the invention relevant sequences can be transferred into expression vectors where expression of a particular (poly)peptide/protein is required. Typical cloning vectors include pBscpt sk, pGEM, pUC9, pBR322 and pGBT9. Typical expression vectors include pTRE, pCAL-n-EK, pESP-1, pOP13CAT.

Furthermore, a protein encoded by said nucleic acid is provided.

The present invention furthermore relates to host containing an aforementioned vector or an aforementioned nucleic acid, or an aforementioned protein. Said host may be produced by introducing said vector or nucleic acid into a host cell which upon its presence in the cell mediates the expression of a protein encoded by the nucleic acid of the invention or comprising a nucleic acid or a vector according to the invention wherein the nucleic acid and/or the encoded (poly)peptide/protein is foreign to the host cell.

By "foreign" it is meant that the nucleic acid and/or the encoded (poly)peptide/protein is either heterologous with respect to the host, this means derived from a cell or organism with a different genomic background, or is homologous with respect to the host but located in a different genomic environment than the naturally occurring counterpart of said nucleic acid. This means that, if the nucleic acid is homologous with respect to the host, it is not located in its natural location in the genome of said host, in particular it is surrounded by different genes. In this case the nucleic acid may be either under the control of its own promoter or under the control of a heterologous promoter. The vector or nucleic acid according to the invention which is present in the host may either be integrated into the genome of the host or it may be maintained in some form extrachromosomally. In this respect, it is also to be understood that the nucleic acid of the invention can be used to restore or create a mutant gene via homologous recombination.

The host can be any prokaryote or eukaryotic cell, such as a bacteria, an insect, fungal, plant or animal cell.

The term "prokaryote" is meant to include all bacteria which can be transformed or transfected with a DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast cells, cells of higher plant, insect cells and preferably mammalian cells. Depending upon the host employed in a recombinant production procedure, the protein encoded by the nucleic acid of the present invention may be glycosylated or may be non-glycosylated. A nucleic acid of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook (1989), loc. cit.).

Preferably, said host is a cell. More preferred, the host is a human cell or human cell line.

Alternatively, said host is a transgenic non-human animal.

A method for the production of a transgenic non-human animal, for example transgenic mouse, comprises introduction of a nucleic acid or vector according to the invention into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate probe. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62: 1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326: 292-295 (1987)), the D3 line (Doetschman et al., J. Embryol. Exp. Morph. 87: 27-45 (1985)), the CCE line (Robertson et al., Nature 323: 445-448 (1986)), the AK-7 line (Zhuang et al., Cell 77: 875-884 (1994) which is incorporated by reference herein). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born as chimeric mice. The resultant transgenic mice are chimeric for cells having either the recombinase or reporter loci and are backcrossed and screened for the presence of the correctly targeted transgene(s) by PCR or Southern blot analysis on tail biopsy DNA of offspring so as to identify transgenic mice heterozygous for either the recombinase or reporter locus/loci.

Methods for producing transgenic flies, such as *Drosophila melanogaster* are also described in the art, see for example U.S. Pat. No. 4,670,388, Brand & Perrimon, Development (1993) 118: 401-415; and Phelps & Brand, Methods (April 1998) 14: 367-379.

Transgenic worms such as *C. elegans* can be generated as described in Mello, et al., (1991) Efficient gene transfer in *C. elegans*: extrachromosomal maintenance and integration of transforming sequences. Embo J 10, 3959-70, Plasterk, (1995) Reverse genetics: from gene sequence to mutant worm. Methods Cell Biol 48, 59-80.

The invention also relates to transgenic non-human animals such as transgenic mouse, rats, hamsters, dogs, monkeys, rabbits, pigs, *C. elegans* and fish such as Torpedo fish comprising a nucleic acid according to the invention.

Also provided is an antibody or aptamer, or fragment or derivative thereof binding specifically to the protein encoded by said nucleic acid as is an antisense nucleic acid, an siRNA, or a ribozyme binding specifically said nucleic acid.

The Figures show:

FIG. 1: Tissue distribution of NOX3 mRNA. A) NOX3 mRNA expression was evaluated in 12 rat tissues by RT-PCR (upper panel); GAPDH mRNA was used as a reference transcript (lower panel). "No cDNA" represents negative control PCR devoid of added cDNA. The first lane of both panels shows DNA size markers. B) Quantification of NOX3 RNA in 14 mouse tissues using real time PCR. NOX3 mRNA expression is shown relative to 18S rRNA expression. The amounts of NOX3 and 18S PCR products were measured using SYBR Green.

FIG. 2: PCR detection of cDNAs encoding NOX activator and regulator subunits in the inner ear. A, RT-PCR amplification of NOXA1, NOXO1, and the reference GAPDH cDNA from the indicated rat tissues. B, RT-PCR amplification of $p67^{phox}$ and $p47^{phox}$ cDNA from the indicated rat tissues. The first lane of each panel shows DNA size markers.

Figure 3:
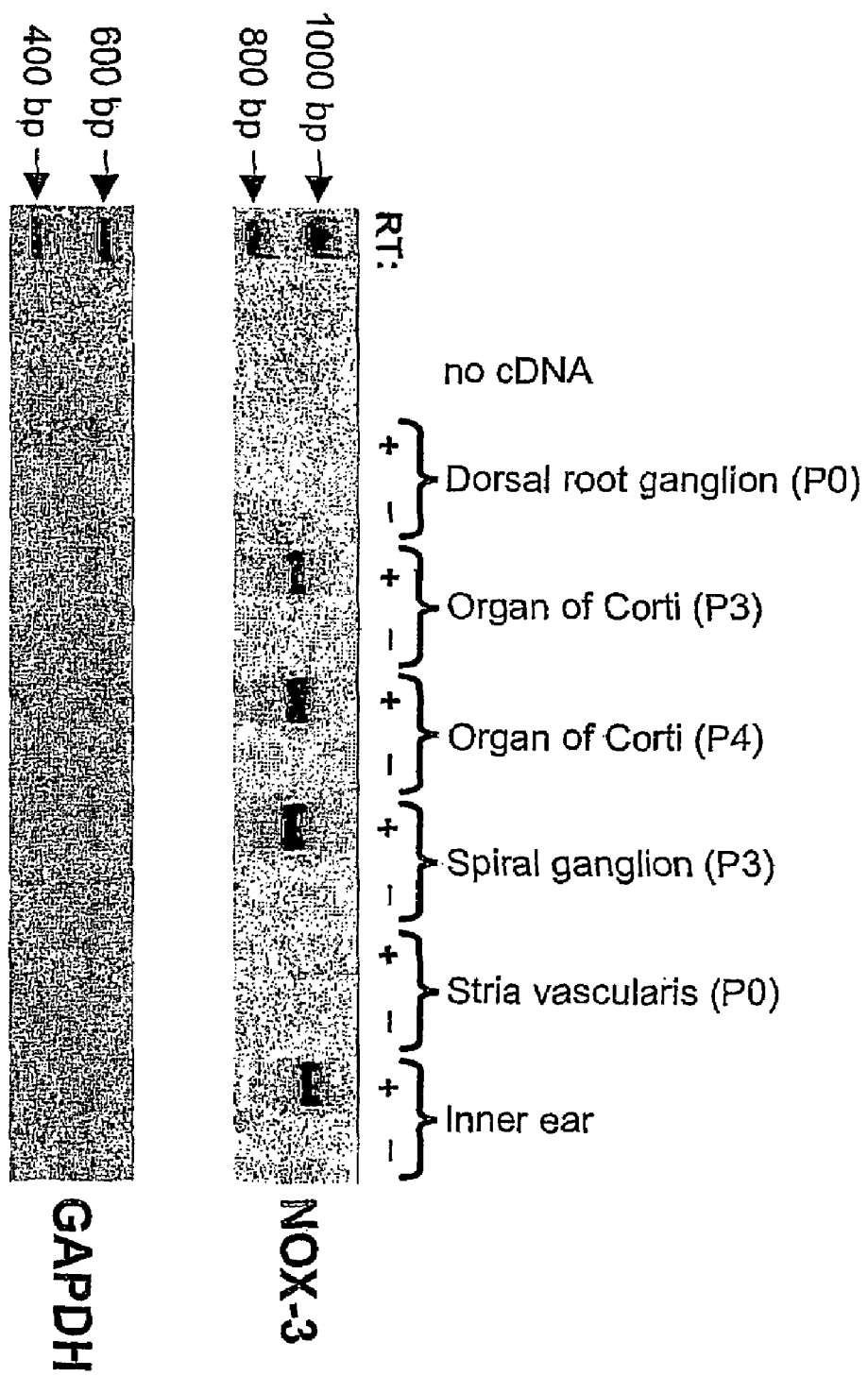

FIG. 3: Expression of NOX3 mRNA in specific regions of cochlea. The indicated regions of the rat inner ear were obtained by microdissection and NOX3 (upper panel) and GAPDH (lower panel) expression were assessed by RT-PCR. "+" symbols represent reverse transcribed (RT positive) samples; "−" symbols represent not reverse transcribed (RT negative) samples. P0, P3, and P4 indicate the postnatal days when samples were taken. Positive control inner ear sample was isolated from adult rat.

FIG. 4: Localization of NOX3 mRNA in inner ear by in situ hybridization. Mouse inner ear sections hybridized with digoxigenin-labeled antisense (A, C, and E) and sense (B, D, and F) probes of NOX3, shown at ×20 (A, B) and ×40 (C-F) magnifications. A, The antisense probe hybridized with the RNA of spiral ganglion neurons. B, The sense probe yielded only a weak, uniform signal and no labeling of spiral ganglion neurons. C, Hybridization of antisense NOX3 probe with the organ of Corti labeled the sensory epithelium. D, Hybridization of sense NOX3 probe with organ of Corti did not yield specific signals. E, Antisense NOX3 probe hybridized with the sensory epithelial cell layer of the saccule. F, Only a week uniform signal was observed with the sense NOX3 probe.

Figure 5:
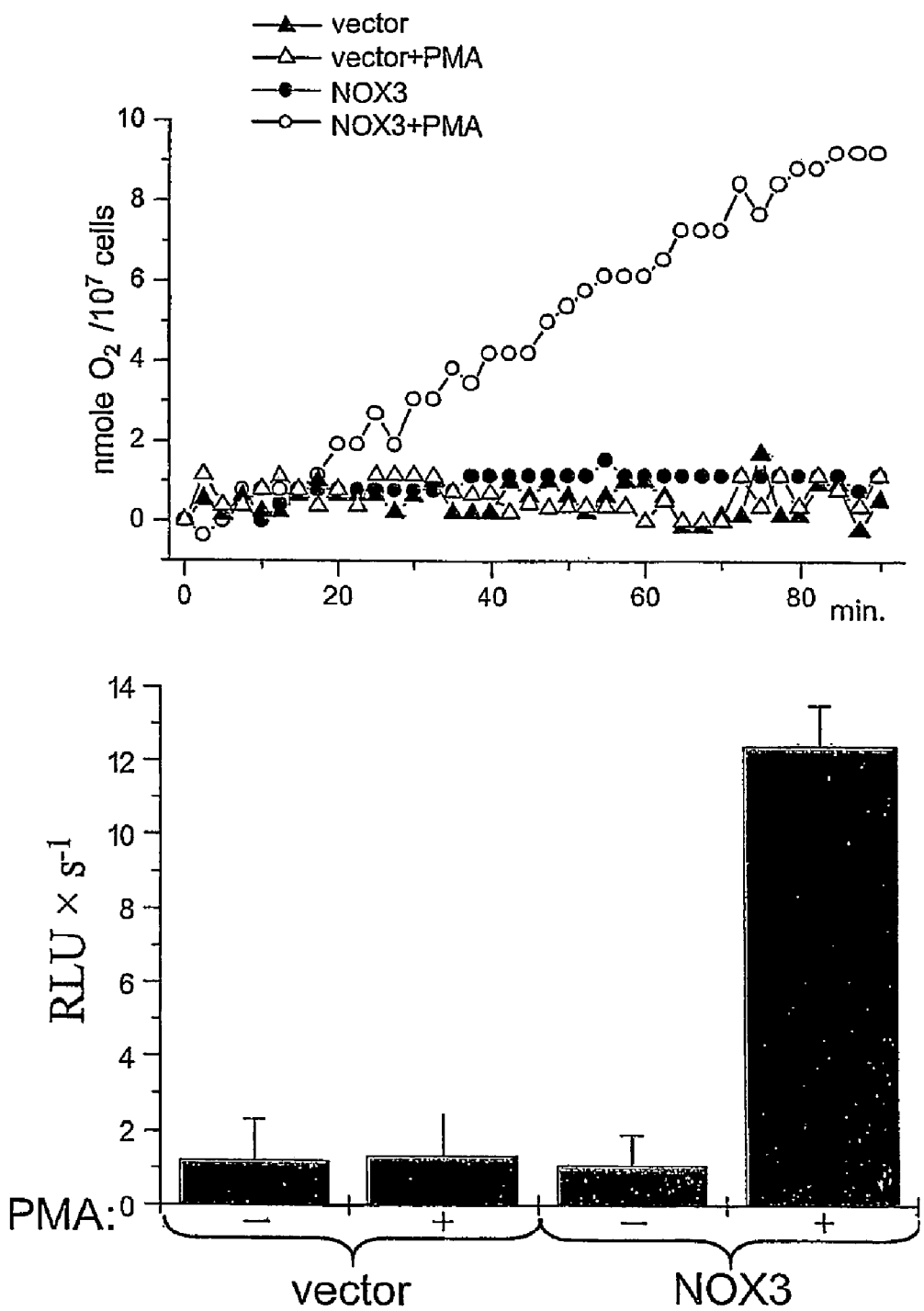

FIG. 5: NOX3-dependent superoxide production in the absence of other NOX subunits. HEK293 cells were transfected with either pcDNA3.1 vector or NOX3, and superoxide generation was measured as cytochrome C reduction (upper panel) or as luminol-amplified chemiluminescence (lower panel) in the presence or absence of 100 nM PMA, as indicated. Upper panel shows the result of a single experiment representative of three independent studies. Lower panel shows statistical analysis of peak superoxide production. Chemiluminescence signals were measured with relative light units (RLU and normalized to 1 second and 150,000 cells.

FIG. 6: Subunit regulation of NOX3 activity. A, B, and C, HEK293 cells were transfected with different combinations of NOX3, NOXO1, NOXA1, $p47^{phox}$, and $p67^{phox}$, as indicated. Superoxide generation was measured as SOD sensitive cytochrome C reduction (lines and symbols) or as luminol-amplified chemiluminescence (bar graphs) in the presence or absence of PMA (100 nM), as indicated. Lines and symbols show typical experiments, representative of at least three independent studies. Bar graphs show statistical analysis of peak superoxide production. Chemiluminescence signals were measured with relative light units (RLU and normalized to 1 second and 150,000 cells.

Figure 7:
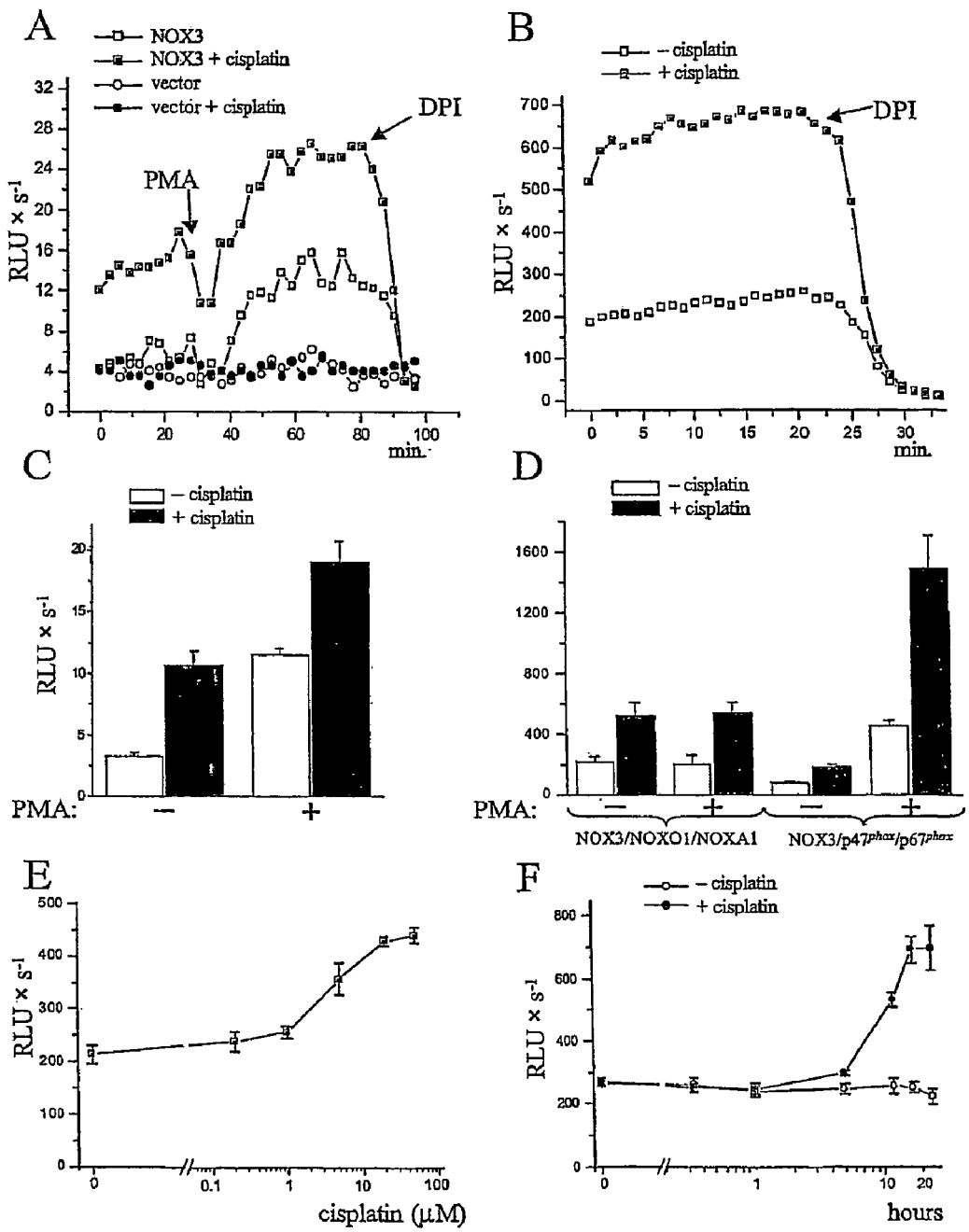

FIG. 7: Cisplatin enhances NOX3-dependent superoxide production. Superoxide production of transfected HEK293 cells were measured either as luminol-amplified chemiluminescence (B, D, E and F) or with a luminol-based superoxide detection kit, Diogenes (A and C). Cells were pre-incubated in the presence or absence of 20 μM cisplatin for 12 hours (A-E). A, HEK293 cells were transfected with NOX3 or control vector (pcDNA3.1) and incubated with or without cisplatin before superoxide measurement. 100 nM PMA and 5 μM DPI were added as indicated. Traces represent a typical experiment, representative of three independent studies. B, HEK293 cells stably expressing NOX3/NOXA1/NOXO1 were pre-incubated with or without cisplatin before superoxide measurement. 5 μM DPI was added as indicated. Traces show a typical experiment, representative of eight independent studies. C, Statistical analysis of peak superoxide production of NOX3 transfected HEK293 cells, after cisplatin- or control treatment, in the presence or absence of 100 nM PMA. D, Statistical analysis of peak superoxide production of HEK293 cells transfected with the indicated constructs and pre-incubated with or without cisplatin. The measurements were carried out in the absence or presence of 100 nM PMA, as indicated. E, Superoxide production of a HEK293 cell clone stably transfected with NOX3/NOXO1/NOXA1 after incubation with various concentrations of cisplatin for 12 hours. F, Superoxide production of a HEK293 cell clone stably transfected with NOX3/NOXO1/NOXA1 after incubation in the presence or absence of 20 μM cisplatin for the indicated periods of time.

The following examples illustrate the invention but should not be construed as being limiting.

EXAMPLE 1

Cloning of Mouse and Rat NOX3 cDNA

Experimental procedures. The first and the last exons of mouse and rat NOX3 genes were identified based on their homology with the human NOX3 gene using the Ensembl Genome Browser (www.ensembl.org). Inner ear samples of mouse (strain C57BI6) and rat (strain Sprague-Dawley) were isolated and total RNA was purified as described [28]. Primers were designed and used to amplify the full length of coding sequences (mouse NOX3 forward 5'-atg ccg gtg tgc tgg att ctg aac-3' and reverse 5'-cta gaa gtt ttc ctt gtt gta ata gaa-3', rat NOX3 forward 5'-gtg ttg gta gta aga gaa gtg tca tg-3' and reverse 5'-c tag aag ttt tcc ttg ttg taa tag-3') with Taq DNA polymerase (Qiagen) under standard conditions. PCR products were subcloned into pcDNA3.1 vector (Invitrogen) and verified by sequencing.

Results. So far, NOX3 mRNA has only been detected in human embryonic kidney, but expression levels were very low [22, 30] and hence the physiological relevance questionable. We reasoned that the physiologically relevant localization of NOX3 might have been missed because previous studies had restricted their analysis to commercially available human RNA sources. To overcome these limitations, we decided to work in mouse and rat and to prepare RNA from tissues that had not been investigated so far. As hitherto only the human NOX3 sequence was known, we identified mouse and rat NOX3 genes by searching genomic DNA databases and designed—based on these results—mouse and rat NOX3 PCR primers.

We then prepared RNA from a variety of mouse and rat tissues, including bone (femur, skull, shoulder blade), cartilage (joints of ribs, outer ear), and inner ear and analyzed them for NOX3 expression by RT-PCR. As shown on FIG. 1A, high levels of NOX3 transcript were detected only in the rat inner ear sample (despite its relatively low mRNA content demonstrated by the low amount of GAPDH PCR product). Using primer pairs designed from the first and the last exons of the mouse and rat NOX3 gene, respectively, we amplified whole length mouse and rat NOX3 coding sequences from inner ear samples. The predicted amino acid sequences of both mouse and rat NOX3 showed 81% sequence identity with the human sequence and 93.5% identity with each other.

EXAMPLE 2

Tissue Distribution of NOX3

Experimental procedures. Total RNA was isolated from different organs of rat and mouse and from specific regions of the rat inner ear using the TRIzol reagent. With the exception of RNA purified from parts of the inner ear, samples were DNase treated, then further purified with RNeasy kit (Qiagen). 2 µg total RNA from each tissue was reverse transcribed using Superscript reverse transcriptase (Life Technologies, Inc.). PCR was carried out with Taq DNA polymerase using the following primers: mouse NOX3 forward 5'-gtg ata aca ggc tta aag cag aag gc-3', reverse 5'-cca ctt tcc cct act tga ctt tag-3'; rat NOX3 forward 5'-gcg tgt gct gta gag gac cgt gga g-3', reverse 5'-gag cct gtc cct ctg ctc caa atg c-3'; mouse GAPDH forward 5'-ggg tgt gaa cca cga gaa at-3', reverse 5'-gtc atg age cct tcc aca at-3'; rat GAPDH forward 5'-cgg tgt caa cgg att tgg ccg tat t-3', reverse 5'-act gtg gtc atg agc cct tcc acg a-3'; rat NOXO1 forward 5'-acc caa acc tct gga tct gga gcc c-3', reverse 5'-gga tgg cac tca tac agg ggc gag t-3'; rat NOXA1 forward 5'-tac tgg ccg tag cac gcg aag act g-3', reverse 5'-gga cct ccc agg ctt gca gtt tga a-3'; rat p47$^{phox}$ forward 5'-gca gga cct gtc gga gaa ggt ggt c-3', reverse 5'-tct gtc gct ggg cct ggg tta tct c-3'; rat p67$^{phox}$ forward 5'-aag cag aag age agt tag cat tgg c-3', reverse 5'-gga gtg cct tcc aaa ttc ttg gct g-3'. Standard PCR conditions were used, and the number of PCR cycles was 30 (FIGS. 1 and 2) or 28 (FIG. 3) for the amplification of GAPDH and 35 for all other amplifications.

Quantitative PCR was carried out using ABI Prism 7900HT Sequence Detection System with standard temperature protocol and 2×SYBR Green PCR Master Mix reagent (Applied Biosystems, Worrington, UK) in 25 µl volume, in triplicates. 300 nM of the following primer pairs were used for the reactions: mouse 18S forward 5'-aca tcc aag gaa ggc agc ag-3' and reverse 5'-ttt tcg tca cta cct ccc cg-3'; mouse NOX3 forward 5'-cga cga att caa gca gat tgc-3', and reverse 5'-aag agt ctt tga cat ggc ttt gg-3'. All amplifications were carried out in a MicroAmp optical 96-well reaction plate with optical adhesive covers (PE Applied Biosystems). The accumulation of PCR products was detected by monitoring the increase in fluorescence of the reporter dye.

Results.

NOX3 is predominantly expressed in the inner ear—Based on the cDNA sequence of mouse NOX3, we designed primers for real time PCR to study quantitative expression of NOX3 RNA in different mouse tissues. 18S RNA was used as a reference gene. The results of real-time PCR demonstrated that NOX3 was predominantly expressed in the inner ear (FIG. 1B). Low amounts of NOX3 RNA could also be detected in skull, brain, and embryonic kidney. However, inner ear contained 50-fold of the NOX3 content of skull and 870-fold of the one of embryonic kidney (FIG. 1B).

Expression of cytoplasmic NOX subunits in the inner ear—NOX1 and gp91$^{phox}$/NOX2 require cytoplasmic organizer subunits (NOXO1, p47$^{phox}$) and activator subunits (NOXA1, p67$^{phox}$) to form a functional enzyme. As NOX3 shows a high degree of homology with NOX1 and gp91$^{phox}$/NOX2 [31], we considered that it might also be a subunit-dependent enzyme and therefore investigated expression of cytoplasmic NOX subunits in the inner ear. RT-PCR analysis (using 35 PCR cycles) showed that mRNA of the activator subunit NOXA1, as well as mRNA of the organizer subunit p47$^{phox}$ was expressed in the inner ear (FIG. 2). mRNA of the activator subunit, p67$^{phox}$, and the organizer subunit, NOXO1, could be detected only at very high cycle numbers (40 PCR cycles; data not shown). Since p47$^{phox}$ mRNA is expressed in phagocytic cells, its detection might be due to blood cell contamination. In contrast, NOXA1 is not expressed in blood cells [24] nor in tissues neighboring the inner ear (FIG. 2A); thus, it is most likely expressed within cells of the inner ear.

Expression of NOX3 in different parts of the cochlea—In order to identify regions of the inner ear that express NOX3, we isolated distinct parts of rat cochlea such as organ of Corti, stria vascularis, and spiral ganglia from newborn rats (postnatal day 1 to 4) as described previously [32]. As a control tissue, we used dorsal root ganglia. Total RNA was extracted from these tissues and tested for NOX3 and GAPDH housekeeping gene expression by RT-PCR. Results showed that NOX3 is expressed in spiral ganglia and in the organ of Corti, while stria vascularis and dorsal root ganglia were devoid of NOX3 mRNA (FIG. 3). Our experiments demonstrated that i) NOX3 is expressed only in selected structures of the cochlea (i.e. organ of Corti and spiral ganglia), and ii) its expression is not a general property of the peripheral nervous system (i.e. it was absent from dorsal root ganglia).

EXAMPLE 3

In Situ Hybridization

Experimental procedures. For in situ hybridization experiments digoxigenin-labelled antisense and sense (negative control) cRNA probes (nucleotides 560-849 of mNOX3) were generated and used as described previously [19] on decalcified, 7 µm thick inner ear sections.

Results. To further define the site of NOX3 expression, we performed in situ hybridization of adult mouse inner ear sections. The antisense NOX3 probe labeled spiral ganglion neurons (FIG. 4A) and cells of the organ of Corti (FIG. 4C). The cellular structures within the organ of Corti were not sufficiently well preserved to identify NOX3-expressing cells more precisely. The sense probe gave only a weak, uniform background signal demonstrating the specificity of the antisense hybridization (FIGS. 4 B and D). Specific labeling for NOX3 was also observed in the vestibular system, namely in the sensory epithelial cell layer of the saccule (FIG. 4 E, F).

EXAMPLE 4

Measurement of Reactive Oxygen Species

Experimental Procedures.

Cell culture and transfection—HEK293 were maintained in Dulbecco's Modified Eagle's Medium/Ham's Nutrient Mixture F12 that was supplemented with 10% fetal calf serum, penicillin (100 units/ml), streptomycin (100 µg/ml), and 4 mmol/liter L-glutamine. NOX3-, NOXO1-, NOXA1-, p47$^{phox}$-, and p67$^{phox}$ cDNAs were subcloned into pcDNA3.1 (Invitrogen, Groningen, Netherlands) and transfected into HEK293 cells with the Effectene transfection system (Qiagen). To obtain stable clones, NOX3, NOXO1, NOXA1-transfected HEK293 cells were selected with 400 µg/ml G418 starting on the 2nd day after the transfection. After 14 days of selection, 24 surviving clones were tested for superoxide production. The positive clones were verified to express NOX3-, NOXO1-, and NOXA1 RNA by RT-RCR.

ROS generation was measured by the peroxidase-dependent luminol-amplified chemiluminescence technique (referred to as luminol-amplified chemiluminescence) in 96 well microplates using Luminometer Wallac 1420 Multilabel Counter (PerkinElmer Life Sciences). Measurements were performed in Hanks' balanced salt solution supplemented with 1 mg/ml D-glucose, 1 unit/ml horseradish peroxidase, and 250 µM luminol. In some experiments, phorbol ester (PMA) was added during the measurements to 100 nM final concentration. When the effect of cisplatin or 5-Fluorouracil (5-FU) was investigated, these compounds were pre-incubated with the cells for the indicated time and concentration in cell culture medium. Before ROS measurements, the cell culture medium was exchanged with the assay solution and chemiluminescence or absorption (see below) was measured at 37° C. After measurements cells were counted, and the results were normalized to 150,000 cells. Extracellular superoxide production was measured in 96-well microplates at 550 nm as the SOD-sensitive reduction of 100 µM ferricytochrome C (referred to as cytochrome C reduction technique). The O$^-_2$ production was calculated using an absorption coefficient of 21.1 mM$^{-1}$ cm$^{-1}$ and normalized to 10$^7$ cells [29].

Results.

NOX3-dependent superoxide generation in the absence of subunits—To investigate its molecular function, we transiently expressed NOX3 in HEK293 cells, which do not show endogenous expression of the enzyme. Superoxide production was measured with cytochrome C reduction technique and with luminol-amplified chemiluminescence. Using either technique, NOX3-transfected cells generated low amounts of superoxide, but only in the presence of a protein kinase C activator (phorbol ester, PMA) (FIG. 5). Since both NOX1 and gp91$^{phox}$/NOX2 have an obligatory subunit requirement, the stimulus-dependent and subunit-independent activity of NOX3 is a unique and distinguishing feature of this NOX isoform.

Figure 6A:
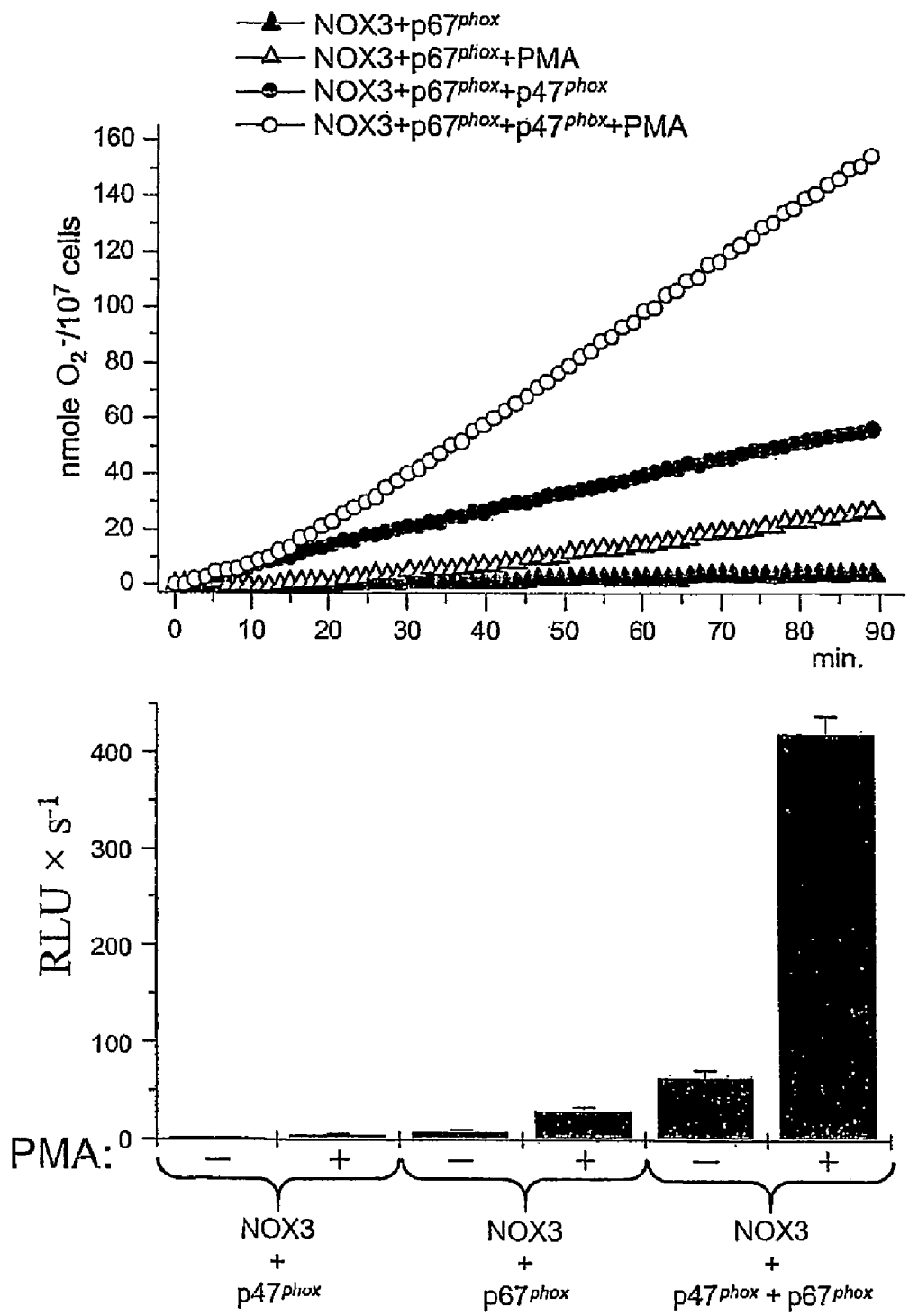
Figure 6B:
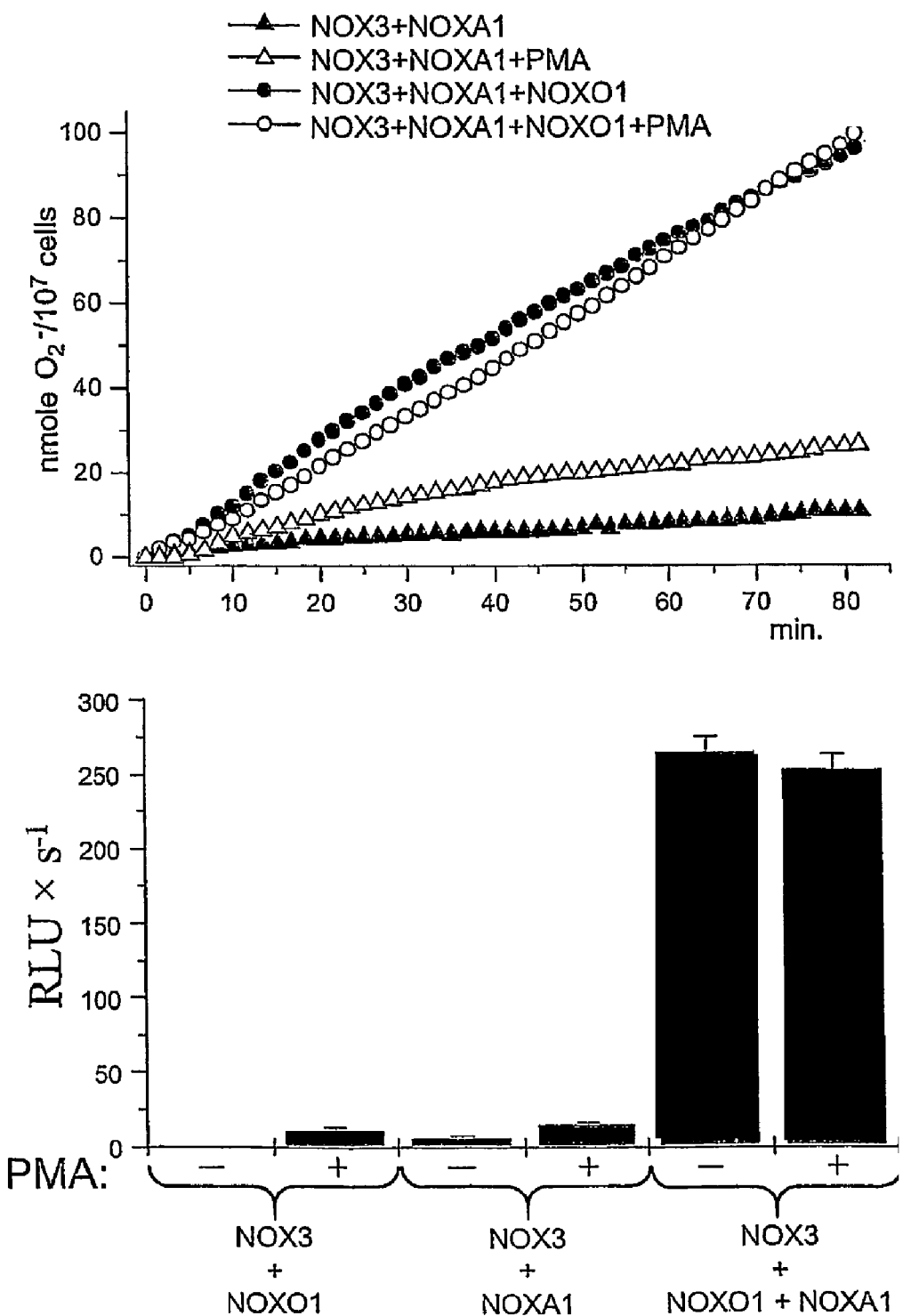

Regulation of NOX3 by the organizer and activator subunits of NOX1 and gp91$^{phox}$/NOX2—Since expression of NOX regulator and activator subunits was detected in the inner ear (see above, FIG. 2), we reasoned that they might influence NOX3 activity. Thus, we investigated superoxide generation by NOX3 upon co-transfection with cytoplasmic subunits. In the first series of experiments, NOX3 was co-transfected with the cytosolic subunits of the phagocyte NADPH oxidase, p67$^{phox}$ and p47$^{phox}$. In these transfectants, the NOX3-dependent superoxide generation was markedly increased, even without an added stimulus (FIG. 6A). The addition of PMA, however, led to a strong enhancement of NOX3 activity (FIG. 6A). HEK293 cells, transfected with p47$^{phox}$ and p67$^{phox}$ but devoid of NOX3, did not produce any superoxide (not shown). Interestingly p67$^{phox}$ alone, in the absence of p47$^{phox}$, was sufficient to double the PMA-induced superoxide generation of NOX3, while p47$^{phox}$, in the absence of p67$^{phox}$, did not modify NOX3 activity (compare FIG. 5 with FIG. 6A). Next it was investigated whether NOX3 could be regulated by the NOXO1 and NOXA1 subunits, which are associated with NOX1 in the colon. Co-transfection of NOX3 with NOXO1 and NOXA1 resulted in a massive increase of superoxide production (FIG. 6B). The NOXO1/NOXA1-enhanced superoxide generation was insensitive to PMA (FIG. 6B). The co-expression of NOXA1 with NOX3, in the absence of NOXO1, had an enhancing effect on PMA-stimulated NOX3 activity. NOXO1 alone, however, did not influence NOX3-dependent superoxide production (FIG. 6B, lower panel).

Figure 6C:
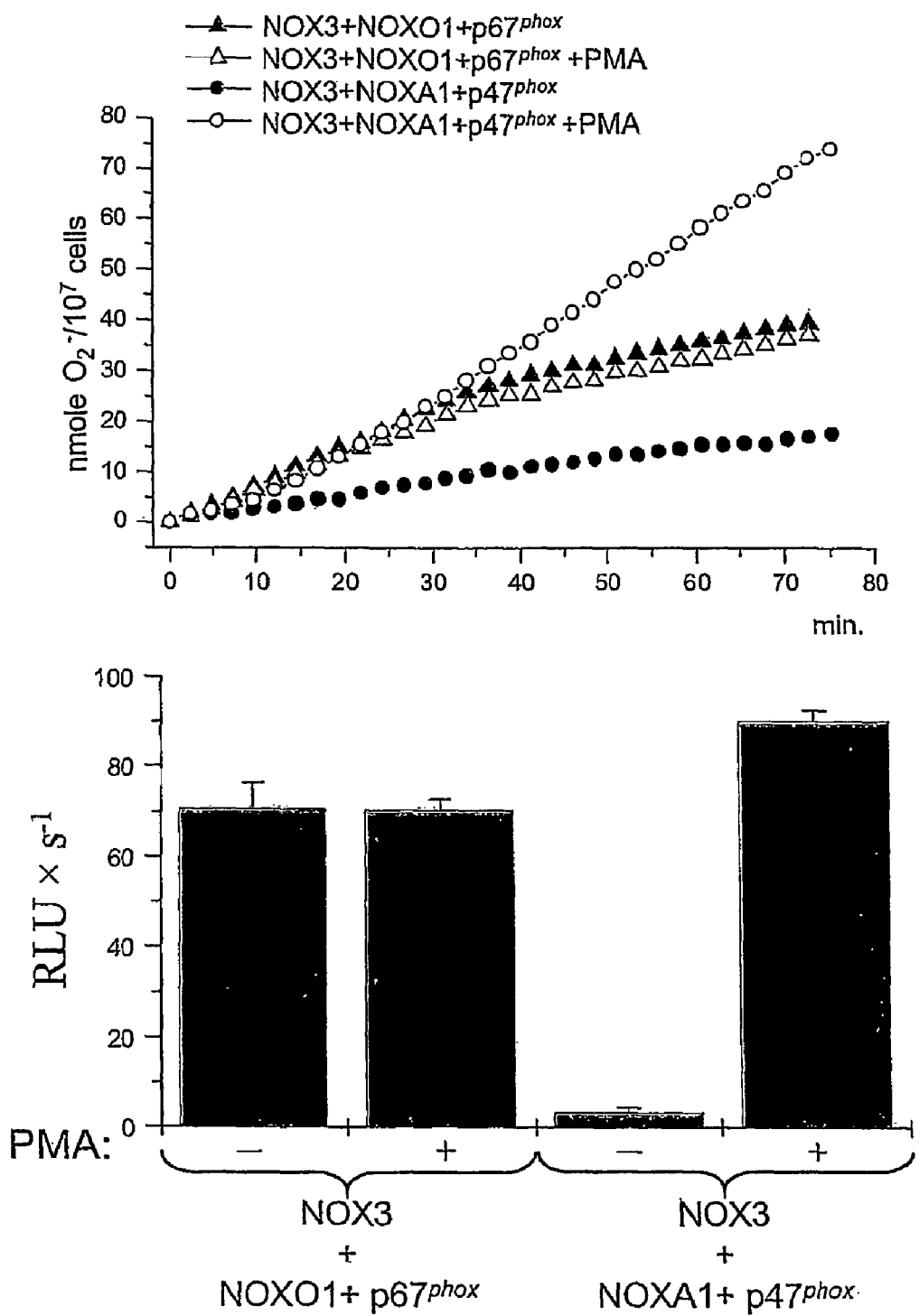

At a least on a biochemical level, there is promiscuity among the organizer and regulator subunits: NOXO1 is able to function with p67$^{phox}$, and NOXA1 with p47$^{phox}$ [24-26]. Therefore, we investigated which combinations of organizer and activator subunits are capable to regulate NOX3, and what kind of properties those complexes may have. Expression of NOXO1, p67$^{phox}$, and NOX3 in HEK293 cells, led to spontaneous superoxide generation that could not be further enhanced by PMA (FIG. 6C). However, when p47$^{phox}$, NOXA1, and NOX3 were expressed, superoxide production by HEK293 cells was largely PMA-dependent (FIG. 6C). Thus, the organizer subunit (p47$^{phox}$ versus NOXO1) determines whether NOX3 activity is PKC-dependent or independent.

Cisplatin enhances NOX3 activity—Cisplatin is an ototoxic drug that exerts its toxic effect, at least in part, through induction of ROS generation in the inner ear [2]. We therefore investigated the effect of this drug on NOX3 activity. HEK293 cells were transfected with NOX3 or with a control vector (pcDNA3.1) and incubated for 12 hours in the presence or absence of 20 µM cisplatin. Cisplatin alone elicited superoxide production in NOX3-transfected, but not in control-transfected cells (FIG. 7A, see traces before PMA addition and FIG. 7C). Addition of PMA further increased superoxide generation, while an NADPH oxidase inhibitor, diphenylene iodonium (DPI), blocked it completely (FIG. 7A).

When HEK293 cells were co-transfected with NOX3, NOXO1 and NOXA1, they produced ROS in a constitutive manner (see FIG. 6B). To investigate the effect of cisplatin under these conditions, we generated HEK293 clones stably expressing NOX3, NOXO1, and NOXA1 subunits. These clones produced superoxide constitutively and spontaneously as observed in the transient transfectants. Upon incubation with 20 µM cisplatin (12 hours), a marked increase of superoxide production was detected by the luminol-amplified chemiluminescence (FIGS. 7B and C), and also by cytochrome C reduction (not shown). The superoxide generation was insensitive to PMA and could be abolished by DPI (FIGS. 7B and D). As control we investigated the effect of another chemotherapeutic drugs 5-fluorouracil, which is devoid of ototoxicity; incubation of NOX3/NOXO1/NOXA1 expressing cells with this compound (100 µM, 17 hours) did not influence superoxide production (data not shown). HEK293 cells were also co-transfected with NOX3, p47$^{phox}$, and p67$^{phox}$, and incubated with 20 µM cisplatin for 12 hours. Cisplatin enhanced the superoxide production of NOX3-, p47$^{phox}$-, and p67$^{phox}$-transfected cells by a factor of approximately 3.3 (FIG. 7D); this superoxide production could be blocked by addition of 5 μM DPI (not shown).

Next the concentration and time dependency of the cisplatin effect on NOX3 activity was investigated using a NOX3/NOXO1/NOXA1 transfected stable clone. After incubating the cells with various concentrations of cisplatin for 12 hours, superoxide production was measured (FIG. 7E). Cisplatin caused an increase of NOX3-dependent ROS generation already at 1 μM concentration, and 20 μM cisplatin had a maximal effect (FIG. 7E). The EC$_{50}$ of NOX3 activation by cisplatin was 3.6+/−1.4 μM.

In order to examine the time course of NOX3 activation by cisplatin, a NOX3/NOXO1/NOXA1 transfected stable clone was incubated with 20 μM cisplatin for various periods of time. Cisplatin enhanced NOX3 activity already after 5 hours treatment and reached its maximal effect after around 17 hours (FIG. 7F); the t$_{50}$ was 11.5+−1.7 hours.

FURTHER REFERENCES

1. Kopke, R., et al., (1999) *Ann. N.Y. Acad. Sci.* 884, 171-191.
2. Kopke, R. D., et al., (1997) *Am. J. Otol.* 18, 559-571.
3. Clerici, W. J., Hensley, K., DiMartino, D. L., Butterfield, D. A., (1996) *Hear. Res.* 98, 116-124.
4. Henderson, D., et al., (1999) *Ann. N.Y. Acad. Sci.* 884, 368-380.
5. Ohinata, Y., et al., (2000) *Brain Res.* 878, 163-173.
6. Van Campen, L. E., et al., (2002) *Hear. Res.* 164, 29-38.
7. McFadden, S. L., et al., (1999) *J. Comp. Neurol.* 413, 101-112.
8. Sergi, B., Ferraresi, A., Troiani, D., Paludetti, G., Fetoni, A. R., (2003) *Hear. Res.* 182, 56-64.
9. Jones, G. E., Balaban, C. D., Jackson, R. L., Wood, K. A., Kopke, R. D., (2003) *Exp. Brain Res.* 153, 293-306.
10. Takumida, M., et al., (2003) *Acta Otolaryngol.* 123, 8-13.
11. Darlington, C. L., Smith, P. F., (2003) *Curr. Opin. Investig. Drugs.* 4, 841-846.
12. Sha, S. H. and J. Schacht, (1999) *Free Radic. Biol. Med.* 26, 341-347.
13. Babior, B. M., J. D. Lambeth, and W. Nauseef, (2002) *Arch. Biochem. Biophys.* 397, 342-344.
14. Bokoch, G. M., Knaus, U. G., (2003) *Trends Biochem. Sci.* 28, 502-508.
15. Lambeth, J. D., (2002) *Curr. Opin. Hematol.* 9, 11-17.
16. Suh, Y. A., et al., (1999) *Nature* 401, 79-82.
17. Banfi, B., et al., (2000) *Science* 287, 138-42.
18. Geiszt, M., et al., (2000) *Proc. Natl. Acad. Sci. USA.* 97, 8010-8014.
19. Banfi, B., et al., (2001) *J. Biol. Chem.* 276, 37594-37601.
20. De Deken, X., Wang, D., Many, M. C., Costagliola, S., Libert, F., Vassart, G., Dumont, J. E., and Miot, F., (2000) *J. Biol. Chem.* 275, 23227-23233.
21. Caillou, B., Dupuy, C., Lacroix, L., Nocera, M., Talbot, M., Ohayon, R., Deme, D., Bidart, J. M., Schlumberger, M., and Virion, A., (2001) *J. Clin. Endocrinol. Metab.* 86, 3351-3358.
22. Kikuchi, H., et al., (2000) *Gene* 254, 237-243.
23. Babior, B. M., (1999) *Blood* 93, 1464-1476.
24. Banfi, B., Clark, R. A., Steger, K., Krause, K. H., (2003) *J. Biol. Chem.* 278, 3510-3513.
25. Geiszt, M., Lekstrom, K., Witta, J., Leto, T. L., (2003) *J. Biol. Chem.* 278, 20006-20012.
26. Takeya, R., Ueno, N., Kami, K., Taura, M., Kohjima, M., Izaki, T., Nunoi, H., Sumimoto, H., (2003) *J. Biol. Chem.* 278, 25234-25246.
27. Banfi, B., Tirone, F., Durussel, I., Knisz, J., Moskwa, P., Molnar, G. Z., Krause, K. H., Cox, J. A., (2004) *J. Biol. Chem.* in press.
28. Yanai, T., et al., (2001) *J. Bone Miner. Metab.* 19, 345-351.
29. Mocsai, A., et al., (1997) *Biochem. Pharmacol.* 54, 781-789.
30. Cheng, G., et al., (2001) *Gene* 269, 131-140.
31. Lalucque, H., Silar, P., (2003) *Trends Microbiol.* 11, 9-12.
32. Malgrange, B., Rogister, B., Lefebvre, P. P., Mazy-Servais, C., Welcher, A. A., Bonnet, C., Hsu, R. Y., Rigo, J. M., Van De Water, T. R., Moonen, G., (1998) *Neurochem. Res.* 23, 1133-1138.
33. Riad-el Sabrouty, S., Blanchard, J. M., Marty, L., Jeanteur, P., Piechaczyk, M., (1989) *J. Mol. Evol.* 29, 212-222.
34. Fekete, D. M., Wu, D. K., (2002) *Curr. Opin. Neurobiol.* 12, 35-42.
35. Fritzsch, B. F., Barald, K. F., Lomax, M. I., (1998) in *Development of the Auditory System* (Rubel, E. W., Popper A. N., and Fay R. R. eds.), vol. 9., pp. 80-145, Springer-Verlag Press, New York.
36. Takumida, M., Anniko, M., (2002) *ORL J. Otorhinolaryngol. Relat. Spec.* 64, 143-147.
37. Ohlemiller, K. K., Wright, J. S., Dugan, L. L., (1999) *Audiol. Neurootol.* 4, 229-236.
38. Zhang, M., Liu, W., Ding, D., Salvi, R., (2003) *Neuroscience* 120, 191-205.
39. Paffenholz, R., Bergstrom, R. A., Pasutto, F., Wabnitz, P., Munroe, R. J., Jagla, W., Heinzmann, U., Marquardt, A., Bareiss, A., Laufs, J., Russ, A., Stumm, G., Schimenti, J. C., Bergstrom, D. E., (2004) *Genes Dev.* in press.
40. Tsunawaki S, Yoshida L S, Nishida S, Kobayashi T, Shimoyama T. Fungal metabolite gliotoxin inhibits assembly of the human respiratory burst NADPH oxidase. Infect Immun. 2004 June; 72(6):3373-82.
41. Yoshida L S, Abe S, Tsunawaki S. Fungal gliotoxin targets the onset of superoxide-generating NADPH oxidase of human neutrophils. Biochem Biophys Res Commun. 2000 Feb. 24; 268(3):716-23.
42. Maack C, Kartes T, Kilter H, Schafers H J, Nickenig G, Bohm M, Laufs U. Oxygen free radical release in human failing myocardium is associated with increased activity of rac1-GTPase and represents a target for statin treatment. Circulation. 2003 Sep. 30; 108(13):1567-74.
43. Seifert R, Schachtele C. Studies with protein kinase C inhibitors presently available cannot elucidate the role of protein kinase C in the activation of NADPH oxidase. Biochem Biophys Res Commun. 1988 Apr. 29; 152(2): 585-92.
44. Holland J A, O'Donnell R W, Chang M M, Johnson D K, Ziegler L M. Endothelial cell oxidant production: effect of NADPH oxidase inhibitors. Endothelium. 2000; 7(2): 109-19.
45. Adv Drug Deliv Rev. 2005 Feb. 28; 57(4):637-51. Epub 2004 Dec. 22.
46. A. D. Frankel, D. S. Bredt and C. O. Pabo, TAT protein from human immunodeficiency virus forms a metal-linked dimer, *Science* 240 (1988), pp. 70-73.
47. S. Futaki, T. Suzuki, W. Ohashi, T. Yagami, S. Tanaka, K. Ueda and Y. Sugiura, Arginine-rich peptides. An abundant source of membrane-permeable peptides having potential as carriers for intracellular protein delivery, *J. Biol. Chem.* 276 (2001), pp. 5836-5840.
48. Homeodomain of Antennapedia (Antp): W. J. Gehring, M. Affolter and T. Burglin, Homeodomain proteins, *Annu. Rev. Biochem.* 63 (1994), pp. 487-526.

49. D. Derossi, A. H. Joliot, G. Chassaing and A. Prochiantz, The third helix of the Antennapedia homeodomain translocates through biological membranes, *J. Biol. Chem.* 269 (1994), pp. 10444-10450.

50. A. Aints, H. Guven, G. Gahrton, C. I. Smith and M. S. Dilber, Mapping of herpes simplex virus-1 VP22 functional domains for inter- and subcellular protein targeting, *Gene Ther.* 8 (2001), pp. 1051-1056.

51. M. Pooga, M. Hallbrink, M. Zorko and U. Langel, Cell penetration by transportan, *FASEB J.* 12 (1998), pp. 67-77.

52. J. Oehlke, A. Scheller, B. Wiesner, E. Krause, M. Beyermann, E. Klauschenz, M. Melzig and M. Bienert, Cellular uptake of an alpha-helical amphipathic model peptide with the potential to deliver polar compounds into the cell interior non-endocytically, *Biochim. Biophys. Acta* 1414 (1998), pp. 127-139.

53. Y. Z. Lin, S. Y. Yao, R. A. Veach, T. R. Torgerson and J. Hawiger, Inhibition of nuclear translocation of transcription-factor NF-kappa B by a synthetic peptide containing a cell membrane-permeable motif and nuclear localization sequence, *J. Biol. Chem.* 270 (1995), pp. 14255-14258.

The invention claimed is:

1. A method for treating hearing loss and/or phantom hearing in a subject afflicted with or at risk of developing hearing loss and/or phantom hearing comprising administering an effective amount of a siRNA inhibitor of NOX3 to the subject; wherein NOX3 protein comprises or consists of the amino acid sequence of any one of SEQ ID NO: 1, 3 or 5.

2. The method of claim 1, wherein said NOX3 protein comprises the amino acid sequence of SEQ ID NO:1.

3. The method of claim 1, wherein the subject has been treated or will be treated with an ototoxic agent.

4. The method of claim 3, wherein the ototoxic agent is selected from the group consisting of salicylates, non-steroidal antiinflammatories, antibiotics, diuretics, cytostatics, quinine derivatives and gastroprotective drugs.

5. The method of claim 4, wherein the ototoxic agent is a cytostatic.

6. The method of claim 5, wherein the cytostatic is bleomycine, bromocriptine, carboplatinum, cisplatin, methotrexate, nitrogen mustard, vinblastine or vincristine.

7. The method of claim 4, wherein the ototoxic agent is an antibiotic.

8. The method of claim 7, wherein the antibiotic is an aminoglycoside antibiotic.

9. The method of claim 8, wherein the aminoglycoside antibiotic is amikacin, gentamycin, kanamycin, neomycin, netilmycin, streptomycin or tobramycin.

10. The method of claim 7, wherein the antibiotic is erythromycin, vancomycin, minocycline, polymixin B, amphotericin B and capreomycin.

11. The method of claim 4, wherein the ototoxic agent is a salicylate.

12. The method of claim 11, wherein the salicylate is aspirin or methyl salicylate.

13. The method of claim 4, wherein the ototoxic agent is a non-steroidal anti-inflammatory agent selected from the group consisting of diclofenac, etocolac, fenprofen, ibuprofen, indomethacin, naproxen, piroxicam and sulindac.

14. The method of claim 4, wherein the ototoxic agent is a quinine derivative selected from the group consisting of an anitmalarial drug and an antiarrhythmic drug.

15. The method of claim 4, wherein the ototoxic agent is the gastroprotective drug misoprostol.

16. The method of claim 1, wherein the hearing loss comprises drug-, noise- and age-related hearing loss.

17. The method of claim 14, wherein the quinine derivative is selected from the group consisting of chloroquine phosphate, quinacrine hydrochloride and quinine sulphate.

* * * * *

SEQUENCE LISTING

<160> NUMBER OF SEQ ID NOS: 26

<210> SEQ ID NO 1
<211> LENGTH: 568
<212> TYPE: PRT
<213> ORGANISM: Homo sapiens

<400> SEQUENCE: 1

```
Met Met Gly Cys Trp Ile Leu Asn Glu Gly Leu Ser Thr Ile Leu Val
1               5                   10                  15

Leu Ser Trp Leu Gly Ile Asn Phe Tyr Leu Phe Ile Asp Thr Phe Tyr
            20                  25                  30

Trp Tyr Glu Glu Glu Ser Phe His Tyr Thr Arg Val Ile Leu Gly
        35                  40                  45

Ser Thr Leu Ala Trp Ala Arg Ala Ser Ala Leu Cys Leu Asn Phe Asn
    50                  55                  60

Cys Met Leu Ile Leu Pro Val Ser Arg Asn Leu Ile Ser Phe Ile
65                  70                  75                  80

Arg Gly Thr Ser Ile Cys Cys Arg Gly Pro Trp Arg Arg Gln Leu Asp
                85                  90                  95

Lys Asn Leu Arg Phe His Lys Leu Val Ala Tyr Gly Ile Ala Val Asn
                100                 105                 110

Ala Thr Ile His Ile Val Ala His Phe Phe Asn Leu Glu Arg Tyr His
                115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
                180                 185                 190

Glu Phe Ile Arg Gln Ala Ser Tyr Glu Leu Phe Trp Tyr Thr His His
            195                 200                 205

Val Phe Ile Val Phe Phe Leu Ser Leu Ala Ile His Gly Thr Gly Arg
        210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
                260                 265                 270

Gly Pro Val Val Leu Tyr Ala Cys Glu Arg Ile Ile Arg Phe Trp Arg
                275                 280                 285
```

-continued

```
Phe Gln Gln Glu Val Val Ile Thr Lys Val Val Ser His Pro Ser Gly
        290                 295                 300
Val Leu Glu Leu His Met Lys Lys Arg Gly Phe Lys Met Ala Pro Gly
305                 310                 315                 320
Gln Tyr Ile Leu Val Gln Cys Pro Ala Ile Ser Ser Leu Glu Trp His
            325                 330                 335
Pro Phe Thr Leu Thr Ser Ala Pro Gln Glu Asp Phe Phe Ser Val His
                340                 345                 350
Ile Arg Ala Ala Gly Asp Trp Thr Ala Ala Leu Leu Glu Ala Phe Gly
            355                 360                 365
Ala Glu Gly Gln Ala Leu Gln Glu Pro Trp Ser Leu Pro Arg Leu Ala
        370                 375                 380
Val Asp Gly Pro Phe Gly Thr Ala Leu Thr Asp Val Phe His Tyr Pro
385                 390                 395                 400
Val Cys Val Cys Val Ala Ala Gly Ile Gly Val Thr Pro Phe Ala Ala
                405                 410                 415
Leu Leu Lys Ser Ile Trp Tyr Lys Cys Ser Glu Ala Gln Thr Pro Leu
            420                 425                 430
Lys Leu Ser Lys Val Tyr Phe Tyr Trp Ile Cys Arg Asp Ala Arg Ala
                435                 440                 445
Phe Glu Trp Phe Ala Asp Leu Leu Leu Ser Leu Glu Thr Arg Met Ser
        450                 455                 460
Glu Gln Gly Lys Thr His Phe Leu Ser Tyr His Ile Phe Leu Thr Gly
465                 470                 475                 480
Trp Asp Glu Asn Gln Ala Leu His Ile Ala Leu His Trp Asp Glu Asn
                485                 490                 495
Thr Asp Val Ile Thr Gly Leu Lys Gln Lys Thr Phe Tyr Gly Arg Pro
            500                 505                 510
Asn Trp Asn Asn Glu Phe Lys Gln Ile Ala Tyr Asn His Pro Ser Ser
        515                 520                 525
Ser Ile Gly Val Phe Phe Cys Gly Pro Lys Ala Leu Ser Arg Thr Leu
530                 535                 540
Gln Lys Met Cys His Leu Tyr Ser Ser Ala Asp Pro Arg Gly Val His
545                 550                 555                 560
Phe Tyr Tyr Asn Lys Glu Ser Phe
                565
```

<210> SEQ ID NO 2
<211> LENGTH: 1707
<212> TYPE: DNA
<213> ORGANISM: Homo sapiens

<400> SEQUENCE: 2

```
atgatggggt gctggatttt gaatgagggt ctctccacca tattagtact ctcatggctg      60
ggaataaatt tttatctgtt tattgacacg ttctactggt atgaagagga ggagtctttc     120
cattacacac gagttatttt gggttcaaca ctggcttggg cacgagcatc cgcactgtgc     180
ctgaatttta actgcatgct aattctaata cctgtcagtc gaaacctttat ttcattcata     240
agaggaacaa gtatttgctg cagaggaccg tggaggaggc aattagacaa aaaccctcaga    300
tttcacaaac tggtcgccta tgggatagct gttaatgcaa ccatccacat cgtggcgcat    360
ttcttcaacc tggaacgcta ccactggagc cagtccgagg aggcccaggg acttctggcc    420
gcactttcca gctgggcaa caccctaac gagagctacc tcaaccctgt ccggaccttc    480
cccacaaaca caaccactga attgctaagg acaatagcag gcgtcaccgg tctggtgatc    540
```

```
tctctggctt tagtcttgat catgacctcg tcaactgagt tcatcagaca ggcctcctat    600
gagttgttct ggtacacaca ccatgttttc atcgtcttct ttctcagcct ggccatccat    660
gggacgggtc ggattgttcg aggccaaacc caagacagtc tctctctgca acatcacc     720
ttctgtagag accgctatgc agaatggcag acagtggccc aatgcccgt gcctcaattt    780
tctggcaagg aaccctcggc ttggaaatgg attttaggcc ctgtggtctt gtatgcatgt    840
gaaagaataa ttaggttctg gcgatttcaa caagaagttg tcattaccaa ggtggtaagc    900
cacccctctg gagtcctgga acttcacatg aaaaagcgtg ctttaaaat ggcgccaggg     960
cagtacatct ggtgcagtg cccagccata tcttcgctgg agtggcaccc cttcacccctt   1020
acctctgccc cccaggaaga cttttttcagc gtgcacatcc gggcagcagg agactggaca   1080
gcagcgctac tggaggcctt tggggcagag ggacaggccc tccaggagcc ctggagcctg   1140
ccaaggctgg cagtggacgg gccctttgga actgccctga cagatgtatt tcactaccca   1200
gtgtgtgtgt gcgttgccgc ggggatcgga gtcactccct tcgctgctct tctgaaatct   1260
atatggtaca aatgcagtga ggcacagacc ccactgaagc tgagcaaggt gtatttctac   1320
tggatttgcc gggatgcaag agcttttgag tggtttgctg atctcttact ctccctggaa   1380
acacggatga gtgagcaggg gaaaactcac tttctgagtt atcatatatt tcttaccggc   1440
tgggatgaaa atcaggctct tcacatagct ttacactggg acgaaaatac tgacgtgatt   1500
acaggcttaa agcagaagac cttctatggg aggcccaact ggaacaatga gttcaagcag   1560
attgcctaca atcaccccag cagcagtatt ggcgtgttct tctgtggacc taaagctctc   1620
tcgaggacac ttcaaaagat gtgccacttg tattcatcag ctgaccccag aggtgttcat   1680
ttctattaca acaaggagag cttctag                                        1707
```

<210> SEQ ID NO 3
<211> LENGTH: 568
<212> TYPE: PRT
<213> ORGANISM: Mus musculus

<400> SEQUENCE: 3

```
Met Pro Val Cys Trp Ile Leu Asn Glu Ser Gly Ser Phe Val Val Ala
1               5                   10                  15

Leu Leu Trp Leu Ala Val Asn Ala Tyr Leu Phe Ile Asp Thr Phe Phe
            20                  25                  30

Trp Tyr Thr Glu Glu Ala Phe Phe Tyr Thr Arg Val Ile Leu Gly
        35                  40                  45

Ser Ala Leu Ala Trp Ala Arg Ala Ser Ala Val Cys Leu Asn Phe Asn
    50                  55                  60

Cys Met Leu Ile Leu Pro Val Ser Arg Asn Phe Ile Ser Leu Val
65                  70                  75                  80

Arg Gly Thr Ser Val Cys Cys Arg Gly Pro Trp Arg Arg Gln Leu Asp
                85                  90                  95

Lys Asn Leu Asn Phe His Lys Leu Val Ala Tyr Gly Ile Ala Val Asn
            100                 105                 110

Ser Val Ile His Ile Val Ala His Leu Phe Asn Leu Glu Arg Tyr His
        115                 120                 125

Leu Gly Gln Ala Lys Asp Ala Glu Gly Leu Leu Ala Ala Leu Ser Lys
    130                 135                 140

Leu Gly Asp Ala Pro Asn Glu Ser Tyr Leu Asn Pro Val Arg Thr Phe
145                 150                 155                 160

Tyr Met Gly Thr Thr Thr Glu Leu Leu Met Thr Val Ser Gly Ile Thr
                165                 170                 175
```

```
Gly Leu Gly Ile Ser Leu Ala Leu Val Phe Ile Met Thr Ser Ser Thr
            180                 185                 190

Glu Phe Ile Arg Arg Ser Ser Tyr Glu Leu Phe Trp Tyr Thr His His
        195                 200                 205

Ile Phe Val Phe Phe Ile Ser Leu Ala Ile His Gly Gly Gly Arg
    210                 215                 220

Ile Ile Arg Gly Gln Thr Pro Glu Ser Leu Arg Leu His Asn Val Thr
225                 230                 235                 240

Tyr Cys Arg Asp His Tyr Ala Glu Trp Gln Ala Ala Leu Cys Pro
                245                 250                 255

Val Pro Gln Phe Ser Gly Lys Glu Pro Ser Ala Trp Lys Trp Ala Leu
            260                 265                 270

Gly Pro Val Val Leu Tyr Ala Cys Glu Arg Ile Ile Arg Phe Trp Arg
        275                 280                 285

Ser His Gln Glu Val Val Ile Thr Lys Val Val Ser His Pro Ser Ala
    290                 295                 300

Val Leu Glu Leu His Met Lys Lys Arg Asp Phe Lys Met Ala Pro Gly
305                 310                 315                 320

Gln Tyr Ile Phe Ile Gln Cys Pro Ser Val Ser Pro Leu Glu Trp His
                325                 330                 335

Pro Phe Thr Leu Thr Ser Ala Pro Gln Glu Asp Phe Phe Ser Val His
            340                 345                 350

Ile Arg Ala Ser Gly Asp Trp Thr Glu Ala Leu Leu Lys Ala Phe Arg
        355                 360                 365

Val Glu Gly Gln Ala Pro Ser Glu Leu Cys Ser Met Pro Arg Leu Ala
    370                 375                 380

Val Asp Gly Pro Phe Gly Gly Ser Leu Ala Asp Val Phe His Tyr Pro
385                 390                 395                 400

Val Ser Val Cys Ile Ala Thr Gly Ile Gly Val Thr Pro Phe Ala Ser
                405                 410                 415

Leu Leu Lys Ser Val Trp Tyr Lys Cys Cys Glu Ser Gln Ser Leu Pro
            420                 425                 430

Glu Leu Ser Lys Val Tyr Phe Tyr Trp Ile Cys Arg Asp Ala Gly Ala
        435                 440                 445

Phe Glu Trp Phe Ala Asp Leu Leu Leu Ser Leu Glu Thr Arg Met Ser
    450                 455                 460

Glu Gln Gly Lys Ala His Leu Leu Ser Tyr His Ile Tyr Leu Thr Gly
465                 470                 475                 480

Trp Asp Glu Asn Gln Ala Ile His Ile Ala Leu His Trp Asp Glu Ser
                485                 490                 495

Leu Asp Val Ile Thr Gly Leu Lys Gln Lys Ala Phe Tyr Gly Arg Pro
            500                 505                 510

Asn Trp Asn Asp Glu Phe Lys Gln Ile Ala Tyr Asn His Pro Ser Ser
        515                 520                 525

Ser Ile Gly Val Phe Phe Cys Gly Ser Lys Ala Met Ser Lys Thr Leu
    530                 535                 540

Gln Lys Met Cys Arg Leu Tyr Ser Ser Val Asp Pro Arg Gly Val His
545                 550                 555                 560

Phe Tyr Tyr Asn Lys Glu Asn Phe
                565

<210> SEQ ID NO 4
<211> LENGTH: 1707
<212> TYPE: DNA
```

<213> ORGANISM: Mus musculus

<400> SEQUENCE: 4

```
atgccggtgt gctggattct gaacgagagt gggtccttcg tggttgctct cttatggctg      60
gcagtaaacg cctatctgtt tattgacaca ttcttctggt atactgaaga ggaggctttc     120
ttttatacac gagttattct gggttccgca ttggcatggg cccgggcatc tgccgtgtgc     180
ctgaatttta actgcatgct aattctgtta cctgtcagtc ggaacttcat ttcactggtg     240
agaggaacaa gtgtgtgctg tagaggacca tggagaagac aactagacaa aaacctcaac     300
ttccacaaac tcgttgccta cgggatagct gtcaattcag ttatccacat tgtggcacac     360
ttgttcaacc tggagcgtta tcacctgggt caggccaagg atgctgaagg gctgctggct     420
gcactttcca acttggcga tgccccaaat gagagctacc tcaatccagt ccgcaccttt     480
tatatgggca caaccactga gctattgatg acagtgtcag gaattactgg cctgggtatc     540
tctctggctc tggtcttcat catgaccctc tcaaccgaat tcatcagaag gtcctcttat     600
gagctcttct ggtacacaca ccatatcttt gtcttcttct tcatcagtct ggccatccac     660
ggaggaggtc gcatcattcg aggccaaact ccagagagtc tccggctgca caatgtcacg     720
tactgcagag accactatgc tgaatggcag gcagctgcct tatgccctgt acctcaattt     780
tctggcaagg aaccttcggc ctggaaatgg gctttgggtc ctgtggtctt gtatgcgtgt     840
gaaagaataa ttaggttctg gagatctcac caagaagttg tcattaccaa ggtggtgagt     900
cacccatctg cagtcctgga acttcacatg aagaagcgag acttcaagat ggcacctgga     960
cagtacatct tcatccagtg cccatctgtc tcccccctgg agtggcaccc cttcactctc    1020
acctccgctc cccaggagga cttcttcagt gtacacatca gagcctcagg agactggaca    1080
gaggcgttat tgaaggcctt tagagtagag ggacaggctc ccagtgagct ctgtagcatg    1140
ccgaggctag cagtggatgg gccctttgga ggctctctgg cagatgtatt tcactacccc    1200
gtgagcgtgt gcattgcaac gggaattgga gtcactccct tcgcctctct tctgaagtct    1260
gtgtggtata agtgttgtga atcacagagc ctgcctgagc tgagcaaggt gtacttctat    1320
tggatctgcc gggatgccgg agcatttgag tggtttgctg atctgttact gtcactggaa    1380
acacggatga gtgaacaagg gaaggctcat ttactgagct accatatata tctcactggc    1440
tgggatgaaa accaggcaat tcacatagct ttacactggg atgaaagtct ggatgtgata    1500
acaggcttaa gcagaaggc tttctatggg cgacccaact ggaacgacga attcaagcag    1560
attgcctaca atcaccccag cagcagcatt ggcgtgttct tctgtggatc caaagccatg    1620
tcaaagactc ttcaaaagat gtgtcgtttg tactcatctg tggatccgag gggcgttcat    1680
ttctattaca acaaggaaaa cttctag                                        1707
```

<210> SEQ ID NO 5
<211> LENGTH: 568
<212> TYPE: PRT
<213> ORGANISM: Rattus norvegicus

<400> SEQUENCE: 5

```
Met Pro Thr Cys Trp Ile Leu Asn Glu Ser Val Ser Phe Val Val Ala
1               5                   10                  15

Leu Leu Trp Leu Ala Ile Asn Ile Tyr Leu Phe Ile Asp Thr Phe Cys
            20                  25                  30

Trp Tyr Ala Glu Glu Glu Ser Phe Phe Tyr Thr Arg Val Ile Leu Gly
        35                  40                  45

Ser Ala Leu Ala Trp Ala Arg Ala Ser Ala Val Cys Leu Asn Phe Asn
```

```
        50                  55                  60
Cys Met Leu Ile Leu Leu Pro Val Ser Arg Asn Phe Val Ser Leu Val
 65                  70                  75                  80

Arg Gly Thr Ser Val Cys Cys Arg Gly Pro Trp Arg Arg Gln Leu Asp
                 85                  90                  95

Lys Asn Leu Lys Phe His Lys Leu Val Ala Tyr Gly Ile Ala Val Asn
                100                 105                 110

Ser Val Ile His Ile Val Ala His Leu Phe Asn Leu Glu Arg Tyr His
                115                 120                 125

Leu Gly Gln Ala Lys Asp Ala Glu Gly Leu Leu Ala Ala Leu Ser Lys
130                 135                 140

Leu Gly Asn Ala Pro Asn Glu Ser Tyr Leu Asn Pro Val Arg Thr Leu
145                 150                 155                 160

Tyr Thr Gly Thr Thr Thr Gln Leu Leu Met Thr Val Ser Gly Ile Thr
                165                 170                 175

Gly Leu Val Ile Ser Leu Ala Leu Ile Leu Ile Met Thr Ser Ser Thr
                180                 185                 190

Glu Phe Ile Arg Gln Ser Ser Tyr Glu Leu Phe Trp Tyr Thr His His
                195                 200                 205

Ile Phe Ile Phe Leu Phe Ile Ser Leu Ala Ile His Gly Gly Gly Arg
210                 215                 220

Ile Ile Arg Gly Gln Thr Pro Glu Ser Leu Arg Leu His Asn Val Thr
225                 230                 235                 240

Phe Cys Arg Asp His Phe Asp Glu Trp Gln Glu Ala Ala Ser Cys Pro
                245                 250                 255

Val Pro Gln Phe Ser Gly Lys Glu Pro Ser Ala Trp Lys Trp Thr Leu
                260                 265                 270

Gly Pro Val Val Leu Tyr Ala Cys Glu Ile Ile Ile Arg Phe Trp Arg
                275                 280                 285

Ser His Gln Glu Val Val Ile Thr Lys Val Val Ser His Pro Ser Ala
290                 295                 300

Val Leu Glu Leu His Met Lys Lys Arg Asp Phe Lys Met Ala Pro Gly
305                 310                 315                 320

Gln Tyr Ile Phe Ile Gln Cys Pro Ser Ile Ser Pro Leu Glu Trp His
                325                 330                 335

Pro Phe Thr Leu Thr Ser Ala Pro Gln Glu Asp Phe Phe Ser Val His
                340                 345                 350

Ile Arg Ala Ser Gly Asp Trp Thr Glu Ala Leu Leu Lys Ala Phe Gly
                355                 360                 365

Ala Glu Gly Gln Ala Pro Ser Glu Leu Cys Ser Met Pro Arg Leu Ala
370                 375                 380

Val Asp Gly Pro Phe Gly Gly Ser Leu Ala Asp Val Phe His Tyr Pro
385                 390                 395                 400

Val Ser Val Cys Ile Ala Thr Gly Ile Gly Val Thr Pro Phe Ala Ser
                405                 410                 415

Leu Leu Lys Ser Val Trp Tyr Lys Cys Cys Glu Ser Gln Ser Leu Pro
                420                 425                 430

Gly Leu Ser Lys Val Tyr Phe Tyr Trp Ile Cys Arg Asp Ala Ala Ala
                435                 440                 445

Phe Glu Trp Phe Ala Asp Leu Leu Ser Leu Glu Thr Gln Met Ser
                450                 455                 460

Glu Gln Gly Lys Ala His Leu Leu Ser Tyr His Ile Tyr Leu Thr Gly
465                 470                 475                 480
```

```
Trp Asp Glu Tyr Gln Ala Ile His Ile Ala Leu His Trp Asp Glu Ser
            485                 490                 495

Leu Asp Val Ile Thr Gly Leu Lys Gln Lys Thr Phe Tyr Gly Arg Pro
            500                 505                 510

Asn Trp Asn Glu Glu Phe Lys Gln Ile Ala Tyr Asn His Pro Ser Ser
            515                 520                 525

Ser Ile Gly Val Phe Phe Cys Gly Pro Lys Ala Met Ser Lys Thr Leu
            530                 535                 540

Gln Lys Met Cys Arg Leu Tyr Ser Ser Ser Asp Pro Arg Gly Val His
545                 550                 555                 560

Phe Tyr Tyr Asn Lys Glu Asn Phe
            565

<210> SEQ ID NO 6
<211> LENGTH: 1707
<212> TYPE: DNA
<213> ORGANISM: Rattus norvegicus

<400> SEQUENCE: 6
atgccgacgt gctggatttt gaacgagagt gtgtccttcg tggttgctct cttgtggctg     60
gcaataaata tctatctgtt tattgacacg ttctgctggt atgctgaaga ggagtctttc    120
ttttatacac gagttattct gggttccgca ttggcatggg cccgggcatc tgccgtgtgc    180
ctgaatttta actgcatgct aattctgtta cctgtcagtc ggaacttcgt ttcactggtg    240
agaggaacga gcgtgtgctg tagaggaccg tggagacggc aactagacaa aaacctcaag    300
ttccacaagc tcgttgccta cgggatagct gttaattcag ttatccacat tgtggcacac    360
ttgttcaacc tggagcgtta tcacctgggt caggccaagg atgctgaagg ctgctggct     420 gcgctttcca acttggcaa tgccccaaat gaaagctacc tcaatccggt ccgcaccttg    480
tatacgggta caaccactca gctattaatg acagtctccg gaattactgg cctggtgatc    540
tctctggctt tgatattgat catgacctct tcaactgagt ttatcaggca gtcctcttat    600
gagctattct ggtacacaca ccatatcttc atcttcctct tcatcagtct ggccatccac    660
ggaggaggtc gcatcattcg aggtcaaact ccagagagtc tccggctgca caatgtcacc    720
ttctgcagag accacttcga cgaatggcag gaagctgcct cgtgccctgt acctcaattt    780 ctggcaagg agccgtcggc ctggaaatgg actttgggcc ctgtggtctt gtatgcgtgt    840
gaaataataa ttaggttctg gagatctcac caagaagttg tcattaccaa ggtggtgagt    900
cacccatctg cagtcctgga acttcacatg aagaagcgtg acttcaagat ggcgcccgga    960
cagtacatct ttatccagtg cccatccatc tccccgctgg agtggcaccc cttcactctc   1020
acgtctgctc cccaggagga cttcttcagt gtacacatcc gagcctcagg agactggaca   1080
gaggcgttac tgaaggcatt tggagcagag ggacaggctc ccagtgagct ctgtagcatg   1140
ccgagactgg cagtggacgg gcccttcgga ggctctctgg cagatgtatt tcactaccct   1200
gtgagcgtgt gcattgcaac aggaattgga gtcaccccct tcgcctctct tctgaagtct   1260
gtgtggtata agtgttgtga atcacagagt ctgcctggac tgagcaaggt gtacttctac   1320
tggatctgcc gggatgctgc agccttgag tggtttgccg atctgttact ttcactggaa   1380
acacagatga gtgaacaagg gaaggctcat tgctgagtt accacatata tctcactggc   1440
tgggatgaat accaggcaat tcacatagct ttacactggg atgaaagtct ggatgtgatt   1500
acaggcttaa agcagaagac cttctatggg cgacccaact ggaatgagga attcaagcag   1560
attgcctaca atcaccctag cagcagcatt ggcgtgttct tctgtggacc caaagccatg   1620
```

-continued

```
tcaaagactc ttcaaaagat gtgccgtttg tactcatcct cagatcctag gggcgttcat    1680
ttctattaca acaaggaaaa cttctag                                        1707
```

<210> SEQ ID NO 7
<211> LENGTH: 371
<212> TYPE: PRT
<213> ORGANISM: Homo sapiens

<400> SEQUENCE: 7

```
Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
            20                  25                  30

Gly Ser Asp Thr Phe Val Arg Arg Ser Trp Asp Glu Phe Arg Gln Leu
        35                  40                  45

Lys Lys Thr Leu Lys Glu Thr Phe Pro Val Glu Ala Gly Leu Leu Arg
    50                  55                  60

Arg Ser Asp Arg Val Leu Pro Lys Leu Leu Asp Ala Pro Leu Leu Gly
65                  70                  75                  80

Arg Val Gly Arg Thr Ser Arg Gly Leu Ala Arg Leu Gln Leu Leu Glu
                85                  90                  95

Thr Tyr Ser Arg Arg Leu Leu Ala Thr Ala Glu Arg Val Ala Arg Ser
            100                 105                 110

Pro Thr Ile Thr Gly Phe Phe Ala Pro Gln Pro Leu Asp Leu Glu Pro
        115                 120                 125

Ala Leu Pro Pro Gly Ser Arg Val Ile Leu Pro Thr Pro Glu Glu Gln
    130                 135                 140

Pro Leu Ser Arg Ala Ala Gly Arg Leu Ser Ile His Ser Leu Glu Ala
145                 150                 155                 160

Gln Ser Leu Arg Cys Leu Gln Pro Phe Cys Thr Gln Asp Thr Arg Asp
                165                 170                 175

Arg Pro Phe Gln Ala Gln Ala Gln Glu Ser Leu Asp Val Leu Leu Arg
            180                 185                 190

His Pro Ser Gly Trp Trp Leu Val Glu Asn Glu Asp Arg Gln Thr Ala
        195                 200                 205

Trp Phe Pro Ala Pro Tyr Leu Glu Glu Ala Ala Pro Gly Gln Gly Arg
    210                 215                 220

Glu Gly Gly Pro Ser Leu Gly Ser Ser Gly Pro Gln Phe Cys Ala Ser
225                 230                 235                 240

Arg Ala Tyr Glu Ser Ser Arg Ala Asp Glu Leu Ser Val Pro Ala Gly
                245                 250                 255

Ala Arg Val Arg Val Leu Glu Thr Ser Asp Arg Gly Trp Trp Leu Cys
            260                 265                 270

Arg Tyr Gly Asp Arg Ala Gly Leu Leu Pro Ala Val Leu Leu Arg Pro
        275                 280                 285

Glu Gly Leu Gly Ala Leu Leu Ser Gly Thr Gly Phe Arg Gly Gly Asp
    290                 295                 300

Asp Pro Ala Gly Glu Ala Arg Gly Phe Pro Glu Pro Ser Gln Ala Thr
305                 310                 315                 320

Ala Pro Pro Pro Thr Val Pro Thr Arg Pro Ser Pro Gly Ala Ile Gln
                325                 330                 335

Ser Arg Cys Cys Thr Val Thr Arg Arg Ala Leu Glu Arg Arg Pro Arg
            340                 345                 350

Arg Gln Gly Arg Pro Arg Gly Cys Val Asp Ser Val Pro His Pro Thr
        355                 360                 365
```

Thr Glu Gln
    370

<210> SEQ ID NO 8
<211> LENGTH: 1116
<212> TYPE: DNA
<213> ORGANISM: Homo sapiens

<400> SEQUENCE: 8

| | | | | | |
|---|---|---|---|---|---|
| atggcaggcc | cccgatacccc | agtttcagtg | caaggggcag | ccctggtgca | gatcaagagg | 60 |
| ctccaaacgt | ttgccttctc | tgtgcgctgg | tcagacggca | cgacaccttt | cgtgcgcagg | 120 |
| agttgggacg | aattcaggca | gctcaagaag | accctcaagg | agaccttccc | ggtggaggcg | 180 |
| ggcctgctgc | ggagatctga | ccgcgttctc | ccaaagcttc | tcgatgcacc | actgttggga | 240 |
| cgcgtggggc | gcacgagccg | cggcctggcg | cgcctgcagc | tgttggaaac | ctattctcgg | 300 |
| aggctgctgg | cgactgcaga | gcgcgtggca | cggagcccga | cgatcactgg | cttcttcgca | 360 |
| ccgcaacccc | tggacctgga | gccgcgctg | ccacccggca | gccgggtgat | cctgcccacc | 420 |
| ccagaggagc | agcctctttc | tcgcgctgcg | ggccgcctct | ccatccacag | tctggaggct | 480 |
| cagagcctgc | gctgcctgca | gcccttctgt | acccaggaca | cgcgggatag | ccttttcag | 540 |
| gcgcaggccc | aggagagcct | ggacgtgctg | ctgcggcacc | cctcaggctg | gtggctggtg | 600 |
| gagaacgaag | accggcagac | cgcctggttt | ccagcgccct | acctggagga | ggcggccccg | 660 |
| ggccaaggcc | gggagggagg | cccgtcccta | gggagcagcg | gtccccagtt | ctgtgcttcc | 720 |
| cgcgcctacg | agagcagccg | cgcagatgag | ctgtccgtgc | ccgcggggc | gcgcgtgcgc | 780 |
| gtgttggaaa | cgtcagaccg | cggctggtgg | ctatgcaggt | acggcgaccg | ggcgggccta | 840 |
| ctccccgcgg | tgctgctgcg | gccggaaggg | ctgggcgctc | tcctgagcgg | gacggggttc | 900 |
| cgtggaggag | acgacccggc | gggtgaggcc | cggggcttcc | ctgaaccctc | ccaggccacc | 960 |
| gcccctcccc | ccaccgtgcc | cacccgacct | tcgccgggcg | ccatccagag | ccgctgctgc | 1020 |
| accgtcacac | gcagggccct | ggagcggcgc | ccacggcgcc | agggccgccc | tcgagggtgc | 1080 |
| gtggactctg | tgccgcaccc | cacgacggag | cagtga | | | 1116 |

<210> SEQ ID NO 9
<211> LENGTH: 349
<212> TYPE: PRT
<213> ORGANISM: Mus musculus

<400> SEQUENCE: 9

Met Ala Ser Pro Arg His Pro Val Ser Ala His Ala Val Ala Leu Val
1               5                   10                  15

Gln Met Asp Arg Leu Gln Thr Phe Ala Phe Ser Val Cys Trp Ser Asp
            20                  25                  30

Asn Ser Asp Thr Phe Val Arg Arg Ser Trp Asp Glu Phe Arg Gln Leu
        35                  40                  45

Gln Lys Thr Leu Lys Lys Thr Phe Pro Val Glu Ala Gly Leu Leu Arg
    50                  55                  60

Arg Ser Glu Gln Val Leu Pro Lys Leu Pro Asp Ala Pro Leu Leu Thr
65                  70                  75                  80

Arg Arg Gly His Thr Gly Arg Gly Leu Val Arg Leu Arg Leu Leu Asp
                85                  90                  95

Thr Tyr Val Gln Ala Leu Leu Ala Thr Ser Glu His Ile Leu Arg Ser
            100                 105                 110

Ser Ala Leu His Gly Phe Phe Val Pro Lys Pro Leu Asp Leu Glu Pro

```
                    115                 120                 125
Met Leu Pro Pro Gly Ser Leu Val Ile Leu Pro Thr Pro Glu Glu Pro
130                 135                 140

Leu Ser Gln Pro Arg Gly Ser Leu Asp Ile His Ser Leu Glu Ala Gln
145                 150                 155                 160

Ser Ile Pro Cys Val Gln Pro Phe His Thr Leu Asp Ile Arg Asp Arg
                165                 170                 175

Pro Phe His Thr Lys Ala Gln Glu Ile Leu Asp Ile Leu Leu Arg His
            180                 185                 190

Pro Ser Gly Trp Trp Leu Val Glu Asn Lys Asp Gln Gln Val Ala Trp
        195                 200                 205

Phe Pro Ala Pro Tyr Leu Glu Glu Val Ala Thr Cys Gln Gly Gln Glu
    210                 215                 220

Ser Gly Leu Ala Leu Gln Gly Ser Gly Arg Gln Phe Cys Thr Thr Gln
225                 230                 235                 240

Ala Tyr Glu Gly Ser Arg Ser Asp Glu Leu Ser Val Pro Ser Gly Ala
                245                 250                 255

Arg Val His Val Leu Glu Thr Ser Asp Arg Gly Trp Trp Leu Cys Arg
            260                 265                 270

Tyr Asn Gly Arg Thr Gly Leu Leu Pro Ala Met Ser Leu Gln Pro Glu
        275                 280                 285

Gly Leu Gly Ser Leu Leu Gly Arg Pro Gly Phe Pro Asp Ser Ala Gly
    290                 295                 300

Ala Asp Lys Val Ala Glu Asp Arg Thr Ile Pro Pro Val Val Pro Thr
305                 310                 315                 320

Arg Pro Cys Met Ser Ala Ile Gln Ser Arg Cys Cys Ser Ile Thr Arg
                325                 330                 335

Arg Ala Leu Gly Gln Glu Gln Gly Thr Arg Val Pro Arg
            340                 345

<210> SEQ ID NO 10
<211> LENGTH: 1050
<212> TYPE: DNA
<213> ORGANISM: Mus musculus

<400> SEQUENCE: 10
atggcaagcc caagacaccc agtatcagcc catgctgtag ccttggtgca aatggaccga      60
ctccagacat ttgccttctc cgtgtgctgg tcagacaaca gtgacacatt tgtgcggagg     120
agctgggatg agttcaggca gctccagaag acccttaaga aaaccttccc agtggaggca     180
ggcctgctac ggagatctga caagttcctt cccaagcttc ctgatgctcc attgctgaca     240
cgtcgggggc atactggtcg aggactggta cgtttgcggc tgctggacac ctatgtacag     300
gcattgctgg caacctcaga acacatattg aggagttcag cacttcacgg cttctttgta     360
cccaaacctc tggatctgga gcccatgctg cctcctggca gctggtgat cctgcctaca      420 ccagaggagc ccttatccca acccagaggc agccttgaca ttcatagcct ggaggctcag     480
agcattccct gtgtacagcc tttccacact cttgacataa gagacagacc tttccacacc     540
aaggctcaag aaattctgga catattacta cgacatcctt caggctggtg gctggtggag     600
aacaaggatc agcaggtagc ctggtttcca gctccctacc tggaggaggt agcaacgtgc     660
caaggccagg agtcaggcct ggctttgcaa ggaagtggga ggcagttctg cactactcag     720
gcctacgagg gcagtcgctc tgatgagcta tccgtgccct caggggcacg tgtccatgtg     780
ctggagacct cagaccgagg ctggtggctg tgcaggtata atggccggac aggcctactc     840
```

```
cctgcaatgt cgctgcaacc tgaagggctg ggctcgctcc tgggcaggcc agggttccca    900
gacagtgctg gggcagacaa ggtggctgag gacaggacca ttcccccctgt agtaccaact   960 cgtccctgta tgagtgccat ccagagtcga tgctgctcca ttacccgcag ggcactggga  1020
caggaacaag ggactcgggt tccccgttga                                   1050
```

<210> SEQ ID NO 11
<211> LENGTH: 482
<212> TYPE: PRT
<213> ORGANISM: Homo sapiens

<400> SEQUENCE: 11

```
Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
    210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
        275                 280                 285

Gly Gly Pro Gly Pro Gly Pro Cys Glu Asp Pro Ala Gly Ala Gly Gly
    290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Gly Ala Asp Leu Ser Ser
                325                 330                 335

Leu Arg Ala Leu Leu Gly Gln Ala Leu Pro His Gln Ala Gln Leu Gly
```

```
                     340                 345                 350
Gln Leu Ser Tyr Leu Ala Pro Gly Glu Asp Gly His Trp Val Pro Ile
                355                 360                 365
Pro Glu Glu Ser Leu Gln Arg Ala Trp Gln Asp Ala Ala Ala Cys
            370                 375                 380
Pro Arg Gly Leu Gln Leu Gln Cys Arg Gly Ala Gly Gly Arg Pro Val
385                 390                 395                 400
Leu Tyr Gln Val Val Ala Gln His Ser Tyr Ser Ala Gln Gly Pro Glu
                405                 410                 415
Asp Leu Gly Phe Arg Gln Gly Asp Thr Val Asp Val Leu Cys Glu Glu
            420                 425                 430
Pro Asp Val Pro Leu Ala Val Asp Gln Ala Trp Leu Glu Gly His Cys
            435                 440                 445
Asp Gly Arg Ile Gly Ile Phe Pro Lys Cys Phe Val Val Pro Ala Gly
            450                 455                 460
Pro Arg Met Ser Gly Ala Pro Gly Arg Leu Pro Arg Ser Gln Gln Gly
465                 470                 475                 480
Asp Gln

<210> SEQ ID NO 12
<211> LENGTH: 1452
<212> TYPE: DNA
<213> ORGANISM: Homo sapiens

<400> SEQUENCE: 12
atggcctctc tgggggacct ggtgcgcgcc tggcacctgg gcgcgcaggc tgtggatcgt      60
ggggactggg cccgcgcctt gcacctcttc tcgggcgtcc ggcgccgcc cgccaggctg     120 tgcttcaacg cgggctgcgt gcacctgctg gccggggacc ccgaggccgc gctgcgggca     180
tttgaccaag ccgtgaccaa ggacacctgc atggcggttg gcttcttcca gcgaggagtg     240
gccaacttcc agctggcaag gttccaggag gctctgtctg acttctggct ggccctggag     300
cagctgaggg gccacgctgc catcgactac acgcagctgg gcctgcggtt caagctgcaa     360
gcctgggagg tgctacacaa tgtggcgtcg gcacagtgcc agctggggct ctggacagag     420
gcggccagca gcctaaggga ggccatgtcc aagtggccgg aggggtccct gaatggcctg     480
gactcagccc tggaccaagt gcagagacgg ggctcactgc cgccacggca ggtccccagg     540
ggcgaggtct tccggcccca ccggtggcac ctgaagcact ggagcccgt ggatttcctg     600 ggcaaggcca aggtggtggc ctctgccatc cccgacgacc agggctgggg cgtccgccct     660
cagcagccac agggaccagg agcgaaccat gatgccaggt ccctaatcat ggactcccca     720
agagctggca cccaccaggg cccctcgat gcagagacag aggtcggtgc tgaccgctgc     780
acgtcgactg cctaccagga gcagaggccc caggtggagc aagttggcaa acaggctcct     840
ctctccccag gctgccggc aatggggggg cctggccccg cccctgtga ggaccccgcg     900 ggtgctgggg gagcaggtgc aggggctcc gagccctgg tgactgtcac cgtgcagtgc     960
gccttcacag tggccctgag gcacgaaga ggagccgacc tgtccagcct gcgggcactg    1020
ctgggccaag ccctccctca ccaggcccag cttgggcaac tcagttacct agccccaggt    1080
gaggacgggc actgggtccc catccccgag gaggagtcgc tgcagagggc ctggcaggac    1140
gcagctgcct gccccagggg gctgcagctg cagtgcaggg gagccggggg tcggccggtc    1200
ctctaccagg tggtggccca gcacagctac tccgcccagg ggccagagga cctgggcttc    1260
cgacaggggg acacggtgga cgtcctgtgt gaagagcccg atgtcccct tgcagtggac    1320
```

```
caggcatggc tggagggcca ctgtgacggc cgcatcggca tcttccccaa gtgcttcgtg    1380
gtccccgccg ccctcggat gtcaggagcc cccggccgcc tgccccgatc ccagcaggga     1440
gatcagccct aa                                                        1452
```

<210> SEQ ID NO 13
<211> LENGTH: 444
<212> TYPE: PRT
<213> ORGANISM: Mus musculus

<400> SEQUENCE: 13

```
Met Ser Ser Leu Gly Asp Gln Ile Arg Asp Trp His Arg Gly Val Leu
1               5                   10                  15

Ala Val Ala Arg Glu Asp Trp Asp Ser Ala Leu Cys Phe Phe Ser Asp
            20                  25                  30

Val Arg Glu Pro Leu Ala Arg Met Tyr Phe Asn Arg Gly Cys Val His
        35                  40                  45

Leu Met Ala Gly Asp Pro Glu Ala Ala Leu Arg Ala Phe Asp Gln Ala
    50                  55                  60

Val Thr Lys Asp Thr Cys Met Ala Val Gly Phe Leu Gln Arg Gly Val
65                  70                  75                  80

Ala Asn Phe Gln Leu Gln Arg Phe Gln Glu Ala Val Ser Asp Phe Gln
                85                  90                  95

Leu Ala Leu Ala Gln Leu Arg Asp Asn Ala Val Ile Asp Tyr Thr Gln
            100                 105                 110

Leu Gly Leu Asn Phe Lys Leu Gln Ala Trp Glu Val Leu Tyr Asn Met
        115                 120                 125

Ala Ser Ala Gln Cys Gln Ala Gly Leu Trp Thr Lys Ala Ala Asn Thr
    130                 135                 140

Leu Val Glu Ala Ile Ser Lys Trp Pro Glu Gly Ala Gln Asp Ile Leu
145                 150                 155                 160

Asp Ile Ala Met Asp Lys Val Gln Lys Gln Val Pro Leu Gln Leu Gln
                165                 170                 175

Gln Val Pro Lys Gly Glu Val Phe Gln Pro Pro Arg Arg Tyr Leu Lys
            180                 185                 190

His Leu Glu Pro Met Asp Phe Leu Gly Lys Ala Lys Val Val Ala Ser
        195                 200                 205

Val Ile Pro Asp Asp His Asn Ala Gln Pro Gln Gln Arg Ser Gln Ala
    210                 215                 220

Glu His Ala Gly His Gln Pro Ser Ser Met Cys Lys Arg Val Leu
225                 230                 235                 240

Ser Thr Thr Gly Gly His Thr Ser Pro Gly Leu Tyr Asp Ser Leu Leu
                245                 250                 255

Ala Ser Arg Arg Pro Gly Pro Gly Pro Ser Glu Val Ser Ser Gly Ser
            260                 265                 270

Glu Gly Ala Ala Thr Lys Asp Pro Glu Ser Leu Val Thr Val Thr Val
        275                 280                 285

Gln Cys His Phe Thr Val Pro Leu Lys Val Pro Arg Gly Thr Gly Leu
    290                 295                 300

Ser Ser Phe Gln Thr Leu Leu Ala Gln Ala Leu Leu His Gln Thr Gln
305                 310                 315                 320

Thr Gly Gln Leu Ser Tyr Lys Ala Pro Gly Glu Arg Ser Trp Ile
                325                 330                 335

Pro Ile Ser Thr Glu Glu Ser Leu Gln Ser Ile Trp Arg Asn Val Pro
            340                 345                 350
```

```
Val Gly Pro Gly Gly Leu Gln Leu Gln Cys Gln Gly Val Trp Gly Arg
    355                 360                 365
Pro Val Leu Tyr Gln Val Val Ala Gln Tyr Asn Tyr Arg Ala Gln Arg
    370                 375                 380
Pro Glu Asp Leu Asp Phe His Gln Gly Asp Thr Val Asp Val Leu Cys
385                 390                 395                 400
Glu Val Asp Glu Ala Trp Leu Glu Gly His Arg Asp Gly Cys Val Gly
                    405                 410                 415
Ile Phe Pro Lys Cys Phe Val Val Pro Ala Gly Ala Tyr Val Glu Ala
                420                 425                 430
Met Leu Val Leu Gly Pro Gln Pro Gly Asp Gln Asn
                435                 440

<210> SEQ ID NO 14
<211> LENGTH: 1335
<212> TYPE: DNA
<213> ORGANISM: Mus musculus

<400> SEQUENCE: 14
```

| | | | | | |
|---|---|---|---|---|---|
| atgagctctc | tagggatca | gatacgggac | tggcaccggg | gtgtgctggc | cgtggcacgc | 60 |
| gaagactggg | actctgcgct | gtgcttcttc | tcagatgtcc | gagagccgct | ggctaggatg | 120 |
| tactttaaca | ggggctgtgt | gcatctgatg | gcagggatc | ccgaggctgc | gctgcgggca | 180 |
| tttgaccaag | cagtgactaa | ggacacctgc | atggctgttg | gcttcctcca | gcggggagtg | 240 |
| gccaatttcc | agctgcagag | gttccaggag | gctgtgtctg | acttccagtt | ggccctggca | 300 |
| cagctgaggg | acaatgctgt | cattgactac | acacaactgg | gtctgaactt | caaattgcaa | 360 |
| gcctgggagg | tcctatacaa | catggcatca | gcacagtgcc | aggcagggct | ctggaccaag | 420 |
| gctgccaata | ctctagtgga | ggcaatctcc | aaatggccag | agggggctca | agacatcctg | 480 |
| gacattgcca | tggacaaagt | gcagaaacag | gtacccctac | agctacagca | agtgcccaag | 540 |
| ggtgaggtct | tccagcctcc | caggcgatac | ctaaaacatc | tggagcccat | ggatttcctt | 600 |
| ggcaaggcta | aggtggtggc | ttctgtcatt | cctgatgacc | acaacgccca | gcctcagcag | 660 |
| aggtcccagg | cggagcatgc | tggccaccag | ccatcctcat | ctatgtgtaa | gagggtcctg | 720 |
| agcactacgg | gtggtcacac | gagccctggc | ctatatgata | gtttgctggc | atccagaagg | 780 |
| cctggtccag | gccctctga | gtttcctca | ggatctgagg | gagcagctac | aaaggaccct | 840 |
| gaatccttgg | tgactgtcac | tgtgcagtgc | cactttactg | tgcccctgaa | ggtcccaaga | 900 |
| ggaactggcc | tgtccagttt | tcagacacta | ctagctcaag | ccctccttca | ccagacgcag | 960 |
| acagggcagc | tcagttacaa | agccccagga | gaggagagat | cctggattcc | catctccacg | 1020 |
| gaggagtccc | tgcagagtat | atggaggaat | gtgcccgtgg | gcccaggagg | gttgcagctc | 1080 |
| cagtgccagg | gggtctgggg | ccggccagtc | ctctaccaag | tagtagctca | gtacaactat | 1140 |
| cgtgcccaaa | gaccggagga | tttggacttc | caccaagggg | acacggtgga | tgtcctgtgt | 1200 |
| gaagtggacg | aagcatggct | ggagggacac | cgagatggct | gcgttggcat | tttccctaag | 1260 |
| tgctttgtgg | tccagctgg | cgcctatgtg | gaagccatgc | ttgtactggg | accccagcca | 1320 |
| ggagaccaga | actag | | | | | 1335 |

```
<210> SEQ ID NO 15
<211> LENGTH: 526
<212> TYPE: PRT
<213> ORGANISM: Homo sapiens

<400> SEQUENCE: 15
```

-continued

| | | | | | | | | | | | | | | |
|---|---|---|---|---|---|---|---|---|---|---|---|---|---|---|
|Met|Ser|Leu|Val|Glu|Ala|Ile|Ser|Leu|Trp|Asn|Glu|Gly|Val|Leu|Ala|
|1| | | |5| | | | |10| | | | |15|

Ala Asp Lys Lys Asp Trp Lys Gly Ala Leu Asp Ala Phe Ser Ala Val
        20              25              30

Gln Asp Pro His Ser Arg Ile Cys Phe Asn Ile Gly Cys Met Tyr Thr
            35              40              45

Ile Leu Lys Asn Met Thr Glu Ala Glu Lys Ala Phe Thr Arg Ser Ile
50              55              60

Asn Arg Asp Lys His Leu Ala Val Ala Tyr Phe Gln Arg Gly Met Leu
65              70              75              80

Tyr Tyr Gln Thr Glu Lys Tyr Asp Leu Ala Ile Lys Asp Leu Lys Glu
            85              90              95

Ala Leu Ile Gln Leu Arg Gly Asn Gln Leu Ile Asp Tyr Lys Ile Leu
            100             105             110

Gly Leu Gln Phe Lys Leu Phe Ala Cys Glu Val Leu Tyr Asn Ile Ala
        115             120             125

Phe Met Tyr Ala Lys Lys Glu Glu Trp Lys Lys Ala Glu Glu Gln Leu
        130             135             140

Ala Leu Ala Thr Ser Met Lys Ser Glu Pro Arg His Ser Lys Ile Asp
145             150             155             160

Lys Ala Met Glu Cys Val Trp Lys Gln Lys Leu Tyr Glu Pro Val Val
            165             170             175

Ile Pro Val Gly Arg Leu Phe Arg Pro Asn Glu Arg Gln Val Ala Gln
            180             185             190

Leu Ala Lys Lys Asp Tyr Leu Gly Lys Ala Thr Val Val Ala Ser Val
        195             200             205

Val Asp Gln Asp Ser Phe Ser Gly Phe Ala Pro Leu Gln Pro Gln Ala
210             215             220

Ala Glu Pro Pro Arg Pro Lys Thr Pro Glu Ile Phe Arg Ala Leu
225             230             235             240

Glu Gly Glu Ala His Arg Val Leu Phe Gly Phe Val Pro Glu Thr Lys
            245             250             255

Glu Glu Leu Gln Val Met Pro Gly Asn Ile Val Phe Val Leu Lys Lys
        260             265             270

Gly Asn Asp Asn Trp Ala Thr Val Met Phe Asn Gly Gln Lys Gly Leu
        275             280             285

Val Pro Cys Asn Tyr Leu Glu Pro Val Glu Leu Arg Ile His Pro Gln
        290             295             300

Gln Gln Pro Gln Glu Ser Ser Pro Gln Ser Asp Ile Pro Ala Pro
305             310             315             320

Pro Ser Ser Lys Ala Pro Gly Arg Pro Gln Leu Ser Pro Gly Gln Lys
            325             330             335

Gln Lys Glu Glu Pro Lys Glu Val Lys Leu Ser Val Pro Met Pro Tyr
        340             345             350

Thr Leu Lys Val His Tyr Lys Tyr Thr Val Val Met Lys Thr Gln Pro
            355             360             365

Gly Leu Pro Tyr Ser Gln Val Arg Asp Met Val Ser Lys Lys Leu Glu
        370             375             380

Leu Arg Leu Glu Gln Thr Lys Leu Ser Tyr Arg Pro Arg Asp Ser Asn
385             390             395             400

Glu Leu Val Pro Leu Ser Glu Asp Ser Met Lys Asp Ala Trp Gly Gln
            405             410             415

Val Lys Asn Tyr Cys Leu Thr Leu Trp Cys Glu Asn Thr Val Gly Asp
            420             425             430

```
Gln Gly Phe Pro Asp Glu Pro Lys Glu Ser Glu Lys Ala Asp Ala Asn
            435                 440                 445

Asn Gln Thr Thr Glu Pro Gln Leu Lys Lys Gly Ser Gln Val Glu Ala
    450                 455                 460

Leu Phe Ser Tyr Glu Ala Thr Gln Pro Glu Asp Leu Glu Phe Gln Glu
465                 470                 475                 480

Gly Asp Ile Ile Leu Val Leu Ser Lys Val Asn Glu Glu Trp Leu Glu
                485                 490                 495

Gly Glu Cys Lys Gly Lys Val Gly Ile Phe Pro Lys Val Phe Val Glu
            500                 505                 510

Asp Cys Ala Thr Thr Asp Leu Glu Ser Thr Arg Arg Glu Val
            515                 520                 525

<210> SEQ ID NO 16
<211> LENGTH: 1581
<212> TYPE: DNA
<213> ORGANISM: Homo sapiens

<400> SEQUENCE: 16
```

| | | |
|---|---|---|
| atgtccctgg tggaggccat cagcctctgg aatgaagggg tgctggcagc ggacaagaag | 60 |
| gactggaagg gagccctgga tgccttcagt gccgtccagg accccactc ccggatttgc | 120 |
| ttcaacattg ctgcatgta cactatcctg aagaacatga ctgaagcaga aaggcctttt | 180 |
| accagaagca ttaaccgaga caagcacttg gcagtggctt acttccaacg agggatgctc | 240 |
| tactaccaga cagagaaata tgatttggct atcaaagacc ttaaagaagc cttgattcag | 300 |
| cttcgaggga ccagctgat agactataag atcctggggc tccagttcaa gctgtttgcc | 360 |
| tgtgaggtgt tatataacat tgctttcatg tatgccaaga aggaggaatg aaaaaagct | 420 |
| gaagaacagt tagcattggc cacgagcatg aagtctgagc ccagacattc caaaatcgac | 480 |
| aaggcgatgg agtgtgtctg aagcagaag ctatatgagc cagtggtgat ccctgtgggc | 540 |
| aggctgtttc gaccaaatga gagacaagtg gctcagctgg ccaagaagga ttacctaggc | 600 |
| aaggcaacgg tcgtggcatc tgtggtggat caagacagtt tctctgggtt tgcccctctg | 660 |
| caaccacagg cagctgagcc tccacccaga ccgaaaaccc cagagatctt cagggctctg | 720 |
| gaaggggagg ctcaccgtgt gctatttggg tttgtgcctg agacaaaga gagctccag | 780 |
| gtcatgccag ggaacattgt cttttgtcttg aagaagggca atgataactg ggccacggtc | 840 |
| atgttcaacg gcagaaggg gcttgttccc tgcaactacc ttgaaccagt tgagctgcgg | 900 |
| atccacctc agcagcagcc ccaggaggaa agctctccgc agtccgacat cccagctcct | 960 |
| cctagttcca aagcccctgg aagacccag ctgtcaccag gccagaaaca aaaagaagag | 1020 |
| cctaaggaag tgaagctcag tgttcccatg ccctacacac tcaaggtgca ctacaagtac | 1080 |
| acggtagtca tgaagactca gccccgggctc ccctacagcc aggtccggga catggtgtct | 1140 |
| aagaaactgg agctccggct ggaacaaact aagctgagct atcggcctcg ggacagcaat | 1200 |
| gagctggtgc ccctttcaga agacagcatg aaggatgcct ggggccaggt gaaaaactac | 1260 |
| tgcctgactc tgtggtgtga aacacagtg ggtgaccaag ctttccaga tgaacccaag | 1320 |
| gaaagtgaaa aagctgatgc taataaccag acaacagaac ctcagcttaa gaaaggcagc | 1380 |
| caagtggagg cactcttcag ttatgaggct acccaaccag gaccctgga gtttcaggaa | 1440 |
| ggggatataa tcctggtgtt atcaaaggtg aatgaagaat ggctggaagg ggagtgcaaa | 1500 |
| gggaaggtgg gcattttccc caaagttttt gttgaagact gcgcaactac agatttggaa | 1560 |
| agcactcgga gagaagtcta g | 1581 |

<210> SEQ ID NO 17
<211> LENGTH: 525
<212> TYPE: PRT
<213> ORGANISM: Mus musculus

<400> SEQUENCE: 17

```
Met Ser Leu Ala Glu Ala Ile Arg Leu Trp Asn Glu Gly Val Leu Ala
1               5                   10                  15

Ala Asp Lys Lys Asp Trp Lys Gly Ala Leu Glu Ala Phe Ser Glu Val
            20                  25                  30

Gln Asp Pro His Ser Arg Ile Cys Phe Asn Ile Gly Cys Val Asn Thr
        35                  40                  45

Ile Leu Glu Asn Leu Gln Ala Ala Glu Gln Ala Phe Thr Lys Ser Ile
50                  55                  60

Asn Arg Asp Lys His Ser Ala Val Ala Tyr Phe Gln Arg Gly Met Leu
65                  70                  75                  80

Tyr Tyr Arg Met Glu Lys Tyr Asp Leu Ala Ile Lys Asp Leu Lys Glu
                85                  90                  95

Ala Leu Thr Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
        115                 120                 125

Leu Met His Ala Lys Lys Glu Glu Trp Lys Lys Ala Glu Glu Gln Leu
130                 135                 140

Ala Leu Ala Thr Asn Met Lys Ser Glu Pro Arg His Ser Lys Ile Asp
145                 150                 155                 160

Lys Ala Met Glu Ser Ile Trp Lys Gln Lys Leu Phe Glu Pro Val Val
                165                 170                 175

Ile Pro Val Gly Arg Leu Phe Arg Pro Asn Glu Arg Gln Val Ala Gln
            180                 185                 190

Leu Ala Lys Lys Asp Tyr Leu Gly Lys Ala Thr Val Val Ala Ser Val
        195                 200                 205

Val His Gln Asp Asn Phe Ser Gly Phe Ala Pro Leu Gln Pro Gln Ser
210                 215                 220

Ala Glu Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Pro
                245                 250                 255

Glu Glu Leu Gln Val Met Pro Gly Asn Ile Val Phe Val Leu Lys Lys
            260                 265                 270

Gly Ser Asp Asn Trp Ala Thr Val Met Phe Asn Gly Gln Lys Gly Leu
        275                 280                 285

Val Pro Cys Asn Tyr Leu Glu Pro Val Glu Leu Arg Ile His Pro Gln
290                 295                 300

Ser Gln Pro Gln Glu Asp Thr Ser Pro Glu Ser Asp Ile Pro Pro Pro
305                 310                 315                 320

Pro Asn Ser Ser Pro Gly Arg Leu Gln Leu Ser Pro Gly His Lys
                325                 330                 335

Gln Lys Glu Pro Lys Glu Leu Lys Leu Ser Val Pro Met Pro Tyr Met
            340                 345                 350

Leu Lys Val His Tyr Lys Tyr Thr Val Val Met Glu Thr Arg Leu Gly
        355                 360                 365

Leu Pro Tyr Ser Gln Leu Arg Asn Met Val Ser Lys Lys Leu Ala Leu
370                 375                 380
```

Ser Pro Glu His Thr Lys Leu Ser Tyr Arg Arg Asp Ser His Glu
385                 390                 395                 400

Leu Leu Leu Leu Ser Glu Ser Met Lys Asp Ala Trp Gly Gln Val
            405                 410                 415

Lys Asn Tyr Cys Leu Thr Leu Trp Cys Glu His Thr Val Gly Asp Gln
        420                 425                 430

Gly Leu Ile Asp Glu Pro Ile Gln Arg Glu Asn Ser Asp Ala Ser Lys
        435                 440                 445

Gln Thr Thr Glu Pro Gln Pro Lys Glu Gly Thr Gln Val Val Ala Ile
        450                 455                 460

Phe Ser Tyr Glu Ala Ala Gln Pro Glu Asp Leu Glu Phe Val Glu Gly
465                 470                 475                 480

Asp Val Ile Leu Val Leu Ser His Val Asn Glu Glu Trp Leu Glu Gly
            485                 490                 495

Glu Cys Lys Gly Lys Val Gly Ile Phe Pro Lys Ala Phe Val Glu Gly
            500                 505                 510

Cys Ala Ala Lys Asn Leu Glu Gly Ile Pro Arg Glu Val
        515                 520                 525

<210> SEQ ID NO 18
<211> LENGTH: 1578
<212> TYPE: DNA
<213> ORGANISM: Mus musculus

<400> SEQUENCE: 18
atgtccctgg ctgaggccat cagactctgg aatgaagggg tgctcgcagc cgacaagaag      60
gactggaagg gggccctgga ggccttcagc gaggtgcagg accccactc gaggatttgc     120 ttcaacatag gctgcgtgaa caccatcctg gaaaacttgc aggcagccga gcaggccttc     180
accaaaagca tcaacagaga caagcactct gcagtggcct acttccagag aggaatgctc     240 tactacgaa tggagaagta cgaccttgct atcaaagacc ttaaagaggc cttgacgcag     300
cttcgtggga accagctgat agactacaag atcctggggc tgcagttcaa gctgtttgcc     360
tgtgaggtat tgtacaatat tgctctcatg catgccaaga agaggaatg gaagaaagca     420 gaagagcagt tggcattggc aaccaacatg aagtccgagc ccaggcattc aagatcgac     480 aaggccatgg agagcatctg gaagcagaag ctgttcgagc ccgtggtgat ccctgtgggt     540
cggctgttcc gtccaaatga gaggcaggtg ctcagctggc caaaaagga ctatctgggc     600 aaggctacgg ttgtagcatc tgtggttcac aagacaact tttctggctt cgcccctctg     660
cagccgcagt cagcagagcc tcctcccaga cccaaaaccc cagaaatctt cagggctctg     720
gaaggtgagc acaccgcgt attgtttggc tttgtgccgg agacgccaga gagctacag     780 gtcatgcctg gaacatcgt ctttgtcttg aagaagggca gtgataactg gccacagtc     840 atgttcaatg gacagaaggg gcttgtcccc tgcaactacc tggagccagt tgagcttcgg     900
attcaccctc agtcgcagcc ccaggaagat acctctccag aatctgatat tccaccacct     960
cctaattcta gtccccagg aagactccag ttgtcaccag gtcacaagca aaaagagccc    1020
aaggaactga agctcagcgt gcctatgcct acatgctca aggtgcatta caaatacaca    1080
gtggtcatgg agacgcggct tggcctcccc tacagccagc ttcggaacat ggtgtctaag    1140
aagctggcgc tctcgccaga acacactaaa ctgagctacc ggcgtcggga cagccacgag    1200
cttctgctcc tgtccgaaga aagcatgaag gatgcctggg gccaagtgaa aaactactgc    1260
ctgactctgt ggtgtgagca tacggtgggt gaccaaggtc ttattgatga acccatacaa    1320

```
aggaaaact  cagacgccag  taagcagact  acggagcctc  agcctaagga  ggggacccag    1380
gtggtagcaa  tcttcagtta  tgaggctgcc  cagccagaag  acctggaatt  tgtggaagga    1440
gatgtaatcc  tggtactgtc  acatgtgaat  gaagaatggc  tggaagggga  gtgtaaaggg    1500
aaagttggca  ttttcccgaa  ggcttttgtt  gaaggatgtg  cagccaagaa  tttggaaggc    1560
attcccagag  aagtctag                                                      1578
```

<210> SEQ ID NO 19
<211> LENGTH: 390
<212> TYPE: PRT
<213> ORGANISM: Homo sapiens

<400> SEQUENCE: 19

```
Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
                20                  25                  30

Gln Asp Leu Ser Glu Lys Val Val Tyr Arg Arg Phe Thr Glu Ile Tyr
            35                  40                  45

Glu Phe His Lys Thr Leu Lys Glu Met Phe Pro Ile Glu Ala Gly Ala
        50                  55                  60

Ile Asn Pro Glu Asn Arg Ile Ile Pro His Leu Pro Ala Pro Lys Trp
65                  70                  75                  80

Phe Asp Gly Gln Arg Ala Ala Glu Asn Arg Gln Gly Thr Leu Thr Glu
                85                  90                  95

Tyr Cys Gly Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140

Gly Lys Ser Thr Ala Thr Asp Ile Thr Gly Pro Ile Ile Leu Gln Thr
145                 150                 155                 160

Tyr Arg Ala Ile Ala Asn Tyr Glu Lys Thr Ser Gly Ser Glu Met Ala
                165                 170                 175

Leu Ser Thr Gly Asp Val Val Glu Val Val Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Glu Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
        275                 280                 285

Gln Ala Gln Arg Gln Ile Lys Arg Gly Ala Pro Pro Arg Arg Ser Ser
    290                 295                 300

Ile Arg Asn Ala His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335
```

```
Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
    370                 375                 380

Lys Leu Ala Ser Ala Val
385                 390

<210> SEQ ID NO 20
<211> LENGTH: 1173
<212> TYPE: DNA
<213> ORGANISM: Homo sapiens

<400> SEQUENCE: 20 atggggggaca ccttcatccg tcacatcgcc ctgctgggct ttgagaagcg cttcgtaccc      60
agccagcact atgtgtacat gttcctggtg aaatggcagg acctgtcgga aaggtggtc      120 taccggcgct tcaccgagat ctacgagttc cataaaacct aaaagaaat gttccctatt      180 gaggcagggg cgatcaatcc agagaacagg atcatccccc acctcccagc tcccaagtgg      240
tttgacgggc agcgggccgc cgagaaccgc agggcacac ttaccgagta ctgcggcacg      300
ctcatgagcc tgcccaccaa gatctcccgc tgtccccacc tcctcgactt cttcaaggtg      360
cgccctgatg acctcaagct ccccacggac aaccagacaa aaagccaga gacatacttg      420 atgcccaaag atggcaagag taccgcgaca gacatcaccg ccccatcat cctgcagacg      480 taccgcgcca ttgccaacta cgagaagacc tcgggctccg agatggctct gtccacgggg      540
gacgtggtgg aggtcgtaga aagagcgag agcggttggt ggttctgtca gatgaaagca      600
aagcgaggct ggatcccagc gtccttcctc gagcccctgg acagtcctga cgagacggaa      660 gacccctgagc ccaactatgc aggtgagcca tacgtcgcca tcaaggccta cactgctgtg      720
gagggggacg aggtgtccct gctcgagggt gaagctgttg aggtcattca caagctcctg      780
gacggctggt gggtcatcag gaaagacgac gtcacaggct acttcccgtc catgtacctg      840
caaaagtcag ggcaagacgt gtcccaggcc caacgccaga tcaagcgggg ggcgccgccc      900
cgcaggtcgt ccatccgcaa cgcgcacagc atccaccagc ggtcgcggaa gcgcctcagc      960
caggacgcct atcgccgcaa cagcgtccgt tttctgcagc agcgacgccg ccaggcgcgg     1020
ccgggaccgc agagcccggg gagcccgctc gaggaggagc ggcagacgca gcgctctaaa     1080
ccgcagccgg cggtgccccc gcggccgagc gccgacctca tcctgaaccg ctgcagcgag     1140
agcaccaagc ggaagctggc gtctgccgtc tga                                  1173

<210> SEQ ID NO 21
<211> LENGTH: 390
<212> TYPE: PRT
<213> ORGANISM: Mus musculus

<400> SEQUENCE: 21

Met Gly Asp Thr Phe Ile Arg His Ile Ala Leu Leu Gly Phe Glu Lys
1               5                   10                  15

Arg Phe Ile Pro Ser Gln His Tyr Val Tyr Met Phe Leu Val Lys Trp
            20                  25                  30

Gln Asp Leu Ser Glu Lys Val Val Tyr Arg Lys Phe Thr Glu Ile Tyr
        35                  40                  45

Glu Phe His Lys Met Leu Lys Glu Met Phe Pro Ile Glu Ala Gly Glu
    50                  55                  60
```

Ile His Thr Glu Asn Arg Val Ile Pro His Leu Pro Ala Pro Arg Trp
65                  70                  75                  80

Phe Asp Gly Gln Arg Ala Ala Glu Ser Arg Gln Gly Thr Leu Thr Glu
            85                  90                  95

Tyr Phe Asn Gly Leu Met Gly Leu Pro Val Lys Ile Ser Arg Cys Pro
        100                 105                 110

His Leu Leu Asp Phe Phe Lys Val Arg Pro Asp Asp Leu Lys Leu Pro
        115                 120                 125

Thr Asp Ser Gln Ala Lys Lys Pro Glu Thr Tyr Leu Val Pro Lys Asp
130                 135                 140

Gly Lys Asn Asn Val Ala Asp Ile Thr Gly Pro Ile Ile Leu Gln Thr
145                 150                 155                 160

Tyr Arg Ala Ile Ala Asp Tyr Glu Lys Ser Ser Gly Thr Glu Met Thr
                165                 170                 175

Val Ala Thr Gly Asp Val Val Asp Val Val Glu Lys Ser Glu Ser Gly
                180                 185                 190

Trp Trp Phe Cys Gln Met Lys Thr Lys Arg Gly Trp Val Pro Ala Ser
            195                 200                 205

Tyr Leu Glu Pro Leu Asp Ser Pro Asp Glu Ala Glu Asp Pro Asp Pro
210                 215                 220

Asn Tyr Ala Gly Glu Pro Tyr Val Thr Ile Lys Ala Tyr Ala Ala Val
225                 230                 235                 240

Glu Glu Asp Glu Met Ser Leu Ser Gly Glu Ala Ile Glu Val Ile
                245                 250                 255

His Lys Leu Leu Asp Gly Trp Trp Val Val Arg Lys Gly Asp Ile Thr
                260                 265                 270

Gly Tyr Phe Pro Ser Met Tyr Leu Gln Lys Ala Gly Glu Glu Ile Thr
            275                 280                 285

Gln Ala Gln Arg Gln Ile Arg Gly Arg Gly Ala Pro Pro Arg Arg Ser
290                 295                 300

Thr Ile Arg Asn Ala Gln Ser Ile His Gln Arg Ser Arg Lys Arg Leu
305                 310                 315                 320

Ser Gln Asp Thr Tyr Arg Arg Asn Ser Val Arg Phe Leu Gln Gln Arg
                325                 330                 335

Arg Arg Pro Gly Arg Pro Gly Pro Gln Ser Thr Asp Gly Thr Lys Asp
            340                 345                 350

Asn Pro Ser Thr Pro Arg Val Lys Pro Gln Pro Ala Val Pro Pro Arg
        355                 360                 365

Pro Ser Ser Asp Leu Ile Leu His Arg Cys Thr Glu Ser Thr Lys Arg
        370                 375                 380

Lys Leu Thr Ser Ala Val
385                 390

<210> SEQ ID NO 22
<211> LENGTH: 1173
<212> TYPE: DNA
<213> ORGANISM: Mus musculus

<400> SEQUENCE: 22
atgggggaca ccttcattcg ccatatcgcc ctgctgggct tcgagaagcg cttcatcccc    60
agccagcact atgtgtacat gttcctggtt aagtggcagg acctgtcgga gaaggtggtc   120
tacagaaaat tcaccgagat ctacgagttc cataaaatgc tgaaggagat gttccccatt   180
gaggccggcg agatccacac agagaacaga gtcatcccac acctcccggc acccaggtgg   240

| | |
|---|---|
| tttgatggac aacgagccgc tgagagccgc cagggcacgc tcactgagta cttcaacggc | 300 |
| ctcatgggac tgcccgtgaa gatctcccgc tgcccacacc tgctggactt cttcaaagtg | 360 |
| cggcctgatg acctgaaact gcccactgac agccaggcca agaagccaga gacgtacctg | 420 |
| gtgcccaaag atggcaagaa taacgtagct gacatcacag gccccatcat ccttcagacc | 480 |
| tatcgggcca ttgctgacta cgagaagagt tcgggaacag agatgaccgt ggcaaccgga | 540 |
| gacgtggtgg acgtcgtgga gaagagcgag acggctggt ggttttgcca gatgaagaca | 600 |
| aagcgaggtt gggtccctgc atcctatctg gagccccttg acagtcccga cgaggcggag | 660 |
| gatccggatc ccaactacgc aggtgaaccg tatgtaacca tcaaagcgta cgctgctgtt | 720 |
| gaagaggacg agatgtccct gtctgagggt gaagccattg aggtcattca taagctcctg | 780 |
| gatggctggt gggtggtcag gaaaggggat atcaccggct atttcccatc catgtatctg | 840 |
| cagaaggctg ggaggagat aacccaggcc cagcgacaga tcagaggccg cggggcacca | 900 |
| cctcgaaggt cgaccatccg caacgcacag agcatccacc agcgttctcg gaagcgtctc | 960 |
| agccaggaca cctatcgccg caacagcgtc cgattcctgc agcagcgcag acgcccgggg | 1020 |
| cgacccgggc cgcagagcac ggatggcaca aaggacaatc catcgactcc gcgcgtcaaa | 1080 |
| ccacagcccg cggtgcctcc gcgacccagc tcagacctca tcctgcaccg ctgcacagag | 1140 |
| agcaccaaac ggaagctgac gtccgctgtg tga | 1173 |

<210> SEQ ID NO 23
<211> LENGTH: 60937
<212> TYPE: DNA
<213> ORGANISM: Mus musculus

<400> SEQUENCE: 23

| | |
|---|---|
| atgccggtgt gctggattct gaacgagagt gggtccttcg tggttgctgt gagtatcact | 60 |
| cttcttactt ggctctaaga gtcctccatt cttagaatga tatttctaaa atggtttaag | 120 |
| tttggaaata ttactttaga tatgagacta aaaacttgtc agcaaacact cattgaatgt | 180 |
| atttaactta ccccttataga atcatgcaaa gttgttttcc aagtccattc attttttgagc | 240 |
| atttttaaag tcaactagtt tgttttgtat ggcacgtgtc tatcaaatga agtctgtgaa | 300 |
| tcagcctgtg aaactagcat tttttttttcc tagagtgctt taaagatgcc ctgactcttc | 360 |
| acaccatggt caattcctgt tgactaagaa gatcctgtgc ttgtcagtaa atactttgaa | 420 |
| gttgacagcc ttatttaaa ataatgtatt tgtaatccct gctgtaatgt aatctgtaag | 480 |
| aaataaatgt atagagtgat tctgaggaat actgacaact tctgcatttc atctgaaaag | 540 |
| aagtttagtg tcgaatgatc ttgagtaggc gaggggtggc ccatagcagt gatctcatct | 600 |
| cttttctccc tacccagct cttatggctg gcagtaaacg cctatctgtt tattgacaca | 660 |
| ttcttctggt atactgaaga ggaggctttc ttttatacac gagttattct gggtgtaagt | 720 |
| agatttaatg acaatctgtt attgtttcaa aaagaaaat gcattctact ttctcaagct | 780 |
| tcaatgttttt catcatcctc cttttttcta tttctaactt atggatagtc cgcattggca | 840 |
| tgggcccggg catctgccgt gtgcctgaat tttaactgca tgctaattct gttacctgtc | 900 |
| agtcggaact tcatttcact ggtgagagga acaagtgtgg taagtactaa aaaattttaa | 960 |
| gcaagctcag ttgttgacag cctgcaacta aagactggaa agatggctta gcaggtaggt | 1020 |
| gctggccagc aaaccttggg aacctgagtt caaatggcca gaatccatgt taaaaaaaaa | 1080 |
| aaaaagcagt gtgtacttgt gtgtttgtga caccagcatg gttgagggtc agaggcagga | 1140 |
| ggataatcag ggactagctg ccaccaacc taactccaag ttcaataagg ccctgatctc | 1200 |

-continued

```
aagagaaaaa aaaagcagag agtgataaaa caggtaacct ggttggtgtt ctctggcctt    1260
ggagtgtgtg catgagtata catatgcaca tgcactcaat atgcagaccc catgcttaca    1320
cacacacaca catacacaca cacacatgca cttttttacag gtatgattga aacatgtatt   1380
ttcctatgaa actcccagca actgtgctta cactagttaa agctaaagat caggacattc    1440
cacttgacgt tggctttcca acaacactg gactcaactt tttcccacat ggagatgcag     1500
gggttatgac tgtttgaacc acaatcattt ctgattgaag aaagataaat aaatcattga    1560
gatgagagcc actcaggaaa cacccccaatt ccttccataa tcaaaatcac aaggcccaga   1620
ttgaacctgg tgattttaac actgatccat ggtaacaccc ctcctaatca tatttatttc    1680
aatatgctta attaccactt cctctgttac tgaaaacagc atgcagaaaa ataagattgt    1740
cagtaacctt tatcagaaga aataacttat tgtgaaatca tcacaatagt aaatactagt    1800
tatagatgca aaacatcttt ctttgtgtaa taaggaacag tgaacaagtc attcaaaata    1860
catgactgga aatggtaatt attacttctt tattctatat caataagctg actaaggcat    1920
gaccataagg tttacttaag cactgtgagt tagagccaga gacctaagaa atcccacttt    1980
tagattgagt tgctattcca gcaaaatagc taaagaaaaa tcttttgcct tgctgtgatc    2040
aaatgccact agttttaag tcccgtgtcc ccacttgaag caacacagag atcagttgag     2100
cctgagtcat atcctcttag atcttgtagc attgttagct ctgtgtccat tttcctaatt    2160
catttattca tttatttttgg tactttagtg ctgtagagga ccatggagaa acaactaga    2220 caaaaacctc aacttccaca aactcgttgc ctacgggata gctgtcaatt caggtgagtg    2280
cttaccaatt gtctttagca ctggctaaga tctaacttca tagttttttg tttaactcct    2340
cccaatcgtg cctttagata atagaagctt tcacccttca tctgaacaca tgaaaccttg    2400
catttacatt ctttcaattc ctaatctata cttaaatgag ttttttccata ataatctctc   2460 aaagatcaaa agaaagttgg tcagatttcc ctttgtgaat aagtagcttc tttgtaatgc    2520
agtgataaat acctatttaa atgaaaattt tgctattcgt atcattcaga actaaaattg    2580
agttatagca aaaacctcat tcatataata ggaaaattga attgtcattc aatgaatgtc    2640
aatatagatg ggatagtgtt cttctttgtg tggtaaggat gtcttaatct ttgccctgac    2700
attagagtct aaaaaaggag gaaaaaaaag aagaagaaga aaagcttggt catgtgacct    2760
gggttcagaa ttgtgttgag ttagtggaca tagaagagcc tttaaaggta gagattgtag    2820
gttgtatagg aactgctact gttacggtta cacttgtcat ttaaggagaa attagtatct    2880
ctgagcaagt ttagacaccc acaaagaagg aaagaatgaa aggagaggta gcaatcaact    2940
ggcttgtggt tttgccgggc aacaaagtca ttgaaataaa agaccattgg aaagataaag    3000
agttatgatt cggtactctt tctctcaaac taatttcact ataaaatgtt ttcctcattt    3060
gtttttcatc ctctcatgca ttaaaaaaat gcagagtaaa aggaacactc gaaccaaatg    3120
ggaatttaat taagcaacaa gacatgacag acggtgcccg agtgccaatt aacacaactc    3180
tgggtgtgta gtgagacatg tggggaagac tctccccatt gattgtctta aacaccggag    3240
caaattaacc cgagataagc gttgcagagg gtctttgtgg tttgtctttt taaaaaaaaa    3300
agtgttaaaa gaaaaatcaa gtcctagctg aaacagctag taaatggggc ggttagggac    3360
aaggttggtc tagctgtatg tctcaggacc tgaagtggtg cagaatacac ctgtgtacat    3420
agagcctttg aaaacaagta ccattaccag gaagtagact ttggcttgca aacggaagcc    3480
gtttccacac tttgaaaaga tacaaaagca gagctcagt gctcacagag ctctgagctc      3540
cctgtggtgt gtggaatcag gcacagggca caaccaccga gctccttggt aaacttgtca    3600
```

```
gagaaggaat tctaggacat ttctgggctt cctttaaacg cttcaaaagt ccttatttc      3660
tcattaagaa tagagattaa acactctaaa gaggcaagaa gaatcttatt accatgcata      3720
gcttaaaggc agagtcagac tttaaaagag agttgtaaag atataaagaa aaaggggat      3780
catcaaaatt catcagaaag gagcacagag catacacgaa aacatgagtt gtgaaaggct      3840
ttcttcttaa atctctgggt acatatcctt tctatgtcct catacatccg tagtataaat      3900
ggatagataa tatacattga atgtatccca tgagcagggc accctgtggg taagacctgt      3960
tgaaccccct gtggcccgtg ctgtttcagg gcactgtgaa attgagagtg agcaagattt      4020
gactagggtc atatgaccag cttcttttat agccctgctg ttgctgggtg tgtgagctca      4080
ggtctcttca gctggctgtg gaatcttgaa agcatcaata gccgtttgat ttctctacct      4140
tggtgagata ctgtagatta ccttcaggac taaatctgat atagcaatct gaaaaataca      4200
aggccattca ttcacttgtt gttattgcga gtgaggtcaa gtccactccc ccaaagcatg      4260
gcggatggac tcacagctct aaccaagttt ttggttctcc acatcctcat ggcctttccc      4320
cttgggtacc cttaagagca agtgttctca acctgtgggc tgtgtgaccc ctttgtaggc      4380
cacatatcag acatcttgaa tatcagatat cactattaca attcacaaca ataggaaagt      4440
tacacttacg tagtagcaat ggaaatcatt ttatgattat gggtcaccac aatattacaa      4500
actgtattaa agggttgcat cattaggaag attgaaaacc actactccaa agtcttctct      4560
ttccttgctc agatgaccct tctgctgaaa ttcctccccc ttcatcgtgc ttcctgggag      4620
gttaagactt gtctatatca ggaacccact gtctgtccta aatgccatca cctacaaggc      4680
tcctgcctta ctcgatagct caagagtggc aatcctcagt ttctgagagg ctcagaggca      4740
gggagcatct cttgcatttt agtaacctgt gtctctaaca caagtagact ataacagact      4800
tgaccaaacc agggcaagtg gcatgtagcc atgtgtgtga ggctaaaaga attgatagga      4860
aaggaacaag acacaaattc tgggcatcgt gtggatgaaa cagcgtttgg gaatgaatg       4920
gatttagaat gatactaatc attcaagatt ataaattcac attctgctgc aaggagaaga      4980
aacaggatgt tctttctcca tctttccctc ccaagtctgc aaaggacatc agttttcttt      5040
ccaacccacg tctcttgaat tgctgctact ctgagctgct cctgagcatc tactgggct       5100
caccccagca gggtcagagc tgtatctccc agcaaagtag cctcatccgg tctgtcatgg      5160
caaccaaccc cagggctgtg gtttccagcc cgacaaaggc aggaaggtgg aaaggaaact      5220
ctttaccttg tccaatcctt gaaaaagcaa ttactgcatt tcacattaac taagaaatgt      5280
ggctggcaac tgtgctttta gagagaggag aaaaaaatgc taagcctggg tttcattgct      5340
acaccttgct cttctcattt gtccttctgc tgtattcacg gaggagcagc tgcaatgtcc      5400
ctgggcttat tttattagcc tcgcccatta tgctgctttt gaaatagcca actggcttaa      5460
taggggtgtg taaccttgga agaaatgcat gcacagagaa gtttgcatgc cagcctctaa      5520
tttcttatcc gttcccctag atgttgaact gcaggctcta attggtcgga taattaaagg      5580
atgtaattag agactggtgg atgtaggcta gggaatgggg ttggggaggc aaaacagtgg      5640
tatctctaat caagggcatc accgaaaatt cagtgccagg agcccttctt cttgccttcc      5700
tgcttgcctg cctgtgataa gcaggagccc cctccaacca ctaaataaat tgtgttcagg      5760
gacctgtaac tccactggta taaaaatcgt tgtctcacag cctttacgtt cttattaatg      5820
tggatctttc tgggttccct ggtccatggc agaccttgaa gaccccagca attgaaaagc      5880
agtatgtgga gcctgggctt ccatcaacgg aggttgtaaa ttgtgaccta tgcagctctt      5940
tccgcaaatt ctgcaacttg tgtctgccag atttcagtgg tgtaagatca ccctgattgc      6000
```

```
aactcctgat gagttgctaa aattagttca caaacatcga taaacagaag aggggcaggc   6060
tgagaagaga gggtacagca taaaggtcct gagaaaataa tgattcggag ctcccaaggt   6120
agagatggtg tcaaaggcac cagttccttg ggatctgaca cctaacaagt tgctaccaac   6180
cagttcctca gttccactga aagtgttcaa agctccaaca gggctccttt atgattttt    6240
ttgtctgctt ctcaataaaa gtttcatatt tgaactcaga agtccacaga ccacttaaaa   6300
gagtgtgtgc agcattgcca acataactgg tctctgtaaa agtactgggt gagaaaata    6360
gaattacagg aagagccacc ctcttacagc ttggatcatt tgggtgagtg atggagagac   6420
gtagcttgag cttttaccaa tatacagcgc tgtatagcat aggaagtcca caggggcaca   6480
caaagagctt gttttcagat attaacccag ttgtcacaaa gctgccatgt atggttatgg   6540
gtattttttc caagtctacc cattttacgg atgagaaaat agagacagga aaaaaaatta   6600
ggtaatcaag aagcatccac tttgctattc ttcctgctag acaccaacat ccagtctaac   6660
atcatggaag tatcacagtg gctgggaagg tgagaattca cccacagcag catcttcaac   6720
ccatttcaga gatagctgtg gccataccac aatagtttgt ttgctcatac taaaaaggat   6780
aagacatata taaagaaaaa aaatagaat gtctgtaagg gaccaaaagc aatacttctc    6840
ctgttactta tcctgcctgg gcagtcctag gtttaacagc ttttatattt ctagttttta   6900
gccatgatca aatctaagag gaacatagag tgtttacgca accaaaatgg cctcaggtgg   6960
tttttacct  taggatctgt cttagtcagg gtttctattc ctgcacaaac atcatgacca   7020
agaagcagtt ggggaggaaa gggtttattc agcttacact tccatgctgc tgctgttcat   7080
caccaaagga agtcaggact ggaactcaag caggtcagga agcaggagct gatgcagagg   7140
ccatggaggg atgctgctta ctggcttgct tcccctggct tgctcagcct gctctcttat   7200
agaaccaagt ctaccagccc agagatggca ccacccataa aggaacctcc cccttgatc    7260
actaattgag aaaatgcctt atagctggat ctcgtggagg catttcccca actgcagctc   7320
ctctctctgt gataactcca gcctgtgtca agttgacaca aaattaacca gtacaggatc   7380
cctgggataa ctaggatatt acaggtttaa tctactttgt gaagcaaaaa caagatggag   7440
agtactgaag gaaaggaatg tatattatat aaaccttaaa gcacataaaa gctacaggta   7500
acagagctct agcttagtcc cgtggagatg gtctcttgag aggctacttg gacttccctc   7560
ctccagtgtt gtcttccgag ctaaaggaag ggaggaggcg gtaaacatga atgagcgctc   7620
cgggtcctaa gtcatctatt ccacacacgc caatctaggt tagctctgtc agattctcct   7680
gtggaagcta acctaagagg aaacagactg agatctgcag ctcattacaa ggaagagggg   7740
tgtcataaaa acaggcgaag acaaagagaa tttgttcatt gctttcttcc tgactgttag   7800
gtatagatga cacattggga aatcagtcct ataatagaaa atgaaaacca gcgtctaatt   7860
ctgtgaaatg gaaatgcccc agtctccatc tccataaaag atttttttgg ttaatcttgt   7920
attcagccac tttggtgaaa gtgtttatca gctacaggac ctccctggtc gaattttgga   7980
ggttgcatgt gtatattatc atatcatctg tgaatagcaa tactttgact tctttctctc   8040
caatttgaac caccttgatc tcctttagtt gtcttactgc tctggctagg acttcaagtg   8100
ctatattgaa tagatgtgaa gagagtagac atcttcatta agacatgaat ttggttgagg   8160
accctggaag gactgttctt ctctgaggag ggttgaagaa agggtagatt gaggaaaggg   8220
gagaagaggg agagactggg gggaagggaa actgaagtca ggatgtaaat atgacagaat   8280
aaataaaaaa gggaaaagga aataagaaaa attcttctaa ataatagttg acattgtgca   8340
gctatgacca caggcacaaa attacctgca atattctcaa aggttctgtg tgtgtgcaac   8400
```

```
atacatgcat gaatgtgcat acagaggcca gatgttggca ttgctggtgt cctcagtggt   8460
tttctgtctc tctgtctctg tctgtctctc tctctcagcc tggagctcac              8520 tgtattttt ttttaaatag actaactggc cagcatctcc aagtatctac ctctttcctt   8580
accacctctg cctcaaccag tactgaggtt ataaacctgc attactgatt atgtacatgt   8640
tgcagataaa actcaagtct ctgtgcttac atggcaagcc cttaccgact tctctgtctc   8700
cccatcccca gtattctcag ccttacatct tccacacctc caatcataaa gaacaaccat   8760
ggaggatgct gtaacacacc cacaatattt atagccatgt acatgttagc ctatacacac   8820
gtacatatat ccatatgtat atatacatag tagccagcac agttacttct tcccattgca   8880
gatgcagaag aacgtgtggg aaattaacta tatcctgagt aatgagtcct tgttcacac   8940 ttgagtctga tcccaatggt gtgtgtcgac tggcagctca tccaggtctc catggaggtg   9000
gcatgactgc tggcttttcca atggagtttc caagctagga aagagcagca cagaggtaga   9060
atctccaggc cagatcacac agtgtccttg aatttgtcct ctttatctaa aatttaaatg   9120
tactaactct cagaatcaga tatcacactt tccttaagag tatagaaaaa atatgttggt   9180
tccacaaata ctggctcatt tcaatgtgcc tgatgatttt gtaagagtta tctatgcaaa   9240
tgtgtgtgta gttgtataaa tgcacatatg tgtatgtacc tatacatata catgtacata   9300
catacatact acatacatac acacatgtat gtgttaaaac atatgaagag aagaacagaa   9360
aatatttctg gaaatgtgta agaaaatatc cctgaaattt tcctgatatc aacctgtgtg   9420
tcaaataaac atatattgct gtgtatgatg catggtattc taagataatt ctttctgaat   9480
tctttaggaa gcttcatatt ctacacccgt catatgccat ctttctttaa gaattatatc   9540
tatattatag tatcctatat tatattatgt tatattatat tatattatat tttgtctgta   9600
attacaataa tgctatgata aaatactgtg accaaaaaag caagttgaag aggaaaaggt   9660
ttatttgtct ccatcattgt aggaagtcat ggcaggaacc tggaaggaag acctgatgca   9720
gaggccatag aggggttctg cttactggct tgttcctcgt agcttgctca ttacagaaac   9780
catcctagaa gtggctccac cccacaatgg ggcaaaagct ctcacatcaa tcactaataa   9840
agaaaatacc ctacagcctg atctgatgaa ggcatttct cagatgagcc tcccttagcc   9900
aacacaacaa caatgttctg atataataac ttcatcact tccaaaatga gtagaaattt   9960
aatatcaaat catgaattaa gatgacttta tttgttaata taattaaaca cttataataa   10020
gccatacact gtatgttcta ctccattcaa gacactggga gagatgcaca aataaatcac   10080
aattccttgt agactgccag agcagagaca cttaaggtag cagcacagta ttttgaatga   10140
actaaaaaga tgtctctgac acagcctctg tccgatgtct cctcatccct agttatccac   10200
attgtggcac acttgttcaa cctggagcgt tatcacctgg gtcaggccaa ggatgctgaa   10260
gggctgctgg ctgcactttc caaacttggc gatgccccaa atgagagcta cctcaatcca   10320
gtccgcacct ttgatatggt gagtcagtcc ttgcacgtta accagtctca cccctgcgga   10380
gtcatttctc ttcccatccc tatatcaaga gcaatagatt tcaaaagctt cacataaaag   10440
agctggataa aagaggttc tgccaaatgc taatatcaat ttcacctttc tgttttaaca   10500
gctagttttt ccaaccatta atatggctgg aaggatatga gcaaggagaa aaacatactc   10560
ggcttaatta atttatagtg aatatatatc cgtgatattt taggtacgca aaaacctgtt   10620
aaagccttaa tattatggat tttagaagca gctcccgatc aaatttcctt cactgatgtg   10680
agattcataa agcaagcacc acccaaaccc agattgaatg cttcatttc aacctgcaaa   10740 ttgttttctg ggtctgttct ctgtgccttg tatcttggca caagtgtgag cagctggttt   10800
```

```
gccaagccat acactgactg atggccattt caaaaagaca agtatgtgac tcatgacacc   10860
atcactgcta atgtctaggt gcacagaaca gcagtgtctc tgggaagaaa aaatacagtc   10920
agcctcggca tcctatcctt agaggtaaac acttccctag gcctcagcat cctatcctta   10980
gaggtaaaca cttccctagg cctcagcatc ctatccttag aggtaaacac ttccctaggc   11040
ctcagcatcc tatccttaga ggtaaacact tccctaggcc tcagcatcct atccttagag   11100
gtaaacactt ccctaggcct cagcatccta tccttagagg taaacacttc ctaggcctc    11160 agcatcctat ccttagaggt aaacacttcc ctaggcctca gcatcctatc cttagaggta   11220
aacacttcct taggcctcag catcctatcc ttagaagtaa acacttccct tgagccactc   11280
ttacatctct cttactggtt catctaaata tcttccatgg actaccatat tggaattgag   11340
actatatatt tttaatctat tttctaaaaa aaaatctcaa ggccacacac cccatcaata   11400
ggattctctc gggctgctgt gacctaggcc cttttTataa gtgatagttt tgttcacatg   11460
tttatttgag aaggaaaatt cagattctag ttatgaggac attcttccaa gtcaaaatct   11520
tgatttcctc gggaaggctt acaattcaag gccattaata aactgaattc ccttttTctt   11580
aactgacacc aattagaagc acatatttca tagctacaaa tcaaaactgc agatgcccga   11640
agcaggcaga gatgtgttta ataccatttc cttgaatctc agaatttatc tggccacctg   11700
tttagatcta catttcttcc ccaataaagc ttaacaaaat tcactgctca caaaagaccc   11760
aagaataaat ctcaacatct tgaataaact atgcaataaa tagtatttat tataaataac   11820
ctttaaagca atttaacaag ctaattaagc tacttcaaac acagttgttt caaaaatttt   11880
agaagcaata tactttgtta gtactaatta ggctcagaag cccctctaat ttgggtattt   11940
ggagagatga ttatcaataa cttgaagcat acattaaagc aattcataag taatgcagtg   12000
gggttacatt agacaactgc cggcaactca gaccagtctg taaatacatt gcagggaaat   12060
gaggagaaat agtctttaat agtcaaaaca gaatgatttg aaattaacac accatgtgct   12120
gttaattgac ttctaaagtg cctgagtata cttacaaaac aaatatttta aatgttctac   12180
gtgtaccctc tttcaatttt attcttctct tctcttctgt gaagagaaga aaataaacaa   12240
tggagaagtc cctgtccaaa ttacttccag atctcatagc agcctaaatt aatgaggttt   12300
tactgacaaa agatatagtg tgagtttatt gagctggtag ttggctcaga gatgagagca   12360
cggggtatga atactaatga ctaagcaagg aatatgggaa ctcacaataa aaacaaaat    12420 gctttgcaat taatattctc aaaggctatt taactgtccc ttgcactcat gggtcagaat   12480
catgctcgtt ggagagtgct gatcagataa gaatagctgt gtccttattg atcacagagg   12540
ctttaccaag ctttattcca aagaccctg aggttatttg aaggaaatgc aagtcatggt    12600
tcttccaatt aaaaagccag aacaaggcat agccaccaag ggaagagtgc atgaaactgc   12660
tttattagga gtgcccctaa ggaaactctc cttcaccccc caaaaaagtg tttattaatg   12720
ttaagatgca attaaacatg gtgagccaca cttttTaatc ttaaaaaagt aaaaacctcg   12780
aatttgagct gattctgcca tgttgttctt ctaatgctct ctggtactga ttcaaaatag   12840
tagctttgac aagaaaatta actcatgcaa atggaaaagt tgtgcttaat ggcacagtat   12900
tttataaaat ttgaacaaag taaatatcca tggtgacaca ggggagaagg aagaatttca   12960
cacctagttt cttgaagtgt gtatggactt tggtgaggtc ctgtgtgttg gcacaaaaca   13020
tcctgaattg ctctttgttt ggatcatcta atactgatcc taaaaatgca aaaatccaaa   13080
atatgaattt ggcggtactt tgtgatcttc tagggcacaa ccactgagct attgatgaca   13140
gtgtcaggaa ttactggcct gggtatctct ctggctctgg tcttcatcat gacctcttca   13200
```

-continued

```
accgaattca tcagaaggtc ctcttatgag ctcttctggt acacacacca tatctttgtc    13260
ttcttcttca tcagtctggc catccacgga ggagggtaag cccatttat aatgaggtgt    13320 tcagatgtat gtctctgtgt acacgtgccc tgactatagt gaatagagca tctgtggaca    13380
ttgttgaaca agcatttgag gcgtggaatg tcaggtttgt tgagcacatg caaagagtgc    13440
tatatctggg tagtatggct gcttctgctt ttagttatta aaggattctc cacacttatt    13500
tccttaatgg ctgtaccagt tacaaccttg ccaatggtga atgaaggttc ccttcctcca    13560
caccccccat tctcagcaat attttaacta tcttgacagg cataaggtga aatctcagag    13620
tggtttaaat ttgcatttct ctaactgtta agaatatcaa ttccttatct gttttttattt   13680 cttcttttga gatctctctg ttcagataca tagccctttt ttaaattggg ttgtttgttt    13740
tcttgactct agtttttgaa tcctttgtat ggagtgggta ttaatcactt atcaaatgta    13800
cagttagcaa acattctctc ctactctgta gatttcctct tctagctatt cttcctttc    13860 ctggacagag catcttagtt ttttgttgtt tgtttgtttg ttttgttttg ttttgttttg    13920
ttttgttttg ttattgtcaa tggctggtct tgcttcttta gtaaaagaaa ctctgtttag    13980
aaactcctct ccatcacatc ttgtaggagt ctgcctatgt tttcagcttc acattgagat    14040
ctttgatcca tttgaagttg atattcatac agagtaagac atagcccata tgggtctaat    14100
tttacccttc tacatgtagg caacctcttc tccgagcatc agttgttgaa gatgctatat    14160
gttctccagt gtgcatcttg gcatctgtca gatgtgaggt ggctgtaatt atgtgcaatt    14220
ttgtctgcat cttctacgtc attccattgg cccacatgtc tgtttttatg tcagtgccat    14280
gctgttttta ttaccatgtc tctgtaacat agcttgaaat acggtgtggc aaccccttg    14340 cccagcattg ttctatttgc tcagcattgc tttgactaac cagagttttt gttgttgttg    14400
ctgctgctgc tgctgctgtt gttttgttg ttgttccatg tgaactttag gattttttc    14460 ctgtttctgt gaatagtgtc ttgaaaagat tgatgaggtt tgtgctgagc ctgtaaacta    14520
cggttaccat cttcacagca ttaattctac ccacctgtga acccaagagg tgtttgcatt    14580
tcctagagtc ttcttccgtg tctttcttca aagacttaaa attctctctg taggtctttc    14640
acctccttgg atgggtttaa tcctacacat cttttgatact attgctaata gtgctttaat    14700 aacctcttt tcagcttctt tgcttctt tgctgtatat aggaaggcta ctgattttg     14760 taagctgact ttagaaatct tagtgcaatc ctcttttaac atggaaagta ttcctataat    14820
cccctaaatc cacatttct gcactcacac cctgggtatt gaaccacaag tccatctcaa    14880
tgggcagtaa cttggctgaa gttaggattt aatgcacaaa taatatttca caaggagaat    14940
tgttgagtta tttcaacatt gctgaaaggc ttatttatgg ataaaaacct atttaatctt    15000
ctcagcttga catattctac aactactatt tacatcaaaa gcgatttgca aattctataa    15060
aaaaaatgcc aagtagacat aagattgttg gaaggcataa agctcactag tctgcctatt    15120
atcccaatgg tataagtgaa aaaattaaac tttttaatat ttttaacagc atacatatgg    15180
aatgacctgg aatctcttct agatagcatg gggaaagtta tcaaacatct aaggatatag    15240
gtactgaaat gtatgacatc cacaatctgg ctcccattta ccactcatcc acccgggcat    15300
catttggcct ggaggttcac agattgtcct gcttacctga ttcaaagtga tgtcatcaag    15360
cttgcatgac ttgcatggaa cagagtcaaa gcctaacata tcttctgtag ctgacaccag    15420
gcagtttcca agagcattga ccactactcc acagacaaac acagcatctc tgtgatgttg    15480
atgttgccca gtctaggaga acctaatttc tcaaaacaaa ccagcgcatc ttatccataa    15540
gtacctagga actgagccac tccagggttc tattatctag gtgtatggtt ctttgccgta    15600
```

-continued

```
agaatacaag ccagtaaagc catcctgaga gttgatgcct aagcaatttg cagaggtcaa   15660
cagactcaag ccagtaagat tacaggactc tttatctagt gctccatcca ttcagacttc   15720
tctttctact tttaaattta tcaatacagc ctcaaagaca catttcaaag tgacctgttt   15780
tgaccttgtc taagcctgct agtaatcact aagcctgcta gtgatcaccg gggggaaaaa   15840
taccattatt ctgggcactt cttttgactt attcacttga aacttctaag tgctcagaaa   15900
caagctaaga agggtagaag ttaaatcaat ccgcagaaga agccaatcgt acaaagttgg   15960
ccaattagcc caaatcagca atcagaatga gatgaaacct aattaaattc aacagtctac   16020
aaaaggatgt gttcaaacaa tttccttcat tatgaattct ctaatataga cactttcaat   16080
gtgacacagg ataccacaga ggggcacttc tttttctggga tcttcaaagt tacccaaagc   16140
tttctaatgc ctattttaa agatgctggg ggaagtgagt gacagcccaa gttttaagag    16200
atgggagtgt tgttttggaa cccactactg agtataaatc tgtgtaaaga tatcgcacaa    16260
aatcagcttg acatttttat gctttccccc ccctctctct ctctgcatgt gtgtgtgtgt    16320
gtgtgtgtgt gtgtgtgtgt gtgtgtgtgt gtgtttctaa gtcgcatcat tcgaggccaa    16380
actccagaga gtctccggct gcacaatgtc acgtactgca gagaccacta tgctgaatgg    16440
caggcagctg ccttatgccc tgtacctcaa ttttctggca aggaaccttc ggtaagagtg    16500
aatccaggag ctttttaaaa ataactgtcc ccacagttaa aataactaga gctttaatag    16560
gcttgaaaaa ataaccgcc catgtcacca cttgacgaag ccatctcttt attaagtggg    16620
ctaatggaga aatcgagtta tggataattt caaaagagat ttactgccaa aagcactttg    16680
ttcagctttg aaatgtattc tactccggct taaatatgga tgtctgatat tgcaaggctt    16740
cataacagca gagtaatgac tctgagggca ttagcctcat ggttcaccac ccgctacacc    16800
cttgctattc ctcagtctat ctcccgggta actggggagga cccagtctt tcctaggttt    16860 actgtgtctc tttctacaac tttggtgatc aaaagaatta agggtgccca gttacttttg    16920
ctataactaa tttctgtttt agccaaaaat agatttttacc aacttaagta ttaatttagt    16980
gatagtgtcc acagattttg aaagtaatgt tttctgtttt ctgggtatgc agcagttgtt    17040
gacttaggta aacaaaaata atactcccat ctggactctg atatattagg aaagtacaaa    17100
cctttggttt aactggtggt tgatatatga cagataataa atgaagtgac tgcattacaa    17160
gtaggaagag gttggcatgt gacttaggtg atggaatgct tgcctaacat acacaaagca    17220
ctgagtttga tccccagcac cacacaaact atgcctgtaa tcccagtaca cagaaagtgg    17280
aagcaggaaa gtcagaagtt caagttcatc agcagcaaca tagggagttc caagagaacc    17340
taaccatcct aaagacagga gactttgtct cagaacaaac aaaaatagaa aacaaaaaag    17400
ttggagagaa caagtaccca agatgtgtta ctctttaaaa tagggggtaat ggactatggt    17460 cacgcataag ccatcagaag aatggaaata gccatttctt taaaaatta caaatacaat    17520 aaattcaatg ccatatttta agggtaaaag tagtaggaga aatgttttaaa actgagagat    17580 gtgaaataga tgtgcccatt agactgtggt tcctttaatg gccagtatag attgtctctg    17640
tcttaaactc agctctctgt agccactacc tggcctgtat attaatgaag aaaatgaata    17700
cctctctaaa attttcagcc acagcatctc catttaaaaa aaaatcaata ctctcccaca    17760
cttcatgaat acagaccagg gcctgctccc accagtgtgc gctagcatta attatgatta    17820 aaaggggggaa cttggccatc tcttgctaac tcccctgcta cacctccttg cacatccaaa    17880
ctcacaccat cactcttttc cattattttt aatggatcct gattcaaagc atgtgtgggc    17940
tgtgcaatta ccgtttggct agactgtacg atactccctc tgatgtctta ttgactctga    18000
```

```
atcagaaagg cattccaagg acatgggggg gggggttccg tgctccacta cactggacct   18060
agctcatctt agtaaggctt catatagtcc tccttgcctc tcttttcctg gggcactttt   18120
ttaatgaaga ttttatctgt agaatatttg tcagctgatg ccatgttgaa tctgagaatc   18180
ttttttctgt caccttgtat aagctggcca gagaaatctg ctgccctagt ttctacctca   18240
atctcacagg cacacaaacc tgcagatctg agagttgctc atgcagtcag tctaatgtca   18300
aaagatgctt ggtcctcctt agccaagaaa ttagctcatt tacctgtaga gaataatcat   18360
atggctctgg gtttcctttt ttagttgttt gttggtttgt ttgggttttt tgtttgtttg   18420 tttgttttt cactttctat ggatgatatt aatggtcaaa gggaaatctt gaatgagggt   18480
agagtcaatc actgaatttc atcaagtggt gagttctcct gcttgctcat ctgtagacag   18540
acacaggact ctgacatggg ggcctgcccc tggaaagctt attgtctaca gcaatcatct   18600
attcataacc acatacataa aataaactca aagccagcct gaccttattt tctggaagga   18660
ataaaagtag aggaatcatg tttcattgct atcactgtta agtcaacacg attttatttc   18720
tgtaataatg caattgctgt actatggttt ttctgcgtgt ttttggagac tagaataaga   18780
aaactaagaa gccatatgaa ttttcagtac taaaaaaact gacacactaa acaattattt   18840
ttttcttatg actaatattc ttttttatt agatattttc tttcactaaa caattcttac   18900
cctttgttta agagctagag aaagtaaggt ggagggtttc aaagggttgc ctctgataca   18960
gagggcattc caagcaaagt cacacctggc gtaaaaagc tcctgacttt gtggcaagtt   19020
gtaacacttc ttttccatat cctatggcct tccttcggat tctctgacct tcttccaaga   19080
attccttagc cagtcctctg cagctatctg caagtacgtt ttcccagcgc cattttatc   19140 cttgtaaata aacccaaaac atttaagagc ttggcaagaa cttcaatgag aattttctcc   19200
aatcatctcc cggtttgaaa aatacaaaac tcaaatatga aaataaagca tgagatgtga   19260
gccagggaga tagtgtctta gtcagggttt ctattcctgc acaaacttca tgatcaagaa   19320
gcaagttggg gaggaaaggg tttattcggc ttacacttcc atactgctgt tcatcaccaa   19380
aggaagtcag gactggaact caggcaggtt aggaagcagg agctgatgca gagaccatgg   19440
agggatgttc attactggct tgcctcccct ggcttgctca gcctgctctc ttatagaacc   19500
caagattacc agtccagaga tggtcccacc cacaaggggc ctttgcccct tgatcactaa   19560
ttgagaaaat gccttgcagt tggatctcat ggaggcattt cctcaactga agctccttcc   19620
tctgtgataa ctccagctgt gtcaagttga cacaaaacca gccagtacaa ttgacccctt   19680
gtcaacttga cacacaaaca catcactagt aagcctcaac ccttacattc ttattcatcc   19740
caagatctag acaactttaa aagtcccact gtctttacat attaaaagtc aatcccttta   19800
aaatgtccaa tatcttttaa aatccaaagt ctttttacaa ttaaatgtct cttaactgtg   19860
gggtccacta aaatagtttc ttccttcaag agggaaaaca tcagggcaca gtcacattca   19920
aaaaaaaaat caatctataa ccatccaatg tctgggatct aactcacgat cttctgggct   19980
cctctaaggg cttggatcac ttctccagcc tgcccttttgt agcacactcg tcgtcctcta   20040
ggctccagat gcctgtactc tactgctgct gctgctcttg gtggtcatct catggtactg   20100
gcatctccaa aacactgcat gaccccttca gtcctgggcc ttcaattgca actgaggctg   20160
caccttcacc aatggccttc catggcctct cacagtgcca agcctcagct gcttttcgtg   20220
accccttcat gccttcaaaa ccagtaccac ctgggtgacc cttacatatt accaagtccc   20280
gctgcagcag gaatacaaac ttggccatct ctggaacaca gcctctttgt gctttcagaa   20340
aacacttccc agaaaatgtc acctcaatga tgctggtctc tttgtttgtt tgtttgtttg   20400
```

```
tttttgtttt ttgagacagg gtttctctgt gtagccctgg ctgtcctgga actcactttg    20460
tagaccaggc tggcctcgaa ctcagaaatc cgcctgcctc tgcctcccaa gtgctgggat    20520
taaaggcgtg tgccaccacg cctggcttgc tggtctcttt ttaagcaccg ctaatttctt    20580
agctccagct aaccagcatc aatagtccca gtaatgcaaa gttttttgctt tagtagttct    20640 ggtatcttgt taatcacagc tgattcttca gccccagcta accagaacta cagaatcttc    20700
acaatcaaaa cagcaatggc cctgaaaagt ctttaattttt ccctctgaaa tttcacaagc    20760
caggcctcca tcttctgcac tgttctcaac attatcttcc aagctcctac aaaacatctg    20820
acagagctct taacaatgaa tggatcttca agcccaaagt tccaaagtcc ttccacagtc    20880
ctccccaaaa catggtcagg ttgtcacagg ataccccac tctgctggta ccaatttgtc    20940
ttagtcaggg tttctattcc tgcacaaaca tcatgaccaa gaagcaagat ggggaggaaa    21000
gggttgattc ggcttatact tccatactgt tgttcatcac caaggaagt caggactgga    21060 actcaagcag gtcaaaaagc aggagctgat gcagaggcca tggagggatg ttcattactg    21120
gcttgcttcc cctggcttgc tcaccctgct ctcttataga acccaagatt accagtccag    21180
agatggtccc acccacaagg ggcctttccc ccttgatcac taattgagaa atgccttac    21240 agctggatct catggaggca tttcctcaac tgaagctcct tcctctgtga taactccagc    21300
tgtgtcaagt tgcacaaaaa ccagccagta cagatagctt agccaataaa gtgctttta    21360 tgcaggtata aggactaaaa gtataaaagc ctggcacaat agagagtgca tgtaatctga    21420
acactggcag gagagatggg cagatccttg gggctcacag agcaattgtc ttagtctgat    21480
cagtaaacct agtgagagat gctatttcaa aaaaaaagt agaaggctcc aaagttcaca    21540
cacacacaca cttcacgatg tatctgatta tacagaataa aagatgggag catggtctcc    21600
ccatctgtac agtgttgtct atgctgatgc tgatccccac agctggacca cttttctagc    21660
atcacttact ggctatatct caccctcact cctgaacttt caaggactc tgggagcatc    21720 acagtataaa taagccgccc tatctcctca tggagcaatt tatatagtag aatagagata    21780
gagcctagga ttaatggctt acattctcct tcctgactaa ccatggaaag aaaaataacc    21840
cttttcattt catcaatgtg gagaaatcag aggccgtggc tgatttggcg ccaacaaaat    21900
gagctatgtg atgtctaaag catgtgtttt caaatggata cggaagatta tttgtgaaaa    21960
tacacaaaga ccatgtgaat atctttgcaa atctttctgt cctgcagaaa gaattgttgc    22020
ctgcattcct ctacatgtcc aaaccatttc ttaaaatact ttcaagcata aggaagctct    22080
ggctttgctt acttggtcca gctccatcct tctgctactt ccctgttttg ccttctctga    22140
ccatcttcac tgccttaccc tagcacgagt ggacctaagg ctttattctc ccctccattc    22200
tgaacgtgtt gttgaatccc actaaggttg aaatgagtaa gtaggtcaac ttgctttgta    22260
ttgcccgaat aaatcatagc ctttgtcaag caagcaagag gaccttagga agaagcaga    22320 gagagctgat gggtgaagac agagatcctg caaacagcca agactgacga aaacagaaag    22380
gaattaaaaa taggaaagat aatttaaaag aaattaaaaa gttatgtcaa agagctggtg    22440
aacttggcga cagagccaag gccagtaagg aaataatcaa tgaccagagt tgaaataaaa    22500
cacaaactct aatcagcttc caaacgctga caccattgca tacactagca agattttgct    22560
aaaaaggacc ctgatatagc tgtctgttgt gagactatgc tggggcctag caaatacaga    22620
agtggatgga tcacagggcc cccagtggaa gagctagaga aagtacccaa ggagctaaag    22680
ggatctgcaa ccctataagt ggaacaacaa tatgaactaa ccagtacccc ccccccccca    22740
gagctcgtgt ctctagctgc atatgtagtc ggccatcagt ggaaagagag gcccattggt    22800
```

```
cgtgcaaact ttatctgcct cagtacagga gaacaccagg accaagaagt gggagtgggt    22860
gggtggggga gtgggtgggg gagcaggtga gggactttg ggatagcatt ggaaatgtaa      22920
atgaaataaa tacctaattt aaaaaataaa taagtaaaaa cacaaactaa aaaaaaaaag    22980
gaggtgtcct ccccgttccc atgatcttat gaaagaacta aggtcgtggt agatttggaa    23040
tggcaaaggg gaaatttaag aacctctccc aagacttgag atccaataag gaactgagaa    23100
ccagcccagc ctcccaagat aactcaaatt gattcccaga gaaccatagt ttattttttg    23160
ttttgttttc ctataagatt aaagcaggat taaaaaacaa aaaacaaaaa ccttgacatt    23220
ctaaaattca ataagctcag gaggctgatg ttttacaaag caagtctctg gacatacect    23280 ggtgttagat agcacacagt aggactccat ttctgctgta tggtaaatat tcaggcaagg    23340
cagctgagac cctgtgaaaa caggctgtgt accaagcctg tctaggccca catcttctcc    23400
acatactttc tcatgtccaa gggatcattt gatcagactg tgcctcagtt tctttctcta    23460
tgaaataaat aggctatcat ataccttgca agattgtttg acattgaacg acaaaaatca    23520
tacattccca tccttcctgt ctactggaga aagacccctc gtgttatatg caacacctga    23580
ggcaagtgta ggctttaaaa tatggtcatt cataatgcag aactcaagaa ataagagtag    23640
taacattttt aagcatgaaa atattcctaa tcatatctct ccagatgatt gttgatgtct    23700
ttgttctgat cctctgagac aaaatctagc ttgatctttt tcattccaca taacattata    23760
gaaggtagag gtatgcacag gggaatgtgg cagtgtgagt gtctgtattc agacagattc    23820
cctacttggg aggcattatt ggcccccaga attactattt gaaactcctt atgttggcta    23880
aaaggatgct ttttctataa gcctttgact ttggctgctt gggagcattt acaacgctag    23940
catacagaac ataaacatca acctgctttc ttatttcttt acaaattcaa ttatttctaa    24000
ttacataaag gcatcattga tcaaggaagc ataaaaacca atagaggaga atttaatctc    24060
ttaaataagc ttgtagactt taaggaataa ttaaatgcta ttgtatttag tacatggaga    24120
catctttgct gttgatagct gggccaaagt tgagggaaat atcttagtcc cgtcatgcta    24180
tatattgata tagttcgaac tagaaatttt ggattctatt ttaacttatc tctctgtgtc    24240
tctgtctctc tgtttctctc actgtctctt attttctgtc tgtctatgtg tctctcccac    24300
ctccctccct gccctccccc tttttctctc catctctctc ttttccccac tctctctgca    24360
ggcctggaaa tgggctttgg gtcctgtggt cttgtatgcg tgtgaaagaa taattaggtt    24420
ctggagatct caccaagaag ttgtcattac caaggtatgt gtgtagcttt atgtctgaat    24480
aaaagcctga gtgtagatga aaatttttta ttagcccaag tttttaattt gccatttta    24540 ttgcagaact gcccgtaatt tagaggctca tcttctggtc taataattgc ttgtatcggg    24600
agcatctttc agtgtgacca attttactgg agacagggat caaagctcca tgctgttatt    24660
cggaattctg ataaaggctt acagcgtaga actggagtta gccatatttc tctttattat    24720
ggtttctctc tagtgaggaa aagacaggaa actactaaga atgctttaca atgatcgtag    24780
taactttaaa tagcccatag aggtgggatt tcgcaaacat gccagcatca tccacacagc    24840
ttcaagcata tgcgttctta acctgggtac tgagcatggg cttggaatgc agccacaggt    24900
tcagagcatg gagggatgct aaggttcaag atgacaatga tggaatggca tgctgctcta    24960
ccctgtttag tgttatgtgc cttggaggca cttctctgcc ttgctgtatt tcatgctgga    25020
ggaagatagg aacagataga cagaaaaagc atatctcaca ggttaacaaa agtacaaatg    25080
ccaggtgtag tggcacacgc ctttaattcc agcacttggg aggcagaggc aggcagattt    25140
ctgagttcta ggccagcctg gtctacagag tgagttccag gacagccaga actacacaga    25200
```

```
gaaaccccgt ctcggaaaaa aaaaaagtac aaagtatgct acccactcct gagtgttagc   25260
tagtgcagtt ttaaccaaat acgtacaccg ttcactgtca cattgaaaga agatggacag   25320
gcattcctat ttctgctttt acatgtttct gtgtttctga gtttaagctt agaaccgtag   25380
aaggtcaatc aagcctggaa caagtgtgga aacctagatc tgttagcagg aaagcacata   25440
gtaggtcctt tagaggcagt gtcgggaggg caagcagaaa tctggaagta aagataaaaa   25500
tgctgtgaag gactcttcat gtagaaaagt gtcataccag tatccacata ctggatcgtg   25560
ttctcatatg catttactac aaaagacacg aaggtgtaca gatattttt cataaggtaa    25620 tggatatata tgaagggcaa atgttccttc cctcagatga tcgttagtgt aaagtccttg   25680
gagaagcttc acggggcttc cctataccaa aaacttagca ccaagacaat atttagtcaa   25740
actgaacaag taaacatttt tggggagaga taaaagatca atattttcc cctcagcatg    25800 aagaaaatct caaattattg ctacatttt ttacatgaag atgatgtggt aactatttta    25860
ataaatgcaa gtaaaattat gagatctcct tccatgacag cttatattca gttggaaatg   25920
gttagctggg ctcagggacg cttggtcacg tggggcatgg agtcatgtgc tgccctactg   25980 cttcctgca cagttattaa aagtcaagtg cagcaccctg cgccatgaac gctgttatca     26040
ctcaaattgc aagcctaggc ataaaagtgc tgacaaatta tacatcaaaa aaaaatccaa   26100
ttaaagattt cgtatggaca gaagaatgtg ctcttgtcat tttacctgag tgagaatccc   26160
cttggctatc ttgctctgtt gtaggtggtg agtcacccat ctgcagtcct ggaacttcac   26220
atgaagaagc gagacttcaa gatggcacct ggacagtaca tcttcatcca gtgcccatct   26280 gtctccccc tggagtggca ccccttcact ctcacctccg ctccccagga ggacttcttc     26340
agtgtacaca tcagagcctc aggagactgg acagaggcgt tattgaaggc ctttagagta   26400
gagggacagg ctcccagtga gctctgtagc atgccgaggt gagacctgcc ccgcctcccc   26460
gcccccaccc gccccaggtc actgttatat acaagctgtg ctacttcaaa cgggaaaaat   26520
atctaaatgg atgaataaac tgtccagttt ggcaatagct ttatattaag ctgcaagctt   26580
gagttcgttc aaaaaaataa taataattga gagtcttcat cagatgtata atttaggaga   26640
agcgaataca tttctgtaaa aataaataaa tgttcaacaa aagtaggtga tgatccaggg   26700
agacggaaga gtttcctttc cagatccaaa agcagctcta gtctaattat gtgcagcctg   26760
ccatgagtca gacaactccc tctgcaagct ctctcccagc acagactgag ttttcaggct   26820
gtgtttgcaa aggttggtct ctggaagaag gatagtttat tctgctcatg ctggacttaa   26880
cccataccat tcctgtatga ctgcatagta acatatagga agcttatata aagactcctc   26940
gtttctgtag ccctcttttc agatacacag tataagttcc tggagttagg gcttctttat   27000
attcatcaga gggaggcatg attctggccg taccactacc ctattcagaa aagcctacac   27060
gtttgaccca agtcactgtg agaatgatca tgtcttgcct catttaagtg aacaagcagg   27120
ttagttccca atcctatagg accattaaat agtacatgaa gtccacagat aggaccccag   27180
aaaaacaaga agacataaaa aaaatatgaa aaaaataaat taaaaacaaa atatttcaat   27240
gaagcatgag aaaaaataat gtctatttgt accattcttg ggggacattg gccaccacgc   27300
atttatttag ttaaaaacac agttgtacat acatacatgg aagttcctgc agatgactat   27360
cttccttctg tatctacaca aatgccagac acataaggat aacataacag aaaaaagtta   27420
acatgttcac caaatatgta tcctttagct cattgaactt gacaaatctt tttgtcaact   27480
gctagcctct ataggcatgc acaaacacac atgtgtgtat ccccactcac ataccaacac   27540
atatgcagac acacactcac atatacgcac atagatagag cacacgaacg ataaaatgat   27600
```

```
agaaaagttt tccaaagagt acctattcca attgcaaggg tgagataaat gtagaccacc    27660
cctccaaaat aaatctaata atgaggttca gagcttgata cataggaagg aagaaatata    27720
taaaatatat tctaaagaaa gcaaaaggta agatccttac agactgcagt aagtcactga    27780
gaagaattgt ctcaaactga accctgccgc tggtataaca aagtgtcttg caggttgaca    27840
ctttgcagag tatgagcagg cctcagacaa gggcatggaa aagctctcaa ttctaaataa    27900
ttagacagat atatgtatgt gtgtgtgtct ctgtgtgtgt atgcttctgg taagatggcc    27960
attttcccta tattaaccct accaatccat gagcatggga gatctttcca ttttctgata    28020
ttttcctctg gcattggatg ctctttctct tacctggact gcctggttgg acctcagtgg    28080
gaaaggatgt gcctagttct gctgggacaa gatgtcccag ggtggggtgg tatgcaggga    28140
aggctcccct tctcctcaga aaagaagaga aacaattttg gaagggattt ggaagggtgg    28200
gacagggagg agaggaggca gaggctgtgg ttgggatgta aagtgactag aaaataaatt    28260
attgaaaaaa taatggagca aaaaaattaa gttttatata tatatttctg caggctttga    28320
gacataggtc tcctctgaat ttaatggata tcttttttaaa atttgtgtca aataatcact    28380
gattattaat tataataata accaacaata agatgcctta atcaatggat aaagtttcta    28440
tttgtcaatc tatttatcta attatttata aaataatcaa cgtgggctaa gatactagca    28500 cttctggtt aatgaccttt attttattct tctatttcca tatatcaata tgtaattaag    28560
ccttattatt taagattaat tcaaggacag tttatttaaa ttattaggaa gtctgggata    28620
tggaatattt ttaaattaat ccatttgaac tttcatgaac acatactaaa gcccaaatgg    28680 gttaacccc acccgctctg tgcaggtgac gggctctcct cagggaatgg ttatgaatga    28740
cttagaaacc ttttcattag catatctttg ttcatatgta aatgtgtact tttggaataa    28800
taggagttat ttaatacatt cggcctactg aaatgctcta aatattccct ttacagttga    28860
ctcaacaaat tgctgttgaa cagttccaga ctgtatcgta agcaagacac caaatacgaa    28920
atgagcaaaa tcagacctgt ttcccacatc caaaacctgg aaacgtagag gtcgtgatag    28980
acaggactaa atcctgagca cccatcgtat aaacgctaat attcagctat gggaaggaag    29040
ggcatatgag ggagtttctc tgagtcacag gggtccaggc agacttccct agggaaataa    29100
agattagaca ggacctagag gaaaggtatt atgtcagcaa gtagaaagag gggaaatttc    29160
aggtattcca tgggaaaaga tcttgtgtgt cagaaggcaa tactgtgtgg tatttaggta    29220
atacaagaaa agccaacatg gagaaccagg aaaagattg agaggaaccc agtggccggt    29280
ctgcataaga acatcttatt tattcaaaga acatgtttat cattataaag aaaaattgct    29340
aaggaaaggc aaaacatttt actgcccctg gactgatgag cataaaggat ttttttttag    29400
caaatatgat ggaaaataga gagttttaca agttgtactt aactgacaaa ttattttaaa    29460
attatgttta ctctgaacaa atcgcctcca ttagactaaa atgatataaa tatataaaca    29520
tgcaaacaaa caaatgaaaa tgagggggggg agttcaccat gaaaagaaaa cacatatcct    29580
ctaagcccct ttgaagtatc tcctttgcct ttgattggca actgagggaa agacagtcat    29640
ggaggctctt catgcaggcg tcccaatgct cacagttgac aggagctccc agaactctaa    29700
caggagcaag ccatgttgac gaggagccac agcaggcgat gacaagcttt gccctccctg    29760
gctcacgtgg agcgtgtgtg tgtgtgtgtg tgtgtgtaca tgagtacaca tgttcatggg    29820
aaggctggaa ggttgcctcc ttgattactt ctctacccta gttttgaga caggttttca    29880 tttgcctgag acttaccatt aggatagctt ggcttgccag aaagctagaa ggatctgcct    29940
gcttctgcct tcctcaccct gggatcacag gcttgctgcc atgcttggct ttttatgcag    30000
```

```
gtcctgggaa ataaactgag gtcctcatga tgatgtagaa agcacacaac taaccaattt   30060
atccttttcc cacccccaaaa gagggaatct ttaaatgccc tagcaacctt cagcccacat   30120
ttgctgaccc acactatgaa attgactagc ttgggatgtc tttgtgtcca agagggagac   30180
gttctgaagg tcaaccgaac tgcattctat gattccaggc tagcagtgga tgggcccttt   30240
ggaggctctc tggcagatgt atttcactac cccgtgagcg tgtgcattgc aacgggaatt   30300
ggagtcactc ccttcgcctc tcttctgaag tctgtgtggt ataagtgttg tgaatcacag   30360
agcctgcctg agctgagcaa ggtatggaaa aatcattagg tcacccttcc atagagtgaa   30420
aggttcaaca ccctcaaatc tctcctctgc cgattcttgg ggaggatttt aattaactat   30480
gagggataaa ctcaaggatc cttaactata cttatgttct taaaaatctc cattcagtgt   30540
tacatttatg agcagggtta tgtctaatct tgttaaagat gacaagacat aaattttatt   30600
gcttcattgc cattacagga catgtaattg ctcatctcga taaaatgtgg acaggctgca   30660
aatggctatg tgactgggct gcagttagtc atattaacag gcgggcttcc ccctcacctc   30720
tttagctcca ctcagtggct gatggtattc aattccacat cttttctcca tggcctctac   30780
taatagacgt tgttattctt ttcacaatgg tgttgccaca tggcaccgag tcctcttttgt   30840 gatttcttgt atgttcttgg actaggcttc tccatttctt tgtcctatcc agtgtgagaa   30900
accatctcat actttgactc tcccaaggtg aaatgagcct tctttttccat ctcctgaaag   30960 tttaataatt gactctgtaa gatactctgt aattaacaga agaaaagata caccaattta   31020
ttgatgtgtt agctgatagg aaccatgcaa agttcaatac tcagagaggg caggtggtgg   31080
aagcctcaat agccttttct ttggctccta tgggcaagtt tatagtaagt gacttttagg   31140
ggagatgaat gagcctaaag aacaaatatt tggaacaaac cttgccgtgt tctgccaatg   31200
gtgtcaactc cctattctcc gtgagacctg gtattttaga aaattcagcg tctaggtcag   31260
cagcagagtt acacagaaag acccttccct gccctcagta gtggcaaagt ggggcaggtg   31320
atgaaggtca ggggaggaat tggttatcct cagctcagac cactcatcat gctaatatgc   31380
cacactctgg actttcattc tctgaaccta aacagtctta ggaccaacat ggggtactac   31440
aagagcagac gaaaagttgg atatgtatct tagggtttct attgctatga cttgagaggg   31500
aaagatttat ttcatcttag agatccatgt aatagtccac cttggaagaa agtcaaggca   31560
ggaagtcagg gaacctggag tcaggacctg aagcagaagc aactctaatt actggcttgc   31620
tcacctgtcc agggatagca ccacacacag tacactgggc cctcccacat caatcacgaa   31680
ttaataaaat atacaacaaa tctgcccaca gaccaagaca gtgggatcat tttctcaatt   31740
gagatttcct ctgccaaatt aaatctagct tgtatcaagt tgaaaagaac aaacagacaa   31800
acaaacaaaa aactagacag cacaccgtgt gaacagaaag tatggaaaca catgaggaag   31860
cagggcactt ggcaagttta gaactaatcc tggtctgccc atatctgctc tgtgtggccc   31920
ttggtcatgg cttcctacca gacctaaaga aaacgctgaa gtcagtaagt ggatcccagt   31980
gaatagtcat tacttttttct ttttgggggg gggagtgagg ggggtcgaga caggatttct   32040
ctgtatagct ctggctgccc tggaactaac tctgtagact aagcaggcct tgaactcaga   32100
aatccacctg cctctcaagt gctgggatta aaggcatgca ccaccactgc ctgtctcatt   32160 acttttttctt attgctctga tcaaataact gtcaaaaaaa caagggaagg gggacttgtt   32220
ttggatcatg acttgaggat ttagtccatc atggtaagaa aaatgtggca gtgagtggcc   32280
ctgtggcagt ggaagaatgt aagagctgtt ctctcatatc ttaacaggcc agaaagcaga   32340
ggctgtacag gatgcaggac gcagcaataa gccttaagct cctctcccaa cacaactcct   32400
```

```
ctaggaaagt ccaacctccc aaagatccca caacctctta aaacagctaa ggaccaagca  32460
taagaacaca tgagcctgtg gcaaacattt tacactcaca ctgttgcaca gcacccattc  32520
tatgggacat tagctgtatg atgtgatatg ctaaacagaa ttttaacacc taagaattgt  32580
tccttcaata cagaattcta gcagattcta gaattatctg caacccttc agacagtgct  32640 tatagaaaaa gaatcttaag aagtcttgat ccacccattc ttcccaaacc aatttagcca  32700
ttgaaccttc cttcatcagc tacatactag ggaattgtgt tctgtgaagc actgagaaaa  32760
atgtaaccca acgacccaaa aattggtgtc ttacctacta agaagaaga gaaaaattaa  32820 ctgtttcctc aggtccaaag tgacagatgc tggacatctg ttttccttt ggtcttggag  32880 ctaatcttca cagctgggga tcaggtgtca ggacacaaga gcctgtgagt aacattttat  32940
actcagacta caacacagta taagaattaa agttctttct cttggataca gaacttgatg  33000
tttagaaaga gtagagggag cttccaaaaa tattcaaaca atcaaaggca gaatccagat  33060
ataggtctga ttagttcttt atatgtcata gaatcagcac cttgtagaca tgacaccata  33120
tgaccctgga actcacctct ctctctctct ctctctctct ctctctctct ctctctctct  33180
ctctctctct ctctctctct ttctctctct ctctctctgt ctctcttct ctctctcaca  33240 cacacacaca ctcctgctct tgctctcctg ctctgtgtgt atatttgtgc acacatgcaa  33300
gtacatggaa tgcacacatt cttggaagtg catctgtaga ttcaagtttc aagtacagtt  33360
gcctacgttc ccaacacata catcagagcc agaggaaaga ctcaaacacc agccctcaga  33420
tatctctact ttttgtttca gacaggatct cctcagcaga ctatttggcc tataagcttc  33480
tagagattca tctatcttac agggaacaca ggcacacact gtcatactgg ctttttcttc  33540
gtaactgacc tcagaccctc atacctgcag ggcaataatt gactgactaa gccaacccct  33600
cagctccact ggtactgatc agagaatctg tacctgaatt ctgctctccc agaggctctg  33660
actgacagct atcactgaaa aaccataact tgcagtgcct ccattcacct ctttagattg  33720
ggattcctat tccatccagt gaagaagtaa gaattcatat gaaacatgga gggtatttt  33780 ttaatagaag aaggaggagg agaaggagga ggtgaaggag gaggaggaga aggggaagga  33840 ggaggggggag gaggaggagg aggggaagga gaaggagaag aagaagagga ggaggagaaa  33900
aagaggaaaa gaggaagaaa agaagaagaa aagaaggagg aggagaagaa gaggaggaga  33960
aggaggagga gcaggaggag gaggagaaga agaggaggag gaggaggagg agaaggagga  34020
ggaggaggag gaggaggagg aggaggaaga gacgaatact atgaaatgca gaattactgt  34080
ggggctagta actaccagaa ccagtctaca gttactgaag attttctacc caaacagtat  34140
agagctggac attgtacata ttttataatc acaatttta agtaatttct ctttatttcc  34200
tttattccca ttttacagag gacaaaataa acaccaatct caaagctaac aagaataata  34260
gattaggctg tcttgatgaa aataactact accctcactt caccaatgga ggacatgaaa  34320
cacagagggc aggtgaacag tagaattagg atttggaccc ttttggtacc caagccactc  34380
atttttaatt gttatttatt attattgtac tatgatgggg gtggtgccac agcatgcatg  34440
tggcagtcag agagcagcta ttgagagttg gttatctgta tccaccatgg gtcccaggaa  34500
tcaaaactgg atcatcagac ctataccaca aacactttca cccaccgagg caccccagtg  34560
gcgccaagcc tttctgtcct tcacagccag tttagcaaag caagcagaat agctttaaac  34620
tgcaggtttg aatctcagag tgaggcctta ctcaccttga tctttcagtc taccaaggaa  34680 aaccctgta taggggtctt gctgcatccc cgtttccatg acactcgagt cacatcatgc  34740
ttctcacaga gatggtatag cctgtgagcc tcactttcac ttgcccattc acacaacata  34800
```

```
tattcagcat ctactataag ccagattctc ttgggctaac acgtctctca catctgtatt   34860
gggacccagt ccagagctga cttaaaataa cttctctgct tttcacctcc cttcctttgc   34920
actgtgctac tgtttcagct agctcccttt tttgtattag catccataaa gcatcttatt   34980
gctctgaaca caccgtgagc tctttaaaac catcctatcc tcttcattag tcaatatgta   35040
gtgcatatct acaccagtga gccactaagt cagcaccaga gtgtgcgatt ctgatatcca   35100
cttcaatagt ctctgttaaa agaagtggca ttctcatact attcaaaggt taggctgaaa   35160
aattatactt aatacctaac tcctaagggt tgacctgcct ggtcacaggg ttaagatgtt   35220
tctgctcttt gaagcagctt tgtgtgtgtg tgtgtgtgtg tgtgtgtgtg tgtgtgtgtg   35280
tgtgtgtgtg tgcagctatc atcaggatta tgcaattaat atttgtcacg gctgtctaca   35340
tgcttttgag atataaatac tattccttcc actgaactgt cagcatctat ataatttga   35400 aagtgcagca gagcaaagtg gtgtgtattt atctaacagc atcttcacaa ttttaggtct   35460
aggccacagc ttccagattg ttatcattca ttacaggaag agagaaacat agcatagaaa   35520
ctcagagctg aaattttcag tgtaaattgt caactgcgat taagtagaat ttttctccta   35580
tggatacaaa aaaaaaaatc tggcatacat atttctatgt tgaagcctca agttgtaact   35640
gcacagcaga ggaaggctgc tgcagctttt tgccagtgtt actgctgtac acaatatctt   35700
ctccttcccc tcttccccc cctcctcctc ctcttcttcc tcttcttctt ccttagtaca   35760
cttttttttg agacagggct tatccctgca gtccagattg gtctggaact cactacacgg   35820
cccaggctgg ccccaagcgt ccagcaatca ttttgccttt gcctctgcct cttaagtgct   35880
aagattccag gtataagtca ctacgtccag ctacacagta gcttccttac tcttctcttt   35940
tgctgtgtaa ttctaaagtc cttctaggga aagacagact cctaaccaaa aaagatggag   36000
gttgtttctt tggctgatat aaagaagcac tgtctattta aatcaaacat tttaaaataa   36060
ttttctgtct tggtatttca agatataaag ttggttggga agatgatgtg gggaacaaag   36120
tgtttgccac acaggtatga ggacttgggt ttgagctccc agggcccag aaattcaatc   36180 cttgtcacaa gtgtctgtag tcccattgtt cctactgtga gatgggaggt agagatggca   36240
gacttcttgg aagctagcct ggagtacgta gttgtagggt taccgggtcc catgtccact   36300
ctgccacagg actctgccag ttggggaggc aggatgcagg agttttgact gcccttaccc   36360
agaactgttg ctgacgggt atcaaccgat cctggggtag gggagagcaa tctgaggaga   36420
gggacaacaa gacaaagcca gggctgtctg gttctcaggc tctctgacac tcaggcgctg   36480
ctagatgctg tggaaaggct gagaacagag tgggggccct caggctggag ctgagaacag   36540
agtgggggcc aaaggggaaa gaggagctcc agctgggtcc cttggggata gagtccttgg   36600
cttgtcggtc acagctggct tgagtttggc ttagtggcca tggctgggga cacagagagg   36660
cattctacgg gaagttacac agtggctctt taagcaaagg ccttctccgt tgttccccac   36720
aacggatccc actgcaaaga ggcagtccat ggttttaagg tatttattgt catagcagga   36780
gcctggttcc caggagctgg gtgaagaaac gctttcaaga cctccaggct tagcacacag   36840
cttactccac tttgcaccag agccttcttt ccaactctca tctcttccct caccttacag   36900
ccttctagcc ttagctcaac caggctgcct ttcagggtac tacaacatga ccaacaaaat   36960
aagaccctga tagtaaacaa actggaaggt gaaaacctga cctaagttgt tctctgacct   37020
ctacatatac ccaggcatct gcactcatac acacaaacac ccagcacatg cacacacatg   37080
atgatgaggg gggtggtagt ggtggtggtg gtgatgatga taatttaaaa gaaaaagaca   37140
gagagtaaat aggaagggac aaattaccta aggaagaaaa ataccttaa gcataatgga   37200
```

-continued

```
gaattgcttg aaagaagtga aaataaaagt tgttatgcgt tgaagagcta tttttagcac    37260
agaagcatag tcatcactag gttaaaggga gacaagagca gtggccctgt aaggtgaggg    37320
aagggatgag agctggaaag agggctctgg tgcaacgtgg agtaagccgt gtgctaagag    37380
tagaaaggcc ctgtagtggt aaaagttttc cgactcccag ttactggctg tgattaattc    37440
tacatcacac ccgatttgtg agaagaactc ttgaaaaaac ttaggacagt ttgcttgtgc    37500
aaactgtcaa gatgatgaat gaaataggtg tgtgtatgtg aatggggagg ggggaggctg    37560
ctgacataaa tatatcggct tacacatttt agttctcttg atatcacctc agtgtagacg    37620
gctctgaggg aagtgccaac tgggagattt ggttcatttt cttaactgca tatgtaatca    37680
tcagaataca ataaaataga ttatagaaaa gctgagataa tctaattcct tcataattgt    37740
ctctcttcat cagctcaata atagataaca gtgataatgg gtatttatag tgtgtcctgt    37800
gcaaaatggc ctttgggttc ctaacctaat ataataaaca gataattcaa ataaaaagac    37860
agcacgggcc agtgggagca aggcaagaac gccaagaagg acaaaaatcc atactctgct    37920
taaagatatt aataaaacaa agaggggcct gctccctttc ctaatgaatg aaaaatgcat    37980
ttaatttaat ccgtttactt tgagaaatta tttacttgca ctctccctca cactggagct    38040
ctggctaccc ctggaattga tcacctctcc cagccacaga aatcaacaat caattgagca    38100
aggtggctga agccatgttt gcttgtcata agcctgtgta ggagccctac tttcattagg    38160
tgacctcaaa agactccagt gccccactag gccttactct tgtcctatgg gaaggtagca    38220
gccctaaccc ttgcagtgcc ttgatttatc acacttgcaa gctttggtga ttattctcct    38280
tgtataagaa aagaattaaa taaaatgtat catttaaaag ctccctttat tgatctcagt    38340
tctcaaatta aatatagccc tggaagtccc caggggagtcg tcctgaagct tgtctcaaaa    38400
ccattctttt cattaccttc acatagtaga tggaatagct ggggtttgtt tgtttgtttg    38460
tttgtttgtt tgcttttaac atatacattt gtaggtgtac caagaagaga gagggagctg    38520
taaccaaagc acttgctttg gtttggacct ccattatacc atggcttgaa gctctgcagt    38580
atcgctatct aacaatctcc ttcattttcc tttttgtttt tattttttgca ttgagacagg    38640 gccttaatat gtagaccaga ctagctcaaa ccacagagat ctacctgtct ctgactgcca    38700
aggacagatc tgtacattga tggaatgcct ctgtgtgtgt gtgtgtgtgt gtgtgtgtgt    38760
gtgtgtgtgt gtgtgtgtgt gtgtgtacac caaggagaga gaggcaattg taccatttgt    38820
attaaaagta tgtgccacca cacccagcta tatctcattt tatttaagta ttccatagaa    38880
tactagtcca ccatcaagat aatcattggt gaatgcttca gtaaggatta ataactataa    38940
ttacagtagt cacaaagatg tctagtcatg gatcagatga caaactggta ataaagttct    39000
gagatggata acatgcagaa tagcagcctt aagaaaaaga atcttggggt gaaaaatgat    39060
ttacaatagc tgatctcagt cttattagta gtataccata aaaataattt tataattta    39120 ttgctttaaa gcagtacatt tttcatgttg gaaagtcttg taaataagaa ttttttaaa    39180 gttttttgtc tctgttatat tcattcagga ttgctctgac actaaaaaca gcagaataga    39240
acctgggaaa aaatagcagc tatttactgg ggagatggaa cattttctaa atggcattgc    39300
agtctctatc tttccaggga taaacgttct tattgctcac aattgtcact atgcagaata    39360
tccatcctag acctggcatg gagcttctct ttgttctatg tcatatgctc agtgaagaga    39420
cagaggtgta ctgtcagatg gaagcaggtc acactgctac cactgctctg ctccttggga    39480
agaggccatg gccaaagtac caagatcaag gccccctgtg aatgctgcc acagagattt    39540 agcacacaag catcctgggg tcccctttcc ctagtgaagg gatactctta agagactaca    39600
```

```
tcattggatt cataccaaaa tttcaattct acgactcaaa aataaggctt tgcctcctct    39660
caatggctcc atctctaaaa ttatttatta gatagtgaga aaaagaccaa gaagggccag    39720
tgtgcctgtc tgctctgagg tataaatacc ttatacctac tccactcatt tctcaaatga    39780
caggaagaga ctaccaatag tggcaaccac cttagcagct acagcttccc tcagacactg    39840
agaaggcgct cacaggctta tactctctac tttcacagaa acatcatgag tgatactatg    39900
cttatggaca tttattacac agtaagagag gctttagcta cacagctagc cccagttcca    39960
ccgcgcctac atggtgaagc caggatccca ggccaggaca caaaacctga ggtcccattg    40020
tgtttagtgg cagtgtcgtg cttctgtgtc tccctggaca cgccccttct ttgtatcagg    40080
ttataaacaa atacttctcc cactcattca tggttaacca acttggggcc taagaatca    40140 catgttataa atgtaactgg actgttgtgt ggacttctga gatagtatgt cctggaaaga    40200
taaattagca gttttttcctt tctttttttt tttttttttg tttataaata attttctttt    40260
tgcaaagatc tctctcctac ttactctgga tcattctgac cattacacaa gtgctacttg    40320 ggaacccttta cagaggagcc tgggctttgg aacatggaaa ggagttgaga caggacagac    40380
tatatcatta tgtatgtagc tcagacccag acataggagt tggatcagac cataagtgcc    40440
agcaaaagat agaaccgtga aaacctgatc caggccatgt gcacagagaa ctgtgtgatc    40500
tcagaatgaa ttcctctaac agctgaacct acactgtctc tccaaaaatg tagggtagct    40560
cttgttgcca cagaagttca aactttatt ttaccgactt tctgcttact gaaatctttt    40620
aaccttgggt attttagacc tctaatatcc acctcgagtt ctcaaagcca gctttgtgc    40680 agggagctgg ttttaggttt gttttacttt tggagagtaa ggtggagaag gcacagatca    40740
cagctttgca gcccattgtt tgggacattt gttcttccag tgtctgtgtc ctttctcctg    40800
ggccaaatac aggggtggaa ttctgatgtc tcttcacagt aagtgtcccc accatcagaa    40860
acatgaaaga gagttgaagt aaatagcct ttcttctgtt caaagtctcc tctttccttt    40920
gtctccctga agcacttcta cagggccaat gcattttctc ttcattgcct cttgcaccaa    40980
aaaggccagt gtccctaaaa gtcagttatg gggtgtgggg ggcagctcac aaggcaacaa    41040
caaggaagca aaggcatgag gcatgaaagg attcacaaac tcgaaggata ctggcacact    41100
gctatgccct gtgaaagcaa ggacaggaat attctatct gaaaaaaaa aaaaaaaaa    41160 agattagaat gtgaagaaag ttaagatgca ggcatctttt caagtgagaa aggtcaaagc    41220
aggctctgat atgagttttt attgttgttg ttgtttcaat aattatttt ggattaccag    41280 gctaacaaag tcagtgagtg ctccaagctt aatgaatcta agcttagaag gagattctgg    41340
gagaaacgtg aattgtggac tcgttgctcg tgaggtttta gaagatggca agagtgtaat    41400
taataataga tggtggggtt ttggtgtgat aattttggcta aaaattgtga acgatgtcat    41460
gttggaggtg aagaaacaac catgattatc aaaaaaaaaa aaaaaagct gtggttccac    41520 tgaggtaaaa gccaaacaca attcactaag acagtggacg ctggccatct ggggctacag    41580
agtcagctgt gatgaatcag atttcagtgg gtgggcacca ttcgggtgat atcttggaag    41640
tgtttcctca gggtcagccc acagatgctg tggtgcacag ctgtatctca gcctgtaac    41700 tgaacctaac actgggtgag agtcacccac ctagtagcca ttttgaaggc ataagagatg    41760
caagactggg gagccatgaa aacaggctaa ggcctacagt ttgtgccagg tcacacagaa    41820
gaggtcatta gggaagctat agccttagtt gtagtggagt ggagaccccca ggatatcaga    41880 aatgccaagg ctccaagaca gagtgggtat agtagaccct gagactgagc caagctcttt    41940
gtgctaagga cagagaagtg ggaaaatggt gcttgcccaa gctctctaaa atctgtaagc    42000
```

```
tcatgagtga gtccaagatt ttggacacag agctacagac cttaaattta tgctactgaa    42060
tttgtgttat tcttttttc tagttgattc tcattctctc tctgtctctg tctctgtctc     42120
tctctgtgtg tgtgtgtgtg tgtgtgtgtg tgtgtgtgtg tgtgtgtgtg tctgtctctc    42180
tctctccccc actacatttt ttgcttttat tgaaaatata ttgtgactgt ggtttcctct    42240
ccctctactc ctcccagttc ctctccacct tctgtactat gcagacctcc tcctttctg    42300 tctctcatta ggcttctaag agataataat aaaataaaat aaaataaaat aaaataaaat    42360
aaaataaaat aaaataaaat aaaataaaat aaaaatataa taatagaaaa ctacagtctc    42420
catgagaggg cctgtattct ccattccctc tggctctaat actctctttg tctcatctct    42480
tctgtagatt ttcctgagct ctgaagaaag ggatttgatg aagatattcc caattagggc    42540
tgaggttcca aggtctctct ctctccctcc ctctctctct ctctctctct ctctctctct    42600
ctctccctcc ctccctccat ccgtacccac ctctctctct gtctctctct ctgtctgtct    42660
gtctctctgt ctgtctctct gttttttctt tctctccctc tgtgtgtgtg tgtggagggg    42720
gattctttgt atttgttctc atctgctgca ggaggaagtt tctctgatga tggttgagca    42780
agacgctgat ctataagcat agtagaatgt cattatgagt cccttatca ataggttttt     42840 ctattttag ttttttggttg attggttggt tggttggttg gttggttggt tggttgggt     42900 tttgttgttt gtttggtttt ggttttggtt ttggtttttg gcttttggtt ttttgagaca    42960
gggtttctct gtgtagcctt ggctgtcctg gaactcactc tgtagatcag gctggcctca    43020
aacttagaaa ttcacctgcc tctgcctcca agggctggga ttaaaggcat gtgccaccac    43080
gcctggcttt agttttgttt taaggccact agtatttggt cccagagaga tctagtctct    43140
gactcttggt cacccaagca atgttggata tgagttccat cttgtagagt gggccttcag    43200
tcaaatcagt tactggctgg tcactaccat aagcattgtg ccaccattgc cctagaatat    43260
cttgcaggca gtacatctgt tcaaagactt tatggctggc ttggtgtgca tatttctcct    43320
tttttagttg ttttgctgggt acatttctgt atcaaagatg ctgaaacata gttctatgta    43380
ggcactagtt tgacgttttc atgttcaatg caatgtgtag gtgttttctt cagcaatgag    43440
acctcactgt caaatagtgg agtgcagcct gttgtcttgg aaacagcttc agttgttgga    43500
gatttccatg agactccttt ggccaacaac tcaattactt gctacccaat cctggtactg    43560
gaagcttcat ttgaagacaa aagttgggac tcggttccc cccaaaattt ggtgatttca     43620
cttagagagc actcatacat gtatatattt tatggagttt ctactgtatt atatcaaatg    43680
gcccttaatt ttcaagtaag agctagtgag ttagccagag agcaagccag ccagcagtgc    43740
tcctccatgg ttcataattc aagatcctgc ttgggtcctt gcttggtgc ccctcagtga     43800 tgggcagtga cctgaaaagc cagatcaacc atcccttcac catgcttctt ttgatttgag    43860
tgttttgcca cagcaatgac ataaaactag aacatcatct gacacctccc ctgcagggtt    43920
gtgctcaagt gtctccatct cagtgaggtc cttttgccac tgtgaccatt cccagattgc    43980 ctttttcta cactgcactg attaccatct aacatagtat atactttata tatttataca     44040
tcaccctcct tttccaagac acaaactcca tgaggatgga caatgtgtgt gtgtgtgtgt    44100
gtgtgtgtgt gtgtgtgtgt gtgtgtgtgt gtgtatgtgt gtgtgtgtgt gtgtgtgtgt    44160
gtgtgtgtgt gtgtgtgttt cggtctgtct gtctttctat ctgtgtacat gtgtatgtgt    44220
ctgtgtttct ctgtgtgtgt gtctgtgtgt gtgtatatat gtttgtgtgt cttgtgtgtc    44280
tgtctgtctg tccatccatc tgtctgccag tccatccatc tgtctgcctg tttgtctcag    44340
acattacgat tattccagag tgcaatttgg tatctgccca tagtaagcat tagtgctgcc    44400
```

```
ctttgttagg gaggactctt gggatattca acattaggca ctttaggctc tgttctgctt    44460
tgaagctatc tggaaggact atgaactata cactccaagg aatattatgg aacatgggag    44520
acgtctttca gtgataataa ttgtgtttaa ggtctatgac aggacttctc aaccttccta    44580
atgctgtgac cctttaatat agttcctcat gttgtagtga tcccaatgat aacatcattt    44640
tcattgcttc tttatagttg taatgttgct agttgtgaat cataatgtca atatctgata    44700
tgcaagatat ctgatatgtg accctcccaa agaaagggat ccagacctac aagttaagaa    44760
ccactgttta agggatctct ccttggatta atattttgaa ttttcatctg agcaggagct    44820
atccagcaaa taggcaacct ttgattctga gatgaaagga gattctcacc tcctgtcctt    44880
cctaactgct aacactacaa atcactgcgt aaatccaaag agaacccgca agatactgag    44940
ccttgaaata cattccttga tttctttttc cttgtgatac taattaaatc tcacttataa    45000
atctgattat atgatggtga gcttacaaac tgagagagag agagagagag agagagagag    45060
agagagaggg agggagggag ggagggaggg agggagagag agagagagag agagagagag    45120
agagagagag agagagagag aggcaaacac tggctctcag agggcgtgtt ttaggtgtta    45180
acacaccaga cagcacctag agtgcagacc aggctccata gaaactgttg cgcccctcag    45240
atgttccttt gagtggacag cagagaatag aaatgtgaac agatttgtgt cccatggttt    45300
cttctagcta gatacaatta tctgaaactc aaagcacaaa gctaagcctt tcttttagca    45360
accccaagct gcttgtcacc tgccatttgc tcaacacaaa gagagtgttt taaaaataaa    45420
taaataaata aataaataaa taaataaata aatatgaaaa caaacccca gaaacaattt    45480
cactgcgtct gctgacacat aggcacaacc tccacccacc tgccttggag gacactgaca    45540
tgtctcactg aagggaaatt tcagtcttgt gagactgcat tctgtaatta ccctaatctc    45600
cattctcaag aggctgtagc aggggaagtg gattagcgcc tgagcctttg ggggtctctg    45660
gagaagagag ctgaaatctc aagcttaggt cataagcaaa gatgaagggg atggcctgct    45720
ggctcatccc ctttgggaag caatgaaagg cacagagagt tgggattatt aatcttgttc    45780
agaagaagct tgtccagaag ctcggaaagt tgattctcat acaaagaggt tggcaaagtc    45840
catggaaacc ctgactcctt gaattcactc tgggcctttt caaatacaat gggatttttt    45900
tttctctctc aaaagaaatc tcggtgtgat tgttcactga tagagaaaaa catatggttt    45960
tgcagaagtg ccaatttggg ctcaaataat ataatggatg taaagtagcc tgtgattatc    46020
agcacattat ggaaagggga acagatgcac cctcctgtct tctctcctga caggtgtact    46080
tctattggat ctgccgggat gccggagcat ttgagtggtt tgctgatctg ttactgtcac    46140
tggaaacacg gatgagtgaa caagggaagg ctcatttact gagctaccat atatatctca    46200
ctggctggga tgaaaccag gtatcagaaa accgaggat ctccattact gcttccattc    46260
ttaaaagaaa cccatttcca taatgagctg gggacttatc aggcaggagc aaagaattat    46320
cctaaagttc cttaaaggga gagggaacg gaatcaagcc agactgaaaa caactactta    46380
agatgtagca ataaaaagac ctctagctgt tgggtaataa actgcagccc agatattagg    46440
actcttaaag ttcgaatttg tcatttaaat agaagaatca gtgtcttgtc attaattgcc    46500
tgggtcatct gctgaattcc taattgcttc tgattctatg ctgctcaaag gaaaacagaa    46560
aagattccat gttgtttctc tacagccttt catattgaaa agtgtgtgag tcagaaaatg    46620
actctggata catgatttac atagagagtt cttttctttta aaacatgcac cctgaatctt    46680
gccaatgctg aggtgacttc tgcttgggta ggtgttccac aagccgttgt agtaatgaag    46740
tataaaagct gagtttgaca aaaatgatgt gtgtcaatgt actgacagta ctgtttcaat    46800
```

```
cctgataaaa gttaccatga ttgggatata aatgacaact agggaatcag agtccagttg   46860
gaatctcaat atagccatga cactagttta tgaaaggcat gttttaaact gtgcatctga   46920
agaagatatt acatggtact gttgatgatg aagataatat tacatggtac ttttagggaa   46980
aatagattca agccaaggag ctttgaccaa atttacagat gattactcta tgagttctgc   47040
aaatattctc tctttctctc tctccctctc tctctctctc tctctctctc tctctctctc   47100
tcacacacac acacacacac acacacacac acacacacac acactgtcta cctccaacca   47160
ttgttataac ttgtctttct cttcttctgt aaatgagtaa gactctgctt gaggttcaaa   47220
atatgttttg gactttatg gccttaattc cagtccttct taaatattta accttctggg    47280
ataatttgaa attgcaggtt tcttgggaac tgggcttgat agatctcaat gagttatatg   47340
gtgttaatta ggttttccaa acaaacattt tccctatcca agcaggattt ttgactgatg   47400
atccatttgg tgaagcacag acgtggcttt tgtcgtttgc ttctgagccc ctgcctgttc   47460
ttccactgct gaagtaaatt ggtcccaagt gttcacttag ccaatccctg tcacttggga   47520
tttatgagac ttggaactct gaagtggatt ttgtgacagc acaactctgc cctgccctgc   47580
cctatctttg ccccttttcaa gactgagata taaaatgtcc ttttttttcct taaatgaacg   47640
taaattaaag ttggtagctt cttaagttttt cccatggcat gtcagaaatt cttcagactt   47700
ccaaatttca accaggaaat cactaatctc aacattgaaa gagttggtgc atttctgtca   47760
gttaactcaa gcactgaggg gctgttttag aaatagccca ttcttaaact gaatccaaca   47820
acctcagaat ggcaaattga caagaacaga agggacagat gggagtggta ctataaaggg   47880
caactcaaaa gagttggaga ttaattgaac attgggctga gaattatgga acagatataa   47940
ttccaaatgt ttgaacacca gagactgagt gttaccaccg tcttaagtag agaaggcctc   48000
cccgctatga gttaatacca gaatgtctta acaagcactt taaggaccat cttaacctaa   48060
cctgtttcaa ggcaagcctc actgtttttc tatggcccca gaactgtcga ctaatggatg   48120
cttatgtatc cttcagtgtg cattcaggtt ttcaagtctt ttgctcctgt tgggtccact   48180
ctccaacatg tcaatcaaga ccccccctcca tttccccacc ctcacacagc atggagtact   48240
gttcccaaac tcttttgcaa ttacaaacac tgttacctaa gctcagactt gcttggtagc   48300
agtatctgca gcctgacatt ctgaaggcca gtctgccctt gtccactggt ctgttagggt   48360
agccaccata acttggatat gaacctccag cactagctgc cttcttgtac taggaacaaa   48420
accattcagg ctagtcatat tcaaagcagg tagccacagc tcgagttggg catagcaagg   48480
ctattattga aactgtcaaa actaagcaag atttagagag tgagagaaaaa actgacacat   48540
gagttttcag agctgatggt tcccaggaac agctcagagc acacatacct gaggcagggg   48600
gaacaaggta gcttctagaa ttcacagcag ctaaagtcaa tggtagacct ggagtagatg   48660
tttataatga gtattgtgcc ccgggctctc atatacaaac ctctaattac acggtgactg   48720
gatgagttca ctgggtttga aggcagtcac tttcagagct ccaagcagac cctgcaatgt   48780
tccctgtccc caacatcaca tcaccacctt caagtatagc ccccaacact tgaaacctaa   48840
tactatacaa gttggctatc catattgttg agttccacat ctgtgtgttt aaccaactga   48900
agactgaaaa tgttgggaaa aaaatacatc tgtgttgaaa acatatgtcc atcttattcc   48960
tttacattat tccctaaaca gtcgaggaca actctttttcc tagttgttgt atggaagtaa   49020
ggttttatag accatctaga tggttttgag aggatgtgag tagcttacac acaaaattctt   49080
ttgaacctct gaagacgttg gtatctggag aagaggacag tcctaatatt tggggatgac   49140
cacccatcaa accatgtcaa ctcaataggc agatctgact gtaagacaca gcttcttccc   49200
```

-continued

```
gggtacttca tggcactttta gtctggaaat ccccaagtcc cctgaattaa atgaatggga   49260
ccatgaggag aagactgatt tttgagatgt tatgcaggaa gaaaactaac ttgggtaacc   49320
acatttactg tattaccctc atcctttaag aaaaaaaaaa tcttttcaag ctctgcctct   49380
gcttatctac tatgtacaca aaagtgtttt gtcccaacaa agacagatga tacctaacac   49440
ttgtcctaaa gcacaacatt gaaggcagct gttaataaag catttcaagc cgtgtttaaa   49500
atattttgaa cacacaagtg atgatagtga gtttatcttt tatttataga tggttctcat   49560
acgttttata atgtcatcta aaactacaat ttttaattta ggcaattcac atagctttac   49620
actgggatga aagtctggat gtgataacag gcttaaagca gaaggctttc tatgggcgac   49680
ccaactggaa cgacgaattc aagcagattg cctacaatca ccccaggtga gcaaagcaag   49740
ctctctctct ctctctctct ctctctctct ctctctcctc tgtctgtcag gatcctccct   49800
gaagtccaga caagctgtca ctggggagag agggggatga gggaggggg ttaatctgaa    49860 gtcataactg agaattttga tccaagactt ttttaaaaaa atatctacct tagaaaatat   49920
gtccatgact ctcttatatt tcagaaacca caaacctctg tttaactggc tgacagattc   49980
agacaattat cgattatgtt cacacttaac ctcaatttaa agttggtatt tcttaaacag   50040
catatgtctt caaaaaaatc ttttcagcag acttagtctc taattaccca gctagagaat   50100
tcatttctcc ccagctctac agtgtgtcta gcacatctag caaaaaagca aagagaaaaa   50160
gtgttctcag acagagtgga ggtttgacat ggtgctaaag aacccagatc tggagctggg   50220
gtatttaagg gtctaccctg gctctgccat tcccatgggt ataccttggt catctaataa   50280
ccctgtgatg acctagtctc ctcctcctct aaaaaactgt aactaatact gcttgcctcc   50340
caggattctg caagaaaaaa atgaatgaag catctaaagt gcctgataca acatctcggt   50400
tagggtttta ccgctgtgaa caggcactgt gaccaaggca actcttgtaa ggacaacatt   50460 taattgggc tggcttacag gtcaggaggt tcagtccatt atcatcaaca caagaacatg    50520
acagcatcca ggcaggcatg gtgcaggagg agctagaatt ctacctcttg ttccaaaggc   50580
aaacaggaga agattggctt ccaggcagct agggtgaggg ttgtaaagcc cacatccaca   50640
gtgacacact taattcaaca aggccacgtg tattccaagg ccatacctct taatagtgcc   50700
acttcttggg tcaagcatat acaaaccaca catacagcaa tctttctcaa ctgccactgc   50760
cattgcttcc atcaattcga ttatcactac tatcatccta accatacaat gtacttcaat   50820
gcatggagga ccttgccatg gggccacaag actagggtac aacctctgac tcccggttct   50880 agaatttttcc atctacatga cctgggttga acaaggtagc ttatttcagt gtatttaact   50940
atattttggg tgtaaatgca aaacacaagt gataaattca tgctcagtgt tgttttctta   51000
agttagcaca tacagtgctg aagagctggg taaagtgtaa gtcgctacga caaagcacta   51060
tccttgctcc taggtcagtc tttgtctgga accttcatca tctatagcat gcactgtctt   51120
catatttgag gaaagagtga aagggaggaa agggagcaac tagaaatgaa caagagccaa   51180
ggccctgagg caagggacat tgttcctgtt gtgattcgat ttgggaggcc agtgggtgga   51240
acagaggcca caagaggaag tatccccaaa gatatcattt aaataggtgg acaggggata   51300
cctgcaagga atcataagac tttggatatg attctcagag gaatagtcac ttagaggtac   51360
aagctcaaga ctggcatgaa agtcacccctt gttactataa gaaaacagac tgcagtgggc   51420
ctaggagaga ggtgaggagg acgatgggga acaggcaggt ggggagcact ggaggaagtt   51480
gtgaagagcg gtttgattct gaacattttta tggaggctga acgggcatga gttatagatg   51540
gactggggca cggacccaag ctggaatgaa ttcccactca ttagcatgga catgaccgtg   51600
```

```
agaattgctg tgtagaagac acaggatatg agaagtttca tttttgatct ttagcttaag    51660
atatgcctta aaaattcaaa tatccagcaa atgatgcctt cagcaggatt tggggtgaga    51720
acctcagctg aaggtatctg catgtaaact gtgtgtggaa ccacaacacc aggataagtg    51780
atcaagagtt ccaagataca ttatattcac gaagcaagaa accataattt ctctctctct    51840
ctctctctct ctctctctct ctctctctct ctctctctct ctgtgtgtgt gtgtgtgtgt    51900
gtgtgtgtgt gtgtgttaca aagtttaaag gacattacta atatttaccct tagcaatcaa   51960 gccatctggg gctttctgac ttttttaatct gtcccttttta tcgctaaatt aaaatctact   52020
cctgtgtctc tgacgacttt ccgttcttcc tgattgcctg tgtgttttct ctttggcttt    52080
ccttctgaga actcatgctt cattaatctc tctctagttc cctgataacct ttttctactc   52140 agtggaattc ttttatggtg agtataaatt catcttttgg tcaattcagc tccttttccat   52200 attttttcctt atattttctt tgtgctagaa ctatgccttt ctatctttat gagctgcctg   52260
tgtgtctgtc tgagttcact ttggatgagc aagggaagaa ggaagtatcg agtagcattc    52320
acagttcata agcatccaat tgcagtatcc ttggtccatg tgaagtcact tggcttctac    52380 taccctagt gctgagagac agaccctctg caaaccagga gtacagcttg tgctatgaca    52440
gccttctgtg gaaaaccctg cattccgaga atgttctgtg agtgagtgtc tcaggcctcc    52500
tggtcataca gcagaggaga gaaattagta gtgacttcca tcagcctaag aggggcagaa   52560
ttctaagagg agagacagga aacatcttaa cttctagctg aaaagtcaag aggaggtaga    52620
tccatcgcac aatgtggcag tctagctttt tcccaccaa ctcagcttta ggtgccctca    52680
cagaactgct gaccccaagg caagtggcct tggcagctct tctttgtcat caaattctgg    52740
tgccctcttg tttactttgc ttccttcctt ggctcttgtg gatgctcagc cttggatcca    52800
gttctggagc accaccttgt ctctaaacaa gagactccat tccaaacacc acccccatcc    52860
cacaagagtc ctctaagcat ccgctcaaca atggatgctg gatgtcaacc tcgtaagacc    52920
ctctaagccc tgggagaagt gttccttcac ctgcacctac ctcgttcttg accagagcaa    52980
atgcagtaat ttcatgaata tgcctatatg taagacctaa gtgggtttgt tactattttc    53040
tcctttggga gaaaaatata gttttgaaca aatttatacc tcttgttttc actgatgaca    53100
aaatagattt cttggctccc tatgggtggt gggggtggca tgtacacata catgtggagg    53160
ctggaagaca acagtgtgtg tcattcctta ggcaccgcat ataccagta ttttggacag    53220 ggtttctcct tactagccca gagacctgtt ttccaagtgg gttgggatgg ctggctaatg    53280
agcctcaaaa attcacctgt ctttacttcc ctagcagctg ggataacaaa cactcatcat    53340 tgttttttg taaaaacaaa cctggttttt atcatatagg ctctgaggag caagctcagg    53400
tctccatcat ttcaaggcaa gcattttctc tatgagatac caccctaccc caacttcaga    53460
ctgcaggctt ctgaaacata catctttaaa ttcatgtaaa tagctccagt cttcacagtg    53520
atttccctac attgatactg cattgtgttt gttttatca taatataaac ttgatggccc    53580
aatgcagaaa gcctttcaaa tcaattcact taatcatctt tcttcacttg gagagtgtga    53640
gccagaagta caagaaatca aaggcaaaaa cgagccttgt gcaatccctg ttcagaaaaa    53700
tgctatttca ggtgagcctg tcccatgtgc atagtgactg tccaggacag ttttatctaa    53760
gctgggaaac atgttcaccc cataccgaaa cacccccctc ccccatcaaa gcacacaatt    53820
gcatggaata gctagctatg tttctcatta tggtagctgt gcaaactctc tttctctggt    53880
gcatgattct atgtcgtcca ggagagaaga gactcctggg gttaagtcat ttcagaacca    53940
agacactact gactacttcc tacctgaaaa aaaaaaaatt taatatcaga tttgtaaaag    54000
```

```
cttgagactc cggaacacgc tggcttatta aattgcttca agcatcaata taattaatat    54060
tagataaatc gatgcaaaat caatcattgt ttcatctctg gaatgccagg tccctggaag    54120
cctgcaaatc tccagcatca agctcagcac tgcccgtcta aagactttt aaaatgacct    54180 cccgtaaaat aatttttgt ttttcttctg cgtaaaagga gatttatgct taatgaagct    54240
tttaatgaag aaattacaga aggagaatgc caataaaatc taattcttaa acaagaaaat    54300
ctaatattga gaagcattgc aatatgctgg cctttgtcca gattgaaatg aaacacaatc    54360
caatcactgt tcggcacaaa ggacaaaata acattaattt tcttcaagat ggttattaga    54420
gagataaaca gtatgttctc ccctatcgt gtcacagaga tgtttgttcc caagcccact    54480
tggctactct cacaaggccg gcttgtcctg caatattagc ttgtatcttt tggcaaagat    54540
aggccaggaa gaattgctgg atttgttagt agcctcagaa aagatccttt gttccccagg    54600
gcctttgaag taggctctcc accatcggag cacaaagctg ggccttctta gcactaactc    54660
ctgtaatcgc atttacctgt tcactcaaag ctggagtttg ctcctgtcct aagaaagagt    54720
tgaatcaaaa gaatggaggg gaaaggaatg caaaaaaatt ttataggaca tgaaaaaaca    54780
ccaccaaaaa taaagctgga agggaagcag atcaaagcgg attgagcaag ttctgaagga    54840
accagaaaat tgcaaaaata acagtaatag agaaacaaat tgatggcatt agaacgaata    54900
caaatgagga acaggagagg cggttttaaa atagatcaaa ggctggaagc agaaaacagg    54960
gaagcacggc ctgctgtttt cttcggtaat taattttggt aattatacca gttgatttac    55020
agaaacacga ggatagtgct aaagacagt caacaaatag caaatgagtg tacatttaaa    55080
gaggtcattt cttgctctgc ccaaactctc atacatgtga caattgtcaa ttacatcaat    55140
tatacaagca cagaaaagta ttcccagcat acagtgggag tcgccctccc attaaagtac    55200
aataggctaa ttagtgcatg cattgacacc taggacttat gaatctatag aaatgtgtct    55260
tatacaaaaa tggaagctct gtttcatttt ctgtaagcat tcttgatatg ctgccaacct    55320
ttagacaagt gttcagaatc agaaaatcat tttcaagaag acaggcagag tgaaaataaa    55380
catagttttg tcatttctag ctatttttt tgacaaacac acattgtaca tccactcacc    55440
catgtggacc tgtggctcag ctattgttag ttaattgact aagaagcttt tctgtatggt    55500
ttcagtcttt gatcttacac ttcggaaaat atttatagtt ttctacttct gacttatctg    55560
ctgatatctt caccatgcct tataggtgtg aactttatgt aattaattag cataaaaact    55620
tttgagattt ttcccagttt tcataacttt aataagaact attgtttaat aatgaagagg    55680
aacagagaaa gagggatgtc agcacttgtc aggacacagc cacccggccc agacatgaac    55740
aaggtgtcag cttactatac aaataagggc acttctaatc catatgacat gaatgtattt    55800
tagaccccca ttgttttcaa atatgtaaaa aaaaaatacc tacctttta ctaaattgag    55860 taaatgtgtc catctggagt tacatttgct tgtgtgcata cccttcagtt ctcatttgta    55920
catgcatatg tgcaaatatg ttgtaaagtg atattttag gaaattagca ttctgattat    55980
agtataccag gtcctttatc taacagggta tcctaaacat tcattatatg actaaaatgt    56040
gcagaatact caaagaaata gatttaaatg caaatccagc acatgataaa ttatagcttt    56100
ataagaaaag taaagcccca taatgcacat tggaaatatt gtccccacag ctaaatgcta    56160
ccttttccac cagagaacat ccagctcact ggttatagcc gagtaaaaat tccatgaaaa    56220
ttactagcct tgtttgtcgt caggggacta agaacataag taaatagaaa gtggagttat    56280
tactctgtta acttactttg atggcattat tccagtaaat taaggattgt agaaaatctt    56340
ttgatatttt ataggtttac atgtcttagt agagcaagga taagggaaaa gataggatgg    56400
```

```
agaaaagttg ttccaccatt ttctgggacc caatactatg aatcaactag ttttctcctt    56460
ttcccccctcc tcctcttcct cctcttcctc ctccctcttca ttctcttctt cctcctcctt    56520
ttttctttct tctctttctc ctccttttt cttttcctcc tactcttctt cccctactct    56580
ttctcctctt ctttctcctt ctcttcttcc tcctcttcct cctcctcttc ctcctcctct    56640
tcatcctcct cctcgacctc cttcccaccc ccatcccata agggcaactg ctttattcac    56700
tcatatctac tgctcagcat gaacaagtga aaggatgatg acgtagagga aacagggatg    56760
agaatcctaa gtgtgcagtg acagtcttat ctgtcaaaag ggacagtttg ttggaaagtg    56820
ggaaaagaag aggcacatgt aagttttgtt agtaacatct gcagcccag ataaacaact    56880
cagtaaggag aacactgcat tagttacttg tcttgttgtc acgaccaaat atctgacaag    56940
aagcagctca gagagaagga gtttatctgg gtccgtggct tgtggaagca gctcatcatg    57000
gctgcagaag caggaggtgc ttgctcacat taatccatag tcaggaagca gaaagcagta    57060
tggatgcctc tgctcaactc gcttcctcct ttgtgttcag tctgagaccc tagcccatgt    57120
ggtcagtctt tcttcctcct cagttaattt tctctaaaac attccttcgg acctccccct    57180
aaggcgtgtc tcctaggtga ttatataagc caagttgaca atcaagattg accaccatac    57240
actgtgagaa ggtcaataca gctggctgct gggcagtgac tatgatgtgg gttagaaagg    57300
gagagaactg accagcacaa ctatcatctg tagttatgaa aaagatggtg ttgtataaaa    57360
tgtaattatg tgataaatca tttggaggca tttctaatga aaacattcc ctgggaaaga    57420
ttaagcagaa cttgtgtgtc cactgtctga aaccgagttt gtagctctcg ctgctgtcgt    57480
cctaagcctt cataaatcca caggaagctc ctgtttatcg atttatttg cagaacacac    57540
tccgagtata aagtaatttg atttttttta acagggttta gggtctgccc caacagggtt    57600
ataacttacc aagcataaaa gccaacacat aaaagcaaac atacaattta aggagaaagg    57660
ggctcatgcc agcagaatca gcgaatcagg gggtggtgag attaccccca ggcatatcca    57720
tgcacccatc tatctgtctg ggaatctggg ggtgaggctg gcaagattat tcccaggaac    57780
accccccatgc cctctaactg ctgggctgaa atctcctggt gagtgatctt ttggatgcct    57840
ttcatgcata gtgttgctca actctttga gagaaaaaac aataataat cccacagaga    57900
aaaacatagt ggttatttaa cagacacggg gcgggtagag agagaacctt ctttcctgtt    57960
tatcagagca ggaaccgttc tgtggatgtt tttaaccatt ttttttcact ctctgtgaaa    58020
tcttcccttt tgtcatcaaa gtcagccact cagactggtc agtgccatct atgagtgtta    58080
tccatgatcc aggtctgcac gcgtgtgcaa gctctgcttg caggctgtaa actgaggat    58140
aaatggtgtc tcacgatttt atacttcttt tgcacagagt cttcgttttt aactctaagc    58200
aattgtggat aattaaattt ttatagaagg aatttttttc tttagcaatc ccattagggc    58260
tctgttgtac ttgtccattg cctcataaag gaaaaggaa gaaaaaaaa aaaaactgcc    58320
acatctgtgc cttaaccatt ttgtgcagat tctctcccgc tccatagttt atgggatgcg    58380
ttcatgaccg gggaacccta tattggtgcc ataaatgcca aggctggtaa aagcaggaga    58440
gcagcagaat gccttacttg tgaagagaga cggaataagg gatgagtgcc aggtcactga    58500
gggcagatag caaatggcct ctgtgagact ttctggtgac cacataaccg tggtagctat    58560
gagccccaag gacagaacag tttggtttta gctggacagt gcaagagcca gagcctcagc    58620
ggagcagggg agttgtgaac cactggaaat cccagtggta cacctgatgg cccaccatca    58680
gaatgctttg aaagggactc ataaaggcag ggcatcaaag aacaccatca acttctcaaa    58740
ctttgactct ggctataaat gaaagggcag tcccaatctg tgggaatagg caacctcttt    58800
```

```
gttgactttc acactaatgg ggaaaatttc aaccccccac cccataacag cacctttgaa   58860
acagagtaca aggacaccct ggcaggatac ccacagcaaa ggtatgactc ctcatcagga   58920
aggacctcca tctgacctct tccactcaga tgtttttgtc cagtgctcaa aaggccaatc   58980
cccataattc tcctgcagcc tctgtgtcca cccctactt cccatcttct gttcagctct    59040
gtgaacatgt gtgatactga tatctgagca cgaacagcta cagagaccac catgtaccaa   59100
gtacagggcc acagcagggc cggccatgcc tcccttcatc ctcagagaaa gcttgggac    59160
acagaggaga ccttgagagg aaaggtctct aatgctcctg attatatcta catgacgtga   59220
tagaactttg aggagataat taatgtgtcc aaagctcatg gcagccaaat gatgaaaca    59280
tcagtctcct taccagttgc ctcctggttt gagaaacacc tggaaattac ctcaagtcaa   59340
attattcagt ataaaacatt tgggggggggg ggaaagatac tttcacaaat taagtcccag  59400
atatcttgga aagtgacact tagacatttt aaatgtgttc tcatttgtag gtgaagccat   59460
ttagtgaatt ctcttgaagg tagttttaaaa tgtggttaaa ccatcaccgt ctaccatggg  59520
catcatggtc tggggacatg ttgttaaaat aggactctgc tatatgatag agaaccacac   59580
tactatataa gctagggagc aaggctatac acgaacttac taacaaaagt caggtggaag   59640
gaagagaagc agtagagcgg gctggccttg gatctgaaga atttctgagg cagtatgtct   59700
catagggcca tctgtctcag tattaactgg cttcatacca aacatattct ccatggatct   59760
caaccaaaga atctcaatta taacaagctg cctaatgatt ttatacatgg taatgtgggt   59820
acttttgatc taggctagag taagtagttt agcttatgct gaagattagg aaaagaaagc   59880
accacagggc acaatgatgt agacaacaag ggaggaaagc ttcggtcttt gtattttca    59940
atagggactg gtgtgacctg aacacttgaa ccagtccttg gcctacacag gagactggag   60000
tgctcttgca atgcgaagca aatctgtgcc ttctacacta ttttttggaag tgcaaggatc   60060
aaaggtcaca ctgtttggaa gactgggtgt tcagcaatgc ttgtctctgc catcttgtac   60120
tttaagcctc ctttgcaggt tgaattctag taggagaaat aagtaagttg ttgttacttt   60180
agatatacat tttattatct ataaaaatgc caaggttgaa caagatatta gtcataacaa   60240
acccttctat aataccttt gaatatactg ttttattttg ctttcattaa aacacacaat    60300
gtaattgtta gctttagatt acatatgtaa gacctccagc cctgcccaaa actatgcagg   60360
taataaccca catgaccatt tacacattcc ttcagcaaat gtatggtttt tgtctactta   60420
agctagacac tatcccaggt tctgagatga agatgatgag tcggaagttc tgatttacac   60480
tttagccaca gatccaagaa gatgttgacc aacttcacct gaccaaaacc cgactgtatc   60540
acaaatcccc tgtgctatta tcaagtacct gcccagcctc tgccttcttg agtttctagc   60600
tcctgtgagt ctggggatca cagggctccg gaaagcttgg ctggagcaat gtactgcaaa   60660
caggaaggac tcttacaaaa gaagtggaca gataagaaaa taagcaaatg gcctcgctag   60720
catgtctgct tcctaattga ctaggcctat cttggcttcc tgctggcctt gcccaggtaa   60780
cactctctcc ttttcttatc cccctccag cagcagcatt ggcgtgttct tctgtggatc    60840
caaagccatg tcaaagactc ttcaaaagat gtgtcgtttg tactcatctg tggatccgag   60900
gggcgttcat ttctattaca acaaggaaaa cttctag                           60937
```

<210> SEQ ID NO 24
<211> LENGTH: 58965
<212> TYPE: DNA
<213> ORGANISM: Homo sapiens

<400> SEQUENCE: 24

-continued

```
atgatggggt gctggatttt gaatgagggt ctctccacca tattagtagt aagtatcatt    60
tttgttattc aactttaaat atatagattg aatagtcttt gattttagg aaaacttgta    120 taggaacgct aaatagcttg aagtattact ctagttaaaa gactaaaact tgttagaaaa    180
cattcagtag atgtatttaa tttcccctta tagaatcatg caaagttgtt ttccgattga    240
gctcattttt aattattttt aaagtcaagt agtttgtttt tgcataatgt atgagtgttt    300
ctctaaatca aatgaagtct ttgaattaga ctatgaaatt ggaacttttc tagagaactc    360
tcggagttgt ttttaaagat ttcttccttc ttgacatcat tgtcaagcaa cgttgattaa    420 gaaggtttg tagtttcatt aaatcactta aagttgactc atatgtgttt aaaatcttt     480 taataaaggt aataatgtat taccatcata atcctattaa aaactaatct atgagaaata    540
aatatgtgga gtaattctga ttaatattga gaagctcttc attccacttt aaaagaagaa    600
ccccaagtga ttttgaatag agaaaaagct tgaaggtagt aatcattggt tctctttcct    660
ttctactcta gctctcatgg ctgggaataa attttatct gtttattgac acgttctact    720
ggtatgaaga ggaggagtct ttccattaca cacgagttat tttgggtgta agtacagttt    780
atgattaaac attattttt cagaaaacaa aatgcatttt attttccctg gatccttgtt    840
ttccctgaat ctctttttta tgtctttaca tgtggacagt caacactggc ttgggcacga    900
gcatccgcac tgtgcctgaa ttttaactgc atgctaattc taatacctgt cagtcgaaac    960
cttatttcat tcataagagg aacaagtatt gtaagtacta aaatatctga ataatctca   1020 actgttacga cttcctcata taagtgccat tgaaaaaaaa tgtactttat tatgaaattc   1080
tcagtaattc tgtttaaact tgggtttctt tgttagagat aacagaaagg ctaagacaga   1140
aaaacggtaa tcagtacatc tatctgattt ggctttggct gttgccattg atttcctaca   1200
tgacactcaa ctcattgcta aacagtttcc tgatatattt gccccatgaa gatggaagca   1260
ttataatagc tggaaccatc attgtttctg actgaaagaa gacagataag cttttgagac   1320
aaacgccacc aggaaacatc tctctgggtt ctcacccaca aaagcataat cacagtacat   1380
agattttatt atgtagattt taacctctac caaacataat gggatatttc tcaattatat   1440
tgatttcact gtgttgggaa cttacctgtg cttcctgtca aacaaaatag catgcagaga   1500
atgagacctt caaaaacttt taccaggtaa aatactgtat tatgcaggca tccctcatt    1560 tattgcactt ccccttattg ttcttctcag atactatggt ttttacaaat tgaagacttc   1620
tggcaaccct gtgtggagca agtatactag cgccattttt tccaatacca tgtgctcact   1680
ttgtgtctct gtgtcttttt tagcaataaa gtgttttta attaaagcat gtactttttt    1740
tagacataat gctattgcac acttaataga ctacaggatg gtataaatat aacttttata   1800
tgcactggga aatcaaaact tttgtgtgac ttgcttattt gcaatatttg ctttattgca   1860
gtggtctgaa atcaaaccca caatatctcc gaggtatgcc tgtataatca tcatcatgat   1920
tttatgaata tttatatata gatgcatatt tgcctttgta tatgtaggaa taattttcag   1980
actacctaaa acacatgaat gaggatgatg gctattacct taaattttta aacaaagaag   2040
ctgagtgagg catgtatttt ggcaggctta ttcaagagtt ttgaattata aacagagaac   2100
taataagtca atcattttg agttgagagt tcagcaaagc aactaataac cttttgattt    2160
gcctgtttga ctaatggcca ttaacttttg tgtcacatag ccccacttta agcagtttag   2220
aggcagagcc tgattcctac tctcttaact ttcatgagat tgttttcact gcaatttttc   2280
cataaatcag gcatattttt ttgttactct agtgctgcag aggaccgtgg aggaggcaat   2340
tagacaaaaa cctcagattt cacaaactgg tcgcctatgg gatagctgtt aatgcaagta   2400
```

```
agtacttatt aattgctcaa tggatttttac aatatctgat gcctaacttc atagttttgt    2460
tttaactctg ccttccccaa gtctcaccct caggtaaaag aaaactttgc cctttatctg    2520
accctgtaaa ccttacacaa atgggttttt acattttcaa tttatactta cctatacgtt    2580
ttccctacc aagacctcaa ttggtcaaag aaaagttggt gaaacttcat ttgcgaatag     2640
ttaagcttgt taataataca ataataaata cttacttgaa aaagggacac tttgttattc    2700
aatataattc actttggaaa taaaattgac ctctgttcaa aatctcattc acagtcgtag    2760
gaaaatgact gtcaaatagt attgtgggca ataaaaaaga aaaagaaaa gaaagatcat     2820
gtgagccaag ttctgaatca tagtgaggta atggacataa aagggtcttg aaaagacatg    2880
aagctttatc ggcatataaa gtgttattgc tattattata tttctaattt aagaggaagg    2940
cactagaaat tagcacccaa ggccaaggtt aaactctgat gaggaagaaa ggaggaggag    3000
cagtcatcaa ccagcttgtg gttttgctgg aaaacaaaga cattgaaata aaaggctatc    3060
tgagcgataa ggagttatga ttcaggactg tttctctcaa actaatttaa ctataaaatg    3120
ttttcctcat ttgtttttat cctctcatgc ataaaaaaaa aagcagagta aaggaacac     3180
tcaaaacaaa tgtgaattta attaagcaac aagacatgac agacggtgcc cgagtgccaa    3240
ttaacacaac tttggggggtg cagtgagaca tgaggggaag atgctcccag tgactgtctt   3300
caacgctgga ttaaaccaac ctgagaactg ctttgtaaaa ggtctttgtg gtttgttagg    3360
aaataagagt aaaaagacat cgtgtcctag agaaaaccag ctcagagata aaggggagga   3420
aataaggctg gttcatcttt gtattccaag gcccacagta gtgctgagta tgcgtaggca    3480
ccaataaccg ttcatgaatg agcgaatgca tgaaggaata aagactcagg gaaagaaatt    3540
ttggctcagg aatggaaatc tttccgcac cttgaaaatt atctaaaatt agaatgaagc     3600
tcccctaaga atactgaatt ccccatcatg ggtgatgtcc aaacagagac cagatcgctc    3660
cttgataggc tcatcacaga agcaattcaa ggaatctcca ggcttccttt aaaatcttaa    3720
atagcttgat ttctgcataa cacagtaaaa tggcaagaat attatcacaa tacaatagct    3780
ttaagacaga cttgaactct aagagaaagt tttaaagata ttacagagag aaggggggaaa   3840
aaaacagcca gcatcaaaag acatcagaaa agaggccggg catggtggtt tacgcctata    3900
atcccagcac tttgggaggc tgaggcaggt gaattgcttg agctcagaag ttcgagacca    3960
gcctgggcaa catagtgaaa gcccgtctct accaaaaatc caaaaaatat tagctgggcg    4020
tggtggtgca tgcctatagt cccagctact tgggaggctt tggtgggagg atagcttgag    4080
cccaggaggc gaaggttgca gggagctaaa attgtgccac tgcactccag cctgggcagc    4140
acagtgagac cccatctcaa aaagaaaaaa aaatacaaca gaaagaaag caaagaataa     4200
gaaaaatgtg ttatgaaata gttttctcct taaacttttg gcatgtaca tttctttata    4260
tgtaatcgtg tatcaataat accaatgcat tagaaacgta taatgaatat cccccgtgtt    4320
aaagatacc tgaaagcagc tataactttc tgaaactagt gtggtcaggg ctgttttagg    4380
atggagtata atttagtata agcagctgtt gactaaaatc aggtaaccaa attattttat    4440
acccctgcta ctgattggta gtgtgatatc tgagaagttc ctcatgctct tcttctgtg    4500
gagttaaaag aatactaata caggccgggc gtggtggctc acgcctgtaa tcccagcact    4560
ttgggaggcc gggcgggtg gattacctga gatcaggagt tggagaccag cctgaccaac     4620
atggtgaaac cctgtctcta ctaaaaatgc aaaaattagc caggtatggt ggttcatgcc    4680
tgtaatccca actacttggg aggctgagga aggagaatca tctgaacccg ggaggtggag    4740
gttgtagtga gccgagaatg ccccattgta ctccagcctg gcaataaga gcaaaactct     4800
```

```
gtctcaaaaa aaaaaaaatt tttcaatgag atgtgcagat tattgtcagg atcagagtta    4860
gttggaagtt tgcagaatac agggttattc acttgctgct attgcaaata aaatcaaatc    4920
caaagccctt agcctgacca agggctccaa tgaccatgca tgtgccccct gcctgtgccc    4980
cctgccacag tcttatctcc tgccatatcc ccctggcttt tccccttggg cacacccagc    5040
tcctaggagt tcctaagcat tctgtgcctt tgatccaggg atcccctttg cctgaaatgc    5100
tctgtcctcc tcatggtgct aaatgggtga gatatggcca tgcccaggac tcatatcctg    5160
gcctacctcc cccagcgcag cctctgaggg gtctaaggtc atactttcta ccacagagtg    5220
aaattcattc cccagaagct gatcacctcc agggctgagc ctgtgcctta cgcctcttgg    5280
ctgccctggt ccctggcgca caggaggtcc tcaagaaatt tggtgaaaac tgaggatgag    5340
tgagagccag caggcaagag aggttgaagg aatcactggg aatggtacag acacatatg     5400
catgagttgt tcagggagtc atgagcagtc tggggtggac tgaacagagt gtggggaggg    5460
aaaagattca acaatgtca attgtccaag ataatacatt cacattctgc tgcaaccaga     5520
gaaagcaggg tgctctttct ccctctttcc ctcacacatc cctggagaca atcaagtgtt    5580
ctctccggcc cccttcctcc tgaacccac tgctttgcca ggctcccaga tatctcctgg     5640
ggctccccca gcagggtcag aactgcaacc cagagcaaag tgcccctcat cccactcctc    5700
catggcgacc agcagagctg cggtgtttcc actccctgca aatgcaggag ctggggagaa    5760
aagctctctg cttctcccaa accctgacaa agcaattatt acatttcaca tgaacgaaga    5820
aatgcgtctg gcaactgcgc tttgggagg aaaaaaaatg ctaagccttg gtttcatgca     5880
aacacctctg cttttcacat tttcttcttc tggtagattc acttgggagc agctgaaaat    5940
gtccctgcgc ttattttatt agcatcgccc attatgctgc atttcaaata gcctgctggc    6000
ttaatagagg tgtgtaacct tggaaaaagt gcgaccacat cgaagtttgc atgccaacct    6060
ctaatttctc atccgttccc ctgtaagctg aactgcaggc tttaattggt caaatcatta    6120
aaggatgtaa ttagagactg gtggaagaag gcgagggagg aggagggaag aggcaaaaca    6180
atggtatctg taatcaagga catcacggaa aatgcagtga caggaactct tcttttggct    6240
tcctgccttc ctgcttgtct gcctatgata agagctgccg gagcattctt caaccactaa    6300
taaatcattt tcagggacct ataaccccat gggtataaaa atcatagttt cacagcctct    6360
tcgttcttat taatgcagat cttttctgga g tccctggtcc acagcagacc ttgaagaccc    6420
ttccaattga aaagtagtac tttgagctcc agcttccatc aagggtgtc taaatagtga     6480
cccaggcagc tctccctggc agagtcggca gcttgcttct gccaggttcc aggagtgaac    6540
aattagccga gtgcagctcc tgatgagttg ctaaaattag tctacaaaca tcaataaaca    6600
taacaagggc agggtgagag gagagagcac agaataaggg tgcccagaaa ataaagattt    6660
ggagacccag gcttgagaat agccctaaag gcacaaactc ttcagtcctg accccctcaag   6720
gattgctcct aaccagttcc ccctgaggct ctgggagctt cagggaagct gcatccccag    6780
ccctgcctga caggatttaa tgtgatttac aaatgcgtgg cacacacagg gtgccagagt    6840
caacgatcct tctacagaaa tcagaccaca ggtttaaaag tttgcagcca aattctggct    6900
gcagaagcag agccagaatc tgtccctggg tccttgtttc tgaaggctgc ttaattagga    6960
ggtgactaac tccaaaatga ctgttatcac tgacaggcag gcagaaagac agcaaggaca    7020
gaccacactt ccaagattcc ccccaattat gctcactttg atctcctgaa aaataaaatg    7080
aaagaaggaa ggtaaaagaa cttttctcagg gcaactggct ctaatagtag cctttatgat   7140
tttttttttt tttttttttg gttcactctt caatggaaag ctccttattt gaactcagaa    7200
```

```
gtccacatac caattaaatg cgcatgtgta gtgtttccaa aattgctgct ctcttaaaag    7260
tactttgggg agaacacaaa attgtagaaa gatccagcta tagcacctt tagcctggca    7320 caattgagtg ggttatggaa atgtgtgtct tgcggtcctc caagggcaga gaagtgcgta    7380
ctgtagaaag tccacagagg cccaggaaga gctcccccgc atagctaatg gcgttggatt    7440
tactgcaaga ctgaagagcc ccaattaagc cagagttggc tttggaaaca tgaaaacatg    7500
agctttgtgt ttgcattact tccatattgg tctacaaatc cctttagat gataaatatg    7560 ctcccagtta acttcagaga aagacacagg agccacacag ctggaagggg cttagataa    7620 ccttgtttag tacaatctac ccatttcaca gatgggaaaa aaagggccta aagaagtta    7680 ggtgactgag aagtatcctc ttcagtattc tttctgttac atactaatat caaatctaat    7740
aacatgaaat gatattgatg actaagggag ggagaaatca aaccatatca ctgttttatc    7800
ccacctctgt agcccttgtc cctgtaacat aaacagcatg gctacttata tttttaaaag    7860
cctaaaatgt agaagggaag gaatagaaaa tacaatgtct aaagaagaac aaaaatagta    7920
tctcccctgg tgtctatcaa gtcacaacaa ttctgaattt agcggttggt atatctttag    7980
ctccaagcca agattgctgt aaaattagga tcagatctaa gaggaaaata aaatgtttag    8040
acaaacaaaa tcggcataag cagttttctc tctgagaatg cctgagataa ataaaatatt    8100
ccactttgta tgttctacct tgtgaaagaa aacaaaatgg aggtagcgag agcaagggaa    8160
catgtaagac atgaaccttta aagtgtgtga caaatactgg agagaatagt ttttacaaat    8220
tccctcagaa gctgcctctt gaaaaccatc tggggctttc tcgtactcct tcattagttt    8280
cttcagctct gttatgggag acctggcaac aagaataagt aaatagttta atatctttgt    8340
tcattcaatc aacatactta aatttagttt aacagtgtca aattctcatg tggaaatcaa    8400
tctaacagaa aacaaattgc aatcaacaac tcattacaga gaagaagaac gttataaaat    8460
ataaagccag gcgtggtggc tcacgcctgt aatcccagca ctttgggagg ccaaggaggg    8520
cagattgcct gagctcagga gtttgagacc agcctgggca gcatgatgaa accccatctc    8580
tactaaaaat tagctgggca tggtggcgtg tgcctgtaat cccagctact tagaggctga    8640
ggcagaagaa ttgcttgaac ccgagaggca gagtttgcag ttagctgaga tcgcgccatt    8700
gcactctggc ctgggtgaca gagggagact ctgtctcaaa aaaaaaaaa aagttataaa    8760 atataaaaac ttatcctgca aaaagaagt tataaaatat aaaaaacgta tcctgccttc    8820 tcttttctgac tatcatatat ggattatgca atggtaaaca catcagttaa cttggtccga    8880
agctcagttt ctatttctgt aaattgggaa cagcttcact ccctgtctgg agtgccctag    8940
tctatggaga gagaattaaa gaaagctagg aggagaggag taagggtcaa ggggcagaat    9000 ataaaggag catttacacc aacctacaat gaggactcca aatgttgtga tcagccagaa    9060
gccttagaaa cggttggact ctagattaaa gacaccaggt aaaccattca gagttttatc    9120
taagcccata gaaaaacta gttttcaatt aaaaatcagg tatgataatt gctcattagt    9180
caaacgaagc aatacagctt gatggtcaaa agatggggca ccgagtcacg caaatcacta    9240
aaccactttc atcacgaatc aacagcaaat tccttaactc tttgaatact ggtctgtcga    9300
atgagaagaa ggctgatacc tgaggagggt taaatcaggt aatatgccta cagcatttac    9360
aacagtgtct gttgtatagt aaatattcaa tatgtttgct atgagacgta ctacctgctt    9420
tttaaagacg tcgagataat tatcagaaaa cagcaattag gaatactgga caatgtttgt    9480
gttcaattta gcaaatagtt tccatttttgc atgtagcata ttggaaaaga ctcctgctag    9540
ataagccttt ccagctttgt ggatgctgag gctaaacaag gcagcacctt catagacatg    9600
```

```
gctgtatatt ttgacaaagc acctagggag gaaacatagt acttcgtggg tgctaacctc    9660
tctgaagcca taaggaagca gtaaacatca cgatgcggaa acactatcga gtgctttgcc    9720
ttcttgggtg agcctcaacc tgaagtatat ttgacttgat tttcaactta aaggctaaag    9780
aaaaatgtgc aatatatata tattatatat atatatatag catatatata ttatatatat    9840
atagcatata tatattatat atctatagca tatatattat atatctatag catatatata    9900
atatatatat atagcatata tatatatata tgtatatgtc agcagagaaa acactactcc    9960
aacaaggttg tatttataga ttgattttcc tacccttcca ttacccctcc tacctttctt   10020
taatctcatt gtcactaagc aaataattgt caaatacaaa ctggtgctga ggtttcaagg   10080
atgaataaag tccatccttg agaagtcaaa gttcatcagg ggtgcaggga taaatagata   10140
ctgcaacagt aatatctgag aaatgctatg gtcatactat catttgtgct ggtgaaattg   10200
aagaatgtgt gatagaagtc aacttttgaa gtgagttgta aggcatgcgt agaaaatttt   10260
gcaaatcaga aaagggagtg atagcaggaa ctcaggtgac aaagaaaaga ggttgcatag   10320
aagatagcat ttctaaataa atctgctcct aggaccacag ggaccaaaat gacacgaata   10380
ttctcagaag ttcttgctgt ttctttttcc ccatcacatc ttcttccaca cctcaaccca   10440
caatgtacaa ccacggagga tcccgtaact cactcacaac ctgtatagac tttatgatag   10500
tcataggccc tgctacttct cactgtgggt gcagaagaaa agaagatatc aactgggaaa   10560
ttatctatac cccgggcaat gaattctcat ttcacacacg aatctgatcc caatggcagt   10620
tatcaactgg ccacccagcg ggagtttcat ttgcaggaaa agcatcggta tgttgttgtc   10680
tagctgtgac tgctggcttc ccaacagatt tggaaagagc agcatcagac acagaatcct   10740
caggccagac gatgctgggt tcttaagctt gttctcttca tttagaattt agacaccacc   10800
aagtcccaga attagaaagc tccatttact tcttaagaat atacagaagg tacatttagt   10860
tccataaata atggcttatt tcaatccacc agaaataaca catgcaaatt tatgtgtgaa   10920
tgtgtatgtg caggggtata tatacatata gagtagtccc tccttgtctg cggggtatac   10980
attccaagac ccacagcaga tgcctgaaac aggggatagt actgaccccg actgccatcc   11040
atcagaacat gttcctttc atgtcttcca cccacaaatg taatgctttt ttcatcataa   11100
ataagcactt atcatgcatt gtggctgtaa cttttgcagt ttgaggtgtg acagcgaaac   11160
tagcacaaat gtcttttttc ttcttcacaa tttcagatag aagatttgtt cttaccgtag   11220
atcttagcaa cttccacata cagttttttt cctttcctta ttaagtagag aactttcacc   11280
ttttcactta aaggaagcac ctgatggctt ccctttggtg tagccgaatt gccagcatca   11340
ctacttttcc gctttgaggc catttttaag taaaataagg atgactcgca cacaaacact   11400
gggataccgt gacagttgat ctgataacca agagggctac tggatatgct ggacaaaggg   11460
attattcaca tcccaggtgg gacagagcgg gatggcatga gatttcatca tgctactcag   11520
aatggcatgc agtgtaaaac acaaattgct tattcctgga attttccatt caatattttc   11580
tgattgtggt tgacctcagg taactgaaac tggagaaagt gaaactttag actgggggga   11640
ctactgtata ctaaaatgtg gaaaggaata aacagaaaat agagtggctg aaagagaaca   11700
aaaacaatat ctctcctggt atctatcatt tacattatat acatacatat cagcatgtat   11760
aatgtacagt attctagaat aatgcttccc gatttcttaa gaagttatat atacttgttt   11820
cttttagaat tatttcatat ataattatgc tgagatatca taacatttat tccacttcca   11880
tgataactat acactttaaa ttatgatgaa ctgagattta ctttatttat taatataact   11940
taaataaatg tggagatttt tgtacagtat catatacata catatcagca tgtataatgt   12000
```

```
acagtactct agaataatgc tttccaattt cttaagaagt tatatatcat tatttctttt    12060
agaattattt catatataat tatgctgaga tatcataaca tttattccac ttccatgata    12120
actatacact ttatgatgaa ctgagattta ctttatttat taatataact taaataaatg    12180
tggagatttt tgtacagtat ctttggaagt attcaatcca ctccactcaa agcactggga    12240
aagatgtgta aatacatcac ttttccttgg agattacaaa aaccagaaca gagaaacttg    12300
agcacagaga cactgtattt tttagtaact agggagaaag caagccacag ggtgcatgtt    12360
tggtgtcatc tccttgtcct agccatccac atcgtggcgc atttcttcaa cctggaacgc    12420
taccactgga gccagtccga ggaggcccag ggacttctgg ccgcactttc caagctgggc    12480
aacacccota acgagagcta cctcaaccct gtccggacct tccccacagt gagttcctgc    12540
atgctaacaa gcttctcccc tgaaaaatcc gtccttttcc agtcctctaa tcaggaacgc    12600
tatattgaaa agcttttaat aaaagagctg gagaatgaat ttatatgtga atttgttttc    12660
aatttcacat tttctaaaaa gttatttttt tctcattaat gttgctggga agttatgagc    12720
aaggagaaaa agatatgtca cctaattaat ttatatatat atacacacac acactagaaa    12780
cgcagtaacc tgttaaattc ctaatatttt aaaatttaac attttaaaag cagttcagga    12840
ttagatattt tttcactgat gttagactca taaagaaggt gaagtgccag ctaaacacag    12900
agattataaa ttggatgtct tcattttcaa tctgcagatt gttttccgga tctgttctcc    12960
gaatgcctca tacattggca catatgtgaa tagctgcttt gccaaatcag atactgggca    13020
aagcagctaa tttcataatg agacctgcat ggccagtgac atcattaatg ctaattacct    13080
gtgtgcacag actgtcagca gctatgggga acaaaaagaa aaccaaaaat gtagccacag    13140
caatctatgt tccgagatga agacggtcgt ctcccttaat tcaccoctac ctctttcttt    13200
gtggttgatc tcagtttttt tccacatacc accatattgg catatgtgtg cagcacgttg    13260
accagactaa aaatatcttt attgcccaag aaaagccgta aggcaataca cttcagcaat    13320
gaaaatccct ccattcttat ccaggccatc tctttaagtg accatttccc catgcagcct    13380
tatttaaaga acaaaaactc aaaatctggt tttgggacac ttgttccatg tcatgtcccc    13440
taattagcct aagataattt tcaatatcag gccattgatc aggtttagtt gagctacctt    13500
ttcttttatt ttttatttat atttatttat ttttttgag acagagtctc actctgttgc    13560
cagagctgga gtgcagtggt gcgatcacgg ctcactgcaa gctccgcctc ccggattcac    13620
gctattctcc tgcctcagcc tcctgagtag ctgggactat aggcacccgc caccacgccc    13680
agctaatttt tgttattttt agtagagacg gggtttcact gtgttagcca ggatggtctt    13740
gatcgcctga cctcgtgatc cgcccacctc ggcctcccaa agtgctggga ttacaggcgt    13800
gagccaccgc gctcggcttg agctaccttt tcttagctga cagctattgg aagcaaaaat    13860
ttcacacttc cgaatcagaa ctacagctgc ccttatgagt ggggatgcct ttgtgtccgt    13920
ccattgaatc acagcatttg tctaggcacc tactgaggtt gctgttttc cccactaaga    13980
cgctggaaaa tccattgcta cacacactca agaataaatc tcaacatttt gcatagtcta    14040
tataataaat agtatttatt aaaaatactt ttcaagcaat gtgattatat atcttactag    14100
aaaaataata aagctactac caatgcagta atttcaaaat tttagaagca atatactatg    14160
taagtactaa ttaagctcag gaaaccctct aatttagggt atttggagag agatgagtat    14220
caataacaca gagtgtacat tatagagcat ttttagagat gcagtgggat tgttttggag    14280
gatacattgc aactgtaacc agtctataaa tgtgttgcaa gaaagagaca tggcgatttg    14340
ccttaatagg caaggaagaa tgatgtgaaa ttagcatatc atatgatgta aatggatttc    14400
```

```
taaaatgcct gaaggtactt gagaagaaaa tattttaaat gtttgagaca taccccttc     14460 aattttattt ccactctttg ctctatgaag aaaaaataat gaagaagtcc ctgtccgaat     14520
tacctccaga tctcaaagcc gcccaaatta atgagatttt actgacaaaa gatatagtga     14580
gtttattgag ctcatggccg tctcaacgat agtaacacaa tgtatgaata ctaatgactt     14640
ggcaagaaca tgggaaactc acaatgaaaa taaactgctg tgtgatgcta ttctaaaagg     14700
ctattttact gtcccttgca ctcacaggtc agaattctgg ccgtttagcc gtgtccacca     14760
gataagaata gctgtacctt tattgatcac ctaggattta ccaagcctta ttccaggccc     14820
ccggagatgg cgtgaaagaa atgcaagtca tggtctttcc aattaaaaag caagagcaag     14880
gaacaactac caagggaact gagtgtgcag ctgctttatt aggaacgccc caagggacct     14940
ctcaaaaaaa tgtgtttatt aatgttaaaa tgcaattaag catggtgatc cacatagtta     15000
ttttgaagat taaaaactta aaactcagat ttattttgca atattttatc ttaaaatgct     15060
cttttcatgc tgccctaatt tcaattcaac ataatcactt tggtttttt tttttttgtt     15120 ttttcttttt tcccatttg ttattgttgt tgttgtttta gacacagggt ctcactctgt     15180
ctcccaggct ggaatgcaga ggcagcatca cggctcattg cagcctcaca ctcctgggat     15240
caagtgatcc tcccacctca gcctactgag tagctgagac tataggctca aaccaccatg     15300
cccagctttt tttttttaat ttatttatgt gggttttttt tccagtataa taactttgat     15360
gtgaaatgat atatacaaaa ataaaaaaat gtgattgatg aaatggtatt ttacgaaatt     15420
ttagcaaagc aagtaaccac cgtaagctgg tgggaagggg gtggaagagt aagctcgctt     15480
cttgagttgc acctgcatcc tcgctgaggc taacgtgctt ctgagtgaaa cattgtgaac     15540
ggctccctgc ttgaaatctc aagtactggt cctaaaaatg aaaaaaaaaa atatgccagg     15600
atatttaatg tcaaggtgtt tttttttgtt tgtttctttt tttgttgttg ttgtttttt     15660 tagaacacaa ccactgaatt gctaaggaca atagcaggcg tcaccggtct ggtgatctct     15720
ctggctttag tcttgatcat gacctcgtca actgagttca tcagacaggc ctcctatgag     15780
ttgttctggt acacacacca tgttttcatc gtcttctttc tcagcctggc catccatggg     15840
acggggtaag tccatactgc gctcctctgc aaggattta tctctgagag tcccaaaata     15900
atcttagaaa gtcctttaga tgaaggagcc ggcgtgcggt gactacagga ctcgtataat     15960
gtgtgaaaag cacattgact gtggcaaacg cttttcagt aacactgaaa ataagctaca     16020
tagatggtga agtattatat ttattttcc tctctgactc tgttagtgag tcttggcatg     16080
tttataaaat tcaggaatcc taatgaatgc aggatgacag tagatctatg tttcattcag     16140
tacctgttct gccatccaat ttatgtgaga ttactcagga tatatatttt tgacaccaag     16200
atttcacttc tgcttaacca aaaccgtcaa ctaggaaacc cactgttcgg gcagggacaa     16260
tgtgtggcat gggcagtctg tgtgtggggtc cagaagcagc tctgacacca gttatcagag     16320
tgagcccttc aggtcctctg agcctcagtt tccccatttg acctctagga ccccattttc     16380
ctcagacatc ccgtaaaaca ctgttctggt attcaatacc tgcctgatat ggttcatctc     16440
ttcttcagga agctagcata gcccctgatg tgttcaccct caaatataat gcttttcaat     16500
cctttaaata ttaataaatg gccctggact aatacatcaa ttgctgtctg tgaactagct     16560
tgtcccttta attatttcaa aaactgattg cctttttttc catttacaa ttttcaaagc     16620 acattcatat acatgatcaa cttgaccccc acaacagtcc tgtcatgtag agaaggtgct     16680
gctgtcccca tttcataaag aggaaaaagg tgttctgagg gttaagtgat gccctcaagg     16740
tcccatgatg aataaacagc agagtcagat ccaggacgcc agtctttaga ctatcaatca     16800
```

```
gacctttact ctggtttgca agcccctgaa gaacaagtct tccattttag gaattaaacc   16860
ttcctcaaca ccagcaagaa tgtggccagc aatgttgcta atgcccttttt tggcttgcca  16920
gcagcaactc ctctgttccc gcaccacaga ataccctctt ccaccccctca ttctcccacc  16980
attgccaccg ctgagcatgg agggtcctgt cccggaggtg gcctccgact ctgcgcggac   17040
ctggaagagc aagcgcatag ctgcagagtg gcatggccta ggaagtcaca cctgccttgg   17100
tgactctggg tccatgtag ggcccacaga caacgctttg ggatttgccc ttccacaagt    17160
caacaacgcc tccaatctcc ctcctcaccc ttaatgctcc tgtcttctca gcccccctact 17220
tctggaaggg ggtggcagtt ctgccgctgc cactgcctgt gcctaagact tctcccgtgg   17280
tccctcagct ggtggacaga aacacattct ccacggaaga agtgcccctg agggtgcatt   17340
ttaccctaaa agactgcctg tgcctctgct gagccttagt aaccgggtca gtccacattc   17400
acccgtactc tgctgcctgg ctagaggctt tccattctct ttcagctaga ggtctctggg   17460
attggctctt ctgaatgtgg aaatctcaac attccttttt gtacttggga tgggcaaggt   17520
ggatggtgtg tagacccagt gtgttccaac tcagagactg tcagtcctcc ctttctactg   17580
ctgattctgc ccccgacgcc ggggttgtta acccctgaag cacatttatg aggctatcta   17640
taactcaggg gaatctagaa gccctattca cagacatgat gtgcttaccc ccctaaacat   17700
acgtccccca catccacacc ctggtgcatt gtagaagcac aagagaattt caatgggcag   17760
tgtttcgttg gagatatttt tgatatccaa ataacatctc ataagatgaa atttttagtc   17820
attttaacct agttgaaaag cttattttag gataagggcc tcatttaatc ttctcagtgt   17880
gaagtattct acagctactg tttacagcga aagcaatttg caaattctac acaaagtgcc   17940
aagtgaaagt aggattattg gaatgtgtta aggcccacta atcttcctat tatgggatgg   18000
catagatgaa gacatttcaa acgtttaaaa tgtttaaaag atacagcatt tgtggaatga   18060
tatgaggctt cttttagaca ctatggggaa tgctgcctac agcctgagaa tgaaagtgtt   18120
aaagtatctg gaatctttcc tctgactctc acttactatt caccctgcct atgtctgggc   18180
atcatttgta cattggagat ttacagatag ttttttctcat ctaactcaga gggatgttat  18240
caagtttgga tggcttccat aaaacagact gggacaaaag ccaagatgtc agttctagct   18300
gacaccaggc tgttttccaa gggcgtatta ctgctccttc ctcccatgcc ctgtgatata   18360
acaggggcca caccactcca caggctgtcc aggacataag tctgtgtgat gctaaggttt   18420
ctcagtctag agtagcatgt ttctcaaaac agatcaatgc atttcattca caaacaccta   18480
ggaactgaac aattcccaga ttccctgacc ttgatgtctt gggctttgct gtctgtgcac   18540
caagaaggaa ccctaggagc ttgtaccaaa gctacttgtc aaaggtcagt caggagtgca   18600
ctcatggcaa atataatata gcaggattat aggactcttc gtccagtgct ccggtcatta   18660
ggactgcctt ctctttccat tcctaaatgt atcaataccg tcttgaagac acactccatt   18720
gtgacctgtt ttgactgagt caaacactgg cttgctggtg gtcactagga ggaaaaatac   18780
cattcttccg gtattttgac tccttcactt gaagacttct gagcattcag aaacaaccca   18840
aggagggtag aagttaaata aatctgcaaa agaaccaaat agtacaaagt tagccaatta   18900
gcccaaatca gcaatcagaa caagatgaaa cctaattaaa ttcaacagtc tacaaaagga   18960
tgtgttcaaa caatttccct tcattatgaa ttctctaata tagacacttt caattttaaca  19020
caggatacca cagagggggcc cttctttttct gggatcttca aagttactcg aagcttctta  19080
aatgcttatt tttaaagaag ctgggggaaa tgaatgacag cccgagtttc aagaactgga   19140
agtgatattt cagagctcac tgtaggatat ataccgtgtgg gagaacaaga ctgctcaaaa  19200
```

```
tcagtttgac gttttttgct ttttgttttg ttttgctttt cttaaataac aagtcggatt  19260
gttcgaggcc aaacccaaga cagtctctct ctgcacaaca tcaccttctg tagagaccgc  19320
tatgcagaat ggcagacagt ggcccaatgc cccgtgcctc aattttctgg caaggaaccc  19380
tcggtaagaa tgaacccagg agcttttaaa aataaatgtc accacagtta aaatacagag  19440
tttttatagg cttggaaaaa agaaagcaca tttcaccact agacaaagcc aactctttat  19500
taagtgtgct aatggagaaa tcaagttaca gataattttt aaagaggttt actgccaaaa  19560
gcactatgtt cagctttgaa atgtattctt ctacttacct ttaaatacta gtgtctgata  19620
tggtgggaat tcataacagc acaatgatgt ccctggagga gtcagccttg ggcctcacca  19680
cccttctttg tgctccctgc atccttagcc acctgtcctc tgcataactt ccatcccagt  19740
ctgagaatta ctggcacccc tgctcaaacc taggtcaatg aacagccaaa tgaggctcag  19800
ggcttcttta taagcttgcc ttctttcttt tgacaacttc aaggatcaaa aacttagtgt  19860
gtcaaacgca tttacttctt gttctaatta agctcctgta actgaaataa tgatgatgtt  19920
agccaagaag atacttaatt aatttgtgta gatgataatg tccacagatc tgaaaagtca  19980
gatttcccgg gtaggtggta accattacag ttggtagcat agggaaagag aagtaatatt  20040
cctatctggc ctcttctggt atcttagaac agtgcaaatc tttgggacaa ccaagtgatg  20100
cttgaaagaa aataaatgca tctggcagat aaacagtagg aggaaataag tgtccaaaaa  20160
tacatcactt aaaacatgga ataacagggt ataatagtat acaaatgatg aagatttagg  20220
aaattaagtc atcaacatat gaagaatata agtgattgcg ttgtttaaaa aaaaaccct   20280 caaatatatt aaattaagca ctggatttta agggtgaaag tactaggagg aatgattaaa  20340
accgagagaa ccggaataga tatgcccatt agactgtggt tctttttaatg gccggtatag  20400 attgtctctg tcttaaactc aactctcagt agccactatc caacctgcat attaatgagg  20460
aacatgaata cctctctaaa attttcagct acagcatctc cataaaaaaa tcaatactcc  20520
cccacacctc atgaatacag accagggcct gctcccagca gcgtttgccg gcattaatta  20580
tcattaagag ggggccttgc tcatctctct ctaactctcc cctgctccac ttccttgcac  20640
acccaaactc agggtgtcac tctctcccat tatttgtaat ggatcctgat tcaaagcgtg  20700
tgtgggctat gcaattaccg cttggctgaa ctgtacgata ttctctctga tgtcttatag  20760
acactgaatc cgaaaggcat cccaaggaca aggaagggtt cctgcgcttc actgcaccac  20820
acctactcgg tctctacaaa gctccatttc tcttcccttg cctctcttaa ctcagggcgt  20880
tttcacggtg ctctgatcaa tagaatatgt atcatttctc cttcagcggt tcactgttcc  20940
cagtgttagg acagataacg ttttgtacct cacctcgtgt aaatggaact gattaaagaa  21000
accaactata cccggcagtc cctcctcccc tacttgtctt acgtggaaaa tatcagagac  21060
caggtctgat ttgacatcac caaaatgaag tgtgtgatgc cccaaactct ctaaaatggg  21120
tggggaagat tatttgtaaa aatatatgaa gactgagtgt ctttgccaat atctcttctg  21180
gcccatttag aaagaactgc attcttgctc tcatttctgt aaacatccaa agcaattctc  21240
aaaaagcttt ctggttcatt caagcataag agacctaagg attcctttgc tcggtccaac  21300
cccatccttc ccagggacgc ttcctacatt tcccttactc tgttcatctt cgcagcttgt  21360
ctcagtctcc ctttccagcc caaatgcact gacaaataca ggactccaga ttcctggttt  21420
gctgctgatg caatccagtc tcaaaagatg cctggtcgtc ctaggccgga gaagcacttt  21480
atgtcattta accacagcat caactcatcg taaccataag gctgacactt tgtaattact  21540
agggaaagct gttagtggta aaggagaaag ccctgatgga ggtagagtca attcagcgaa  21600
```

```
cttcaccgag tgcctaagtg cattgcttgg caatgcagta gacaggattc agacacgtgg   21660
gacctgcccc aggagatctg attgtctaga aaaagaggct attcataaac acacacataa   21720
aataaaatca aagccagcat gttcttattt tctggtagga atgaaaaacc aggagtgaaa   21780
gtgaaggaaa caagtttcat tattgctgct tttgaatcaa catcgtttta tttctatcat   21840
aaaatactca ctgtagcgtg acttttgag catttttga agaagaagaa aagaaagcca    21900
agaagccacg gagtatttta gcattaagga aacttagata ctaaatagtt cttccccatt   21960
atttaatagc tgaggaaatt gaggtccaag cagtttcagt gtcttaccca tggtcacaaa   22020
aagcattccc agtaaagcca ccttaaagaa ccagagcccc taactctgtg gccatgaact   22080
ttctcctcca ttcacagcat tcactctaag tctctggctt ccataaccgc cattttgtca   22140
gcactctgct gctagctgct acaagtacat agccccaacg ttctacttat ctctgtgaat   22200
aaagccaaag tgtttaagag cttggaggga actaataat aattttctcc agctagttcc    22260
cattttacaa acaggacgt tatgaacata ataaatctca agatgtgcct agtggcacag    22320
agtgaggggt ggtggcccca aggccagaat ccaggtcttc agacacccag cctagcatct   22380
actttgacac acggccctct tgctctgaat caaggcctcc ttgtcttgat tctctcttgt   22440
ctgtcccggg tatcactgca aggacagttt cctaatattc atccctggcc atctctccct   22500
caggccctga cttccagggg ctccaggcac aacacaggta acgacactgg ctacttcctc   22560
ccggagcaaa ggatatacta agattgagat ggagtcgggg attaatagct tatattctcc   22620
tacctgaacc atggaaagaa aaataatcca ttacatttta tcaacgtgga aaatatcaga   22680
gatcgtgtct gatttgacat caccaaaatg aagtttgtga tgccccaaac tctctaaaat   22740
gggtggggaa gattatttgt aaaaatatat gaagactgag tgtctttgcc agtatctctt   22800
ttagcccatt tagaaagaac tgcattcttg ctctcatttc tataaacatc caaagcaatt   22860
ctcaaaaagc tttctggttc attcaagcat aagagaccta aggattcctt tgctcggtcc   22920
aaccccatct ttcccaggga cgcttcctag atttccctta ctctgttcat cttcaccacc    22980
tcatccacag catagggga caaaaggttt attctctttg ctgttctgaa cacattgctg     23040
ggccctactg aggcagaaaa aataagtggg tcaaattgtg ttgccttgtg ttgccccat    23100 aggtctagct tttatgaggc caagagcccc cccaggaaaa aaagcagaga gggttgatgt   23160
aggtgagaag agggaccatg cgaagagacc cagaaatcaa caaaaagcaa tagacaaaac   23220
gagaaaggtg actcaaagga agtaaaaata atgctaaaag acttgtgacc catcaacaga   23280
agagacagag ccagatgact ggtcaggag cactgagtaa tgagtcaatc ggggaggggt    23340
ggtgaatgtc tgagttctga agaccgagac atccttcctg cccccacccc ccgccccaga   23400
tactattcaa ggagtaaggt ggtggattta gaaaacctag gaggaagtgt agggacatat   23460
gaaaaggctt gagttctggc cctggctatc tctggtccac ctcagactct ccaggcaact   23520
cagacccatt cccagaatgt caggattttc cttctttaa ttctaaaaga attagaggat    23580
attgaatgtt cccaatacaa agaaataatc agtgtttgag atgatggata gagtaattta   23640
ccctgacctt atcatgatac attgtatgta tcaaaacatc actatgtacc tcgtgaatat   23700
atacaattat tatttgtcta ttgaaaacaa taaaaatttt aaaagaaaa aaagaatta     23760 gagtagattt ccaagagcat gcagtatcct aaaattcaat gagttcatga gtttctaatg   23820
ttttggaaaa caagcctcag tatcaattta gcgctggaca gaaaggacca cgataaatatg   23880 gcaatgcaca tggagggtag cctggggtcc tggtaagaac tcaggctggg tagtcaggca   23940
tacctgagtt cacatctcta cgaaacacct tcgtcccttt atgaccttgg acaatttggt   24000
```

```
tgatctgact gagtcttaac tccttcctct gtaaaatcaa ggtaatacat atgcctcatg   24060
ggattgttca gtacaaatag aactcttcaa aaattgtaac ttcccatttc ttcccttca    24120 ctgaggaaga caccttatgt tgtacagagc tcctgataca atagcctgct ggtaaattga   24180
tcatcagtaa tgcacattat actcatcaaa agttaacata gcatctgatt tgtttaaaat   24240
ggacattttc accatcacaa ttctctagac aattattgag ccttttgctg tgattagata   24300
aacttaaatt taaggtgcca ggaaattgac tttatatttt actccaaata actgtgtgtg   24360
tgtgtgtgtg tgtgtgtgtg tgtgtgtttc tgtgtttatt caggcagacc ctgtagttgt   24420
gatgcattct tggcccaaaa aattactatt tgagatttta aaatgtaatt tcttatgtcc   24480
tgtgttgggt gagtaatgta gctttgactt tggcttgagt ttgggagcat ttacgaccct   24540
atcatatgta atataaacat caatctgctt ttttatttct ttgcaaattc aattatttct   24600
aattacataa aggcatcatt gatcaagtaa gcataaaaac caatatagaa gagtttaatc   24660 tcttaaaataa gcttgtagac ttcaataaat aattgaatgt tatagtatat aatacaagga   24720
gacatctttg ttgctgataa ctggcccaaa gttaaggaa aaatatctaa tccccatcat    24780
gttgtatatt gatttggttc aaattgaaaa tatttggatt ctattttcat ttcctttttc   24840
tctctctctc tgctactctc ttcaggcttg gaaatggatt ttaggccctg tggtcttgta   24900
tgcatgtgaa agaataatta ggttctggcg atttcaacaa gaagttgtca ttaccaaggt   24960
atgcatgtag ctttatgtct gaataaaagc ctgagtgtag atgaaaattt tttattagcc   25020
caaattttta atttgccatt tttattgcag aactgtctgt aatttagagg ctcatcttct   25080
gttctaataa ttgcttgtat cctgagcatc ttttagtgtg actaattttg ctgaagacag   25140
ggatcagggc tccagacggc acacagaatt ctgataaagg tttattgtac agcactggaa   25200
tgatctgctt tgtctttatt ttgctttctc tctagggga aatgcaaggg gagtgagtgt    25260
actttacatg ggtcatagtg acttgaagga taatcacttc ttcaccacgt aaaggcacaa   25320
attttgcaaa caaataacat tttcaaatct atacactctc actggggact accaagcaga   25380
ggaaagggaa acagtcacca taaggttcag agcaagaggg accactgtgg ggaagaaaaa   25440
tggagatgaa ggatgaagat agagttctac cctcatgagc agcatgctcc tggtagcatt   25500
tttcagtctt gctccccatc ctcacatctc tacgtcctca caatgtttac ctcttgctgg   25560
aggaagacgg gaagggtag accaagacca aaaaatgca tgcctaggag agtgaaaagg    25620
tgccaaatac tctcccccag cttttgaaat gtccaagaag aaactctccg ttagccaagc   25680
ctatcccact ttgctaatac aatttttaaca gaatcctgta tctctgtagc cgccttcatg   25740
aaagcagatg tatagaaatt gcttcctatt tctgctttaa gctgtttctg tgttgctgtt   25800
tttaagttaa gcaccaaagg atgtcaggct gtatcaaaag ctagactgta aaacttctgg   25860
aaacctactc gagctgttac gagggagacc atttaacagc aatgtcagaa cagataccag   25920
tagggagagg gaaaacttag aaccaatgat gaaaatgctg tgaaattctc ttttgaacgg   25980
aaaaatactg tcacagtatc tagatgctag attttgttcc cttatacctc ttgtcacaaa   26040
agaagacagg agggcctgga gagattttc aggaaacaag attgaaatct aagaagggaa    26100
attagctctt tccctctgat aagcagtaag tcataaagct tttataaaca ctactagaaa   26160
ccttgtccaa tgcttcccta catctaaaac tcagagcgga gtcaggacac aggatgagac   26220
tcaaccaaaa agaaaacaaa acaagaaaag agtttgaagt gagtttgaag attgttttc    26280 acttagcctg aagaaataag agggttaatt cacaagacat tgagaaaaga tgcagatcat   26340
tgaaaaaggt aacaaaatgt tcctagatgt taaaaacaca gagataatgt ggtgacttat   26400
```

```
tttaataacc ctaagcataa taatatgcaa gcttctactg tcttgggtct ggttgactgt   26460
gctgtggaaa gcctggccat tggacacatg gactcacatg ctgggcacca attgcacctg   26520
ggtgcagcta tttcaaatgc caccctctga aggagaggag catcattctt gctggagttg   26580
caaacacaga tgtgaaagcg atggcacata tctttgggag ctaacagcag atgggatatg   26640
taaattacac ctgaaacaag ctgatctaaa attttcaaca cctttgatgg aatgaaaggt   26700
gtttctttat tatttcgagg acaaaggcaa acaactctct cactctcaca taggtggtaa   26760 gccaccccte tggagtcctg gaacttcaca tgaaaaagcg tggctttaaa atggcgccag   26820
ggcagtacat cttggtgcag tgcccagcca tatcttcgct ggagtggcac cccttcaccc   26880
ttacctctgc cccccaggag gacttttttca gcgtgcacat ccgggcagca ggagactgga   26940
cagcagcgct actggaggcc tttggggcag agggacaggc cctccaggag ccctggagcc   27000
tgccaaggtt cgtgcccatt tctctcatgt ataaattgca gtattataaa agtaaggta   27060 tcttaatgta tcaacatgct acctgattca gcaatatctt tattaaatgg tgagtttgag   27120
actgtgtcta aatttgagaa tgtgtgtaaa aagtataatt ttgtagactt ctaggagaca   27180
cacatctgtt cctgtaaaaa aaaaaaaaaa aaagaaaaa aagactaatg ttcagccaag   27240
agagggtgat ccaggaagga ggtttctctt ccaggtccta aagcatcacc tggttacttc   27300
tatgcagcct gcaatgagtg agacaactct gggcattttt ttctatcaca gtctgagttt   27360
tttttattgt atttgtaaag tcaggtcttc ataacaagga tgctatgttt ctgtgtcctc   27420
ttcttataaa gacccaagtc atattggata taagggccca taccactcca gcatgacctc   27480
atcttagctt tattcattat gtctgcaacc ctatttctaa ataaggtcac atcctaagta   27540
ctgaggttag gactttaaca tatcaatggg ggacacactc aacccacagc atcactctat   27600
tcagaaaagt ctgggctcac gcctgttatc cgagcacttt gggaagccaa ggcgggcgga   27660
tcacttgagg tcaggagttt gaggccagcc tggccaacat ggcaaaaccc catctctact   27720
aaaaatacaa aaattagccg ggtgtggtgg cacatgcctg taatcccagc tatctgggtg   27780
gctgaggcag gagaattgct tgaacctggg aggcagaggt tgcagtgagc cgagatcgcg   27840
ccactgcact ccagcctggg tgacagagtg agaccttgtt tcaaaaaga agaaggagga   27900 ggaggaggag gaaagaaaaa gaaaaagcct gggcacataa cagaagtccc aaagtaaatg   27960
accactcctc agctctgttc agtaaacaat ggcttcgggt caattcccac tgttcataca   28020
gggttaccca aaagcatgca aagcacacat ttggggctct ggaagaacag ggacaccaaa   28080
aaaaatgaga aaaacatttt tggaagaatt tcatatttga aaagaagcat caagagattc   28140
ctacttctgc catccttgga gggtatcagg aactaccaag aagcagccac tgtcatgagc   28200
actgtggtag ggagctcggt agagacactt caaatggaag ttcctgaggg caggacattg   28260
tctttcctcc tcggaatctc cagtgcctac aacagtgtct gacatgcagt gcgtacagag   28320
gaaagatttg acaaaagaat taatgaagcc ctggggccaa tatggattct ttatctcatt   28380
tagtttgaca aatatttatt ggtgacaaac aaggtaccac aataaatttg agacacaaaa   28440
tgtagtcagc ttattgtcct gctttccctg ttttcgtagg ctactgagct gtaactgcac   28500
cctgggcttg gttgtatttta gtgggtagga agagtcacag gcctcctttc agacactggt   28560
cctgaagaat ggtatgccaa gccaagtaga agcatcatct gctcaagcca gagccccaaa   28620
tcagatgaga acacatgact atttttcttt tttataatgga aaggaagcaa tgtaataaaa   28680
ttttaaggtt cagagtgcag agcaaatgcc taaaatcaaa aataaaagta gatgcactgc   28740
acagcacccc caccctcacc aacccccca gcacacacac acacacacac acacacacac   28800
```

```
acacacacac acacacgcca cagtgtctaa ctgctttctc ggtccctgct ctcccttgg    28860 catcgccaag gcaaaagttt tcatcctttt tgctaactgg cttctgccct gtgtgtatac    28920
acttatctgt tctatcaacc acccttcccc ttcacaaacc agatagcatt tcaaccagtc    28980
ccccaagaag aactcagtac tggttactca gtagctgaca tgctttctgc ctatggagtg    29040
catcgccagc tgcaagttcc aacaggatcc ccagggcctc cctgggctca tctgttccac    29100
ctcctgctcc ctcatgggct tagctcttcc agctttcttg ttgttcacac acactgagaa    29160
tgtagtcctc agtgcctttg ccattgctgt tccctccacc tggaatgctg ttccccacat    29220
ctctgctggg cagctccctc tcttccttca ggtctctgtt caaatgtccc cttcagtga    29280 ggcctttgct tcccactgca catgaaacaa ccccagcag tcactcaatc gccatgatgc    29340
cacatgctga ctttatttt ctttatagta cataccacca cctggcatgt taaatattta    29400
tatttgcttg attgtttact gtctatctct ccacactaga atggaagctc tatgagaaaa    29460
gggcctctgt ttgcttcact ttaccatcca cagggcctag aacaggccct gactgtcagt    29520
cactcagtaa gtcattatgg gctcgataaa aatgagttgt cataaacaga gctgcttccc    29580
tccattcact aatttgtttc gccctctgcc tctgtatgtg tgtaggcata tgtattagtg    29640
gcaaagcctt ccaaaaaact agaatttgtt taaatcttca acatacaaag aatcaggatg    29700
ttattggact tccttggatg attttacagt tccccactgt tttaattttg aattaaatca    29760
tattggggag agcactatat ctttttactg ctttggatcc cagacaaatt taatccagcc    29820
cctggaattt gtgagtgaga tgcccaggag gggaagcaag cccaaaaaaa gaacagggaa    29880
acctcttcct ctaaacccaa gaaaagggga gagaatgtga gctctttcaa aagactagac    29940
cttctgaagg aaaacagagg aatttctcag ttgatggagt ttccagctat cctttgccca    30000
gagctggggc ccacactgtg agaggagctg ggttcaaagc ccaactttgt gtgtgatctt    30060
ggagaatgta tgtaacacac tgcctcagtt tcctcatctg tacaatgaag atgcaataa    30120 tagtactcat ggctttgttt aggatcacac ataacagtcc ataaaacac ttaacataat    30180 acttagcaca cggtaagtgc tcaaagagtt agctactatt attattaaca acataagaat    30240
ggtcacctac cacagaaata gcaatggaag tgtttgttag aggagtaaat gcagtcagtt    30300
cagagagctg agactggaac ttaatggggt agggtggggt gctgctgaac tacccagcaa    30360
ggactcacag gacagggatg caggcaagac aaatcatttt ctgagcctca ttattagaaa    30420
cgctgtgtct aaatcaaggc agggatagct gcataaacgt gataaacaag aatttgtgca    30480
aatgaagctg attcagattg ttaaaaatct ggagaaatgg agaaatttgg gcccaaaaaa    30540
gaacaactgg gatgtcatga tagctatgtt caactattta aaggcctgag atgccaaaaa    30600
ggaaaaagat ctggaatgtg cttctcagaa aggcaaaaga tgagagttgt cagaagacag    30660
atttcagtaa gacatgagaa caaattgtct aatatttaga attgccccta agtggaacaa    30720
ggtgccccgc agtttaacat aggtatatga gcatctctca ggaatgtggc aggaggatta    30780
ctgtattagc agggaactta gaccaaatat tttctcctgt agctttgagt ttcaattcta    30840
aagatgtaga aatttgttta ttgtatattt ctgtggatta atttacaaaa ttcttcttgg    30900
gatttaattg acatcttttt aaatcagtgt caaataaatt cccaatatga ctgattattt    30960
tttaaaaatg aacagtaaga catttgaatc tatggacagg ttttcttct ctctttctct    31020 caatttcctt tatgtaatta tttatggaat aatctacagt gggctaagat actaaccatt    31080
tctggttaat gaccttttat ttttattctt ccatttccat atatcaatat gtaataaagc    31140
cttattaatt aagattaact tgaggagagt tcatttgaat tattaggaag tctggcatat    31200
```

```
agaataattt aaaataaacc caattgaact tcatgaaca catagtaaag ctcaaatggg   31260
ccaacctccg gtgtcttcaa cagacacccc ttagggaatg gttatgaata actcagaaac   31320
cttttaatta gcatatcttt gttcatatgt aaatgtgtgc ttttggaata gttgaggtta   31380
tttaatacat tctgctgact gaaatatttt aaacattccc tttacaattt attcaaccaa   31440
ttgttattga acaacttcat gtcagggagt gctgggatta cagcagtgag caaagacagc   31500
cctgactcct actttcctag acctcacagc tctacacaga aatcaatcag atcacgcata   31560
cacaccaata aattgtaaaa ttacagctgt gatgaggact atagaggagg gaaacatgga   31620
gctataaatt atataagagg ggatttaacc taatctgagg ggttcaagaa ggcttccaca   31680
ggaaaggaat gattgggata agacctacca gagaaataac tattaaccaa ctaaggagag   31740
agggaaggaa ctggagaaga tgccaggtgc agtggctcac gcctgtaatc ccagcacttt   31800
gggaggccga ggtgagcgga tcatgaggtc aagagatcaa gaccatcctg gccaaaatgg   31860
tcaaacctcg tctctatgaa aaatacaaaa aaattagctg ggcgtggtgg cacgtgccta   31920
cagtcccagc tacttgggag gctgagtcag aagagtcgct tgaacccagg aggcaaaggt   31980
tgcagagagc ggagatcgca tcactgcact ccagcctggt gacagagcaa gactccatct   32040
caaaaaaaaa aaaaaagaa aaagaaaaag aaaagaacag aaactggaga agattattcc   32100
aagggaaaat ggtatcgcat gcaaaggccg tgtggcagta gggagtactg tgtatttaat   32160
attttaagaa tattaatatc tcaccagtgt gagaaccagt gatgagtgat ggaaaagaac   32220
tcagggacca gtctgcatag gaccatgcta aggaccctct tatttattca atgaatatac   32280
tttatcctta ttaagaaaaa tttgctaagc aaagaaaaat accagtgcta cccaaggcct   32340
aattaccaca gattttgagt cagtataatc taaaataatg ggttttagaa gttccacata   32400
actgacaaat gacttcaaaa ttatatttat tccaaatgaa tagcttccat tagactaaaa   32460
ttacataaac ctactaagat gtgtgaccaa atgtaaacag gggagaatga cattaggaag   32520
aggaaataga agcctgctaa gcttccttga tgcttccaga ttttccctc tgatggcagc   32580
tggggtggaa agggaaatag ctcttccagc agcctcaatg atacttggag ccaaaacaag   32640
cttctaagcg ctgtaaggag agcatgccac atggacgagg cctgagctat agcgagagat   32700
gtcaggcttt gtccttccat gaacagtgcc tgggccagga caacctcgtt gtctcccaat   32760
aaggcagagc tggaaatcct catgctaacc ccaggctctc caaatagggc attttcaggc   32820
acagagtcaa cctctgcatg cactggcaaa cacgtcctgt aaaaagcacc agctccggat   32880
ggttctgggt tcacgagcaa ggtgttctga aggtcaaata ggctgcattc ctctatgatt   32940
ccaggctggc agtggacggg cccttggaa ctgccctgac agatgtattt cactacccag   33000
tgtgtgtgtg cgttgccgcg gggatcggag tcactccctt cgctgctctt ctgaaatcta   33060
tatggtacaa atgcagtgag gcacagaccc cactgaagct gagcaaggta cggaaaaatc   33120
attagttcac ccttccatgg attaaaaggt tcaatgtcct tatatctatc atctgccgat   33180
tcttggggag gattttaatt aactatgagg gataaactca aggatcctta actatactta   33240
tgttcttaaa aatctccact cagtattaca tttatgagta gggttatgtc taatcttgtt   33300
aaagatgaca agacataaat tttattgctt cattgccatt acaggacatg taattgctca   33360
tctcagtaaa atatggacag gctgcaaatg gctatgtgac tgggtggcag ttcgcaatat   33420
taagaggcaa cctctcctta gtctctttag cttcagactg tggttgcaag tgtacaattc   33480
gatgtcctcc tctcgtggac tcagtcctaa caagaagcca caattgggat ttattggccg   33540
gcttgctgtg gggtggccat cccgctctga atctcccttt tgtcatttcc tgtatgtttt   33600
```

```
acaactagat gcctctagaa tttctttccg tcctttgtcg tatctagaca ctccatccga    33660
tacttggacc ctcttaggac cagcagcagg cactagagca atggtaggca aagagccctg    33720
ataacccaaa gccgtatgaa tgcaggagga gtgaggatgg cagacgagct tggtgctggg    33780
ccgtcctgca tatcttctct gcttaaccct ttgtccacag tgtcctcatc tatcaaaggg    33840
agacgcttga cttaaccacc aggtctcaat gtgtaaacca tgggacatct gtcacctgac    33900
atgatccact agagagaatt ccgtagtcaa aggaacttaa gcaacgctcc tgcaacatcc    33960
cactctagaa gacatcatcc actagccatt aaataagttc tgcggggtg gggcgcagta     34020
gctcatgcct gtaaccccag cactttggga gattgaagtg ggaggatcac ttgaggccag    34080
gagtttgacg ctagaccagc ccgggccgca tagagagaca tcatctctgc aagaaaatta    34140
aatattaggg agttcaaagc agtgagccgt gatcgcacca ctgcactcca gcctgggcaa    34200
cagagcgaga ctctgtctct aaaaaaagtt ccgcagaaaa gatcctcatt cagttttgtt    34260
tcatctatct ttcccaagct tatttagcta cagaaccttt cctcacctaa cacctatcaa    34320
gaattcgtat tctgtgaagc atcccaggca atgagggcta aagatctct aaactcgggt     34380
ctctgccaac taagaaacag cagttaacta tttcatgagt ttccaagtga caggtccttg    34440
acatacattt tctcatttga attttttaat ctccccaaca accttataaa gtaagtaaca    34500
caaggcctgt tttccaggta aggaacctga agcttggaga gattaaattg attttcctga    34560
aaagacatgg gtaatcaaag gcagaatcag gattcaaact taggttcatc tggctctttc    34620
catgacaaaa ccaacacatg gtagacgtga cccccagctc ctcctgcaac cctggagcaa    34680
tattttagga agacggtggg attcctgctc atagaatcgg cacctgaatt ttgctgtcat    34740
caaagaacat gcctgattcc accctgactg aaatactgcc tgcagttcac ctctctgagc    34800
tgagtttcct gatccacata acggagaaat aagaatccat atccaacagg gagttttaat    34860
gctaaataag acaaataata tggaaatatt accatagaaa tgtgtataca gaaatataga    34920
tgattatcta aatgctgatt gtatctacca aaggtataaa taggttacca gtactgctat    34980
tactaatggc ctagatttat caagcactga ctacctaaca ggaaggaaac tgggcatttt    35040
acatgcacta tctcatgcca tcttttcgtc atacttatca tttttattcc cattttacag    35100
atgagaaaac taaggcctga tcacaaagct aatagaaatg acagtcattt tactaaatgc    35160
tcataatagc tcattcagat aggtaatatt ctcaatactg atgaggaccc tgacacacag    35220
agagctaaat aatactagaa ctagagtttg aatctagatc cttctggcac caaagctcat    35280
cttctttcct ctacgccata atatatttaa caaagcaagc aaaacagtga ctgggatatt    35340
tggacctcac agcaatgctt tgttttggtt cgtgatgatt tttcagccac cctaagttct    35400
tccttccctc ttgctgccta ccaagtaaat cccactcaga gaggtggctc actgcttcat    35460
ggtttccacg acactaaaag tcacttcatg cttcacagga agatggtggt ggatagcgtg    35520
tctcattttc attcactcac taatccaact aatatttcaa gtcctgctca gagacatgca    35580
aagtctcatt gtcattacac ccgactcaca atcacctccc ccttctctta acctccacca    35640
ctcctttgct gccctactgt tatgtcacat atctttcctg tattaagatt cgtgaaataa    35700
tcttatttc tctaacagac tgtgagttcc ttgaacatag cttctctgga tatcttcata    35760
catatatata tatacacata caacatgtga taactatata tatagtaaaa atattgaata    35820
aatcaatgag tgaataaatg tctacatgtc caaaaagaat aaacaatggc ttctgtacac    35880
aattttcttt aaaatttaag ggtattaagg ttttgtttat gtaaccaaaa aaattcttca    35940
atgattttta ctaaattcca attatttac taggaatata gaggaaaaat cttataagaa     36000
```

```
cccccaaaaa ttttaaaatt catacaggag cctacaaaat cttaattttg cctcctttct   36060
cagcattcca ttgtcattcc tgggctctgc ttgtggcgtt tctcaaggct ttcagcactg   36120
cagtcaccac aaaaccataa aatagggaca ttgatctcta ttccaagaaa cagaaacagt   36180
agagtaaaaa atataaaagc aatgttttca tcgcttataa aaatgtgagg gactatttgg   36240
acacgactca ggtgaaaata agggcagaaa taatgtcata tgggagaaag gaagctaaag   36300
tgtggaatca taaaataact taaaggtcct aatctcctag ctttgcatag gaccatgaaa   36360
gtcagtatct gcacctcgag cggagatgat ttgtccaaag tcacccagct tgttcaccac   36420
tgagtcagga cctgagcatg tgtttctgat ttctgcttca aagttctttc atggaagaag   36480
tgaggttttc atgctattga aagtttgggc tgaaaattac agttcagatc caattcctta   36540
agcgtctgca ggcatgagaa caggtttagg aagtttctct cttttaaagc aactttgtgt   36600
tggtttgagt atagctacta ttaggcttat gtaactaata tttgtcaggg ctacctacat   36660
gcttttgaga tataaagact actccttcca ctaaactgtc agagtctata aattttga   36720
agtgccacag agcaaagcag tacatattta tctaacggtg tcttcacaat tttaagtctg   36780
gactatagtt ttcagattgt cctcttttgt aataaggaag gaaaggacaa ctcgcatagg   36840
cgttgagagc cagaatttta agcttaaatg gttaactgcg attaggtggg attttttttt   36900
cctccatgtg taaaaacact ggttggcata aggcatacat ttttacacac aaaactcaag   36960
ttgcaagtct ataggaaaaa atgtgcacca aagttttctc aattgtcacc gttgcaaact   37020
agaacttctt tacccttctc ctctgttgca ttattctaga aaacttctaa gtaaaatgca   37080
ggagcacaac caataaggcg cctgccactt cctcagtggg aagcgtcata agtagtactt   37140
tccatttgaa gctgatgtct taaaatatct ttgtttctaa gtacttttgt tttgaaagat   37200
ctgggagggg gcggggagtg aaggggagg gggaagaatg ggcaggaggg gatttcccaa   37260
gaaggccaaa taacaagaag tataatgatg gcttgctgtg atgaaaatgg aaaaagttg   37320
taatacatga aagaaatatt ttcaacgcag aagtaagagc caaacttcac tgagttgaag   37380
gcagctgaga acgctgtgcc cctgtgggat gagggaaggc tgagggtggt tgagaattct   37440
ctgtgatgca atatggagga agctgaatgc tgggggtgaa aaatgccctc tagcaataaa   37500
gtcctccacc tcctgcctaa cgggtatgat taattctaca tcacactcaa tttgtgaaaa   37560
gagctcttga aaaaaaatta ggacggtttg cttgtgcaaa ctgtcaaaat gatgaatgaa   37620
ataggtgtgt atgaatgggg agggaggggg aggattgctg acataaatag attggcttac   37680
acattttagt tctccctaat atcacagctg tgcagtcagg actgagacaa ctgccaactg   37740
caagatgcgg ttcgttttct taactgcata tgtagtcttc agactacgat acaacagatt   37800
atacaagaac tgagataatc tcatttcttc ataaattgtc ttccttcatc agctccataa   37860
tatataacca tgataatggg tatttatagt gtgtcccatg caaaatggcc tttgggttct   37920
taacctaata taataaacag ataattcaaa taaaagaca gcacgggcca gtgggaacaa   37980
gggaaagagg ccaaaaaaga caaaaaatcc atactctact aaaatatatt aataaaacaa   38040
aggagggcct gctctctttt ctagtgaatg aaaaatgcat ttaatttaat ctgtttactt   38100
tgagaaatta tttactttca ctttccctca cactggagct ctgactactc ctggaactga   38160
tcatctctac taatcaccaa gattcctgcc atcagttggc ctctttagga ggggccattc   38220
atgcttctcc taaagaaatg tatgcttctt gtctttcctc ggagggcctc aaaaggcctc   38280
agtaccccat cagccctcac cattgctctg tgcggaagtg accagtatta atatgtttaa   38340
tatcttggtt tattaaccac agattgcgtg actacagtct tcttgcaaaa gagtccaatg   38400
```

```
aaatacacaa acattttaaa atctcccttc acctccctcc ccaaactaaa cacctcccca    38460
actttgctcc ctaagaaact caccattaaa cagttgaata tgtctcattc cattcctttt    38520
ccatgcattt atatgcatat acctatacac attcatgcat aaatagggt gtgtgtgtgt     38580 agaaggcaga ggaagtgtaa tttgttttgt ttttcattaa agcataactt cgggcaccgt    38640
cagtgtcaat acctgatgat ctatttcatt ttgtttggtg tctttagagt attccatagt    38700
gtggataggc cacaatttat ggaatcattc tgctattaaa taatgtttca ggccaggtgt    38760
ggtggctcac acctgcaatc ccagcatttt gggaggtcga ggtgggcgga cacctgagg    38820 ccaggagttg gagaccagcc tgaccaacat ggcaaaaccc catctctact aaaaatacaa    38880
aaattagccg ggcgtggtgt caggtgcctg taatcccagc tactcgggag gctgaggcat    38940
aagaattgct tgaacctggg aggtggaggt tgcagtgaac tgagattgca ccactgcact    39000
ccagcctgga ggatagcgcg agactccgtc tcaaaaaaaa aaaaaaaaaa aaaaagaat     39060 gtttcagatg tttcagttgt ccaacaagga ttattaactg taattagacc aaacggaggc    39120
ccaaaagaga tcagtcctca gccacagggc gaagtagcaa tatagtcatg aaatagttaa    39180
cattgaggat aatcacattc agaaaatgtc ttaaggatga aaaattattg acaaagcctg    39240
gtcttggcct tataatggtt caccagaaaa acaatttat aactgtatca ctttaaacta     39300
gaacttttac acattaggta ggcttatcat taagaagaaa tatttcttct tttatttctt    39360
cttatttgct attgtattaa tccaggattc ccttaacaaa aacaaaataa aaccaggac    39420 aataagagtg atcatttatt gaggaggtaa tatattttct aaaaccagt ctttatcttt     39480 tcacagagag aaattctcct tttggaaaat gatcctgatt cccctctatg cagagcttct    39540
gtcatcctgc tggtttcaag cttctgtctg ttctgttctt tcttttgcac agtgtggggt    39600
acagaggcgt gctgcccagc aggaggcagg tggcactgca agccactgcc cttctccttg    39660
aggaggcgat ggtcaaggtg ggcccctggc tccctgtaaa acgcctctag gtgagtttag    39720
cacacaccga gcctggtgag gggcttcccc ttcatggagc acatcttcat gatgaatgct    39780
gagattctgc ttctgacact ggtgctagag gtcaagtttg gcttcccttc tcagtgacca    39840
ggagtgacca gtgggaacac atgccaagca aggcgcatgt ccctctttgc tctataaat    39900 actgtcttca ttcttcattc tctaagctcc tccaaatgac aaacaaggat agtaacaata    39960
gcagctaaca tcttctgagc acttactgtg tctgccagac gttgcattaa atgcttcagt    40020
aaaacatatc ctttcatcct cacaataacc tcaggagcta ttgttctgtg tttattgcca    40080
ttttacatac gcagtaatct aggttggagt taaataactt tgcccagtt gcacaagtta    40140 tttgcaactt ctacctgcat ggtgaagcca gcagcagtct accacagcag atgggcttca    40200
taggctcaca acgctgagct gttgtaccat gctacactat atcctaaacc tgtattcttg    40260
tgtacacttt ccttgtttag aggggttctg ggccataaat aaatacatag gtaaataatt    40320
ttttttctgt ttcattctct ggaaatttat tttggatata aagacataca gattgcattt    40380
gtgaaagtgc cctctgcctg tgttcatgga tatctattca agatacggca caagttttgg    40440
agatgtaatc gcctgaaagc atccaacttt gattagagag tctgagctct catagtaaca    40500
cagattggta gtgcttctca attcattttc tgaaactgtt tatcaaaatt tagcacagtt    40560
ccatttccta ctggccccag acctctttga cctggtccct atgtgctgct gaagaattct    40620
taaagagaag ccttggcttg ggaaaacatg aaaatgagaa gggacacaca gagagcccaa    40680
acttgtgact gtcgctcaga cccaagcccc ttgcaaatgg acatggctga gtttgggctg    40740
atcattagcg cttgggaatg atgtgaaact aaggtctatg acgggccaca tgcacacaga    40800
```

```
aaccctcaac gccatgacag tcccagagtg gtctcccaaa acatctaggc atccactata   40860
tctacaagaa tgtggctggg cacgatggct catgctggta atcccagcgc tttgggaggc   40920
cgaggtgggt ggatcacttg aggtcaggag ttcgagacca gcatggccaa catggtgaaa   40980
tcccatctct actaaaaaat aaaaacttcg tcgtgcatgg tggcacatgc ctgtaatccc   41040
agctacttgg gaagctgagg caggagaatc acttgaaccc gggaggtgga ggttgcagtg   41100
agccaagatc ccaccattgc actccagcct gggcaacaga gagagactcc ctctcaaaaa   41160
aaaaaaaaaa aaaaaagaa agaaagaaa agaaaaaaaa gtgttggatg agtcctgtaa    41220
aaaaaaataa ttttattact atgaaagttc agaactttg ttattttact gagaatgact    41280
ttctatttaa taaaatcttt taaagtaaac tcaggtattt ttggtctctg agatcagcta   41340
tgaaattctg aaaaggcatg ctttctacag gtagctgatt tcagggttgt tttattttg    41400
gagactaagg tggggtgagc attggaaagc acagatcaca gagttgtagc ctattgtttg   41460
ggatacttgg tctctcattg accaggtcct ttctcatggg cgaaatgcag acttggaact   41520
cttatgtccc ttcccagtga gtgtccccca ccattagaaa gatgaaagaa agtcaaagta   41580
aatacctttt gcttctgttc aaagtcccctt tctttctttt tctgcctgaa acacttctac   41640
tgagcctatc cattttttcct ccatagcctc ttacaccaaa gctgcccagt gtcacttaca   41700
agtcaattac ggagggaaaa acacacaaag ccattacgag gaagcaaaaa gtataaaagg   41760
cttgacaaac cctaaggacg ctgacatgca gctaggccac gagaaagtaa ggaaggattt    41820
ctatttgaaa agataaagtt tcatgtacgg aggaagctaa gatggggata gttttcaaga   41880
aaggacgact gggactagat ttgaaattgg aggattttt tataaagcaa atgttctggt    41940
ttattatcca tctatgaatg tgttttaagc atgttcctta aagaatggga aagagagaaa    42000
ataaatcaat gatatttgct ctatgcccaa tgccaactct gagatgaaac aggctaccaa   42060
ggccagggag gagggggtca tgcataggtg agcactgcat taattcagcc agtagatttt   42120
tcatttccac ccagagcaaa gcaaggcaaa atgaaagcta aggttttcaa agagtaattt   42180
agattaggca caatacaaag cgaaaagaaa gcagatagtg gtattcatca ccaacctcga    42240
atataaaatc caccccctaac tggtctcctt tcctcctccc ccaccctcca taccctgggt   42300
ctattctcaa tacagcagcc agagagatcc tgccacctgc tgcgggccat ggaactccct   42360
gctcgccaac tccctgtgct ttcctgtctc tcggagggaa agtctacaac ggcccccaaag   42420
ccctacaacg ccatggctcc cccagccctc ccctcgccca tctccttgct ctccccaccc   42480
tctctgggct ccagccacac aggcctccag gctcttcctg gaaaggtctc actcaggacc   42540
tccgcacttc ccaccatctg catctgcact tcccacctaa gcatttgact ccctcaactt   42600
ttccaggtct ttgctccaat gtcccccttct catgaagagg ggacatgaat ctccacgaat   42660
tgatggttca tgtccatcca ttactgattc aacaaatatg tgttgaatgc ctcctatgtc   42720
tccagactgt tctactccct ggaattataa aagtgaacac aagaggccaa aaacaagaga   42780
gggctcattg agcccccgtt tgaccattca acttaatatt gcaacacttc taacccgcct   42840
ggggttctg catgcacttc tcaccatctg acataaccta tattctactt atctatcatc    42900
ttccttctcc ctctaagatg caaattttaa gaggacagca attttttttg gccctgtctt   42960
gttcacttgt atagttccag agcacagaag agtctggaca ggtaggaagc actcaataca   43020
tatttgttga atcagtgaac ggatggatga acgtgagccc cttgctcatg ggattcaga    43080
gggtgtcaca aagggaaccc cggcttagct ctgcctggag aggctgtgca gagatcatcc   43140
ctaggaagaa ataagtgtca ggaaaggaaa ggcaaccctc tctcttcctg agaaaagcag   43200
```

```
gtcattgtgc ttagagactg agggattatt tgtcctgaaa ttagtatctt aagtcccctt    43260
gtgaacagga gctgtccaac aaatatgtgg gcccagtttt tgaaagaaga ggccttattc    43320
tcagcatctt ttactcttac aaataattaa tattataaag tcctgcctaa acatgaagag    43380
aatagacaag atgtttagct ttgagataaa cttttttatt tttgtctcat gaatttgatc    43440
tattcattaa atctcattta tatctctgat tatatgatcg tgagcttaca agctggccgg    43500
cagagaggga gagaagagaa cattgatcac tggatgaggt atttccaggt ggggatttac    43560
caggcagcag ctggaatcaa gaccagccct catggatatt gttaagccat acagatgtct    43620
cttttgggga aggcacgag agagagaggt gtgggcagca aggggtggga gtgtgagaaa     43680
aatgggagaa ttaatagatt tatctcctgt ggtttcttct agatgcaatt atttgaaact    43740
cgcagcacaa aaactaagct tttattttag caaacccaag ctacttttg tcacatgcca     43800 tttgcttaat accgagagtt aaaaaaataa ttcttcccag tcataatttc attatagcag    43860
ttgacacaca ggcacagccg ccacccacca gctttcttgg acaccgatat gtttcactga    43920
gaggaaattt ctggcctgtg tgacttgatt ctgaaattac cataatctcc actctccaga    43980
ggccgtagct agtgaagtgg attagtgtcc aagcctttgg ggtctctgga gaagaaagtt    44040
caaatccaga gcttaggtca taagtaaaga tgaaggggtt ggtctaacgg tttatccccc    44100
tttgggagca gtgaaaggca cagctagtta tgattattaa tcttgttcag aagcagcaca    44160
gccagaaatg tggtgagttg atcctcatcc agagaaactg gcacggccca caggctcctg    44220
actctctgaa ttcactctgg cttttttcaa acacattgtg aattttttca aaagaaatca    44280
cagtgtgact gtttgttcac tgacacacac aaaaaaaagc atgttatttt gcagaagtgc    44340
ccatttgggc tcaaataatt taatgggagat aaagtagtct gtgattatca gcacatatga    44400
aaagagaata gatccgttca cttgccttct ctcttgacag gtgtatttct actggatttg    44460
ccgggatgca agagcttttg agtggttttgc tgatctctta ctctccctgg aaacacggat    44520
gagtgagcag gggaaaactc actttctgag ttatcatata tttcttaccg gctgggatga    44580
aaatcaggta ctgataagac tctgagaata agcaatattg ctgaactcat ctaatagcaa    44640
tgaggaacaa tttcaataat gagctatgta gcactctgat agcatgacag aattattttt    44700
atgttcttaa aagggaaagg agaataaaat aaaaccagat tagcaagagt gattcaagtt    44760
gtaacaatca aagaaccaaa aaaagaagct acagttaact tgctgaggaa tagaaagggt    44820
cagacaatgg aagacaatcc agaggctgga aatcccaaac aaatttgcat tgtccccttt    44880
aaaagtgaca tcaaatgaat attactgatt ggctgtatca tcttgttgag ttcctgactg    44940
gttctgtttc tgtgccttga gctgttcaga gctaagcaaa aaagattcct aggtgtttac    45000
attcaacatt ttgtattgtg aagtatgtga gcatctatag aaaataatta ttatgaatac    45060
atgatttgtc cagagtttgt tctcttaagg tgttcttaga aattgtgtgc acgtatgttt    45120
atttacctaa gatgaagatg atcttttgtt ttggcaggtg ttctgcagta tattgtatta    45180
atgaaatatt aagattgaat ttaccaaaaa taatgtatac caaaatattg actatggtag    45240
tatttcaatg ttgatactat tgaatgataa ctactacatt gtaatccatt ttaactcctc    45300
aaacagggga attaacaacg aagtgattac taggttacac aatatatatt ctaatcagca    45360
gctattattg atatatactt ttaaggaaag tgtatttgag cctgggagat tgacattaat    45420
cactacattt acaaatgaat gctctgtgta tgtacatcac acatacacac acatgcgtgc    45480
gcacacacac acacacacac acactggcct tatagaacat cactgtaatt tgactctgct    45540
tctgcaaatg aataagactc tgctagaaat tcagtagctt aatgaatttt tatggtctta    45600
```

```
tttgcagtcc ttcttaaata tttaatcctt tgggataatt tgaaatgtag cttcttggg    45660 aactaggctt gaaacatctt aatgaattat atagtgttaa ttatgttttc caaacaaaca    45720
ctttccttat tcaagtggga ttttttgactg atgaacagtt tggtgaagta gagacagctt   45780
ctgtcttctg ctctcaagta ctgtgcctgc tcttctactc taaggtgcat tgatcccagt    45840
gtgcacctag gtattccttg ccaactggga gctgtgggac tgaggttctc ataactgaga    45900
actgaagttg atttggcgac aacacaatcc tgcccctcc cgtctctact acttccaaga     45960
atatgctata aaacatatat ttttttttcta aacacaagta gattaaaata gatgtcttac    46020 attttttgcca tgacatgttg aaaattattt cgactcctaa atttcaggca gaaaaatcac    46080
taatttccac atttaaagga aaaataattg gtgcattctg tcgggaaaga atcaagaggc    46140
tgttttagaa atacccaatt gttaaactga attcaacaac ctcaaagtgg caaaatgaca    46200
agaacagaag ggacagatgg aagaggtatt gtgaagggta aatcaacaga gtttggagac    46260
taattgaaca ttgggctgag aaatatggga caaatatcat tccaaatgtt tgaacatcag    46320
tgattggcgg taccacaagt gtaagtaggg aaggccctt ttgtgtgtga aatggtgccc     46380
gaacttctca gcaaggacct taagaccctt cccagcctga ctcccactca ctagctgtgt    46440 cccacccca tcggtttcct ctggcaccag agccaccaaa ggatgcgtgt tcacccatca     46500
cactgtgcac agtcacacgt ccatggcttt gctcgttctc tccccacacc tggcgtgtca    46560
cttaacaccc tctgccactg ttccccacct tcttttttgct cggagtccta taccccaact   46620
cttttccagc agtagctctg ccacctggtg tcagacttgc ctgctcacaa cttcctacga    46680 cctggattc ttttttatatt ttcttttattt tttagattca gagggtgcgt gtgcccattt    46740
gttacatggg tatagcgcat actggtgggg ttacccatta cccaaacagt ggatatcata    46800
cccagtaggt tctttgtcaa ccctcactcc cttctcaccc tccccccctt ttggagcccc    46860
cagtgcctgt tattcccatc tttatgtcca tgtgtgccca ttgttgagct gctgcttgta    46920
agtgagaata tagagtattt cgtttttgt ttctgagtta gttcacttag gataatggcc     46980
tccagctcca cccatgttgc tgcaaagaac atgatttcat tcttttatg gctgcatagt     47040 attccacagt atgtatataa cacgtttct ttgtccagtc aactgttgat ggacactcag     47100
gttagttcca tgattttgct attgtgagta ctgctgtgat gaacatatga gtcttttta    47160 tataattggc ctggatttct gagatctaac ctaccattgt ctcctgacct gttgggacac    47220
ttccactatt ttcagctgaa cctccctaga ttcaactact tttttagact ggagagaagg    47280
tcagccagga aagtcaggct tacagtggga acctggggca tgagttgcac ccagcaaggt    47340
tgttagccaa actggtcagg gtcaggatga gtcagagggt gagaatgaat agagcaccac    47400
ataggggtct aagggatgag cactgggaac acagatcccc agaagtgaga agcaaggtag    47460
ctaccagaat gcagaagggg ctaaaataaa tgacagcaac ttaaaacatg atcatggcca    47520
ggtgcagtgg ctcatgcctg taatcccaac aatttgggag gccaaggcgg gtggatcatg    47580
aggtcaggag atcgagacca tcccggctaa cacagtgaaa ccctgtctcc aataaaaata    47640
cacacacaaa aaaaattagc caagcatggt ggtacacacc tgtagtccca gctactcgag    47700
aggctgaggc aggagaatcg cttgaactca ggaggtggag attgcagtga accgagatca    47760
cgccactgca ctccagcctg ggtgacacag caaggctctg tctcaaaaaa cacaaaaaca    47820
tacaaacaaa caaaaacaaa caaacaaaaa tgatcacaag ggattatgct gtgggctgtc    47880
atttattgac cactagctac atgacgcctg gatggagttg cttaattcca aggcaaatga    47940
ttaggcacag atctccagcc aagccgcctg ccaggctctg gccaccattt tccgcctgcc    48000
```

```
aggctccaca tcctcccagc acttgaaact ggacagtata catcacaccg tttaaaccca   48060
ctaggcaggt ctcattgtaa gatgcagttt cttcccagac atttcatacc actttaatct   48120
ggcaatgccc ttctcaactc cccaggagcc aatgttaagt gaaggggat agcaggtaga    48180 cattaattgt tgaaaagttt ggcaggaaaa gaaggaagtc gtttagtgct tgctttctct   48240
taaccacatt tactatatta ctttcatcct tttaaaggaa aatattcttt ctaggttaat   48300
gttattgcac atctactagg tataaagagg cacttggttc caacaaggcc tgattcagac   48360
ataaatgaga tatgatgctt gccctaaagt gcagcattgg agacatctgc aaatagtgat   48420
aagcattgcc agccctgtac acatttttaa ttaaatctac aaatgaacat gattacttta   48480
ttctttattt atagaagtct tatttttttt ttctaaatgt catctaatgc cacaaattta   48540
ctttaggctc ttcacatagc tttacactgg gacgaaaata ctgacgtgat tacaggctta   48600
aagcagaaga ccttctatgg gaggcccaac tggaacaatg agttcaagca gattgcctac   48660
aatcacccca ggtaaggcaa gctcttgctc ctctccctgc caggctcttc tctggagaaa   48720
tgcaagggct gctggagtga aaagttaatc tgcagtaccg tatatctcca ttagagacaa   48780
aacatctacc ttagaaaagg tgatcaatgg tatatttcag gggccacaag cctctcctga   48840
actggcttac aacctctgac agttattgat tatgttgcaa ttttcacac ttaacctcca    48900 tttaaagatg gtatttcttc aactacatat gctttcaaga catctttggt gggtacagtt   48960
gatctctaat tacccaactg gagaattcac tcctgtccaa ctgtacacta tctagcatgt   49020
ctagcaaaag cagagagaaa atgttagaag acaaagcagg gatttcgggt ggtggttaag   49080
aacccagcat ctggctgtaa atcctggttc tgcctttacc attggttgac cttggacagg   49140
ttatctaccc tggtactgac tctgtctcct cctctgcaaa ctgcagaaaa taatagtgct   49200
ttcctcctaa gagtctgcaa ggataaaatt aatgaatgca tgtaagaggc ttaaaacggt   49260
gctttgtatg gagtttgcaa gaagcactag ctgctatcac tgctattatt atttttatta   49320
tcgtttccat tattactatt attattatca ttatataata aatttcaata tagaaaagca   49380
agaatacttg ttctggggtc acaaaactga agtgaagcct gcacttcctg gttctagaag   49440
ttactggctg tgtgaccttg gaagaggcag cttatttgag ctttcgcacc ccattgaaaa   49500
atatggatga taatatccat tcacagtgtt gttttcataa cgtaaatata cttgtagtat   49560
ggggcactaa tgcaaacagt tatcattgtt atgatgtctc ctaagtcagt cttttgctttg   49620 aaccttcatt gtctacggct cttaaaagtc ggcatgtcct aatattgtct tcattaaaga   49680
acagttccca tatttgagga aagatctgaa ggcagtgaag gagtgtgcca tgtgggcaac   49740
tggagcatgt gccaaggccc tgaggcagga gacatcattc ctggcatgat cccagaacag   49800
aggaggtgag agggagagca gcaagagcca tgctgtagga gaggtaacaa agacagctgc   49860
gagtcattgt aaaactttgg attttattca cacaggggaa ggcacttaca ggtttgagca   49920
gtagagtgac gtgggatcac tctgcaagag aatggaacgt gaggggcctg gacagaggt    49980 ggagaggcca gagaattcag cagtggtggc agtttggatt agggagcagc agaggaggtg   50040
atgagaaatg gttagattcc ggagtctttg cgggttgagc tgaattgact atggatggga   50100
tgtgaggtgt gacccaagct attcaataga gtggaatccc cacttaccat atggtgatga   50160
ctttaagagg agcagctggt tggcagacat ggggtgtcag gagttcagtt tgtgacatgt   50220
ttagcttatg atgcctgtca tacatccacg tggaattttg gagtgggcag atgaatataa   50280
gaagcaaacg ttcaggggag aatttcagcc agaggtgtga gcacatggac tgtttggagc   50340
cgtgaaactg gatgagatga ccagacaggc agatatagat ggacaagagt tccaagaact   50400
```

```
gcactgttgg atggtcaggg aacagacact gtattgacag gtcacagagt ttaatacgtg    50460
acactcatat ctgccttaat aatcatgccc cttgggtctt ctataccctg accttctttc    50520
catccacttt ctctgtattg caccagtaag agtacattaa agcccactaa ggtacctctg    50580
actgcttcca tatccccggc gatgttccca ttgtcttgca tccttcaaag cctcagtcct    50640
tgcatttctg cctcgtgggc ttcctgcaga gacagcatgc ttcattaaac tctttgtact    50700
tccttcatat ttgttctgct tcacagagta cttctctggt gaatattatt tatcttatgg    50760
tcattttggc tgctcctttt taacattttt ttcacactct ttctgtacca gaaagatgcc    50820
attttctttt ttatcagttg tcatggaatt cattagactc cctggaccag ctatttgaag    50880
gaggttaatg aggagggaga tgtggaagga gtgatcaggt agctgtccaa gattcataac    50940
catctgattc cagtcaccat cttgcctgtg aagttactca gacctcaact gccctgtgct    51000
ctgtgagacc cctgccaacc ctctctgcac cctgcaccca gcaacctgta gagaaacagg    51060
agtgtttaca ccctgggaag agatggtttg aaggcatgct tgtggggatt actcctgacc    51120
cacattcagc cagggagtaa aggctttcca gcaggagacc ccaagaaaag catcactttg    51180
agcatagggt tggggaggga gggcgtggac cagctgcaca acctcacaat cttgctcttg    51240
ccccacgggg ctcattctga tgcctcataa gctgtggcag tggccttgga gacttttcca    51300
ggtgtcactt cctgacacct ccttgctcca ttttgcttct tgccctgact cctgctgaca    51360
tatggcctag aatccagttc tggttctacc ttctctccaa atgaggtgct tccaacccat    51420
cctggcttct gcagccacag aatccggttc ctctgagctc ctgctccaca cccagccctg    51480
gctccagggc ccccagtgct tctgagtcta agtcaccaca cccacctcac acccacccag    51540
aggagagacg agatcatttc atctgccatt tccttgaaaa gattgtaggt agaaactaac    51600
aaaatattaa aagcttatat gagaaaactc aaggggtttt tgttgctatt ttctcctttt    51660
gggaaaaaaa aaatatatat atatatatat tcactgataa atgttttacg ttcggttttc    51720
agtcatcatg gaataaatgt tctcacttcg caggcttttg acatggacat ctatatcttg    51780
gttttcagtt cttctagata gtctcagtct ttattaggat tgtcccttt tgacatctca    51840 tatggtgttt gtttgtttat tatttattta tttatttatt tatttttaca cacaaagctt    51900
gcagcccagt gcggaaggcc tttaaaacca aactatttaa ttatctccct tccctcaaaa    51960
aggcatgagc caggaacacg gagcatcaag agaccaagga taaaactggg tttgcacaaa    52020
ctctgcctag aaaattatgt aactcagtgc tgagaagtgg gcctgtccaa ttttttcgca    52080
gggagtaaag agtaatcagt tttaaggtgg caaaactgta ttaccatcac tttccctgtt    52140
gctcatacct ttctagaagc cataatcaaa gtgaagtgcg gaaacgtact taatgctcaa    52200
ttgtattttg cagcacggta gctatgcaaa ctctctctcc ttgatggatg acttcatctc    52260
ttccagagta gacgaggccc ccaaggtttg gaatcactga atcaaacctc tacagcatac    52320
ttcccagtcc caaattttt aatatcatat ttgtaatagc cttagactct agaacatggt    52380
aacttgttat atagcttcaa gcatccatgt cattaatatt agacacatga aggcaaagtc    52440
aatgattttg tccctggaat gccagatccc tgggaaaaga caagccttcg gtcaaaagct    52500
tagcaccacc ctttcaaaag gctttttaaa tgacctcctt aaaataattt tgttttctgc    52560
tgtgtaaaag gagatttatg tttaatgaag cttttaatga agaaatctcg gaaagagaat    52620
gccaataaaa tctaattttt aaacaagaaa atctaatatt gagaagtatt tcaatatcct    52680
ggcctttgtc cagatgtaaa tgaaacacac aatccaatta ctgttctgca caaaggacaa    52740
agtaacatta attttcctcg ggatggttat taaagagata aacagtatgt tttcccctta    52800
```

```
ttatgtcaag gatatgtttg ttcccaagcc tgcctggcta ctcttacaag acggttctgt    52860
cctgtcgtta gctcatatct tttggcaaag atgggtcaga agaaattggt ggatttgtta    52920
gtggcctcag aaaaggttct ttgttcttga gggcctttga agtaggctct caaccatttc    52980
tattcatcga cacgaagccg aggattctcc ggacttactc tttcaaaaat atttacctgt    53040
tcactcaaag ctggagtttg ttcttgttct aagaaggagt aaatcaaaa gaataaagtg     53100
aagaggggca aaaagatttt ttatagaaca tgaaaacag gaccaaaaat aaagcttgaa     53160
gggaagcaga tcaaagagag tagtacaagc tataaaggaa ccagaaaatt gcaaaaataa    53220
cagtaataga gaaacaaatt gatgggcatc aaaatgaata caaataaggg agagagaaga    53280
aaaattaaaa atagatcaaa ggctgacaga aaatagaaaa gtgtgttcta ttgttttttgt   53340
ttgtaattaa ttttggtaat tatattagct atattacaaa aacacaagta tagttttgaa    53400
agacagtcaa caaatattaa gtggatgcat tataagcctt ttattgatat attcaaattc    53460
acatgcatgt gaaaattgta tagtatttca gttagataaa gcacagaaaa gtactatgaa    53520
acaaaaacat taaaaattat tctcccaatt aaaatatagt aggctaatta aatacattca    53580
ttgccatcta tgtcttacta atctagagaa aggtatcttt ttcaaaaatg gaaactgtat    53640
tgcattttt gtaaacattg tcaatacgtt cacaagcttt aggtaaatgt tcagaaaatc     53700
aggaaaatat ttccaagaag gtagacagaa tgaaaataaa aataccgttg tcacatctag    53760
ttactttttt gataaacaca cattgtacgg atactcagct ttctgaattt gtggatcagt    53820
tgcttttaat taattgaata aaataatttt ccataggcct taaatctttg atcttaccct    53880
tcagataata tttgtagttt tctacttttg acctatctgt taataacttc accacgcctt    53940
ttaggtgtaa atttgatgta attaattacc ataaaaactt taaagtttgg tcattttttt    54000
ttttttttt gtaatttcag tagacgtatt tcttttaact ttgaagaaaa aaaaatagaa     54060
gagtactacc atttgttaga acagtttaac ccaacctaac gatgaagaaa ggtgtcaact    54120
taccatatga ttgggggctt ctaatccata ttgcatgaat gtattttaga ccacctattg    54180
ttttcagaaa cgtgaaaata cctttatact aaattgagta aatgtgtcca tctggaccca    54240
catttgcttg tgtatgcacc cttcaattct catttgtatg tgcatatgtg caaatgtttt    54300
taaaatgata ttttaagaa attagcattc tgattatagc atacagggcc ctttatctaa    54360
caggatatcc taaacattca ttatgtgact aaaatgttca gaatactcaa agaaatagac    54420
ttaaatggaa atacaacaca tgataagtta cagcttcatg ggaaaaataa agacaccata    54480
aacttatgat gaggaaattg tcagcatatt cccatagttc cttcccatga gagggcatca    54540
atctctctgg ttagacccaa gtgaagattc aataaaaatt gctgaaatta ctccatttgt    54600
ggtaggggg attggagaga tgggtgagta cagggtggat ttatcattat actgcaaaat    54660
ttcttcaatg gcattaccta tctatcaaat tattagtttg gcaaaatatt tggttactta    54720
tgcatgaagg catatatatg ttactgtttt attggggtgg ggaagggttg gcaaaaatgg    54780
ctctaccatt ccctgggatc ggatgctaca agtcatctgc tttcatttt cttccccatt     54840
tgaccataag cttctcaagg gcttatagct ataagcaact ttatctatgc acctcagagc    54900
ctagcaaaat ggccagtatg tgcaagtggc agcaccatga gaccaatgag ggagctggga    54960
caagtgtccg aacagcacag ttctggctgc caaagaaaac agagcctgtg gagtgtgggc    55020
aggagcagaa tcacaacagt gagcctggtt agggacatct gcagcaactc atgagcaact    55080
gagtaattag gacacagaga aaagtaatgt cgtaggctgc tacaaattaa ctgggagata    55140
ggttaaaaaa aaaaaaaaag ctggccagca caattatcat ctgcggttct gaaaaaagaa    55200
```

-continued

```
ggtgttgtac aaaatataat tatgtgatga atcatttgga ggcatttcta atgaaaaaca   55260
ctcactagaa aggattaacc agaagttgtg tccattgtct gatacagagt ttgtagctct   55320
catcttcttt ctaagcctcc ataaatccac gggaagcttc tgtttatcga ttttatttgc   55380
agaatgcact cagggtataa agtaatttgc ttttttttaa atagggttta gggtctgccc   55440
ctacagggtt ataacttacc aagcataaaa gccaacacat aaaacaaac atacaattta    55500
aggagagaag ggctcacggc agcagaacct gggaattcag cgaggtggtg ggatcactcc   55560
cgggcgcacc cacacgccca tatatctgct gggctgaaat ctcctggtgg gtgatatttt   55620
ggatgccttt catgcatggc atcgctgaac tgttttttgaa aaatgcacca accccacaga  55680
gaagagcaca atagttattt agcagacata gagagggaaa ggagaatttt ctttattgtt   55740
tatcagagct aaaaataatg ctgtgaatgt tagccatctt tgcagcttgt gtaaaatttg   55800
tccttttctc atcaaagtca gcagcccaga ctgatcaatg ccattaacat tgtccccgat   55860
ccagctcccc catgcgtgtg caagctctgt ggcttgcagg ctgtaaactg aagaatagca   55920
ccttgcgttt ttatacttct tttgcggaga atctctattt aattccaagc gattgtgggt   55980
aattaaattt tatagaagaa ttttttcttt accaaccccca ttagggttct gttgcacttg  56040
tccgttgcct cataaaagaa aaaaaaaaaa gggaagctgc cacatctgtc ccttaaacac   56100
ttggcttgga ttctctgccc tgtgattcac agtatgcatt tgtgacaaga agttctccat   56160
acttggagtc acaaatgccg agaagagtaa gccaggcaaa ctgcttgtgc tgtctgtggg   56220
gacagtgatg cacagagagc cagtgaaggg ctgaccttc cacctttagca gaaggtagat    56280
aataaatggc cttttgtgaga cttttggtg attgcatcac cacggcggat atggcccctg    56340
agtaaagtgt ggacttagct gtgcagtgtg atagccacaa cttcaaaaga ctcaggggag   56400
ctgtgaactg ctggggacac caggagaaca ccaggcagca gcaatcagaa tcctttgaaa   56460
tggagtctta aaggcagagc atcaagggc accatcaggt ctgcagttac tgttgctgca    56520
aacgaaagag cagtcttagc ccattggagt gggccagtgg gcaatctctt tggtgacatc   56580
tacactaatg gaaaaatatc accacccata acagcatctt tgaaaataga tgcaaggaca   56640
cctctgggca tcagacacaa agcaaagctg tgactcctca ctgggaaggg tctcgcctga   56700
tccatctacc attcaaaatg tttcagtcca gagctcaaaa atctagtgct gatctcagta   56760
agtctacata atcacctctg tgttaacacc ccgcaccacc tcttctgttc agcttcacgg   56820
agcaggcaga caccaatagc catcgcgtgg gaaaataata tcaggaagct agccattcct   56880
gagagcacac catgtgccaa gcacaggacc agcggccaga cctgcaatgt cttgcttgat   56940
cctcacagag attctcggag ctagattcta taattctccc cattttatag atgagaaact   57000
gggggctttg tgaaggtaat tgacatgccc aaagttaccc agcaacgaag tggtggagcc   57060
aagagcactc ttaaccattg ccttttattt ccataaacac ctcaaaatct cttcattaag   57120
ccataaactc atacctttcc atgggaaata ttttctgaaa aattactttc tcaaatttag   57180
ccatgggaat gatttctttg aaagtagtac tgctacattt taaacatatt gtcatttgta   57240
aattaagcca ttgataagtt cctttgaagc tggagtttga aatgcagggg aaccatcaat   57300
ttctactgtg gatgtgatgg tcctggaaca cacagttaaa atgtggctat gacacatggc   57360
agagaaccat gttaacatat gagctaagaa gaactaggct ctataggcac ttcccagcaa   57420
gatccatgtc tgaagaaaca gagatggtat agtgagctgg tcctgaagcc caaagaatgt   57480
cttgatgaca gtgtttctca aagtgaggct cacagggcga tctgcctcaa caccacccga   57540
gatcctcact aaacatgcat tccttggatt cgagcctagg aatctacatt tcaacaatct   57600
```

```
gcctagatga tttatgcac agtaaagctt gagaactttt gatccacact agagtaacta    57660
attcagctta tactagagat tggaaaaaat gctacaaaga atagtaatat tcaagacaag    57720
agaaaaaaga catggtctct aaaaatctct atagagactg atgcacccca acttccagaa    57780
acaactttga aaccctgtgc agatgtggtg tttatatgta ggctaagttg caaggcattt    57840
gagcagctct gggatagcca ctatatgcaa aaagtatctc tctgacatag ttttctgaaa    57900
tgtcaagatt agagatgaca acgtttgggt gactatattt tcagcaatgt cttttctt     57960 tccagctctc ccttctggcc ttctttgaaa attaaagtaa ttccaacagg agaaattaat    58020
taaattgcta ttactttagc attaatttta ttatctataa aaaggcaggg ctgaacagga    58080
tattagtgat aactaacctt tttaaaaccc ttttgaatgt attatctcat cttgcttttg    58140
ataaaacata caacgtagtc cttatcatct tttccacatg cagaaactga ggtcagtga    58200 cttgcccaag accacgcaga tactactcag gaaagccatt tagtcattca ttcagcaaat    58260
gtgtgttgat tgtccactgt atgccaggca ctgttccagg tgctggaata aaacagacca    58320
ggtttatgtt ctcaggaagt taacatctgg tcacgtatcc aagaagacat gaatcaaggt    58380
cacctggcca aaaaggaggt caagtccagg cattgtgtaa gtggctgcaa tcatataggt    58440
cagggattgg gaaactcttc ccataagggg ccaaatagta atcattttag gctctatgga    58500
ctgtatggtc ccactctcaa ctactgaact ctgccattgt aaagtgccaa cattgcaggg    58560
tgttgtatca aaccccctca acagtttcat ggccccttc cagcctcagt cttcttggct    58620
ccacctccct gattaattta ggggaggatg ctgggaacct aggagagagc atggtgctga    58680
aagtaggtag aaaaaaagaa tctaagaaaa aacgacatgg agggagaaaa ataaataagt    58740
aaagccacaa ccacttcatt aatcttatca ttgtcttggc ttctggctgg ccttgcctcc    58800
tggtgacatt ttatttcctt tcttaccccc tactgcagca gcagtattgg cgtgttcttc    58860
tgtggaccta aagctctctc gaggacactt caaaagatgt gccacttgta ttcatcagct    58920
gaccccagag gtgttcattt ctattacaac aaggagagct tctag                   58965

<210> SEQ ID NO 25
<211> LENGTH: 16
<212> TYPE: PRT
<213> ORGANISM: artificial sequence
<220> FEATURE:
<221> NAME/KEY: source
<223> OTHER INFORMATION: note="Description of artificial sequence:
      synthetic peptide"

<400> SEQUENCE: 1

Arg Gln Ile Lys Ile Trp Phe Gln Asn Arg Arg Met Lys Trp Lys Lys
1               5                   10                  15

<210> SEQ ID NO 26
<211> LENGTH: 18
<212> TYPE: PRT
<213> ORGANISM: artificial sequence
<220> FEATURE:
<221> NAME/KEY: source
<223> OTHER INFORMATION: note="Description of artificial sequence:
      synthetic peptide"

<400> SEQUENCE: 26

Lys Leu Ala Leu Lys Leu Ala Leu Lys Ala Leu Lys Ala Ala Leu Lys
1               5                   10                  15

Leu Ala
```